US007951070B2

(12) United States Patent
Ozaki et al.

(10) Patent No.: US 7,951,070 B2
(45) Date of Patent: May 31, 2011

(54) OBJECT OBSERVATION SYSTEM AND METHOD UTILIZING THREE DIMENSIONAL IMAGERY AND REAL TIME IMAGERY DURING A PROCEDURE

(75) Inventors: Takashi Ozaki, Hachioji (JP); Koichi Tashiro, Sagamihara (JP); Masaya Fujita, Sagamihara (JP); Masakazu Gotanda, Kanagawa (JP); Akinobu Uchikubo, Iruma (JP); Takeaki Nakamura, Hino (JP)

(73) Assignee: Olympus Corporation, Tokyo (JP)

( * ) Notice: Subject to any disclaimer, the term of this patent is extended or adjusted under 35 U.S.C. 154(b) by 1117 days.

(21) Appl. No.: 11/716,308

(22) Filed: Mar. 9, 2007

(65) Prior Publication Data
US 2007/0173689 A1 Jul. 26, 2007

Related U.S. Application Data

(62) Division of application No. 10/858,440, filed on Jun. 1, 2004, now abandoned.

(30) Foreign Application Priority Data

| Jun. 2, 2003 | (JP) | 2003-157041 |
| Jun. 2, 2003 | (JP) | 2003-157042 |
| Jul. 1, 2003 | (JP) | 2003-189784 |
| Jul. 1, 2003 | (JP) | 2003-189785 |
| Jan. 30, 2004 | (JP) | 2004-024828 |
| Jan. 30, 2004 | (JP) | 2004-024829 |
| Jan. 30, 2004 | (JP) | 2004-024830 |
| Jan. 30, 2004 | (JP) | 2004-024831 |
| Jan. 30, 2004 | (JP) | 2004-024832 |
| Jan. 30, 2004 | (JP) | 2004-024833 |

(51) Int. Cl.
*A61B 1/00* (2006.01)
*A61B 1/04* (2006.01)
(52) U.S. Cl. .......... 600/118; 600/117; 600/104; 600/109
(58) Field of Classification Search .................. 600/109, 600/117, 118, 407, 476, 166, 104
See application file for complete search history.

(56) References Cited

U.S. PATENT DOCUMENTS 4,989,083 A * 1/1991 Eino .............................. 348/135
5,217,003 A 6/1993 Wilk
(Continued)

FOREIGN PATENT DOCUMENTS
JP 07-194616 8/1995
(Continued)

OTHER PUBLICATIONS
Japanese Official Action dated Mar. 16, 2010.

*Primary Examiner* — John P Leubecker
(74) *Attorney, Agent, or Firm* — Scully, Scott, Murphy & Presser, P.C.

(57) ABSTRACT

An object observation method and system including an endoscope, at least one treating device, a first detecting portion for detecting information indicating an observation direction of the endoscope, a second detecting portion for detecting information indicating a treatment direction of the treating device, a three dimensional virtual image data storing portion for storing three dimensional image data prepared in advance, a virtual image data processing portion for creating virtual image data based on the information indicating the observation direction and the treatment direction, first and second three dimensional image display monitors, each having first and second image display devices, and switch sections for instructing change of display mode of the second image display devices.

8 Claims, 91 Drawing Sheets

U.S. PATENT DOCUMENTS

| | | | |
|---|---|---|---|
| 5,261,404 A * | 11/1993 | Mick et al. | 600/425 |
| 5,274,551 A * | 12/1993 | Corby, Jr. | 600/433 |
| 5,765,561 A * | 6/1998 | Chen et al. | 600/407 |
| 5,776,050 A | 7/1998 | Chen et al. | |
| 5,873,822 A * | 2/1999 | Ferre et al. | 600/407 |
| 6,591,130 B2 | 7/2003 | Shahidi | |
| 2005/0085717 A1* | 4/2005 | Shahidi | 600/424 |

FOREIGN PATENT DOCUMENTS

| | | |
|---|---|---|
| JP | 08-280695 | 10/1996 |
| JP | 11-309 | 1/1999 |
| JP | 2000-135215 | 5/2000 |
| JP | 2003-093493 | 4/2003 |
| JP | 2003-127076 | 5/2003 |

* cited by examiner

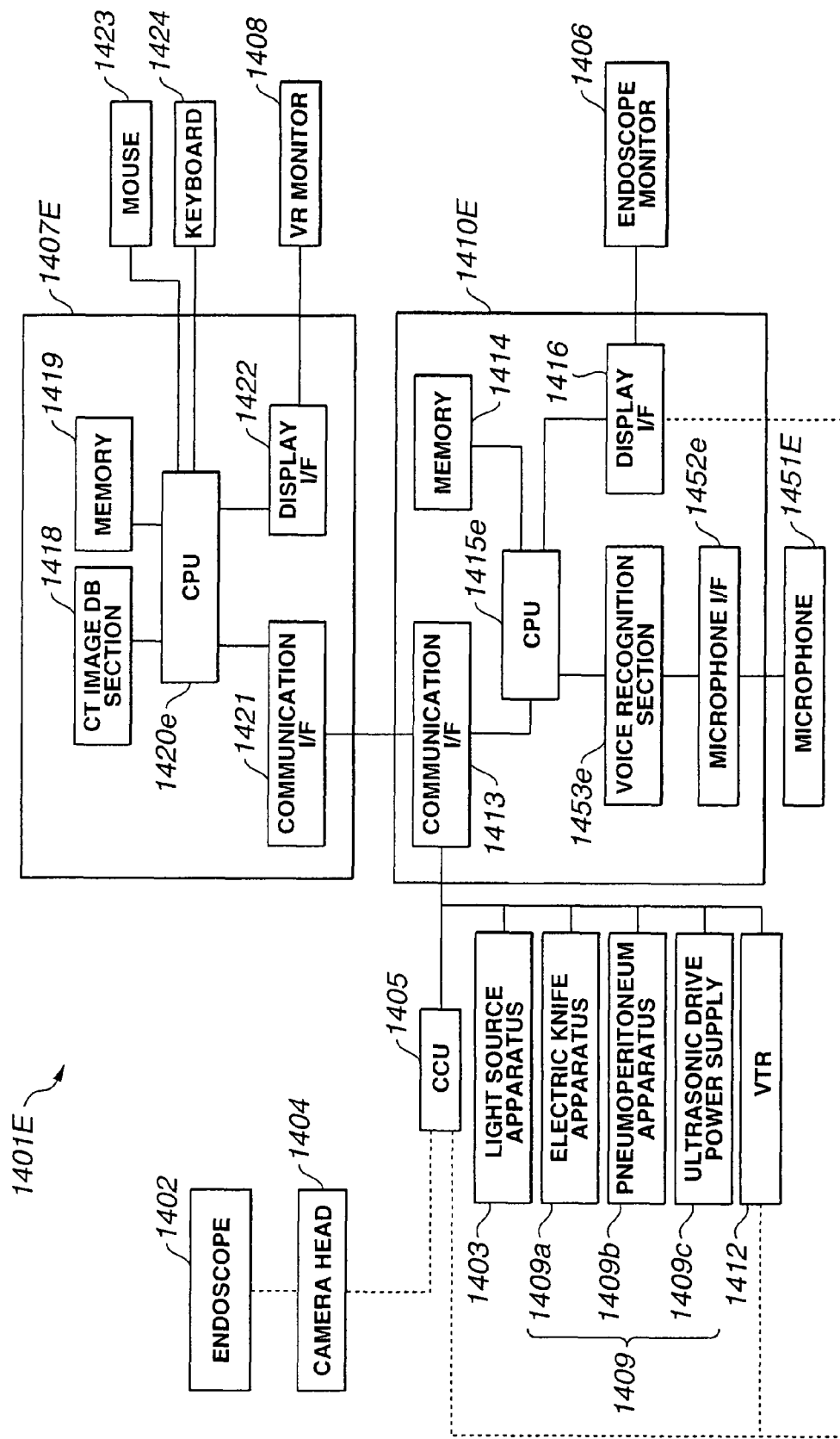

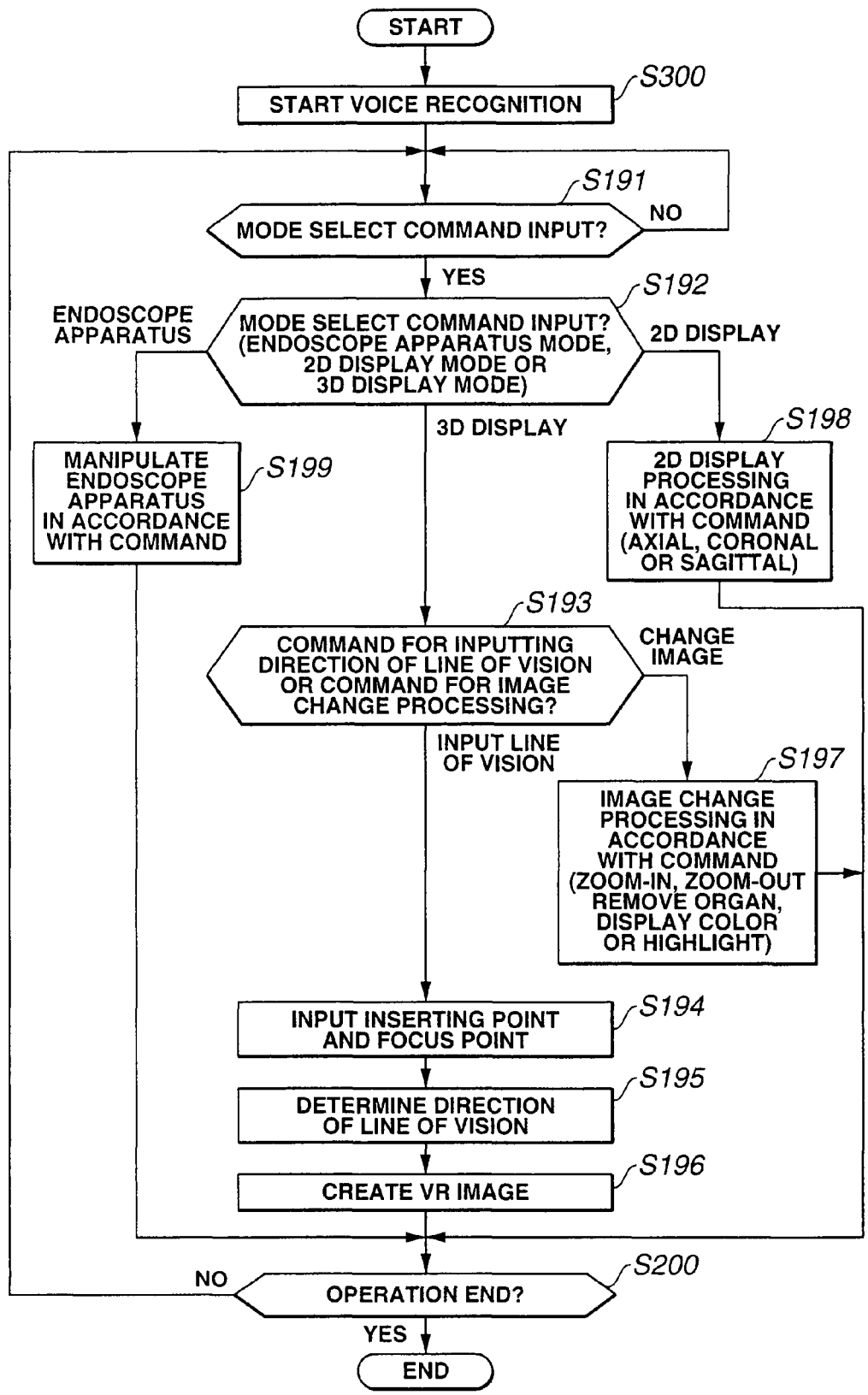

OBJECT OBSERVATION SYSTEM AND METHOD UTILIZING THREE DIMENSIONAL IMAGERY AND REAL TIME IMAGERY DURING A PROCEDURE

This application is a divisional application of U.S. application Ser. No. 10/858,440 filed on Jun. 1, 2004, now abandoned, which claims benefit of Japanese Application Nos. 2003-157041 filed on Jun. 2, 2003, 2003-157042 filed on Jun. 2, 2003, 2003-189784 filed on Jul. 1, 2003, 2003-189785 filed on Jul. 1, 2003, 2004-024828 filed on Jan. 30, 2004, 2004-024829 filed on Jan. 30, 2004, 2004-024830 filed on Jan. 30, 2004, 2004-024831 filed on Jan. 30, 2004, 2004-024832 filed on Jan. 30, 2004, 2004-024833 filed on Jan. 30, 2004, the contents of each of which are incorporated herein by this reference.

BACKGROUND OF THE INVENTION

1. Field of the Invention

The present invention relates to an object observation system and a method of controlling an object observation system.

2. Description of Related Art

Endoscope apparatuses have been widely used in medical fields and industrial fields. In the endoscope apparatus, an endoscopic image obtained by a television camera externally installed endoscope in which a television camera is attached to an eyepiece portion of an optical endoscope or an electronic endoscope self-containing an image pickup apparatus at the distal end of an insert portion thereof is displayed on a monitor. With reference to the endoscopic image, observation and/or treatment may be performed.

An endoscopic surgery system using the endoscope apparatus is used for performing an operation under endoscopic observation by using a pneumoperitoneum apparatus and/or a high-frequency cautery apparatus, for example, as multiple peripheral apparatuses in addition to a camera control unit (called CCU or video processor, hereinafter) including a light source apparatus for supplying illumination light to an endoscope and/or a video signal processing circuit for displaying endoscopic images and/or a TV monitor for displaying endoscopic images. In the endoscopic surgery system, the multiple peripheral apparatuses are connected to a system controller in order to centrally control the multiple peripheral apparatuses.

With the recent increase in processing speed of computers, the endoscopic surgery system can reconstruct a volume rendering image (simply called rendering image or VR image, hereinafter) as a virtual three dimensional image (called virtual image, hereinafter) instantly by using medical image data in a three-dimensional area and can display a rendering image on a display screen of the monitor as a navigation image for guiding an endoscope, for example, to a target part of a body to be examined and/or a reference image for checking the surroundings of a target part.

As this kind of conventional endoscopic surgery system, a system used in a bronchial endoscope apparatus has been proposed as disclosed in Japanese Unexamined Patent Application Publication No. 2000-135215.

The endoscopic surgery system disclosed in the publication creates a three dimensional image of a tract within a body to be examined based on medical image data in a three-dimensional area of the body to be examined, obtains a path to a target point along the tract on the three-dimensional image, creates a virtual rendering image of the tract along the path based on the medical image data and displays the virtual rendering image on the monitor. Thus, a bronchial endoscope can be guided or navigated to a target part.

With the endoscopic surgery system used in the bronchial endoscope apparatus, a rendering image of a predetermined path is displayed. In this case, an operator does not have to operate or instruct in the middle in particular. Therefore, the endoscopic surgery system is useful for navigating the bronchial endoscope to a tract in the body such as the bronchial tubes, which limits a direction of line of vision.

On the other hand, a conventional endoscopic surgery system can display a rendering image as a reference image in addition to an endoscopic image when the conventional endoscopic surgery system is used for surgery.

Generally, in surgery, an operator performs surgical treatment by using a treating device such as an electric knife with reference to an endoscopic image. In this case, the operator uses rendering images of a target part and the surroundings as reference images in order to check the state of the blood vessels around an internal organ and/or the back of an internal organ.

Therefore, the endoscopic surgery system must display a rendering image as a reference image that an operator needs to check on the spot during surgery more than a case where a rendering image is used for navigation of a bronchial endoscope, for example.

Therefore, the conventional endoscopic surgery system displays a rendering image in response to a manipulation on a mouse and/or a keyboard by a nurse or an operator in an unclean area based on an instruction by an operator in a clean area.

Recently, in a surgical operation, various progressions and results of the surgery are often recorded, and endoscopic images may be also recorded. During surgery, an operator takes photographs by manipulating a release switch in order to store in patient's charts and records and saves still-image data of endoscopic images as a record of the surgery.

In order to create a three-dimensional image as described above, a three-dimensional virtual image data of the inside of a body to be examined is obtained by picking up a tomographic image of the body to be examined by using an X-ray computed topography (CT) apparatus, for example. Thus, an affected part can be diagnosed by using the virtual image data.

In the CT apparatus, X-ray irradiation/detection are rotated continuously, and, at the same time, a body to be examined is fed in series in the body axis direction. Thus, continuous helical scanning can be performed on a three-dimensional area of the body to be examined. Therefore, a three-dimensional virtual image can be created from tomographic images of serial slices of the three-dimensional area.

One of this kind of three dimensional image is a three dimensional image of the bronchi of the lung. A three-dimensional image of the bronchi is used for three-dimensionally identifying a position of an abnormal part, which is suspected as a lung cancer, for example. In order to check the abnormal part by performing a biopsy, a bronchial endoscope is inserted, and a biopsy needle and/or a biopsy forceps are extended at the distal end. Thus, a tissue thereof can be sampled.

In a tract inside of the body having multi-level branches such as the bronchi, when a position of an abnormal part is close to the end of the branch, bringing the distal end of an endoscope to a target part accurately in a short period of time is difficult. Therefore, for example, a navigation apparatus is proposed in Japanese Unexamined Patent Application Publication No. 2000-135215 above.

By the way, for a diagnosis on an internal organ of the abdomen area, which is a body to be examined, an image analysis software is conventionally in actual use which creates a three-dimensional virtual image of the body to be examined within the abdomen area mainly as described above and displays the image for diagnosis.

An image system using this kind of image analysis software is used for diagnosis so that a doctor can identify a change in a lesion of a body to be examined within the abdomen area of a patient before surgery, and the diagnosis is generally performed on a desk.

SUMMARY OF THE INVENTION

An object observation system of the invention has an observation apparatus for observing a body to be examined, a three-dimensional image recording apparatus for recording three-dimensional images, which are obtained in advance, of the body to be examined, and an image constructing apparatus for constructing a three-dimensional image based on images in synchronization with the observation apparatus, which are recorded in the three-dimensional image recording apparatus.

BRIEF DESCRIPTION OF THE DRAWINGS

FIG. 82 is a diagram showing a state in which the head band in FIG. 81 is put on;

FIG. 120 is a flowchart showing a processing operation, which is a feature of the fifteenth embodiment;

FIG. 121 is a screen display example of a virtual image display screen for illustrating an operation of the fifteenth embodiment;

FIG. 122 is a screen display example of a virtual image display screen on which the virtual image in FIG. 121 is enlarged;

FIG. 123 is an entire configuration diagram showing an object observation system according to a sixteenth embodiment; and FIG. 124 is a flowchart showing a processing operation, which is a feature of the sixteenth embodiment.

DETAILED DESCRIPTION OF PREFERRED EMBODIMENTS

First Embodiment

An embodiment of the invention will be described below with reference to drawings.

Figure 1:
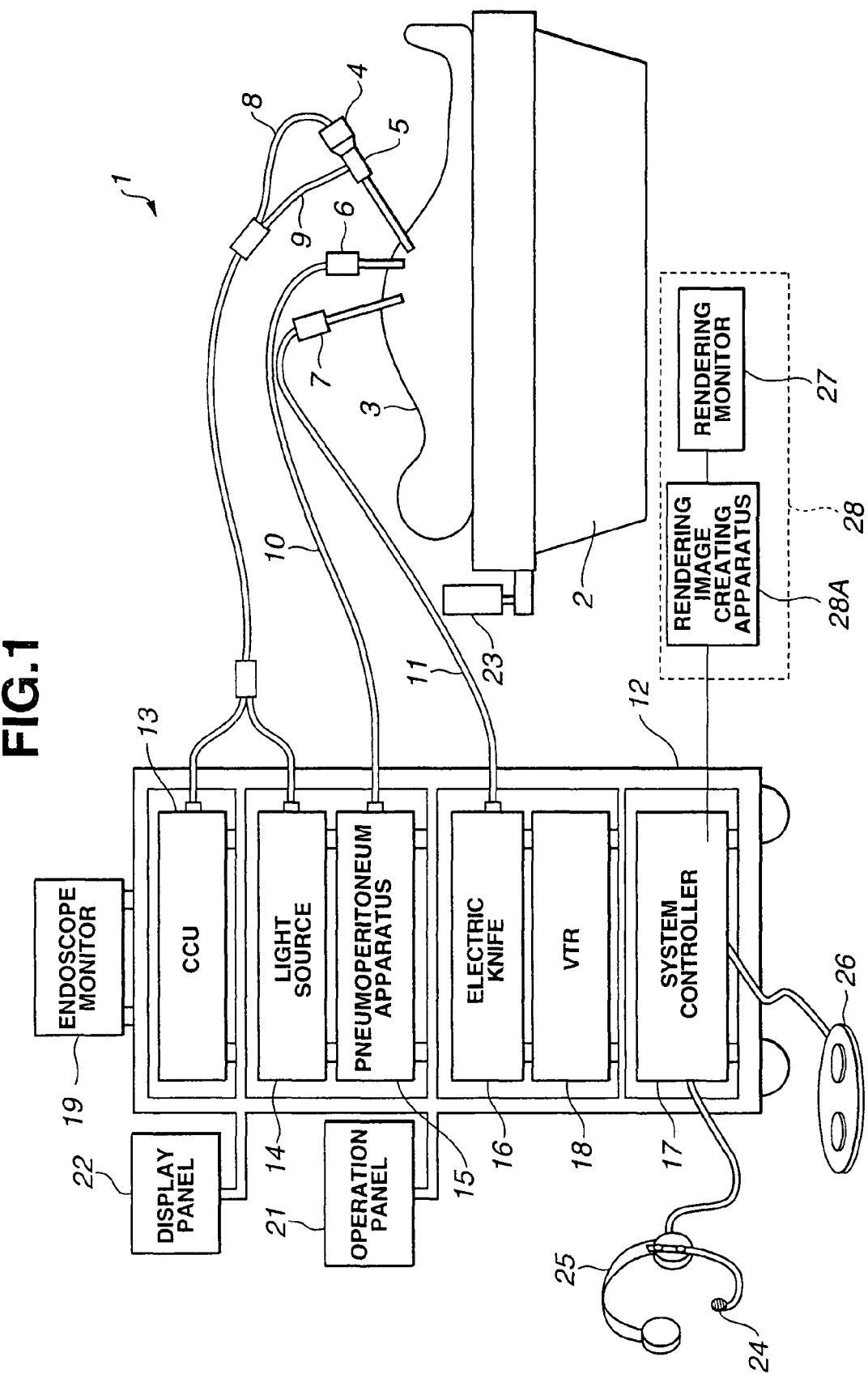
FIG. 1 is an entire configuration diagram showing an endoscopic surgery system according to a first embodiment.
Figure 2:
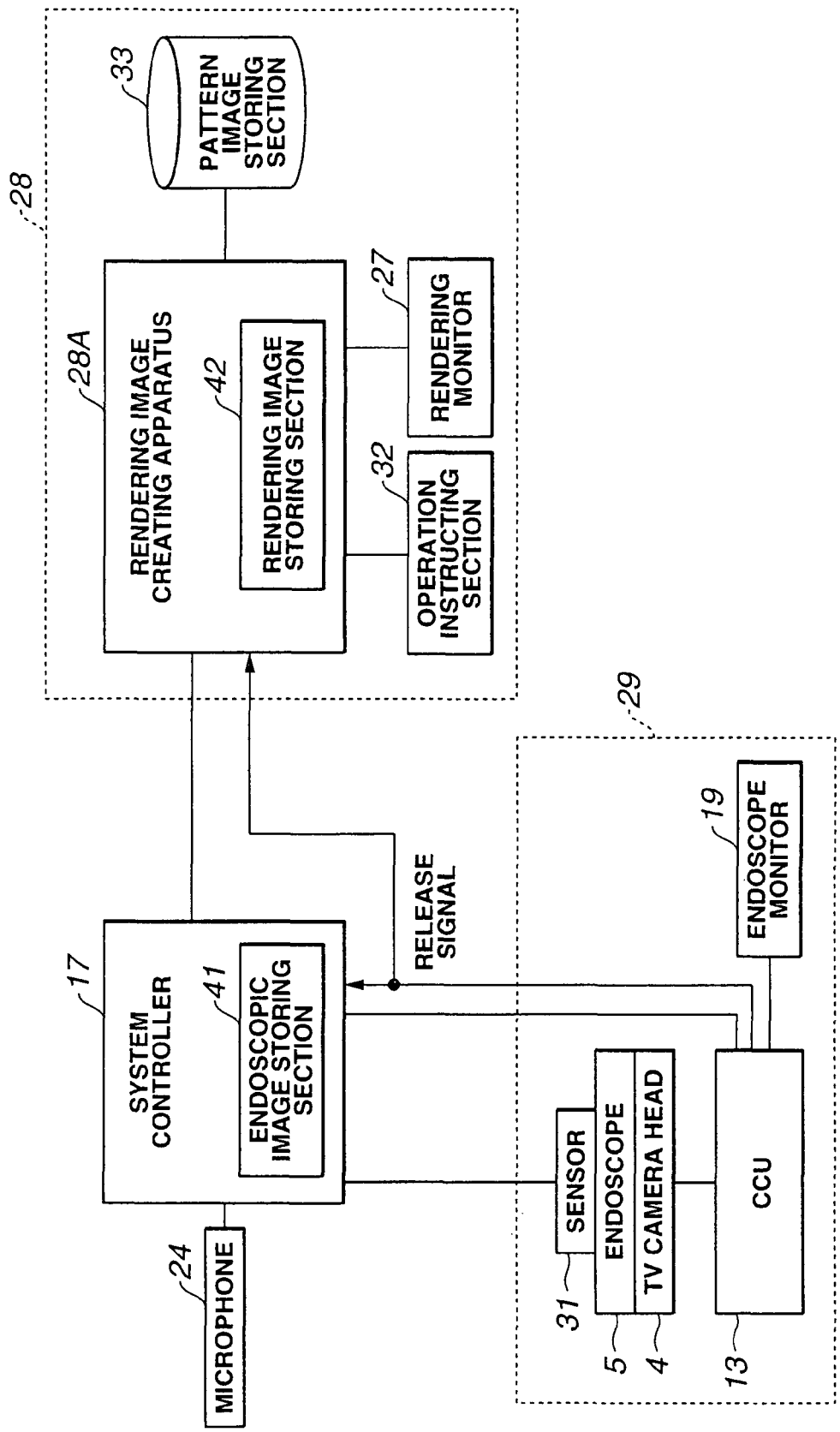
FIG. 2 is a circuit block diagram of an endoscope apparatus and rendering apparatus in FIG. 1.
Figure 3:
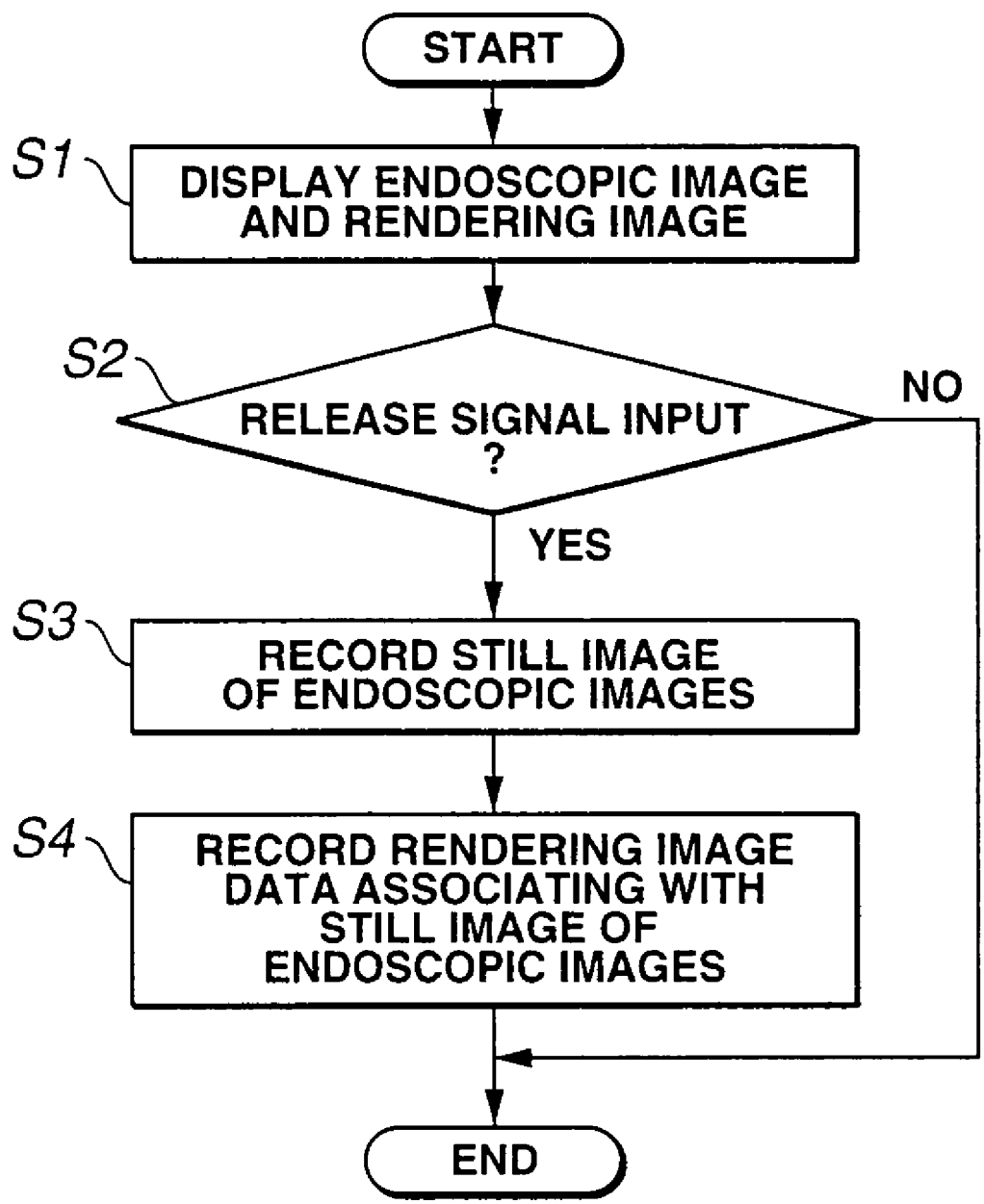
FIG. 3 is a control flowchart of a system controller in FIG. 1.

FIGS. 1 to 3 relate to a first embodiment of the invention. FIG. 1 is an entire configuration diagram showing an endoscopic surgery system according to the first embodiment. FIG. 2 is a circuit block diagram of an endoscope apparatus and rendering apparatus in FIG. 1. FIG. 3 is a control flowchart of a system controller in FIG. 1.

As shown in FIG. 1, an endoscopic surgery system 1 according to the first embodiment is an object observation system. The endoscopic surgery system 1 has a rigid endoscope (often simply called endoscope, hereinafter), which is inserted to an abdominal cavity of a patient 3, which is a body to be examined, lying on an operation table 2 through a trocar (not shown). A TV camera head 4 self-containing an image pickup apparatus is attached to the rigid endoscope 5. The endoscopic surgery system 1 includes a pneumoperitoneum guide tube 6 and an electric knife probe 7, which are inserted to the patient 3. The pneumoperitoneum guide tube 6 is used for performing a pneumoperitoneum. The electric knife probe 7 is used for electrically performing a cautery treatment on an affected part.

In the endoscopic surgery system 1, a signal cable 8 connecting to the TV camera head 4, a light guide cable 9 connecting to the endoscope 5, a pneumoperitoneum tube 10 connecting to the pneumoperitoneum guide tube 6 and a signal cable 11 connecting to the electric knife probe 7 are connected to a CCU 13, a light source apparatus (which may be called light source hereinafter) 14, a pneumoperitoneum apparatus 15, and an electric knife 16, which are mounted in a trolley 12, respectively.

A system controller 17, a VTR 18 and an endoscope monitor 19 are mounted in the trolley 12 in addition to the CCU 13, the light source 14, and the pneumoperitoneum apparatus 15 and the electric knife 16. The CCU 13 performs signal processing for an image pickup apparatus contained in the TV camera head 4. The light source 14 supplies illumination light. The pneumoperitoneum apparatus 15 supplies gas for pneumoperitoneum. The electric knife 16 supplies cautery high frequency power. The system controller 17 performs entire control. The VTR 18 records image signals output from the CCU 13. The endoscope monitor 19 displays image signals output from the CCU 13 as endoscopic images.

In the endoscopic surgery system 1, a central operation panel 21 for performing central operation and a central display panel 22 for performing central display are attached to the trolley 12. A remote controller 23 for performing remote control operation is removably provided in the operation table 2.

Medical equipment such as the CCU 13 are connected to the system controller 17 through a communication cable (not shown) and are centrally operated by the central operation panel 21, the remote controller 23 and the central display panel 22.

The system controller 17 has a microphone 24 for capturing voice as instructing means. The microphone 24 is removably connected to the system controller 17 through a signal cable extending from the head set 25. The microphone 24 may be a pin microphone. The system controller 17 and the head set 25 may be adjusted to communicate voice information by radio communication such as infrared rays. The microphone 24 may be attached to a goggles type or glasses type apparatus called face mount display (FMD) or head mount display (HMD).

A foot switch 26, which is a remote operation unit, is connected to the system controller 17. A hand switch (not shown) may be connected to the system controller 17 instead of the foot switch 26.

The system controller 17 receives image signals output from the CCU 13 and causes the VTR 18 to record the image signals. When a release switch (not shown) is manipulated, the system controller 17 receives and records still-image data from the CCU 13.

The endoscopic surgery system 1 according to this embodiment includes a rendering apparatus 28 which can create and display a rendering image as a virtual three-dimensional image of the inside of a body cavity by using medical image data in a three-dimensional area. The rendering apparatus 28 is included in a three-dimensional image recorder in which three-dimensional images, which has been acquired in advance, of a body to be examined are recorded.

As shown in FIG. 2, the endoscope 5, the TV camera head 4, the CCU 13 and the endoscope monitor 19 are included in the endoscope apparatus 29 as an observation apparatus for observing a body to be examined. The endoscope 5 has a sensor 31 as a positional relationship detecting portion for detecting a relative positional relationship between the distal end part of the insert portion and a body to be examined, positional relationship information with respect to a twisting angle, insert length, and insert point and focus point with respect to a body to be examined of the insert portion can be detected. According to this embodiment, a rigid endoscope is used. However, when a soft endoscope having a soft insert portion is used, an inserting speed of the insert portion, a bending angle of a bend and so on can be detected as the positional relationship information.

Positional relationship information detected by the sensor 31 is captured by the system controller 17 and is output to the rendering apparatus 28. The sensor 31 may perform radio communication by infrared rays, for example, and may give the positional relationship information directly to the rendering apparatus 28.

The rendering apparatus 28 reconstructs and displays on the rendering monitor 27 a body cavity rendering image following the distal end of the insert portion of the endoscope 5, that is, in synchronization with an endoscopic image displayed on the endoscope monitor 19 based on the position relationship information obtained from the sensor 31.

The rendering apparatus 28 has a rendering image creating apparatus 28A, an operation instructing section 32 such as a mouse and a keyboard, and a pattern image storing section 33 for storing extracted image, which is created by instructing to set a predetermined parameter relating to image display in response to an instruction from the operation instructing section 32 and extracting a predetermined part.

The endoscope apparatus 29 has a release switch (not shown) in the TV camera head 4 or the CCU 13. By manipulating the release switch, photo-shooting is performed, and still image data of endoscopic images is recorded as records of surgery. When the endoscope is an electronic endoscope self-containing an image pickup apparatus, the release switch is provided in the electronic endoscope.

In order to recognize details of surgery easily, the endoscopic surgery system 1 according to this embodiment is adjusted to store still image data of endoscopic images and rendering image data substantially at the same time in response to a manipulation on the release switch.

More specifically, the system controller 17 includes an endoscopic image storing section 41 as recording means for recording still image data of endoscopic images in response to a release signal output from the CCU 13. The rendering image creating apparatus 28A includes a rendering image storing section 42 as recording means for recording rendering image data in response to a release signal output from the CCU 13.

The rendering image creating apparatus 28A associates still image data of an endoscopic image stored in the endoscopic image storing section 41 and rendering image data stored in the rendering image storing section 42 by using a time stamp, for example.

Therefore, the endoscopic surgery system 1 according to this embodiment stores rendering image data in association with still image data of an endoscopic image substantially in synchronization with the still image data of the endoscopic image in response to a manipulation on the release switch. The endoscopic image storing section 41 and the rendering image storing section 42 may not be provided separately like the pattern image storing section 33.

The endoscopic surgery system 1 having the above-described construction has a construction as illustrated in FIG. 1 and may be used for an endoscopic surgery.

The insert portion of the endoscope 5 is inserted to a body cavity of a patient, and an endoscopic image obtained by the endoscope 5 is picked up by the TV camera head 4. The TV camera head 4 picks up and optoelectronically converts an endoscopic image and outputs image pickup signals thereof to the CCU 13. The CCU 13 performs signal processing on the image pickup signals and generates image signals.

On the other hand, the rendering image creating apparatus 28A reconstructs a body-cavity rendering image in accordance with the distal end of the insert portion of the endoscope 5, that is, in synchronization with an endoscopic image displayed on the endoscope monitor 19 based on positional relationship information obtained from the sensor 31.

Here, the CCU 13 and the rendering image creating apparatus 28A are controlled by the system controller 17, and processing is performed in accordance with the flowchart shown in FIG. 3.

As shown in FIG. 3, the system controller 17 controls the CCU 13 to output endoscopic image signals created by the CCU 13 to the endoscope monitor 19 and display the endoscopic image on a display screen of the endoscope monitor 19. Furthermore, the system controller 17 controls the rendering image creating apparatus 28A to output rendering image data created by the rendering image creating apparatus 28A to the rendering monitor 27 and displays the rendering image on a display screen of the rendering monitor 27 (step S1).

An operator uses an electric knife 16, for example, to perform treatments with reference to endoscopic images and rendering images.

Here, an operator manipulates the release switch in the TV camera head 4 or the CCU 13 to take photographs and records still image data of endoscopic images as records of surgery.

The system controller 17 judges the presence of a release signal (step S2). If a release signal is given, still image data of endoscopic images is recorded in the endoscopic image storing section 41 (step S3).

Next, the system controller 17 controls the rendering image creating apparatus 28A to record rendering image data associated with the still image data of an endoscopic image in the rendering image storing section 42 (step S4). If a release signal is not given or if surgery ends, the system controller 17 terminates the processing. In this way, the system controller 17 constructs a rendering image from images recorded in the rendering apparatus 28 in synchronization with a still image of an endoscopic image.

The still image data and rendering image data of an endoscopic image may be recorded in reverse order. In other words, rendering image data associated with the still image data of an endoscopic image may be recorded in the rendering image storing section 42 first, and the still image data of the endoscopic image may be then recorded in the endoscopic image storing section 41.

Thus, the endoscopic surgery system 1 according to this embodiment can record rendering image data in association with the still image data of an endoscopic image substantially at the same time and can attach the rendering image data to patient's charts along with the still image data of the endoscopic image.

Here, rendering image data does not have the unnecessary blood, fat and so on. Thus, viewing the rendering image data along with the recorded still image data of an endoscopic image helps recognizing which technique step of what surgery the endoscope image relates to.

Therefore, with the endoscopic surgery system 1 according to this embodiment, details of surgery can be grasped easily.

The endoscopic surgery system 1 according to this embodiment includes a sensor 31 as a positional relationship detecting portion for detecting a relative positional relationship between the distal end part of the insert portion of the endoscope 5 and a body to be examined, positional relationship information with respect to a twisting angle, insert length, and insert point and focus point with respect to a body to be examined of the insert portion can be detected. However, the invention is not limited thereto. A relative positional relationship between the distal end of the insert portion of the endoscope 5 and a body to be examined may be detected by a positional relationship detecting portion by detecting a position and/or angle of a body-cavity tissue through image processing on an endoscopic image.

Second Embodiment

Figure 4:
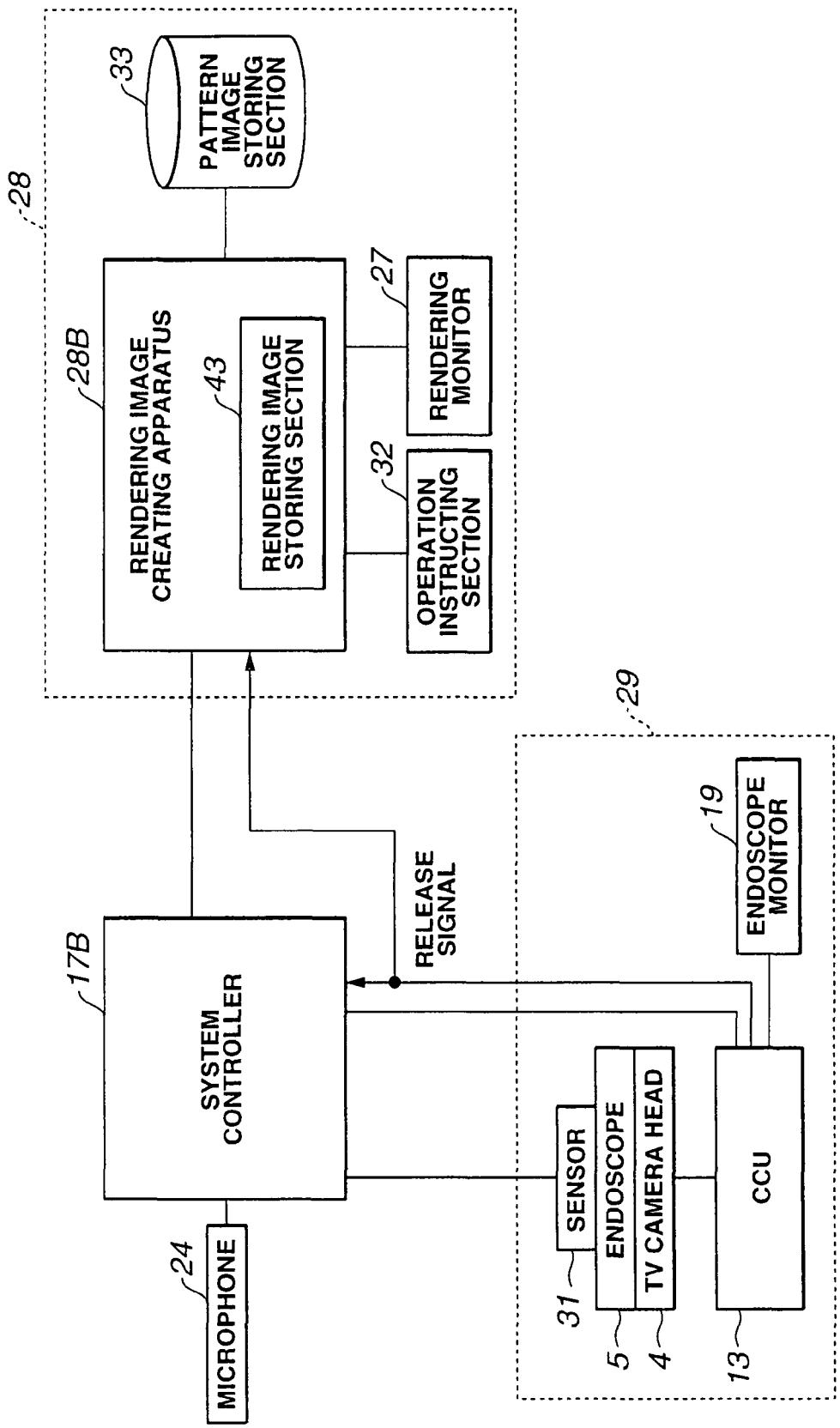
FIG. 4 is a circuit block diagram of an endoscope apparatus and rendering apparatus included in an endoscopic surgery system according to a second embodiment.
Figure 5:
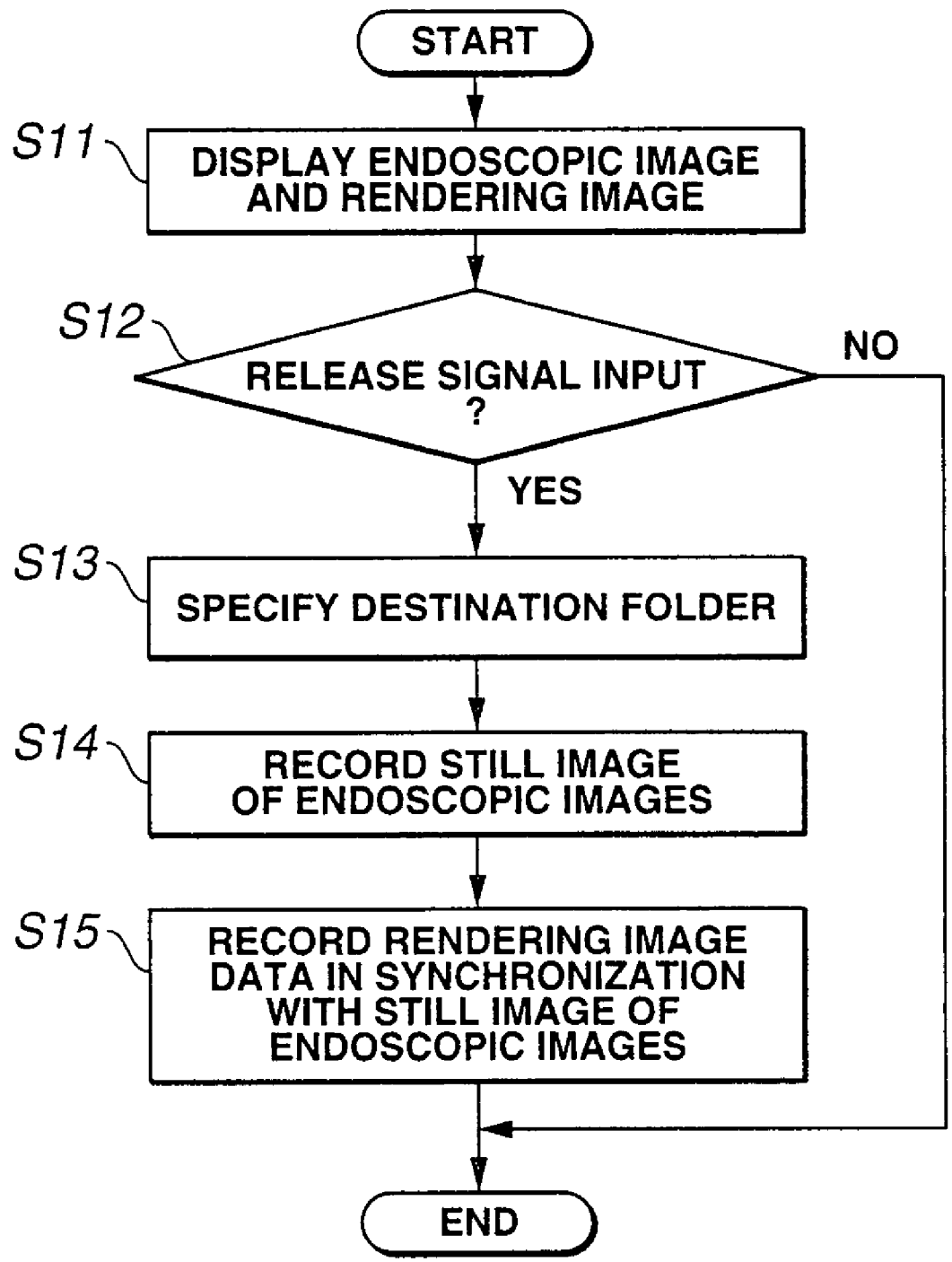
FIG. 5 is a control flowchart of a system controller in FIG. 4.
Figure 6:
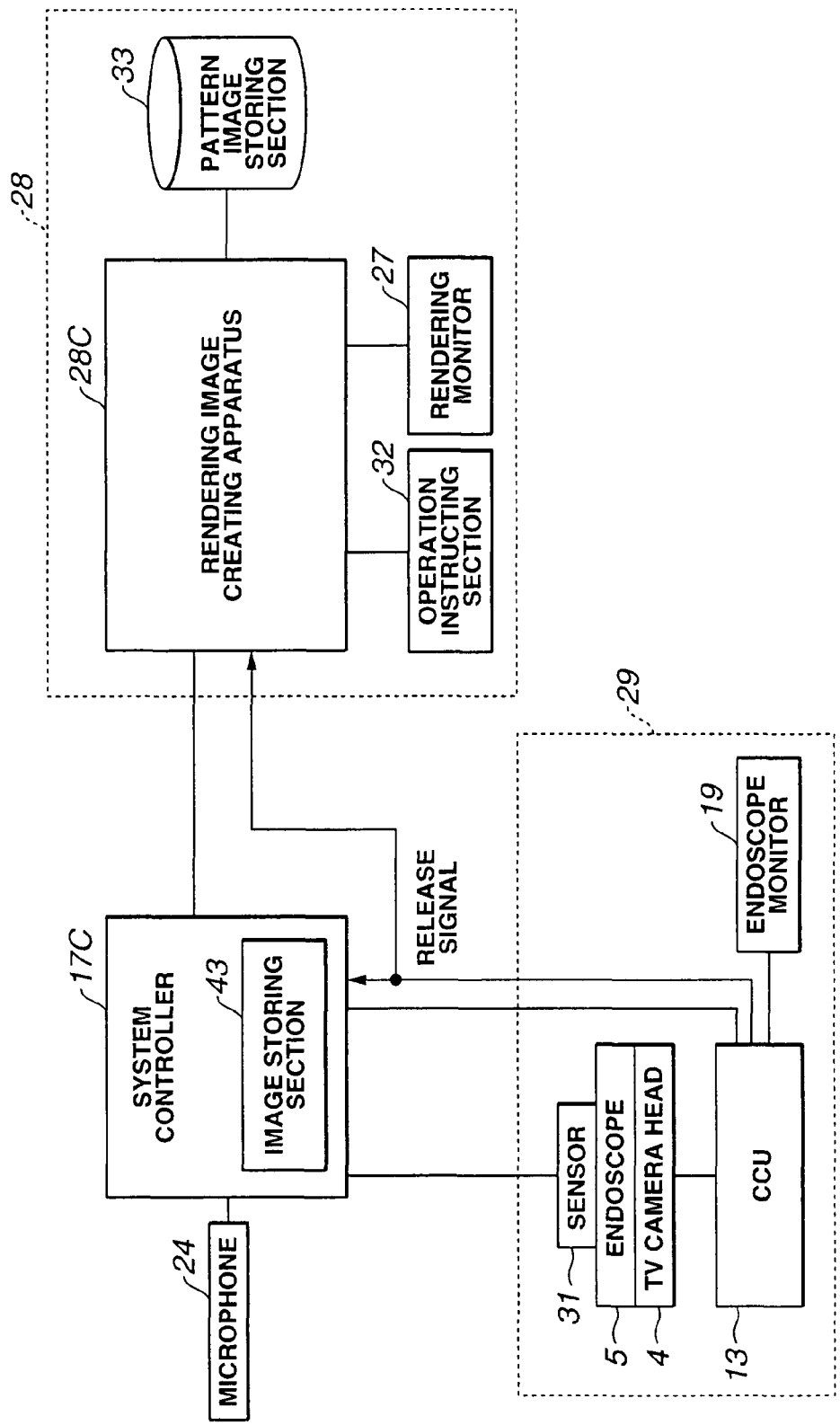
FIG. 6 is a circuit block diagram of an endoscope apparatus and rendering apparatus showing a variation example of FIG. 4.
Figure 7:
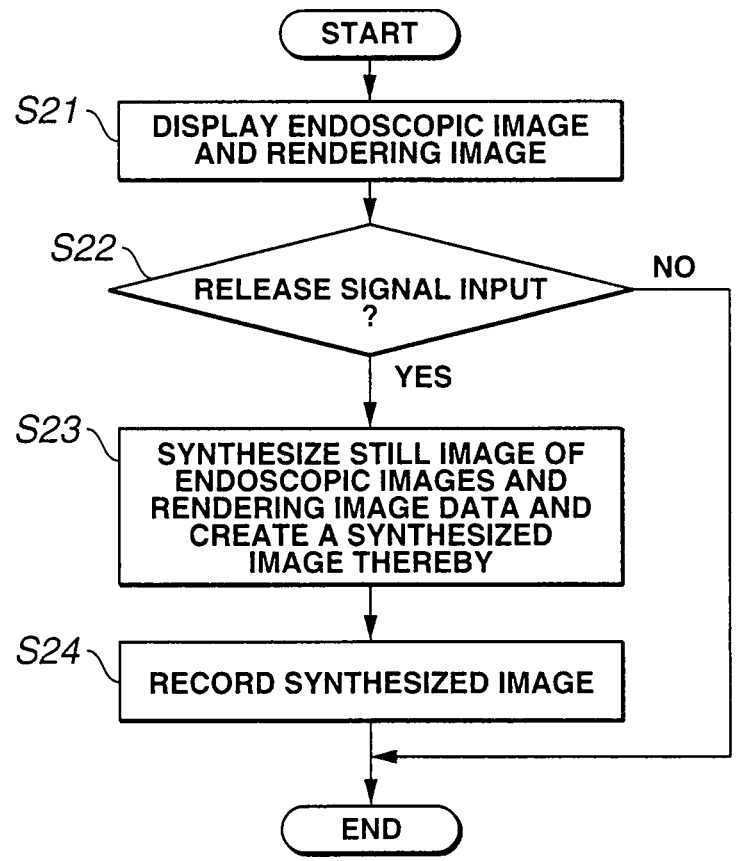
FIG. 7 is a control flowchart of a system controller showing a variation example of FIG. 5.
Figure 8:
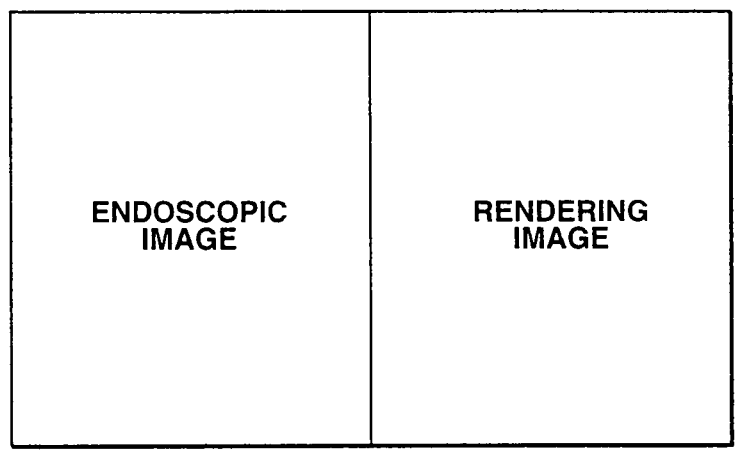
FIG. 8 is a diagram showing a display example of a synthesized image.

FIGS. 4 to 8 relate to a second embodiment of the invention. FIG. 4 is a circuit block diagram of an endoscope apparatus and rendering apparatus included in an endoscopic surgery system according to the second embodiment. FIG. 5 is a control flowchart of a system controller in FIG. 4. FIG. 6 is a circuit block diagram of an endoscope apparatus and rendering apparatus showing a variation example of FIG. 4. FIG. 7 is a control flowchart of a system controller showing a variation example of FIG. 5. FIG. 8 is a display example of a synthesized image.

While, according to the first embodiment, rendering image data and the still image data of an endoscopic image are associated and are recorded in separate storing portions, rendering image data and the still image data of an endoscopic image are recorded in a same storing portion according to the second embodiment. Since the other construction is the same as the one according to the first embodiment, the descriptions thereof will be omitted here. The same reference numerals are given to the same components for description.

In other words, as shown in FIG. 4, an endoscopic surgery system according to the second embodiment records still image data of an endoscopic image and rendering image data thereof in a same storing portion. More specifically, a rendering image creating apparatus 28B includes an image storing section 43 as recording means for recording still image data of an endoscopic image and rendering image data thereof.

Then, still image data of an endoscopic image is output to the rendering image creating apparatus 28B through the system controller 17B in response to a release signal output from the CCU 13. The rendering image data is recorded in the image storing section 43 along with the still image data of the endoscopic image. As described later, the image storing section 43 records the still image data of the endoscopic image and the rendering image data in a same folder simultaneously.

The endoscopic surgery system having the above-described construction has the same construction as that of the first embodiment and can be applied for an endoscopic surgery.

The insert portion of the endoscope 5 is inserted to a body cavity of a patient, and an endoscopic image obtained by the endoscope 5 is picked up by the TV camera head 4. The TV camera head 4 picks up and optoelectronically converts an endoscopic image and outputs image pickup signals thereof to the CCU 13. The CCU 13 performs signal processing on the image pickup signals and generates image signals.

On the other hand, a rendering image creating apparatus 28B reconstructs a body-cavity rendering image in accordance with the distal end of the insert portion of the endoscope 5, that is, in synchronization with an endoscopic image displayed on the endoscope monitor 19 based on positional relationship information obtained from the sensor 31.

Here, the CCU 13 and the rendering image creating apparatus 28B are controlled by the system controller 17B, and processing is performed in accordance with the flowchart shown in FIG. 5.

As shown in FIG. 5, the system controller 17B controls the CCU 13 to output endoscopic image signals created by the CCU 13 to the endoscope monitor 19 and display the endoscopic image on a display screen of the endoscope monitor 19. Furthermore, the system controller 17B controls the rendering image creating apparatus 28B to output rendering image data created by the rendering image creating apparatus 28B to the rendering monitor 27 and display the rendering image on a display screen of the rendering monitor 27 (step S11).

An operator uses an electric knife 16, for example, to perform treatments with reference to endoscopic images and rendering images.

Here, in order to record still image data of endoscopic images as records of surgery, an operator manipulates the release switch in the TV camera head 4 or the CCU 13 to take photographs.

Then, the system controller 17B judges the presence of a release signal (step S12). If a release signal is given, the saving folder is identified (step S13). Then, still image data of endoscopic images is output to the rendering image creating apparatus 28B and record the still image data of the endoscopic images (step S14).

Next, the system controller 17B records rendering image data in association with the still image data of an endoscopic image in the image storing section 43 (step S15). If a release signal is not given or if surgery ends, the system controller 17B terminates the processing.

Thus, in addition to the same advantages as those of the first embodiment, the endoscopic surgery system according to the second embodiment can obtain an advantage that still image data of an endoscopic image and rendering image data thereof can be searched easily without consideration of a combination of the still image data of the endoscopic image and the rendering image data. This is because the still image data of the endoscopic image and the rendering image data are recorded simultaneously.

The image storing section 43 may be included in a system controller 17C as shown in FIG. 6 instead of providing in the rendering image creating apparatus 28B.

In this case, the system controller 17C records rendering image data output from a rendering image creating apparatus 28C in response to a release signal in the image storing section 43 in synchronization with the still image data of an endoscopic image.

A control flow of the system controller 17B may have a construction as shown in FIG. 7.

As shown in FIG. 7, the system controller 17B controls the CCU 13 to output endoscopic image signals created by the CCU 13 to the endoscope monitor 19 and display the endoscopic image on a display screen of the endoscope monitor 19. Furthermore, the system controller 17B controls the rendering image creating apparatus 28B to output rendering image data created by the rendering image creating apparatus 28B to the rendering monitor 27 and display the rendering image on a display screen of the rendering monitor 27 (step S21).

Then, an operator uses the electric knife 16, for example, to perform treatments with reference to endoscopic images and rendering images.

Here, an operator manipulates the release switch in the TV camera head 4 or the CCU 13 to take photographs and record still image data of endoscopic images as records of surgery.

The system controller 17B judges the presence of a release signal (step S22). If a release signal is given, the system controller 17B causes still image data of endoscopic images to output to the rendering image creating apparatus 28B and synthesizes the still image data of the endoscopic image and the rendering image data. As a result, a synthesized image thereof is created (step S23).

Next, the system controller 17B records the synthesized image data in the image storing section 43 (step S24).

Here, a synthesized image is one image in which an endoscopic image (still image) and a rendering image are placed in parallel, for example, as shown in FIG. 8. In a synthesized image, an endoscopic image (still image) and a rendering image may be placed vertically instead of placing in parallel. Alternatively, a synthesized image may be displayed on a sub-screen with respect to an endoscopic image (still image) in P-in-P display form.

If a release signal is not given or if surgery ends, the system controller 17B terminates the processing.

Thus, in addition to the same advantages as those of the second embodiment, the endoscopic surgery system in this variation example can obtain an advantage that still image data of an endoscopic image and rendering image data thereof can be searched easily without consideration of a combination of the still image data of the endoscopic image and the rendering image data. This is because the synthesized image of the still image data of the endoscopic image and the rendering image data are recorded.

An endoscopic surgery system of this embodiment has an advantage that details of surgery can be grasped easily.

Third Embodiment

Figure 9:
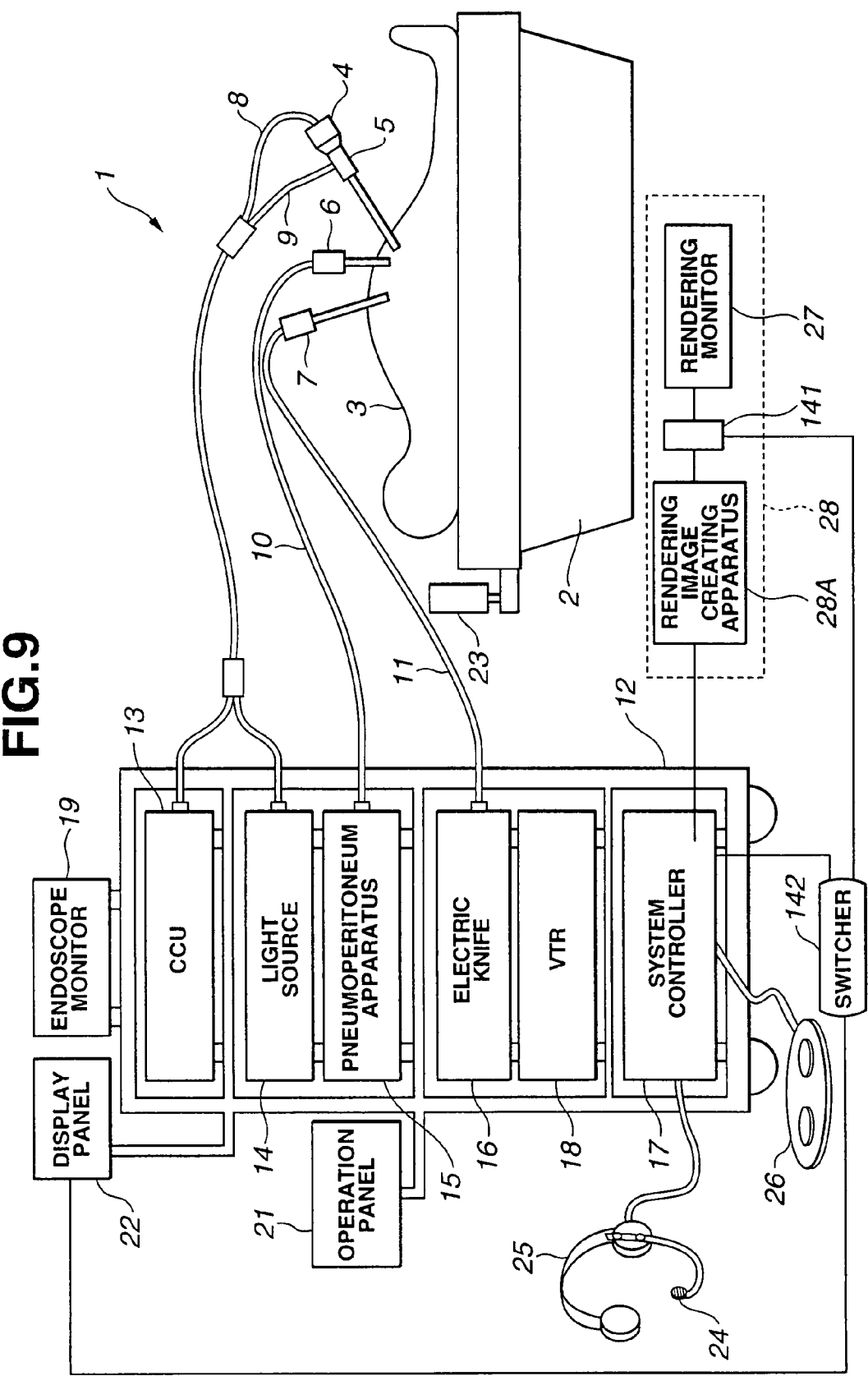
FIG. 9 is an entire configuration diagram showing an endoscopic surgery system according to a third embodiment.
Figure 10:
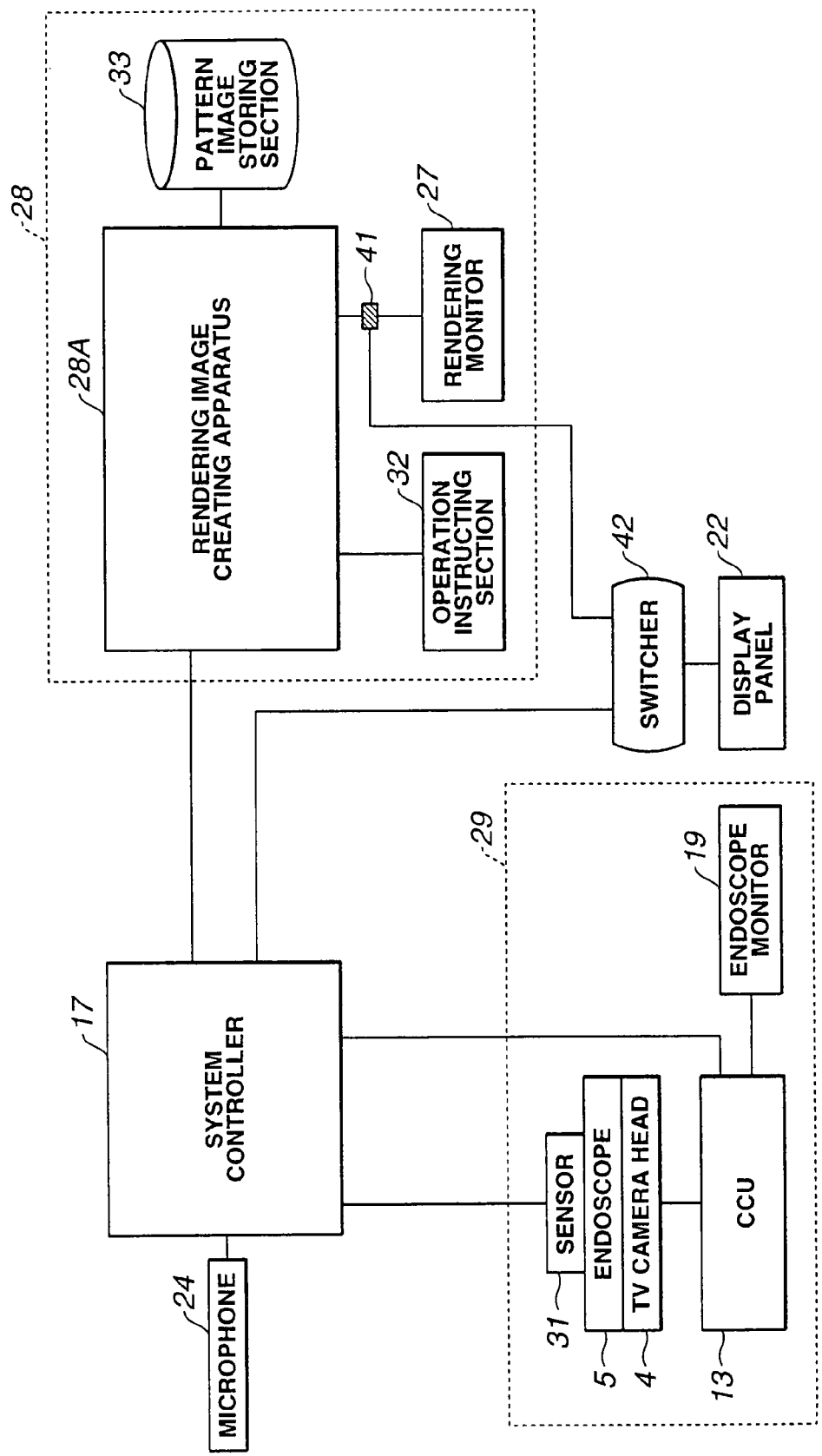
FIG. 10 is a circuit block diagram of an endoscope apparatus and rendering apparatus in FIG. 9.
Figure 11:
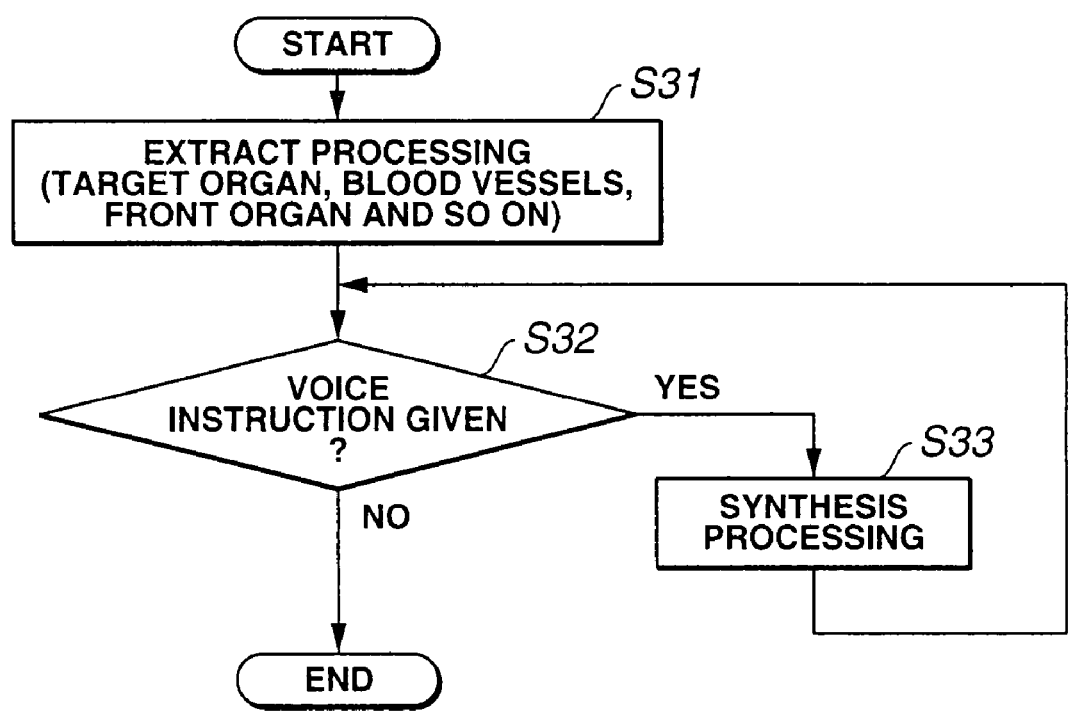
FIG. 11 is a flowchart of image processing to be performed by a rendering image creating apparatus in FIG. 9.
Figure 12:
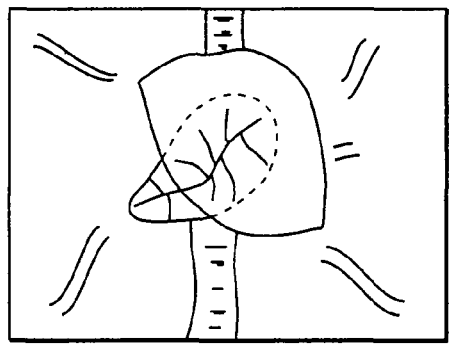
FIG. 12 is an image display example showing a rendering image of the inside of a body cavity around a target part, which is created by the rendering image creating apparatus in FIG. 9.
Figure 13:
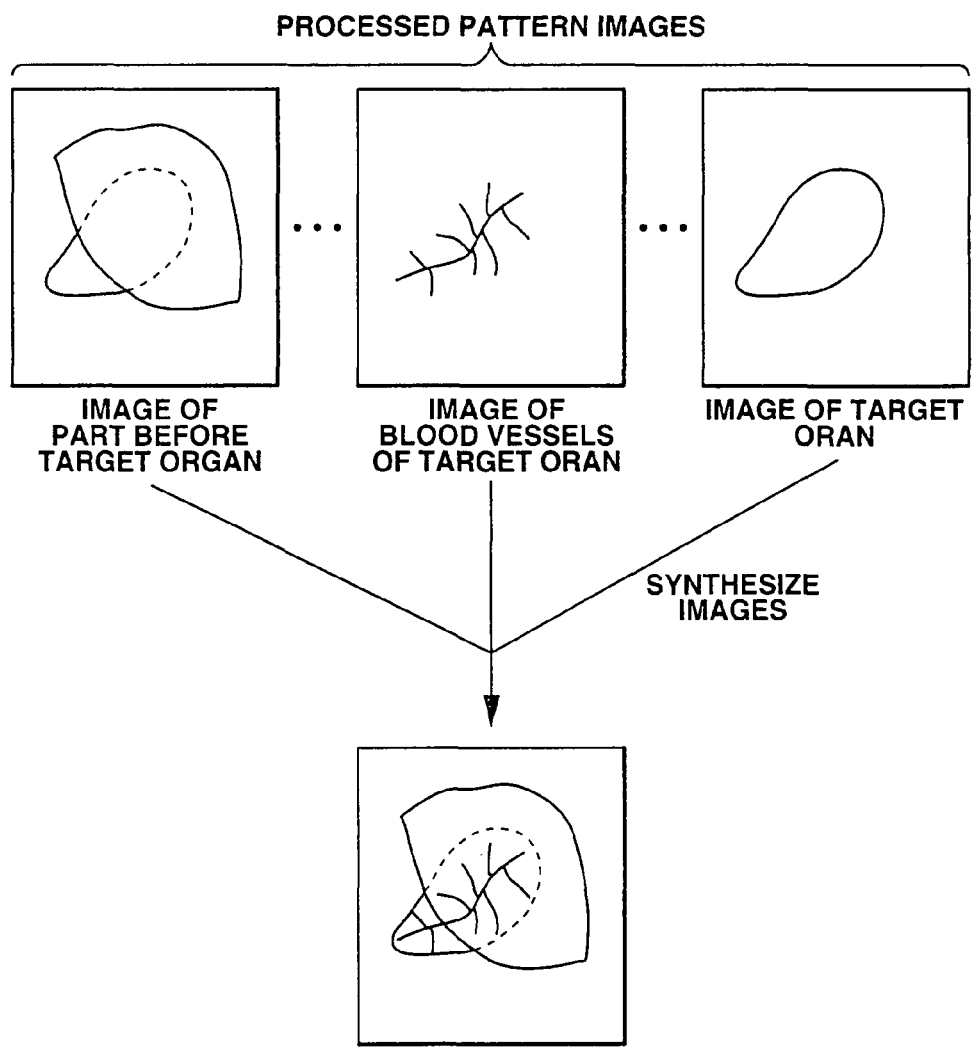
FIG. 13 is a conceptual diagram showing processing pattern images extracted from a three-dimensional image of the inside of the body cavity in FIG. 12 and a synthesized image created by synthesizing these processing pattern images.
Figure 14:
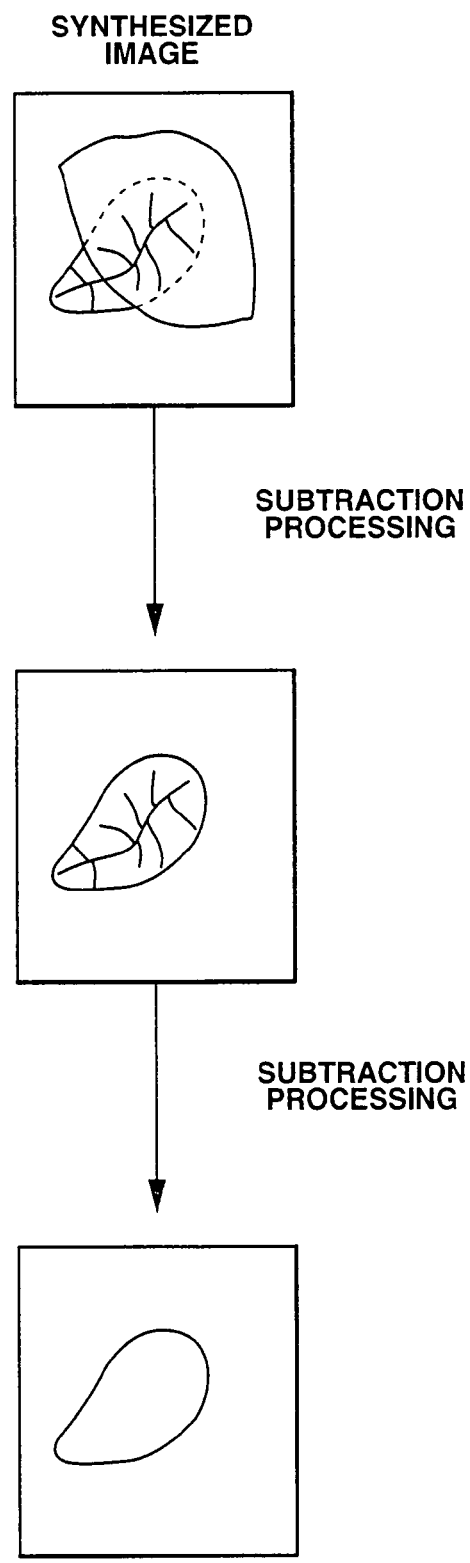
FIG. 14 is an image display example of the synthesized image in FIG. 13 after subtraction processing.
Figure 15:
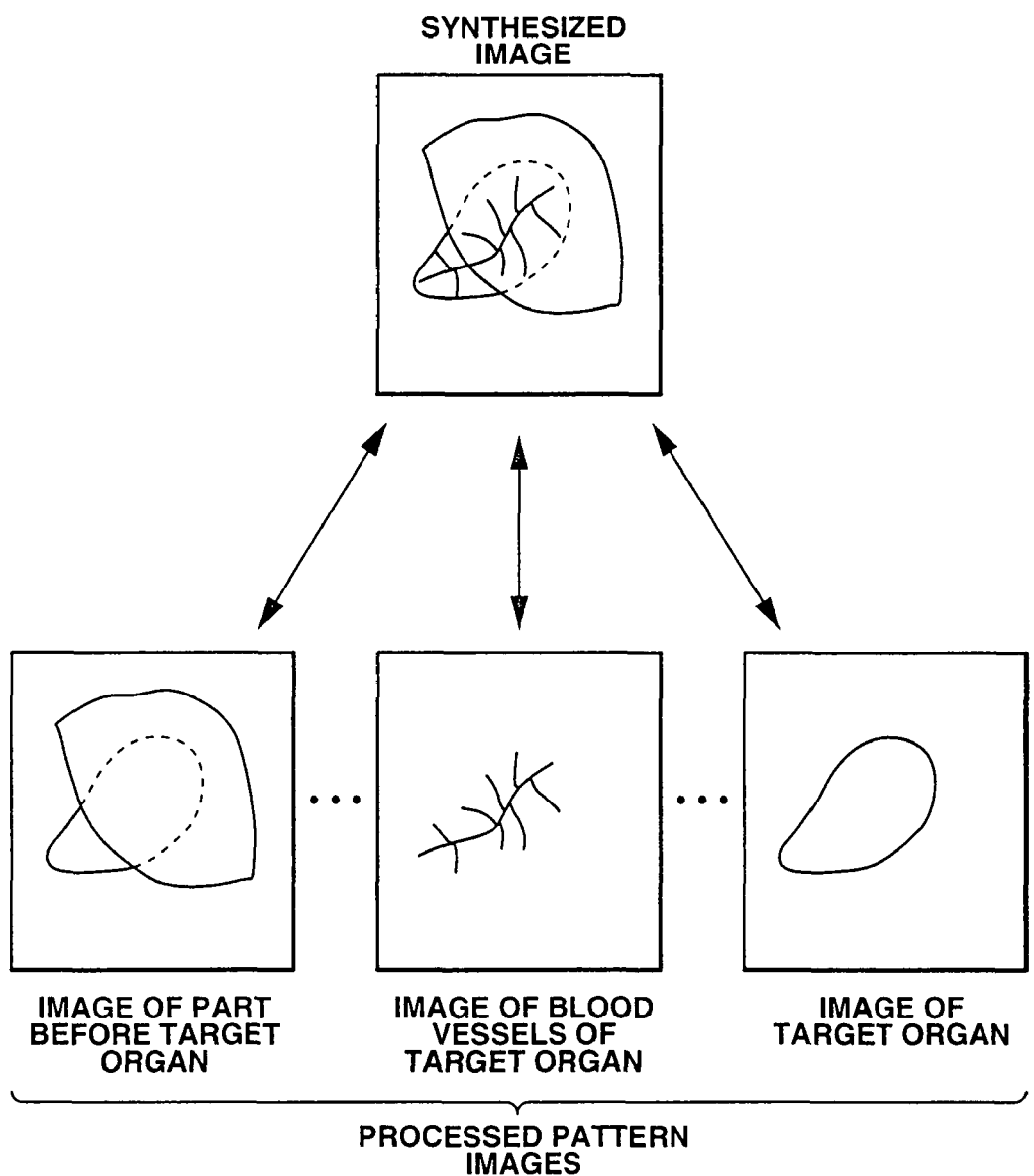
FIG. 15 is a conceptual diagram in which a desired rendering image is obtained by directly instructing selective display of the synthesized image in FIG. 13.

FIGS. 9 to 15 relate to the third embodiment of the invention. FIG. 9 is an entire configuration diagram showing an endoscopic surgery system. FIG. 10 is a circuit block diagram of an endoscope apparatus and rendering apparatus in FIG. 9. FIG. 11 is a flowchart of image processing to be performed by a rendering image creating apparatus in FIG. 9. FIG. 12 is an image display example showing a rendering image of the inside of a body cavity around a target part, which is created by the rendering image creating apparatus in FIG. 9. FIG. 13 is a conceptual diagram showing processing pattern images extracted from a rendering image of the inside of the body cavity in FIG. 12 and a synthesized image created by synthesizing these processing pattern images. FIG. 14 is an image display example of the synthesized image in FIG. 13 after subtraction processing. FIG. 15 is a conceptual diagram in which a desired rendering image is obtained by directly instructing selective display of the synthesized image in FIG. 13.

The same reference numerals are given to the same components as those of the first embodiment. The descriptions will be omitted herein, and different components and operations will be mainly described below.

Conventionally, based on an instruction by an operator in a clean area, a nurse or operator in an unclean area manipulates a keyboard, for example, and causes a rendering image to be displayed as a reference image.

With an endoscopic surgery system 1A of this embodiment, an operator can give an instruction by voice directly through a microphone 24 and easily operate. Thus, a desired rendering image of a surrounding of a target part can be obtained. An operator may give instructions by using not only the microphone 24 but also a mouse and/or keyboard or a remote controller.

Image data of a rendering image is output to a switcher 142 through a splitter 141, is switched by the switcher 142 from peripheral equipment information from a system controller 17 and is output to a display panel 22.

As described above, a rendering image creating apparatus 28A creates an extracted image by extracting a predetermined part from an in-body-cavity rendering image around a target part when a predetermined parameter relating to image display is instructed to set in response to an instruction of the operation instructing section 32. The rendering image creating apparatus 28A outputs the created extracted image data to a pattern image storing section 33 and causes the pattern image storing section 33 to store the created extracted image data.

Further describing the extracting processing, the rendering apparatus 28 creates multiple processing pattern images as shown in Table 1, for example, by performing extracting processing in response to a setting instruction by the operation instructing section 32 in advance with respect to an in-body-cavity rendering image around a target part.

TABLE 1

| PROCESSING PATTERN IMAGES | PARAMATERS | | | | | |
| --- | --- | --- | --- | --- | --- | --- |
| | AMBIENT LIGHT | DIFFUSE LIGHT | SPECULAR LIGHT | LIGHT STRENGTH | TRANSPARENCY | CLEARNESS |
| TARGET ORGAN IMAGE | *** | *** | *** | *** | *** | *** |
| IMAGE OF TARGET ORGAN BLOOD VESSELS | *** | *** | *** | *** | *** | *** |

TABLE 1-continued

| PROCESSING PATTERN IMAGES | PARAMATERS | | | | | |
|---|---|---|---|---|---|---|
| | AMBIENT LIGHT | DIFFUSE LIGHT | SPECULAR LIGHT | LIGHT STRENGTH | TRANSPARENCY | CLEARNESS |
| IMAGE OF PART BEFORE TARGET ORGAN | *** | *** | *** | *** | *** | *** |

Table 1 shows processing patterns for three images including an image before a target organ, an image of blood vessels of the target organ and an image of the target organ as processing pattern images for a target organ in accordance with progress of surgery.

Parameters shown in Table 1 include ambient light, diffuse light, specular light, light strength, transparency and clearness. The processing pattern images, which will be described later, are defined based on these parameters.

Here, ambient light refers to light in the environment. Diffuse light refers to scattered light. Specular light refers to light having reflected waves traveling in a constant direction on a diffusive reflecting surface. Clearness refers to contrast at the edges of an image. The parameters may further include light attenuation and angle of view.

The rendering image creating apparatus 28A performs synthesizing processing on multiple extracted processing pattern images and creates a synthesized image. In other words, the rendering image creating apparatus includes an image extracting processing portion and a synthesizing processing portion. The rendering image creating apparatus 28A may be constructed so as to perform subtraction processing on a synthesized image and create subtraction-processed image.

As an in-body-cavity rendering image a target part and surroundings, the rendering apparatus 28 creates a synthesized image from the processing pattern images read from the pattern image storing section 33 in accordance with a voice instruction by an operator from the microphone 24 to the rendering image creating apparatus 28A through the system controller 17 and displays a desired rendering image on the rendering monitor 27. The microphone 24 may be constructed so as to communicate voice information by radio communication with infrared rays, for example, and may give a voice instruction directly to the rendering image creating apparatus 28A.

The endoscopic surgery system 1A having the above-described construction may have the construction as described with reference to FIG. 9 and can be applied to an endoscopic surgery.

Here, the rendering image creating apparatus 28A performs image processing based on the flowchart shown in FIG. 11.

First of all, before surgery, the rendering image creating apparatus 28A performs extraction processing in response to a manipulation on the operation instructing section 32 by an operator, a nurse or an operator and in accordance with the parameters described with reference to Table 1 from in-body-cavity rendering image of a target part and surroundings shown in FIG. 12 (step S31). Then, the rendering image creating apparatus 28A creates a processing pattern image as shown in FIG. 13. Image processing is performed on blood vessels such that the blood vessels can be seen through organs therebefore.

Here, as processing pattern images, an image before a target organ, an image of blood vessels of the target organ and an image of the target organ are created in accordance with the parameters defined in Table 1.

The created processing pattern images are stored in the pattern image storing section 33.

The operations up to this point are included in a preparation stage before an endoscopic surgery.

Then, an operator advances to an endoscopic surgery.

The insert portion of the endoscope 5 is inserted to a body cavity of a patient, and an endoscopic image obtained by the endoscope 5 is picked up by the TV camera head 4. The TV camera head 4 picks up and optoelectronically converts an endoscopic image and outputs image pickup signals thereof to the CCU 13. The CCU 13 performs signal processing on the image pickup signals and generates image signals. The CCU 13 outputs the image signals to the endoscope monitor 19 and causes the endoscopic image to be displayed on the endoscope monitor 19.

An operator uses an electric knife 16, for example, to perform treatments with reference to the endoscopic images and rendering images.

Here, a rendering image creating apparatus 28A reconstructs a body-cavity rendering image in accordance with the distal end of the insert portion of the endoscope 5, that is, in synchronization with an endoscopic image displayed on the endoscope monitor 19 based on positional relationship information obtained from the sensor 31. Then, the rendering image creating apparatus 28A displays the body-cavity rendering image on the rendering monitor 27.

Here, an operator instructs to "synthesize images" through the microphone 24 with respect to a body-cavity rendering image (refer to FIG. 12) of a target part and surroundings displayed on the rendering monitor 27.

Thus, the rendering image creating apparatus 28A judges whether a voice instruction from the microphone 24 is given or not (step S32). If the voice instruction is "synthesize images", the three processing pattern images are read out from the pattern image storing section 33 and the three processing pattern images are synthesized as shown in FIG. 13 (step S33). The resulting synthesized image is displayed on the rendering monitor 27.

Then, in accordance with progress of the surgery, the operator gives a voice instruction from the microphone 24 and displays a desired rendering image on the rendering monitor 27 with respect to the synthesized image.

Here, the operator performs treatments on a target organ by using an electric knife, for example, with reference to the endoscopic images and the rendering images. Then, the rendering image creating apparatus 28A repeats the steps S32 and S33 in accordance with a next voice instruction until the operator instructs to finish.

Thus, the operator can refer to a desired rendering image and can check a target organ from the desired rendering image when an endoscopic image is not clear enough to view.

Therefore, the endoscopic surgery system 1A of this embodiment can be easily operated, and a desired rendering image can be obtained.

The rendering image creating apparatus 28A may perform subtraction processing as shown in FIG. 14 as synthesizing processing.

More specifically, in response to a voice instruction, "part before target organ, delete" by the operator, the rendering image creating apparatus 28A subtracts an image of a part before the target organ from the synthesized image and displays an image having blood vessels in the target organ on the rendering monitor 27.

In response to a voice instruction, "blood vessels in the target organ, delete" by the operator, the rendering image creating apparatus 28A subtracts an image of the target organ blood vessels from the image of the blood vessels in the target organ and displays a target organ image of the target organ only on the rendering monitor 27.

Thus, the operator can refer to rendering images in accordance with progress of the surgery and can check the target organ from the rendering images when an endoscopic image is not clear enough to view.

The endoscopic surgery system 1A may obtain a desired rendering image with respect to a synthesized image by directly instructing selective display as shown in FIG. 15 regardless of progress of the surgery. More specifically, in response to a voice instruction, "target organ image" by an operator, the rendering image creating apparatus 28A reads out "target organ image" data from processing pattern images stored in the pattern image storing section 33 and directly switches from a synthesized image to the target organ image.

Thus, the operator can obtain a desired rendering image directly regardless of progress of surgery.

An endoscopic surgery system according to this embodiment has an advantage that the endoscopic surgery system can be easily operated, and a desired rendering image can be obtained.

Fourth Embodiment

A fourth embodiment of the invention will be described below with reference to drawings.

Figure 16:
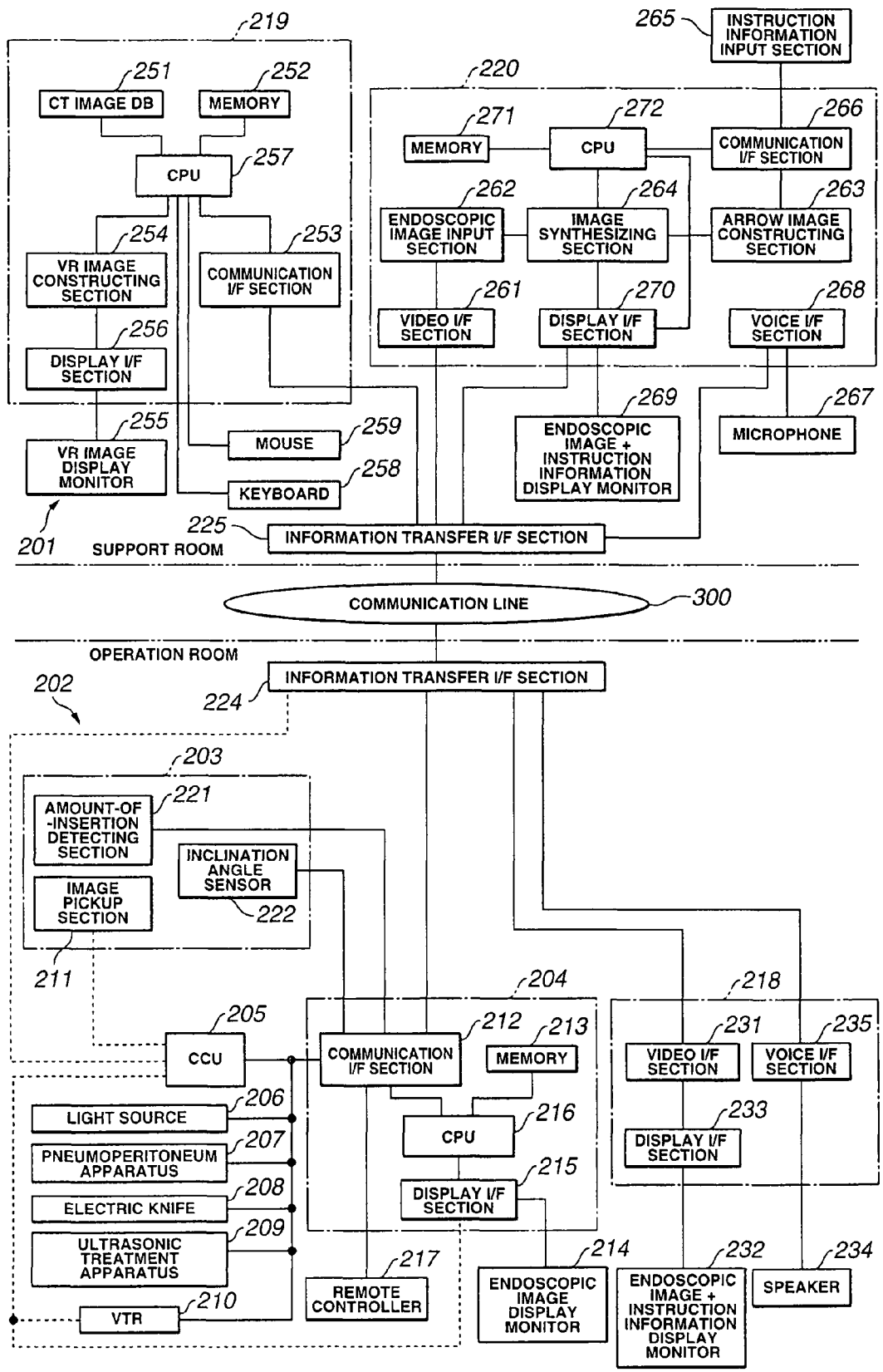
FIG. 16 is a configuration diagram showing a configuration of a remote surgery supporting apparatus and surgery system according to a fourth embodiment of the invention.
Figure 17:
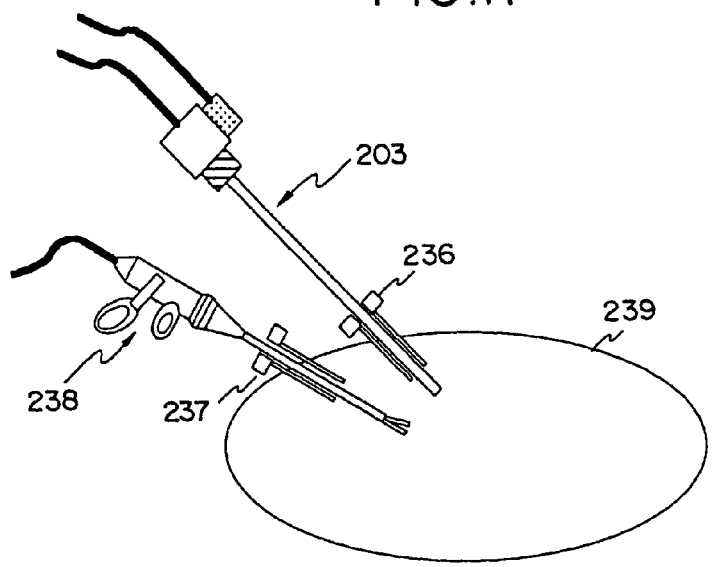
FIG. 17 is a diagram showing a state in which a rigid endoscope in FIG. 16 is being used.
Figure 18:
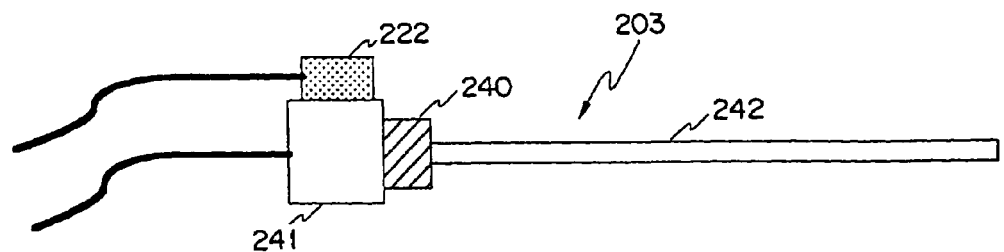
FIG. 18 is a diagram showing a construction of the rigid endoscope in FIG. 17.
Figure 19:
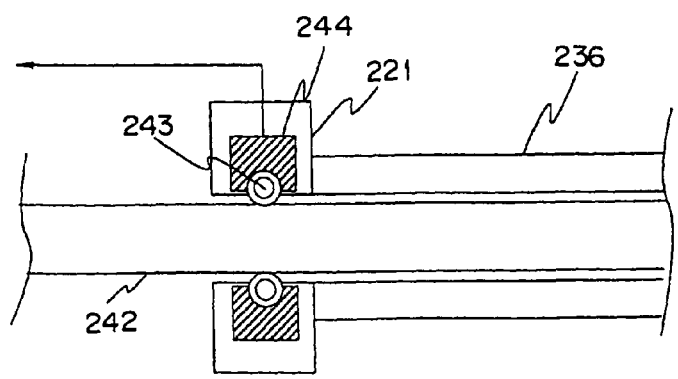
FIG. 19 is a diagram showing a construction of an essential part of a trocar in FIG. 17.
Figure 20:
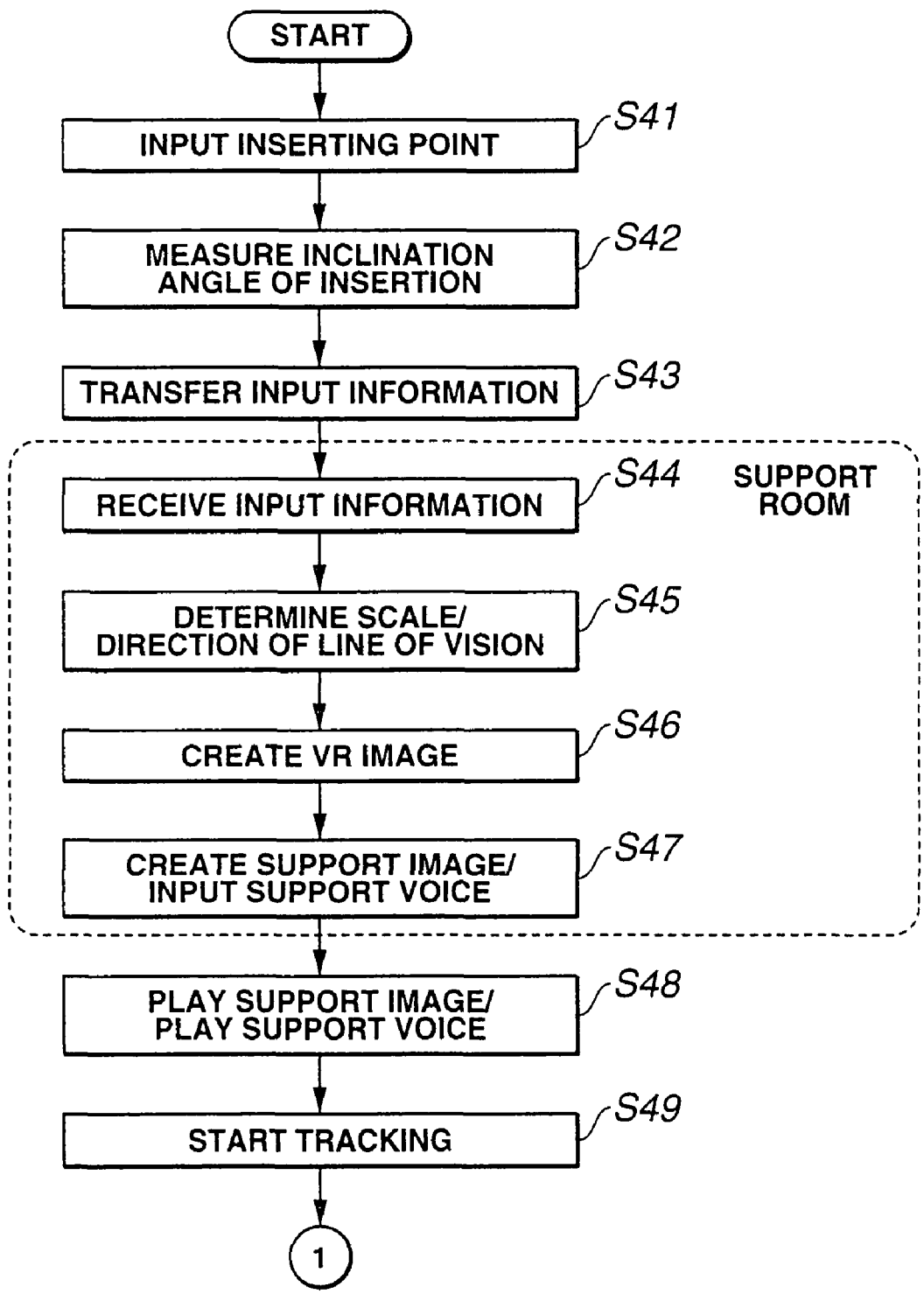
FIG. 20 is a first flowchart showing a processing flow of a remote surgery supporting apparatus and surgery system in FIG. 16.
Figure 21:
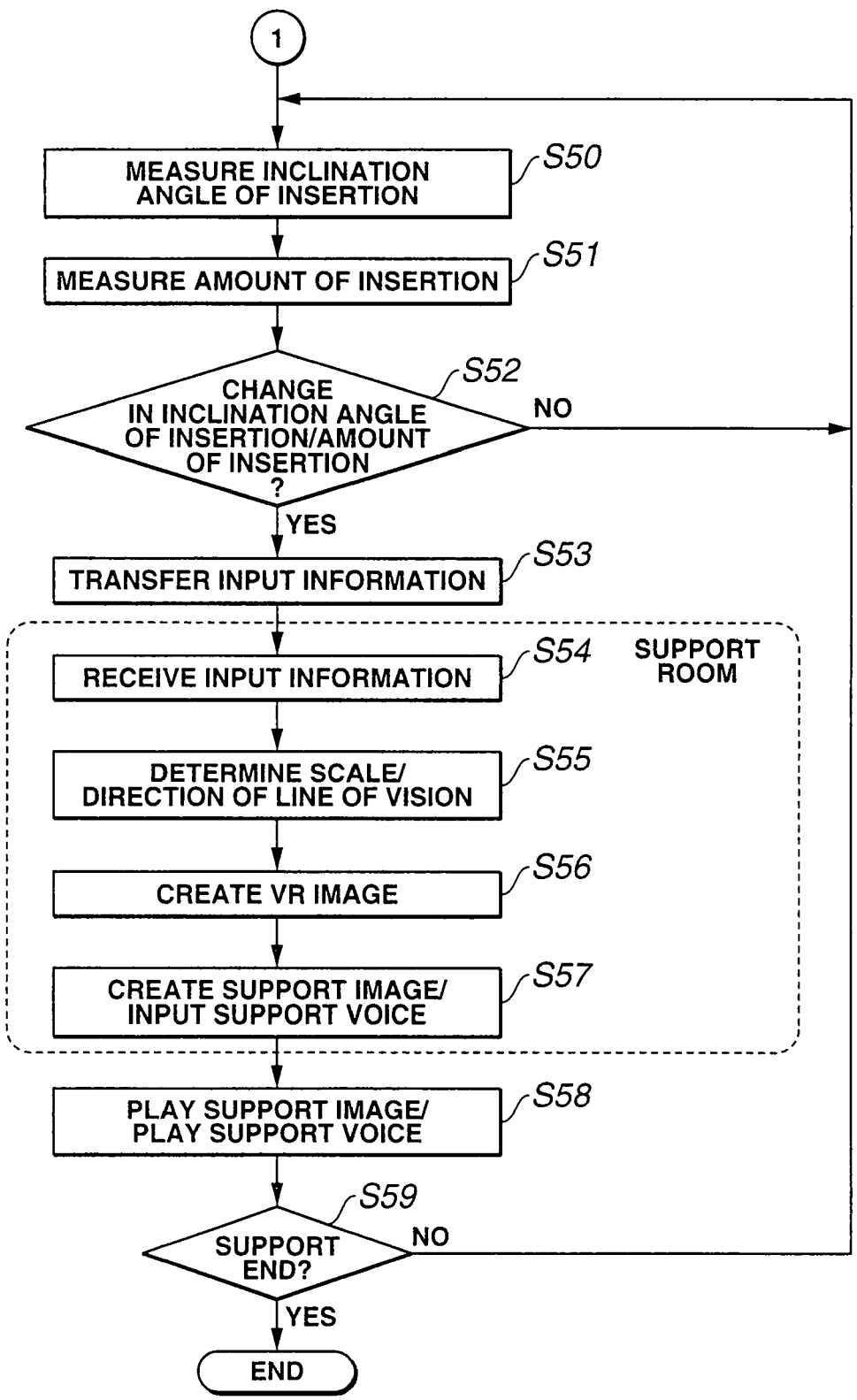
FIG. 21 is a second flowchart showing a processing flow of a remote surgery supporting apparatus and surgery system in FIG. 16.
Figure 22:
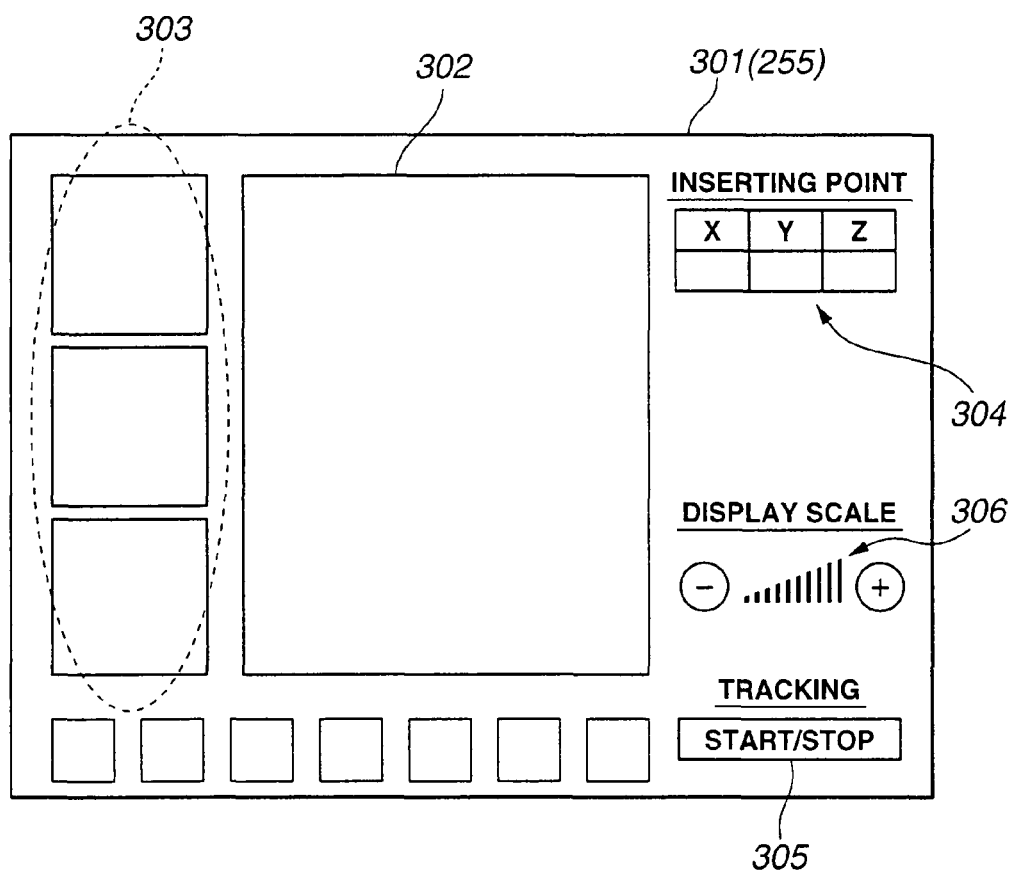
FIG. 22 is a diagram showing a VR display screen to be displayed on a VR image display monitor in FIG. 16.
Figure 23:
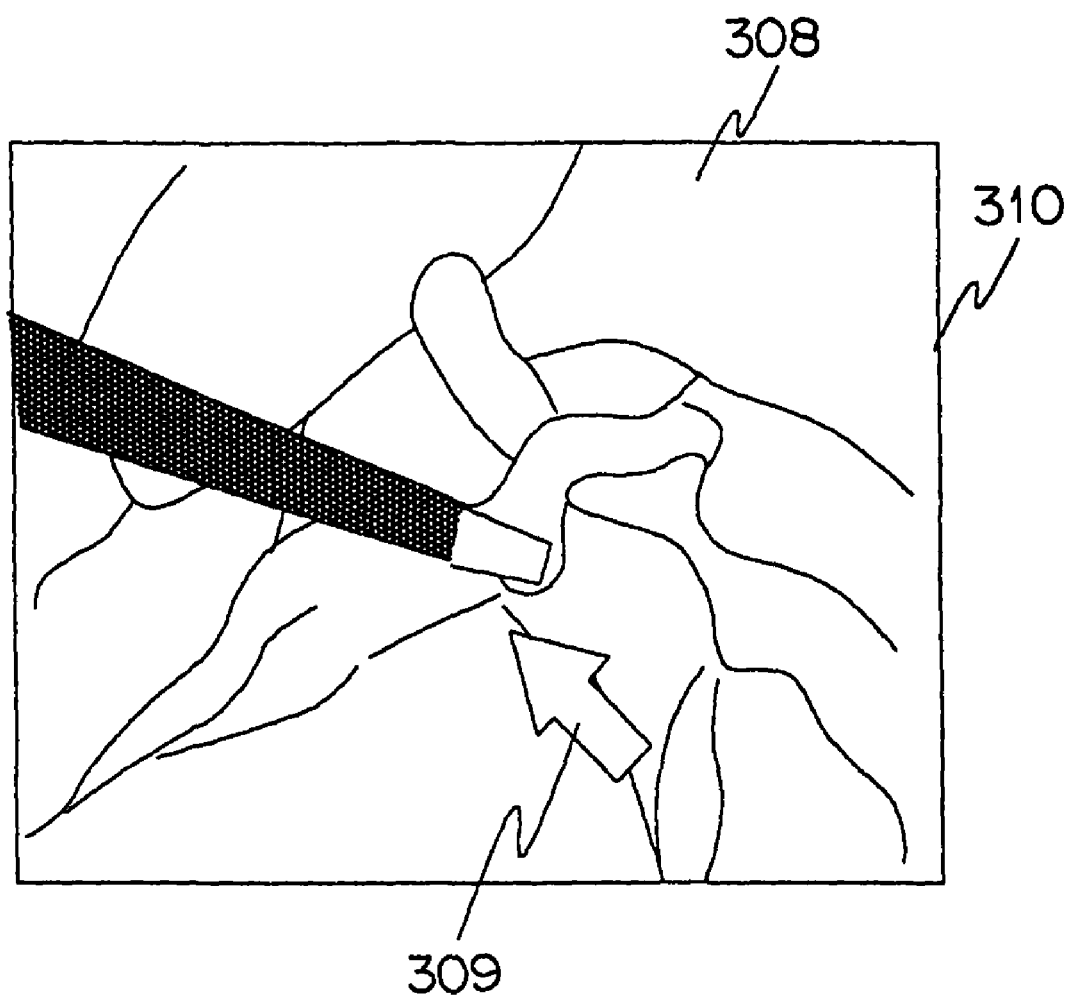
FIG. 23 is a diagram showing a support image created by a support information creating apparatus in FIG. 16.
Figure 24:
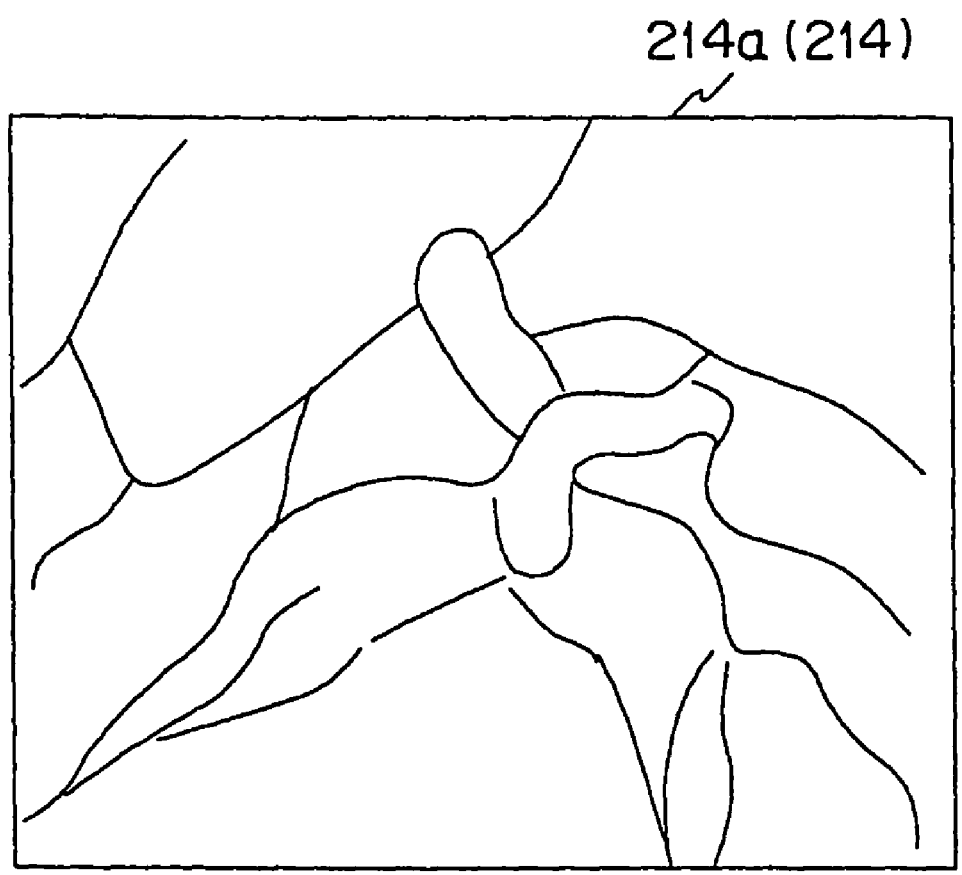
FIG. 24 is a diagram showing a first example of an endoscopic image displayed on an endoscopic image display monitor in FIG. 16.
Figure 25:
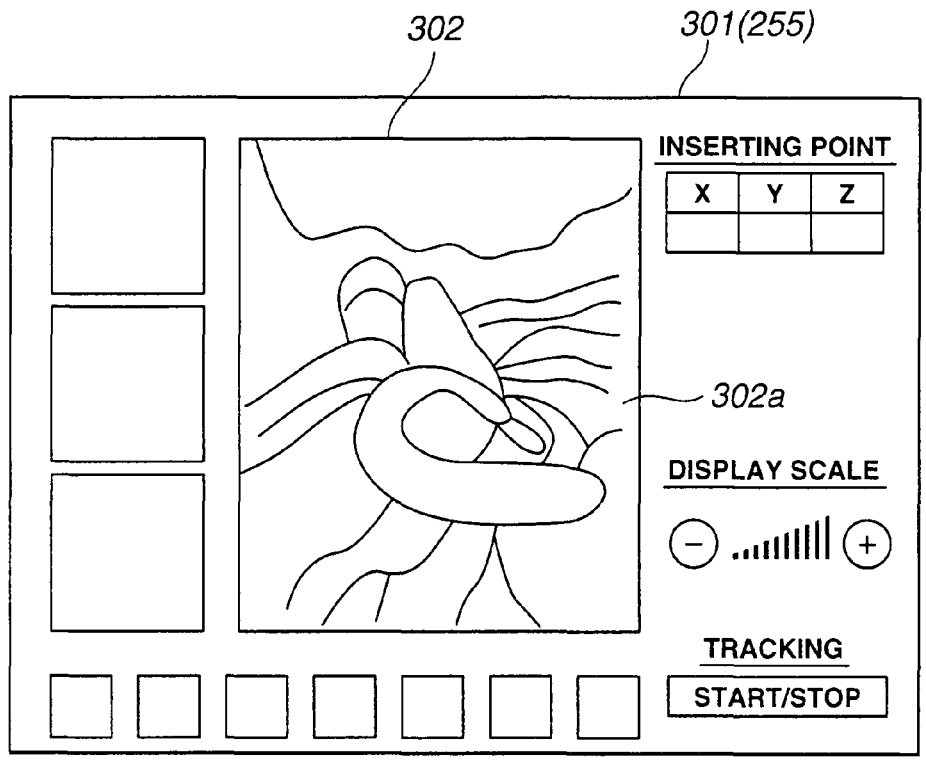
FIG. 25 is a diagram showing a VR display screen to be displayed in accordance with the endoscopic image in FIG. 24.
Figure 27:
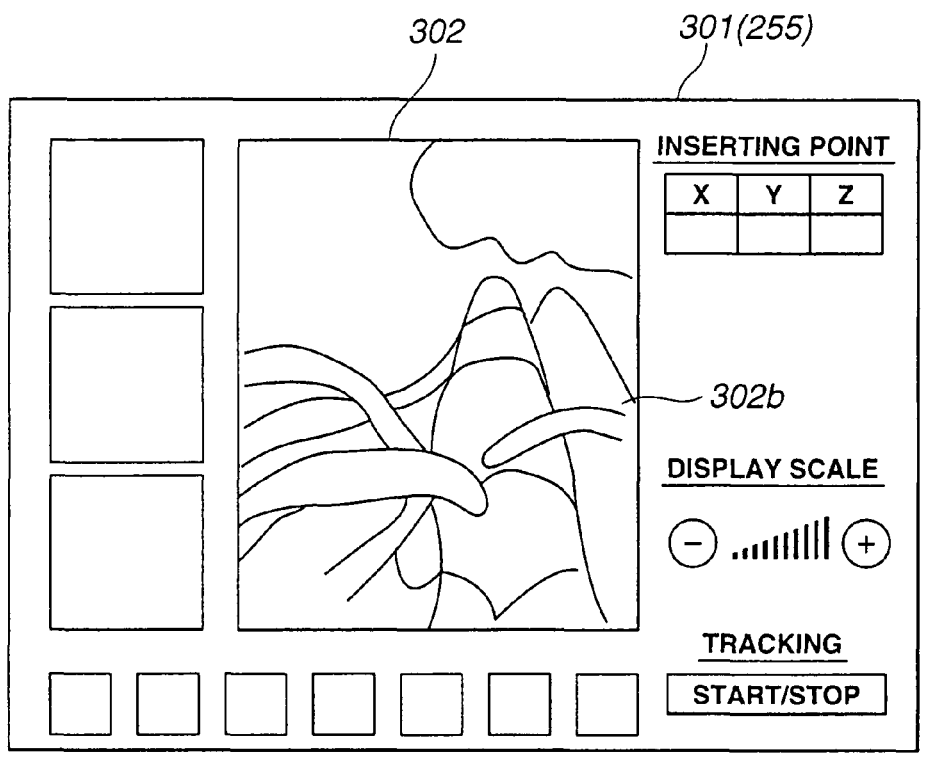
FIG. 27 is a diagram showing a VR display screen displayed in accordance with the endoscopic image in FIG. 26.
Figure 26:
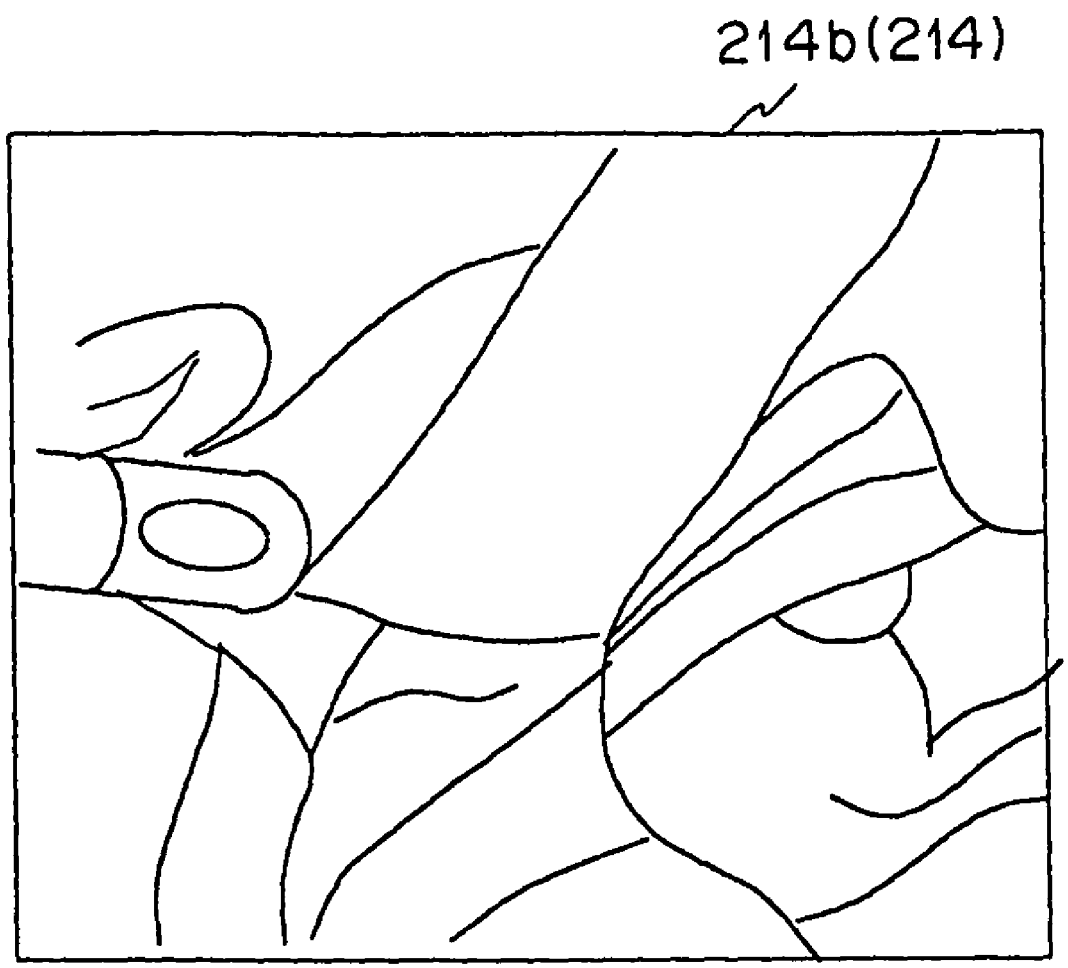
FIG. 26 is a diagram showing a second example of an endoscopic image displayed on the endoscopic image display monitor in FIG. 16.

FIGS. 16 to 27 relate to the fourth embodiment of the invention. FIG. 16 is a configuration diagram showing a configuration of a remote surgery supporting apparatus and surgery system. FIG. 17 is a diagram showing a state in which a rigid endoscope in FIG. 16 is being used. FIG. 18 is a diagram showing a construction of the rigid endoscope in FIG. 17. FIG. 19 is a diagram showing a construction of an essential part of a trocar in FIG. 17. FIG. 20 is a first flowchart showing a processing flow of a remote surgery supporting apparatus and surgery system in FIG. 16. FIG. 21 is a second flowchart showing a processing flow of a remote surgery supporting apparatus and surgery system in FIG. 16. FIG. 22 is a diagram showing a VR display screen to be displayed on a VR image display monitor in FIG. 16. FIG. 23 is a diagram showing a support image created by a support information creating apparatus in FIG. 16. FIG. 24 is a diagram showing a first example of an endoscopic image displayed on an endoscopic image display monitor in FIG. 16. FIG. 25 is a diagram showing a VR display screen to be displayed in accordance with the endoscopic image in FIG. 24. FIG. 26 is a diagram showing a second example of an endoscopic image displayed on the endoscopic image display monitor in FIG. 16. FIG. 27 is a diagram showing a VR display screen displayed in accordance with the endoscopic image in FIG. 26.

As shown in FIG. 16, a remote surgery supporting apparatus 201 according to this embodiment is disposed in a support room away from surgery room and remotely supports surgery system 202 disposed in the operation room through a communications line 300.

The surgery system 202 includes, in an operation room, a rigid endoscope 203, a system controller 204, a CCU 205, a light source apparatus 206, a pneumoperitoneum apparatus 207, an electric knife 208, an ultrasonic processor 209, a VTR 210 and a support information player 218. The remote surgery supporting apparatus 201 includes, outside of the operation room, a VR image creating apparatus 219 and a support information creating apparatus 220. The surgery system 202 and the remote surgery supporting apparatus 201 are connected through the communications line 300.

First of all, details of the surgery system 202 will be described. Image pickup signals picked up by an image pickup section 211 of the rigid endoscope 203 are transmitted to a CCU 205, undergo image processing and are output to the VTR 210 for recording images and the system controller 204.

The system controller 204 includes a communication I/F section 212, a memory 213, a display I/F section 215 and a CPU 216. The communication I/F section 212 exchanges setting information with the CCU 205, the light source apparatus 206, the pneumoperitoneum apparatus 207, an electric knife 208, an ultrasonic treatment apparatus 209, and the VTR 210. The memory 213 stores different kinds of programs. The display I/F section 215 causes an endoscopic image display monitor 214 to display image signals from the CCU 205. The CPU 216 controls these portions.

A remote controller 217 is connected to the CPU 216 of the system controller 204 through the communication I/F section 212. Various kinds of data can be input through the remote controller 217.

The rigid endoscope 203 includes an amount-of-insertion detecting section 221 and an inclination angle sensor 222. The amount-of-insertion detecting section 221 detects an inserting amount of the rigid endoscope 203. The inclination angle sensor 222 detects an inclination angle of insertion of the rigid endoscope 203. Insert amount data detected by the insert amount detecting portion 221 and insertion inclination angle data detected by the inclination angle sensor 222 are input to the CPU 216 through the communication I/F section 212 of the system controller 204. The CPU 216 outputs the inserting amount data and the insertion inclination angle data to the information transfer I/F section 224 through the communication I/F portion 212. The inserting amount data and the insertion inclination angle data are transmitted by the information transfer I/F section 224 to the information transfer I/F section 225 of the remote surgery supporting apparatus 1 through the communications line 300.

The support information player 218 plays support information including support image information and support voice information from the support information creating apparatus 220 of the remote surgery supporting apparatus 201, which are input from the information transfer I/F section 224 through the information transfer I/F section 225 of the remote surgery supporting apparatus 201 and the communications line 300. The support information player 218 includes a video I/F section 231, a display I/F section 233 and a voice I/F section 235. The video I/F section 231 inputs support image information. The display I/F section 233 displays on the monitor 232 support images including (endoscopic images+instruction information) based on image information input by the video I/F section 231. The voice I/F portion 235 inputs support voice information and causes the speaker 234 to play the support voice information.

As shown in FIG. 17, the rigid endoscope 203 is inserted into the body of a patient 239 through trocars 236 and 237 along with a treating apparatus 238 such as the electric knife 208 and the ultrasonic treating apparatus 209.

As shown in FIG. 18, the rigid endoscope 203 includes an image pickup section 211 at the inserted proximal end and the inclination angle sensor 222 at a handle 241 on the inserted proximal end side. The inclination angle sensor 222 measures an insertion inclination angle of the rigid endoscope 203 by using a gyroscopic compass and outputs the result to the system controller 204.

As shown in FIG. 19, the amount-of-insertion detecting section 221 is provided on the proximal end side of the trocar 236 for guiding an insert portion 242 of the rigid endoscope 203 into the body of the patient 239. The amount-of-insertion detecting section 221 includes a roller 243 and a rotary encoder 244. The roller 243 is in contact with an outer surface of the insert portion 242 and rotates in accordance with the insertion of the insert portion 242. The rotary encoder 244 detects an amount of rotation of the roller 243 and outputs the amount of rotation to the system controller 204 as an amount of insertion of the insert portion 242.

Next, details of the remote surgery supporting apparatus 201 will be described. The VR image creating apparatus 219 obtains inserting amount data and insertion inclination angle data of the rigid endoscope 202 from the surgery system 202 through the communications line 300 in real time. Based on the inserting amount data, the insertion inclination angle data and CT images obtained by a CT apparatus (not shown), the VR image creating apparatus 219 creates a volume rendering image (VR image), which is a virtual image in real time and in a same direction of line of vision as that of an endoscopic image picked up by the rigid endoscope 202. The support information creating apparatus 220 creates support image to be transmitted to the surgery system 202 with reference to VR images thereof.

More specifically, as shown in FIG. 16, the VR image creating apparatus 219 includes a recording portion 251, a memory 252, a communication I/F section 253, a VR image constructing section 254, a display I/F section 256 and a CPU 257. The recording portion 251 stores a CT image database (DB) including multiple CT images. The memory 252 stores different kinds of programs. The communication I/F section 253 receives inserting amount data detected by the amount-of-insertion detecting section 221 and insertion inclination angle data detected by the inclination angle sensor 222, from the surgery system 202 through the information transfer I/F section 225. The VR image constructing section 254 constructs a VR image based on inserting amount data and insertion inclination angle data obtained by the communication I/F section 253 and a CT image in the CT image DB. The display I/F section 256 causes the VR image display monitor 255 to display a VR image constructed by the VR image constructing section 254. The CPU 257 controls these portions. A keyboard 258 and a mouse 259 used for inputting various kinds of data are connected to the CPU 257.

The support information creating apparatus 220 includes a video I/F section 261, an endoscopic image input section 262, an arrow image constructing section 263, an image synthesizing section 264, a communication I/F section 266, a voice I/F section 268, a display I/F section 270, a memory 271, and a CPU 272. The video I/F section 261 receives an endoscopic image from the CCU 205 through the information transfer I/F sections 224 and 225 and the communications line 300. The endoscopic image input section 262 converts an endoscopic image obtained by the video I/F section 261 to digital endoscopic image data. The arrow image constructing section 263 constructs an arrow image to be superposed on endoscopic image data. The image synthesizing section 264 creates a synthesized image by superposing an arrow image from the arrow image constructing section 263 on endoscopic image data from the endoscopic image input section 262. The communication I/F section 266 receives instruction information from an instruction information input section 265 for inputting position information of an arrow image to be superposed on endoscopic image data. The voice I/F section 268 is used for inputting voice data from a microphone 267 used for inputting instruction voice. The display I/F section 270 is used for displaying a support image including (endoscopic image+instruction information), which is a synthesized image from the image synthesizing section 264, on a monitor 269. The memory 271 stores different kinds of programs. The CPU 272 controls these portions. The voice I/F section 268 and the display I/F section 270 output voice data and support image, respectively, to the support information player 218 of the surgery system 202 through the information transfer I/F sections 224 and 225 and the communications line 300.

An operation of this embodiment having this construction will be described. As shown in FIGS. 20 and 21, at a step S41, the CPU 216 of the system controller 204 inputs coordinates of an inserting point (of an endoscope) where the rigid endoscope 203 is inserted into the body of the patient 239 by using the remote controller 217 connecting to the system controller 204 of the surgery system 202. The coordinates system agrees with the coordinate system of the CT image.

At a step S42, the CPU 216 measures and inputs insertion inclination angle data of the rigid endoscope 203 by using the inclination angle sensor 222. At a step S43, the CPU 216 transfers input information including inserting coordinates data of an inserting point and insertion inclination angle data to the VR image creating apparatus 219 of the remote surgery supporting apparatus 201.

At a step S44, the VR image creating apparatus 219 of the remote surgery supporting apparatus 201 receives inputs and inputs information including coordinates data of an inserting point and insertion inclination angle data. Then, at a step S45, the CPU 257 of the VR image creating apparatus 219 determines a scale and/or direction of line of view of a VR image based on the coordinates data of the inserting point and insertion inclination angle data of the endoscope. At a step S46, the VR image constructing section 254 creates a VR image based on the scale and/or the direction of line of view and causes the VR image display monitor 255 to display the VR image through the display I/F section 256.

The VR image is displayed on a VR image display area 302 of a VR display screen 301, which is displayed on the VR image display monitor 255 as shown in FIG. 22. The VR display screen 301 includes a VR image display area 302, a two-dimensional image display area 303, an inserting point display field 304, a start/stop button 305 and a display scale change input portion 306. The VR image display area 302 displays a VR image created by the VR image constructing section 254. The two-dimensional image display area 303 displays multiple two-dimensional CT images relating to a VR image. The inserting point display field 304 displays an inserting point (x0,y0,z0) of the rigid endoscope 202. The start/stop button 305 instructs the start and stop of tracking. The display scale change input portion 306 is used for changing a display scale.

At a step S47, in the support information creating apparatus 220, the CPU 272 creates a support image 310 having the arrow image 309 indicating the position of an affected part as shown in FIG. 23 on the endoscopic image 308 with reference to the VR image. The CPU 272 further causes the monitor 269 to display the support image 310 through the display I/F section 270.

At the step S47, not only the support image 310 is created and/or is displayed but also support voice to an operation room is input through the microphone 267. The CPU 272 transmits the created support image data and input support voice data to the surgery system 202 through the communications line 300.

In the surgery system 202 having received the support image data and input support voice data, the support information creating apparatus 220 displays the support image 310 on the monitor 232 and causes the speaker 234 to play the support voice at a step S48.

Once the first support image 310 is displayed in this way and tracking (in accordance with live images of VR images) is started at a step S49, the CPU 216 of the system controller 204 measures insertion inclination angle data of the rigid endoscope 203 by using the inclination angle sensor 222 at a step S50. At a step S51, the CPU 216 measures inserting amount data of the rigid endoscope 203 by using the amount-of-insertion detecting section 221.

At a step S52, the CPU 216 judges whether or not either inserting amount data or insertion inclination angle data is changed. If not changed, the processing returns to the step S50. If changed, the CPU 216 transfers input information including inserting amount data and insertion inclination angle data to the VR image creating apparatus 219 of the remote surgery supporting apparatus 201 at a step S53.

When the VR image creating apparatus 219 of the remote surgery supporting apparatus 201 receives (the input of) input information including the inserting amount data and insertion inclination angle data at a step S54, the CPU 257 of the VR image creating apparatus 219 determines a scale and/or direction of line of view of a VR image based on the inserting amount data and insertion inclination angle data at a step S55. At a step S56, the VR image constructing section 254 creates a VR image based on the scale and/or the direction of line of view and causes the VR image display monitor 255 to display the VR image through the display I/F section 256.

Then, at a step S57, in the support information creating apparatus 220, the CPU 272 creates a support image 310 having an arrow image indicating the position of an affected part on endoscopic image data with reference to the VR image and causes the monitor 269 to display the support image 310 including (endoscopic image+instruction information) through the display I/F section 270.

At the step S57, not only the support image 310 is created and/or is displayed but also support voice to an operation room is input through the microphone 267. The CPU 272 transmits the created support image data and input support voice data to the surgery system 202 through the communications line 300.

In the surgery system 202 having received the support image data and input support voice data, the support information creating apparatus 220 displays the support image 310 on the monitor 232 and causes the speaker 234 to play the support voice at a step S58.

Then, at a step S59, the CPU 216 of the system controller 204 judges whether or not an instruction for support termination from the remote controller 217 is given or not. If not, the processing returns to a step S60. If so, the processing ends.

Through the processing at the steps S50 to S59, in the VR image creating apparatus 219, when a live endoscopic image 214a as shown in FIG. 24, for example, is displayed on the endoscopic image display monitor 214, a blood-vessel included virtual image 302a without an organ part, for example, as shown in FIG. 25 is displayed in the VR image display area 302 on the VR display screen 301. Here, the blood-vessel included virtual image 302a is in real time and has a same direction of line of vision and size (scale) as those of the live endoscopic image 214a.

When the rigid endoscope 203 is inclined from the state in FIG. 24 and the live endoscopic image 214b as shown in FIG. 26 is displayed on the endoscopic image display monitor 214, a blood-vessel included virtual image 302b without an organ part, for example, as shown in FIG. 27 is displayed in the VR image display area 302. Here, the blood-vessel included virtual image 302b is in real time and has a same direction of line of vision and size (scale) as those of the live endoscopic image 214b in accordance with (by tracking) the display.

In this way, according to this embodiment, by transmitting an inserting amount and insertion inclination angle of the rigid endoscope 203 to a support room separate and far away from the operation room through the communications line 300, an instructing doctor in the remote support room provides the operator in the operation room with support images and support voice with reference to VR images tracking (in accordance with) live endoscopic images in real time. Thus, proper technique support can be provided to the operator easily at low costs.

Fifth Embodiment

Figure 28:
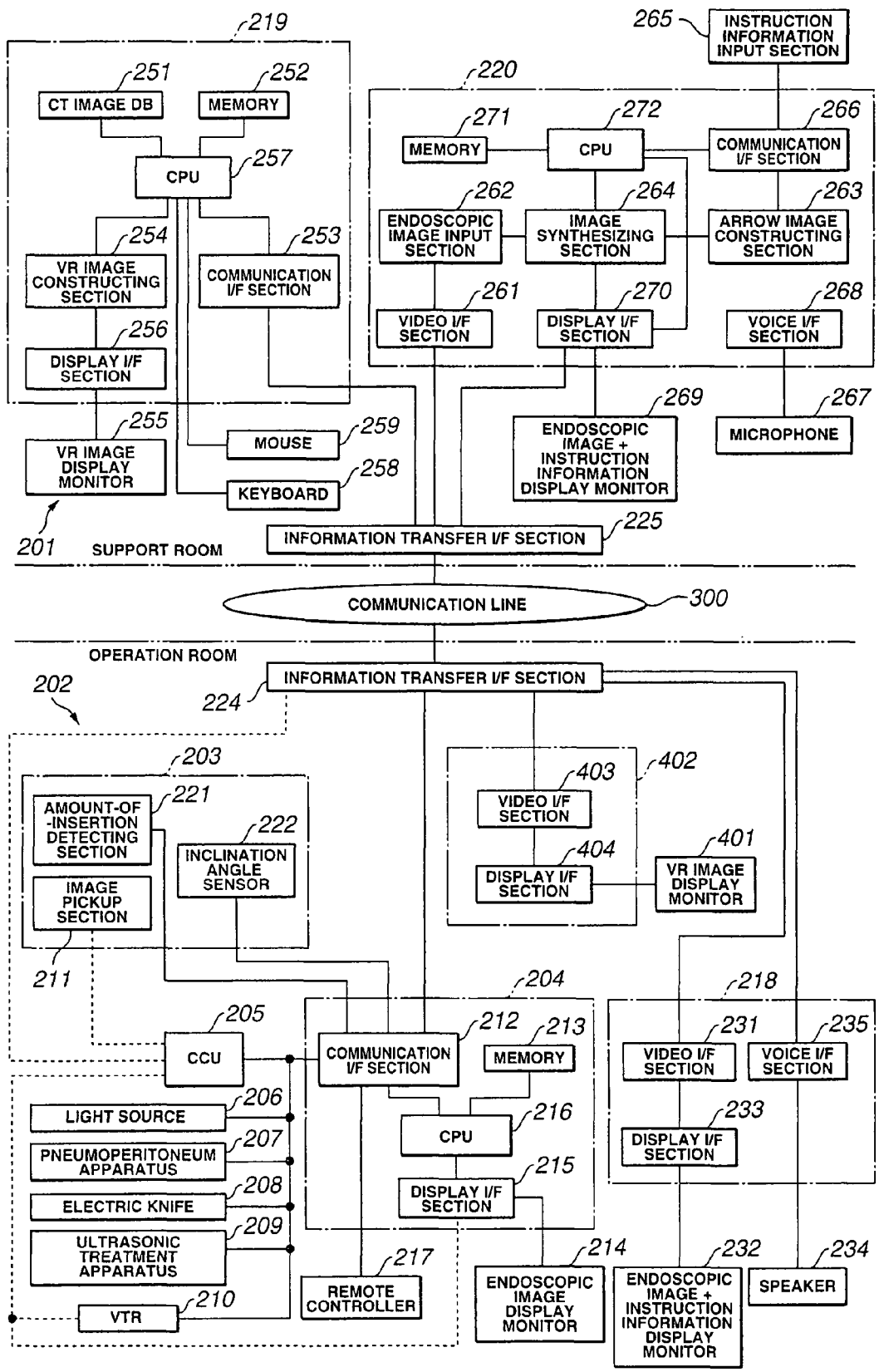
FIG. 28 is a configuration diagram showing a configuration of a remote surgery supporting apparatus and surgery system according to a fifth embodiment of the invention.

FIG. 28 is a configuration diagram showing configurations of a remote surgery supporting apparatus and surgery system according to a fifth embodiment of the invention.

The fifth embodiment is substantially the same as the fourth embodiment. Therefore, only difference therebetween will be described, and the same reference numerals are given to the same components, the descriptions of which will be omitted herein.

As shown in FIG. 28, the surgery system 202 includes a VR image display apparatus 402 for receiving the input of VR image data created by the VR image creating apparatus 219 of the remote surgery supporting apparatus 201 and causes the VR image display monitor 401 to display the VR image. The VR image display apparatus 402 includes a video I/F section 403 and a display I/F section 404. The video I/F section 403 is used for inputting VR image data through information transfer I/F sections 224 and 225 and the communications line 300. The display I/F section 404 causes the VR image display monitor 401 to display a VR image based on the input VR image data. The rest of the construction is the same as that of the fourth embodiment.

According to this embodiment, at the step S47 or S57 according to the fourth embodiment, not only support image data and input support voice data are transmitted to the surgery system 202 through the communications line 300 but also VR image data is transmitted to the surgery system 202 through the communications line 300. The VR image is displayed on the VR image display monitor 401 in the operation room. The rest of the processing is the same as that of the fourth embodiment.

According to this embodiment, in addition to the advantages of the fourth embodiment, a support environment with a supporting doctor can be more robust since an operator in an operation room can refer to a VR image displayed on the VR image display monitor 401.

Sixth Embodiment

Figure 29:
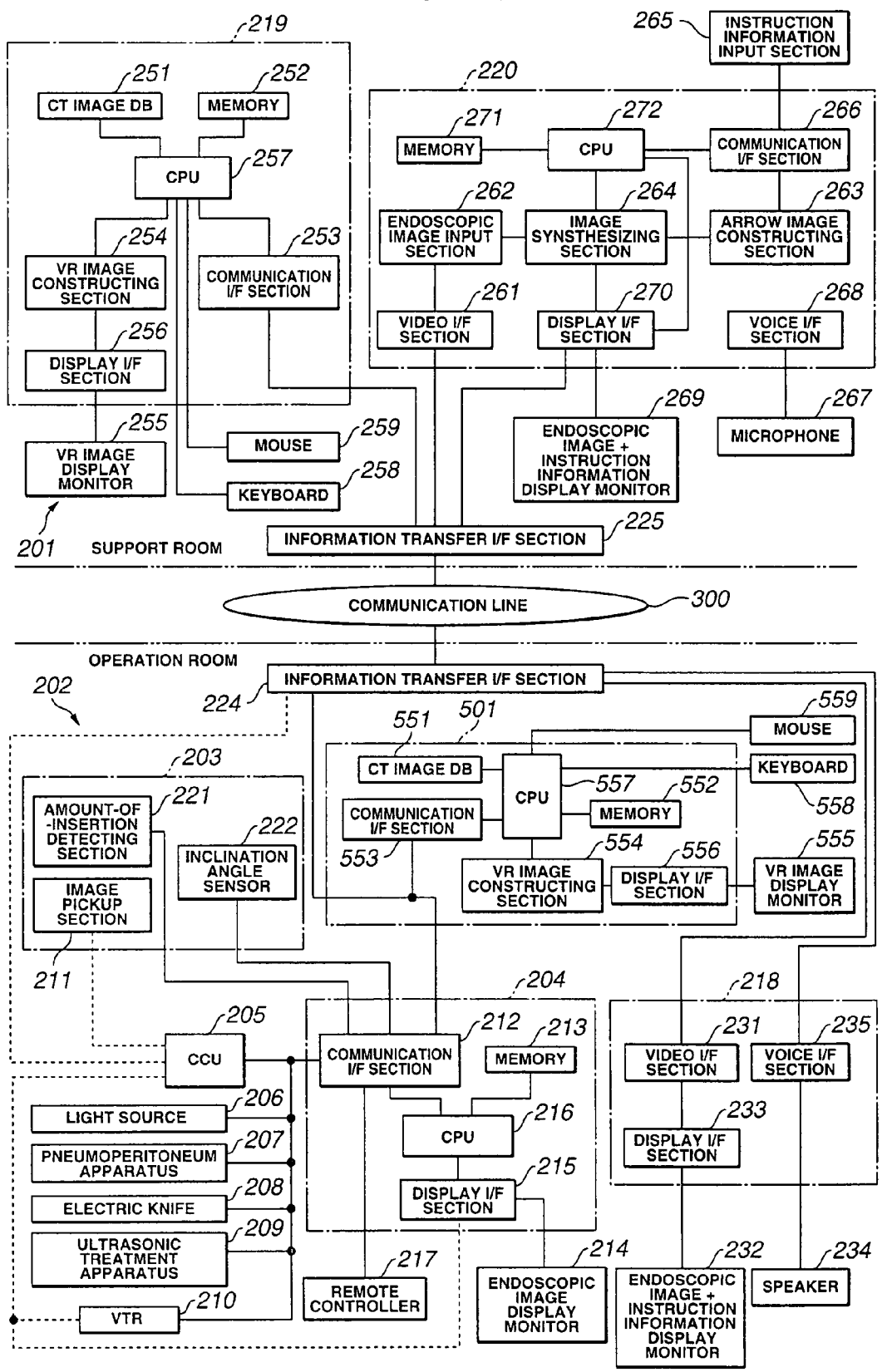
FIG. 29 is a configuration diagram showing a configuration of a remote surgery supporting apparatus and surgery system according to a sixth embodiment of the invention.

FIG. 29 is a configuration diagram showing configurations of a remote surgery supporting apparatus and surgery system according to a sixth embodiment of the invention.

The sixth embodiment is substantially the same as the fifth embodiment. Therefore, only difference therebetween will be described, and the same reference numerals are given to the same components, the descriptions of which will be omitted herein.

According to this embodiment, a VR image creating apparatus 501 is provided in a surgery system. The VR image creating apparatus 501 has the similar configuration with that of a VR image creating apparatus 219 in a remote surgery supporting apparatus 201 and creates a VR image to be displayed on a VR image display monitor 555.

Like the VR image creating apparatus 219, the VR image creating apparatus 501 includes a recording portion 551, a memory 552, a communication I/F section 553, a VR image constructing section 554, a display I/F section 556 and a CPU 557. The recording portion 551 stores a CT image database (DB) including multiple CT images. The memory 552 stores different kinds of programs. The communication I/F section 553 receives inserting amount data detected by the amount-of-insertion detecting section 221 and insertion inclination angle data detected by the inclination angle sensor 222 from the system controller 204. The VR image constructing section 554 constructs a VR image based on inserting amount data and insertion inclination angle data obtained by the communication I/F section 553 and a CT image in the CT image DB. The display I/F section 556 causes the VR image display monitor 555 to display a VR image constructed by the VR image constructing section 554. The CPU 557 controls these portions. A keyboard 558 and a mouse 559 used for inputting various kinds of data are connected to the CPU 557. The rest of the construction and operation is the same as that of the fifth embodiment.

According to this embodiment, in addition to the advantages of the fourth embodiment, a VR image is not required to transmit by the VR image creating apparatus 219 of the remote surgery supporting apparatus 201 through the communications line 300 since the VR image creating apparatus 501 creates a VR image to be displayed on the VR image display monitor 555. Thus, the communication traffic of the communications line 300 can be reduced, and the communication environment can be improved significantly.

As described above, according to this embodiment, by providing a proper instruction from a remote facility with reference to a live endoscopic image, surgery can be supported easily in real time at low costs.

Seventh Embodiment

A seventh embodiment of the invention will be described below with reference to drawings.

Figure 30:
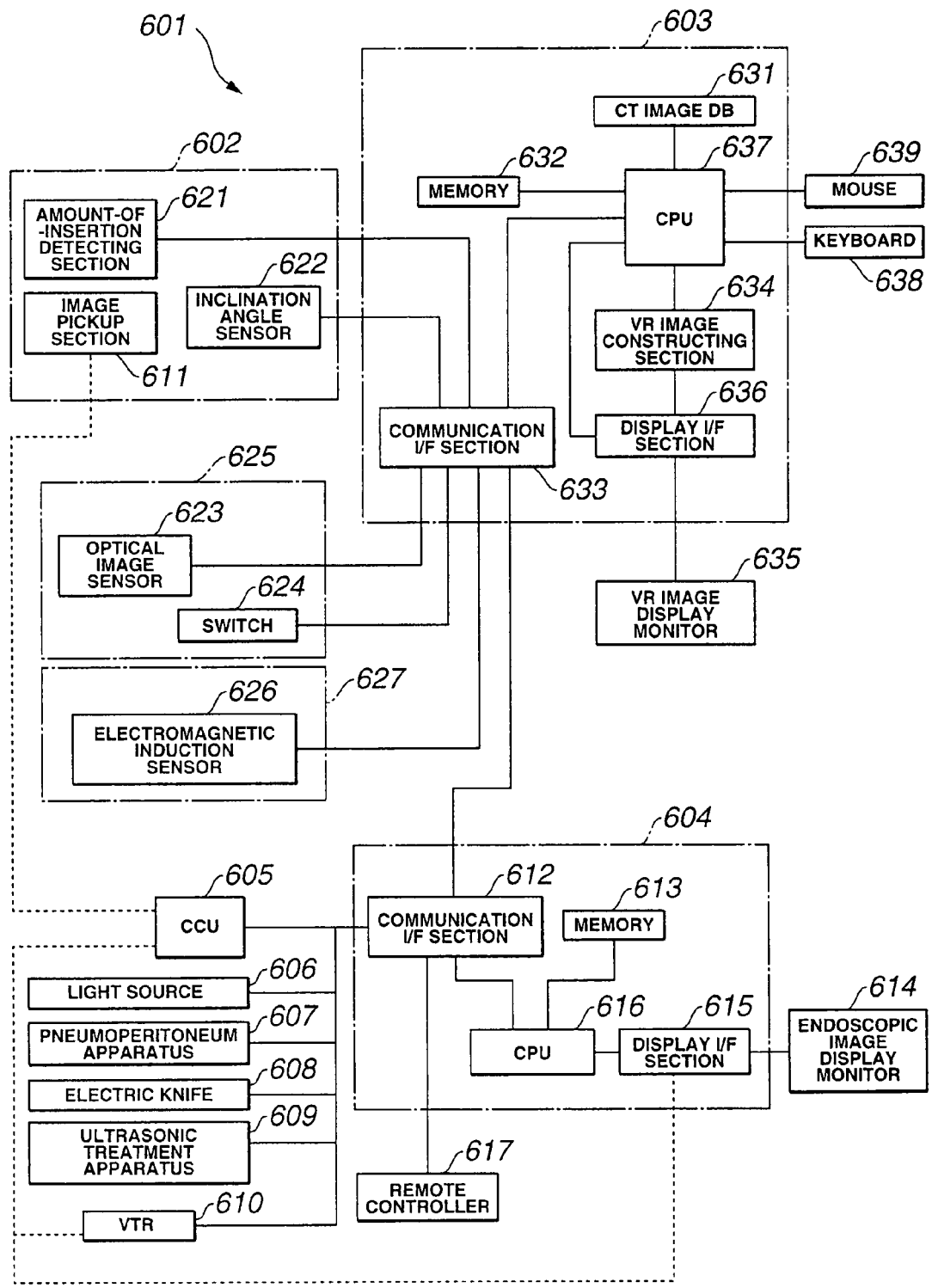
FIG. 30 is a configuration diagram showing the rigidity of a surgery supporting apparatus according to a seventh embodiment of the invention.
Figure 31:
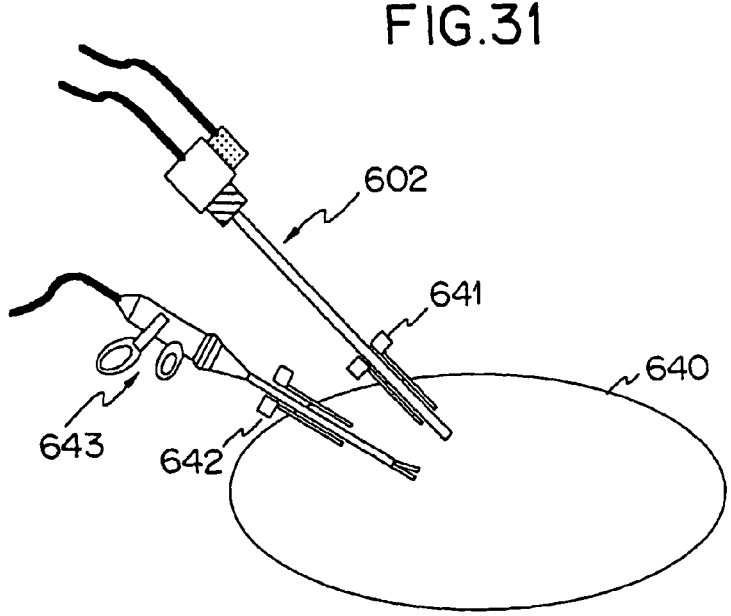
FIG. 31 is a diagram showing a state in which a rigid endoscope in FIG. 30 is being used.
Figure 32:
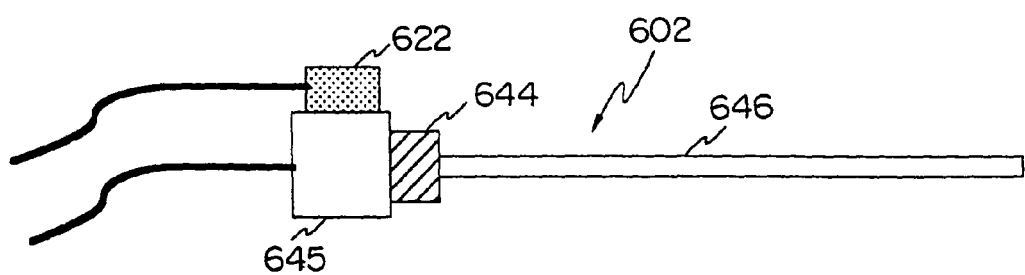
FIG. 32 is a diagram showing a construction of the rigid endoscope in FIG. 31.
Figure 33:
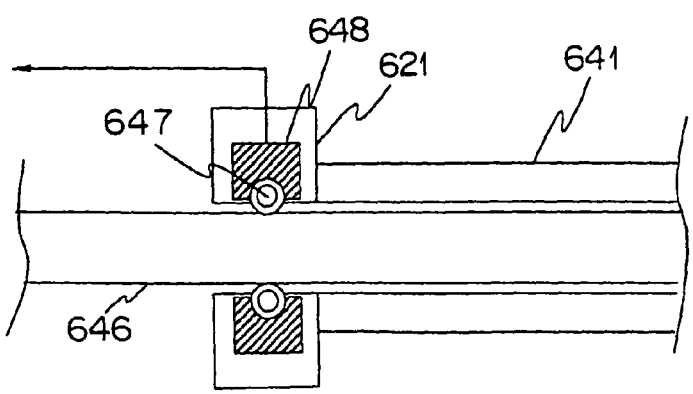
FIG. 33 is a diagram showing a construction of an essential part of a trocar in FIG. 31.
Figure 34:
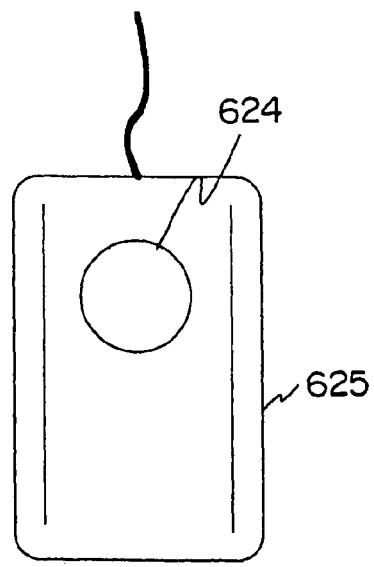
FIG. 34 is a top view showing a top face of an XY-inserting point measuring apparatus in FIG. 30.
Figure 35:
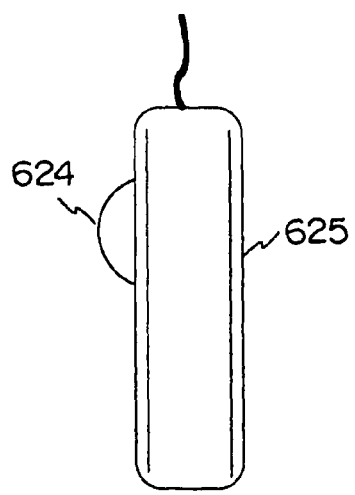
FIG. 35 is a side view showing a side of the XY-inserting point measuring apparatus in FIG. 30.
Figure 36:
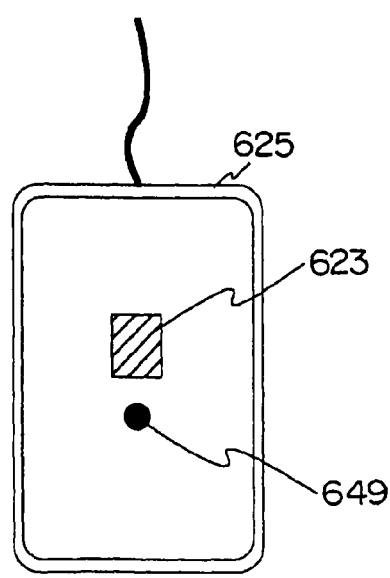
FIG. 36 is a back view showing a back face of the XY-inserting point measuring apparatus in FIG. 30.
Figure 37:
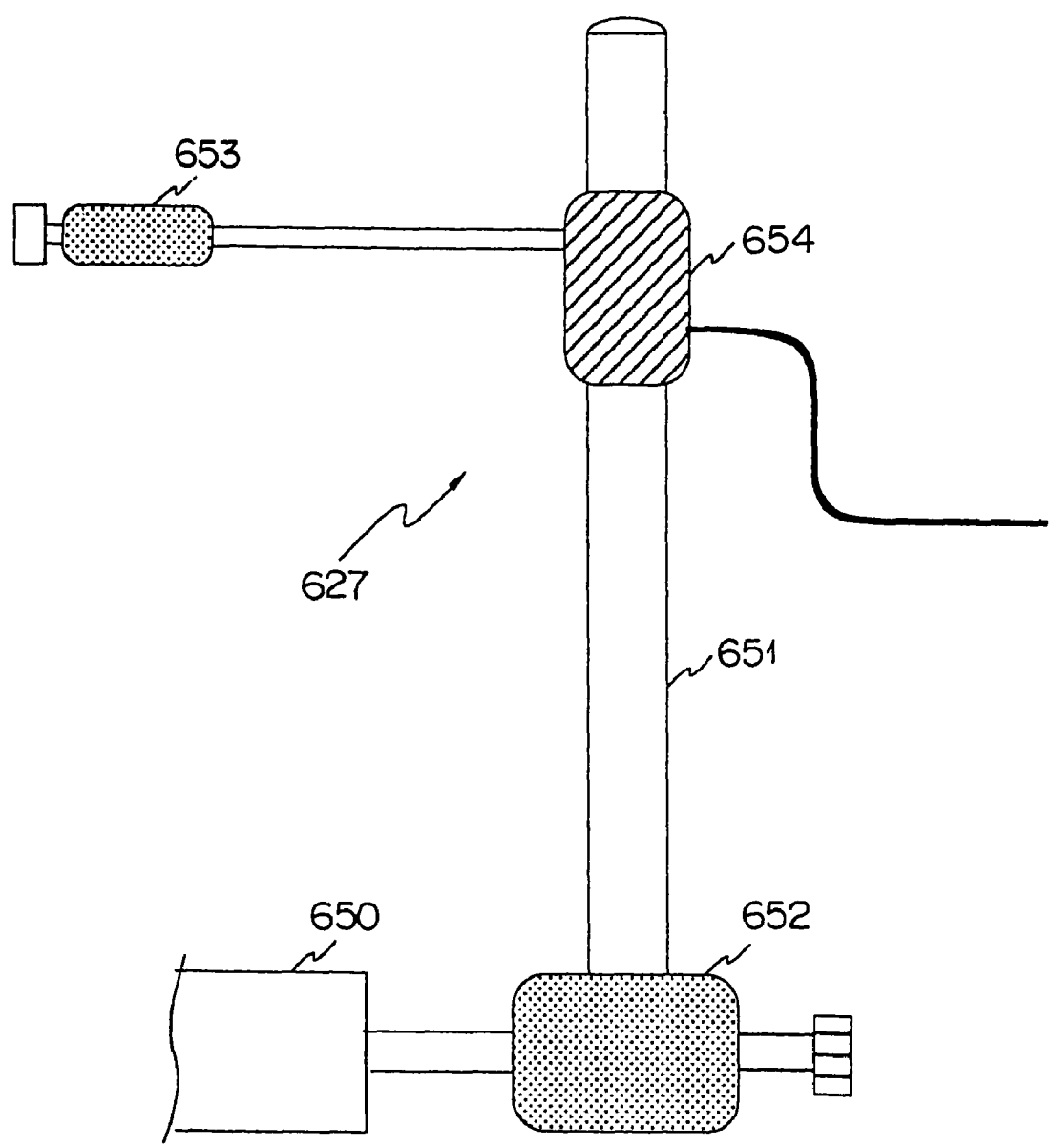
FIG. 37 is a diagram showing a construction of a Z-inserting point measuring apparatus in FIG. 30.
Figure 38:
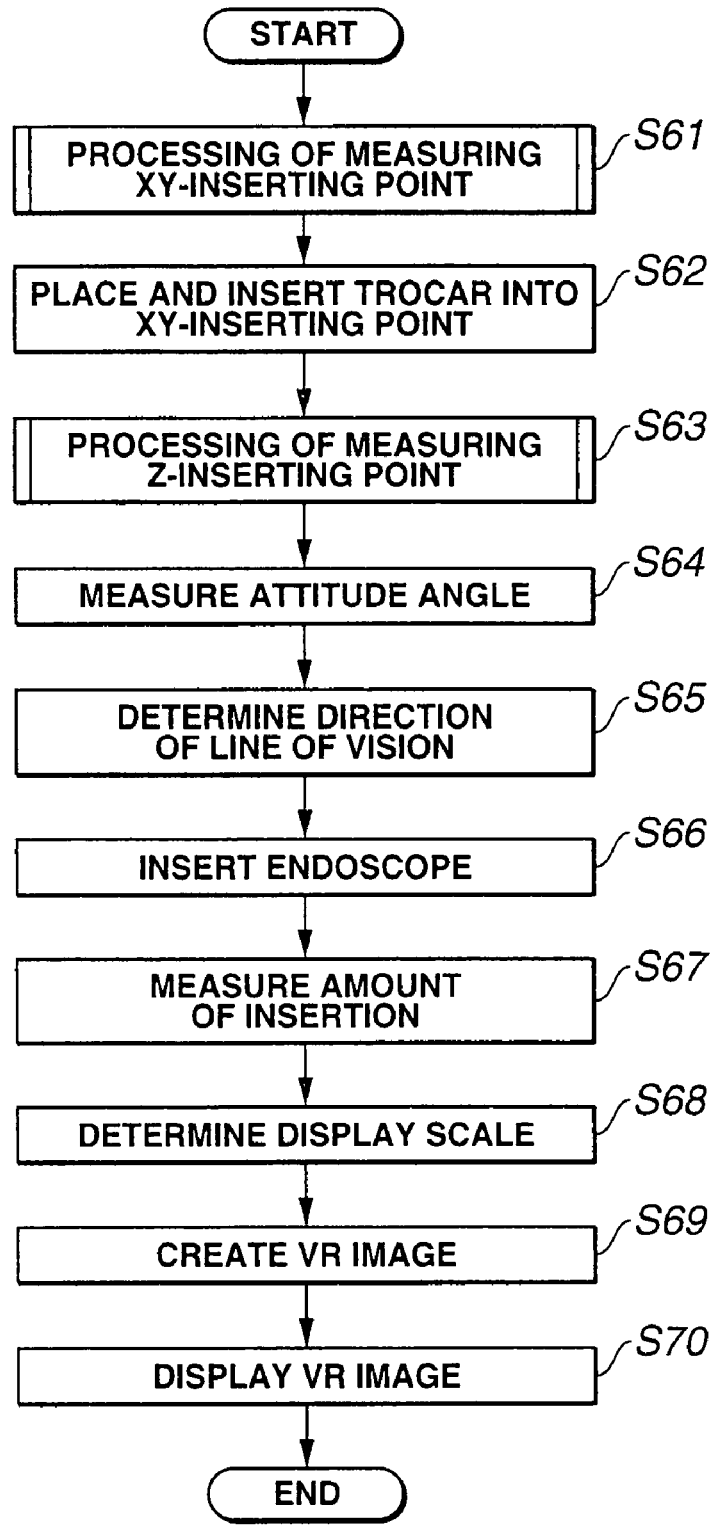
FIG. 38 is a flowchart showing a processing flow of a surgery support apparatus in FIG. 30.
Figure 39:
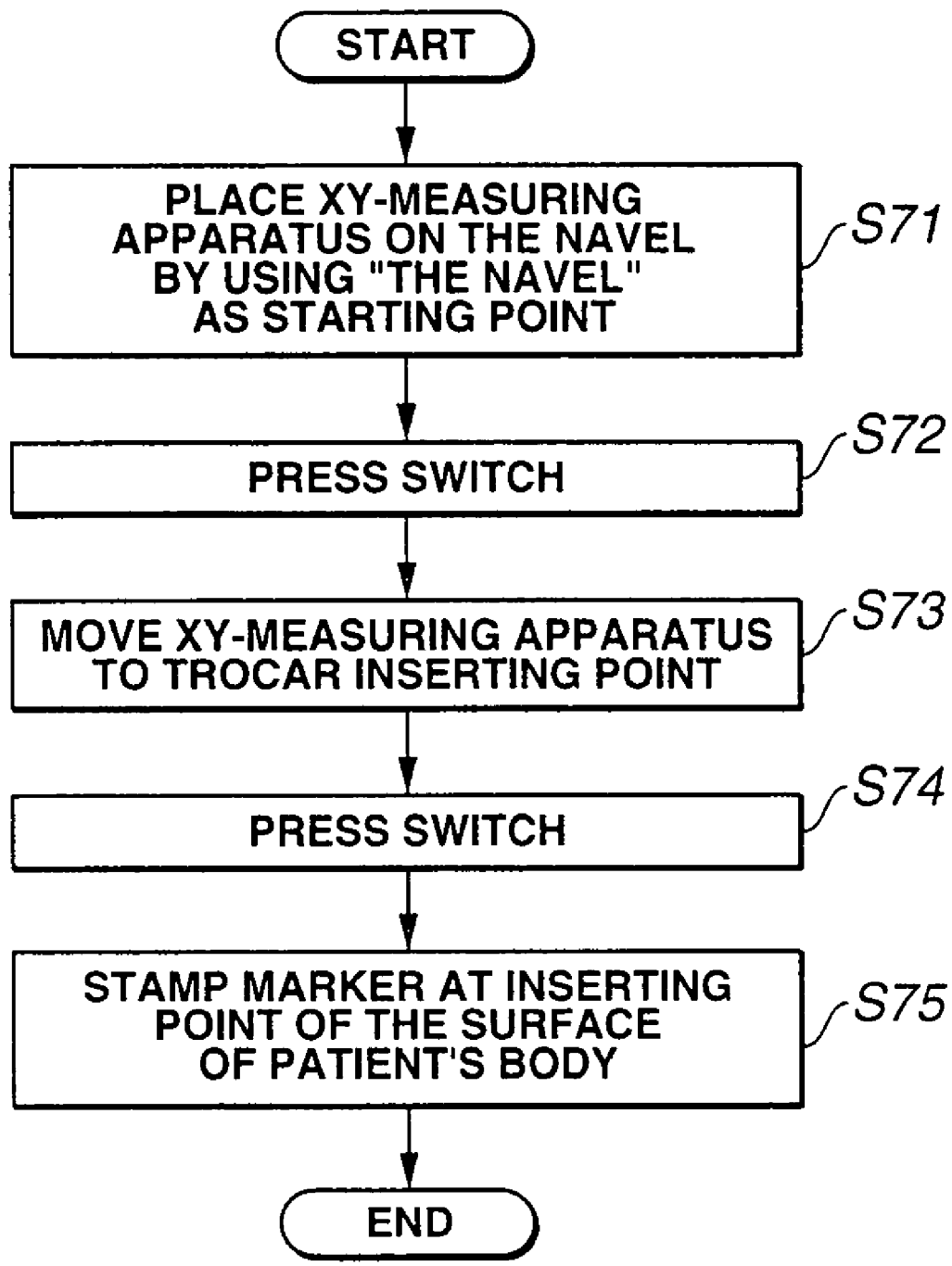
FIG. 39 is a flowchart showing a flow of XY-inserting point measuring processing in FIG. 38.
Figure 40:
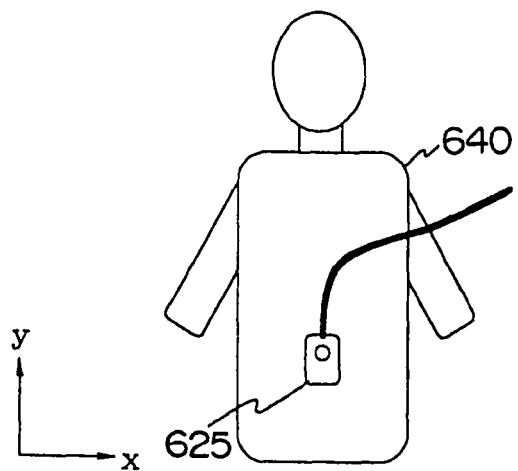
FIG. 40 is a first diagram illustrating the XY-inserting point measuring processing in FIG. 39.
Figure 41:
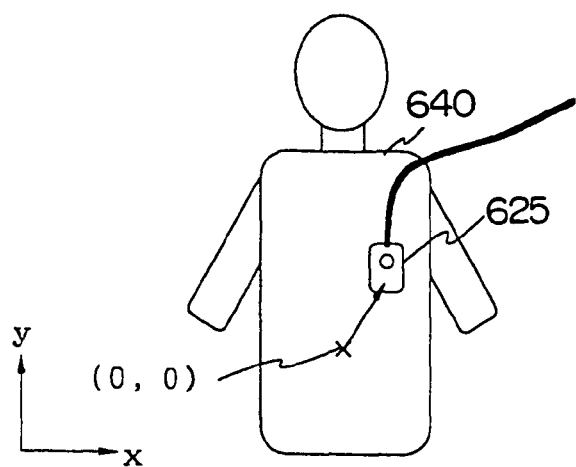
FIG. 41 is a second diagram illustrating the XY-inserting point measuring processing in FIG. 39.
Figure 42:
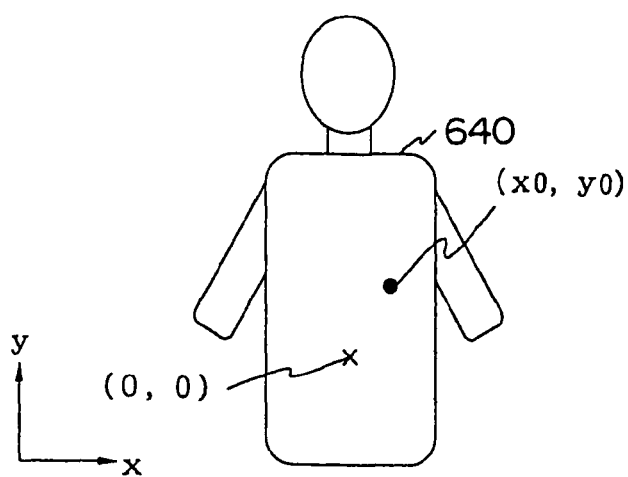
FIG. 42 is a third diagram illustrating the XY-inserting point measuring processing in FIG. 39.
Figure 43:
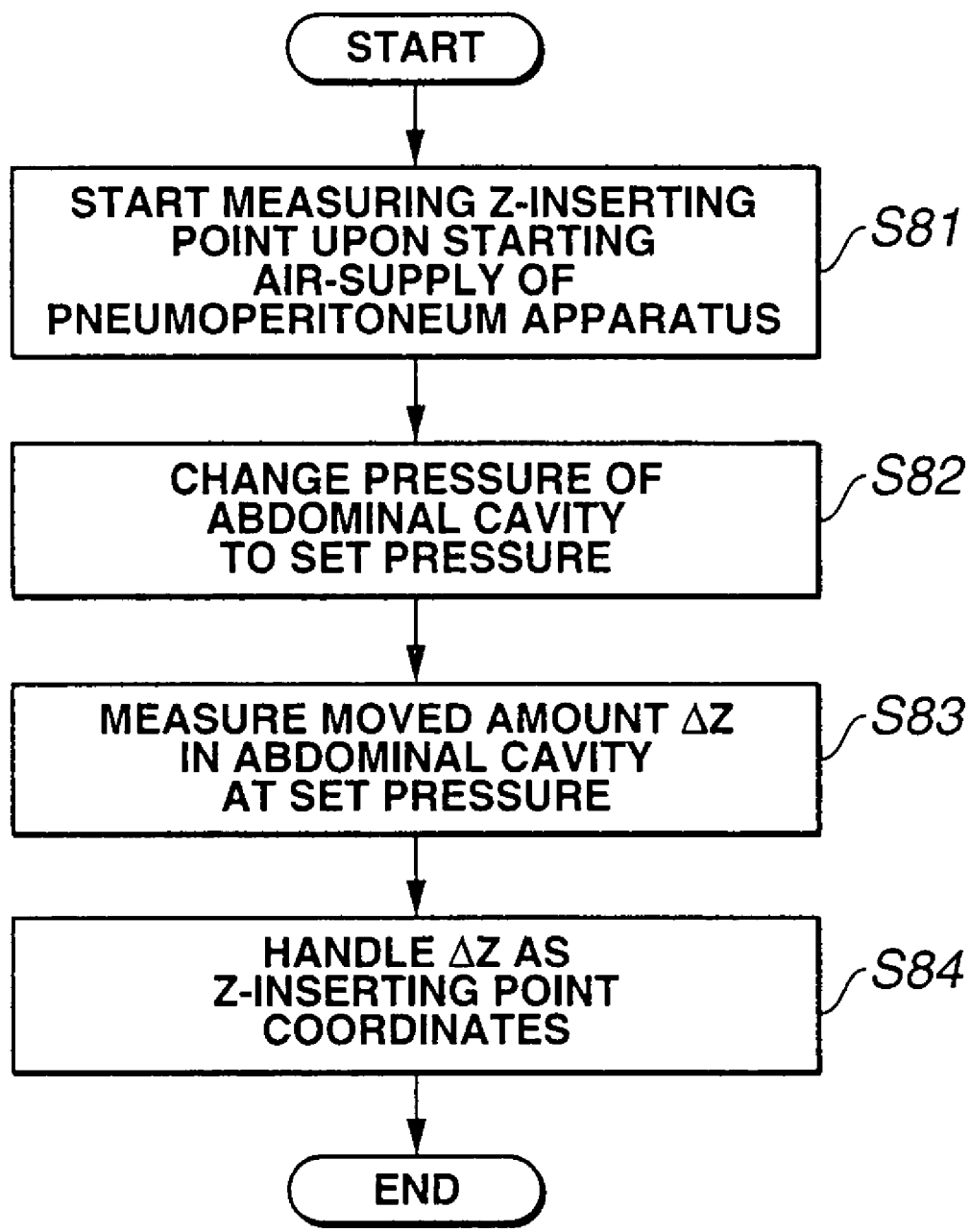
FIG. 43 is a flowchart showing a flow of Z-inserting point measuring processing in FIG. 38.
Figure 44:
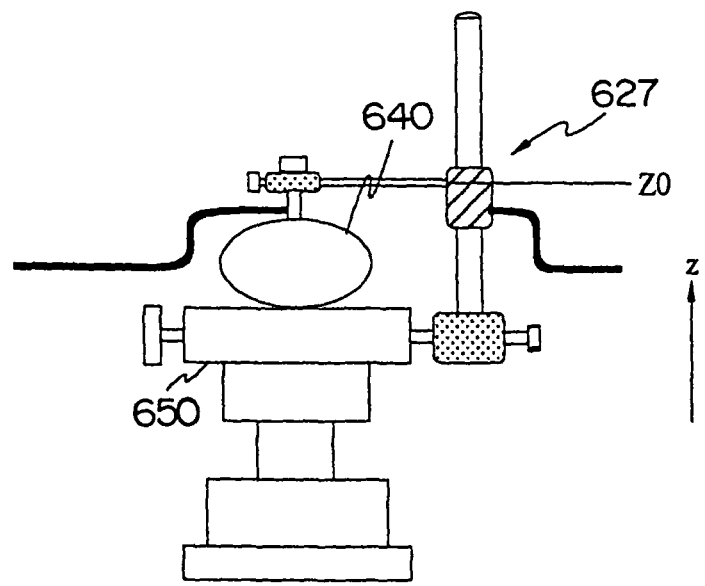
FIG. 44 is a first diagram illustrating the Z-inserting point measuring processing in FIG. 43.
Figure 45:
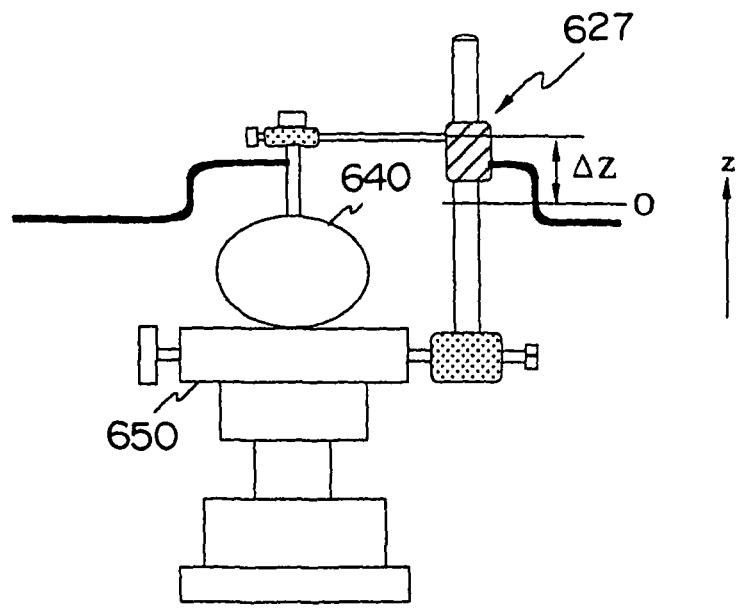
FIG. 45 is a second diagram illustrating the Z-inserting point measuring processing in FIG. 43.
Figure 46:
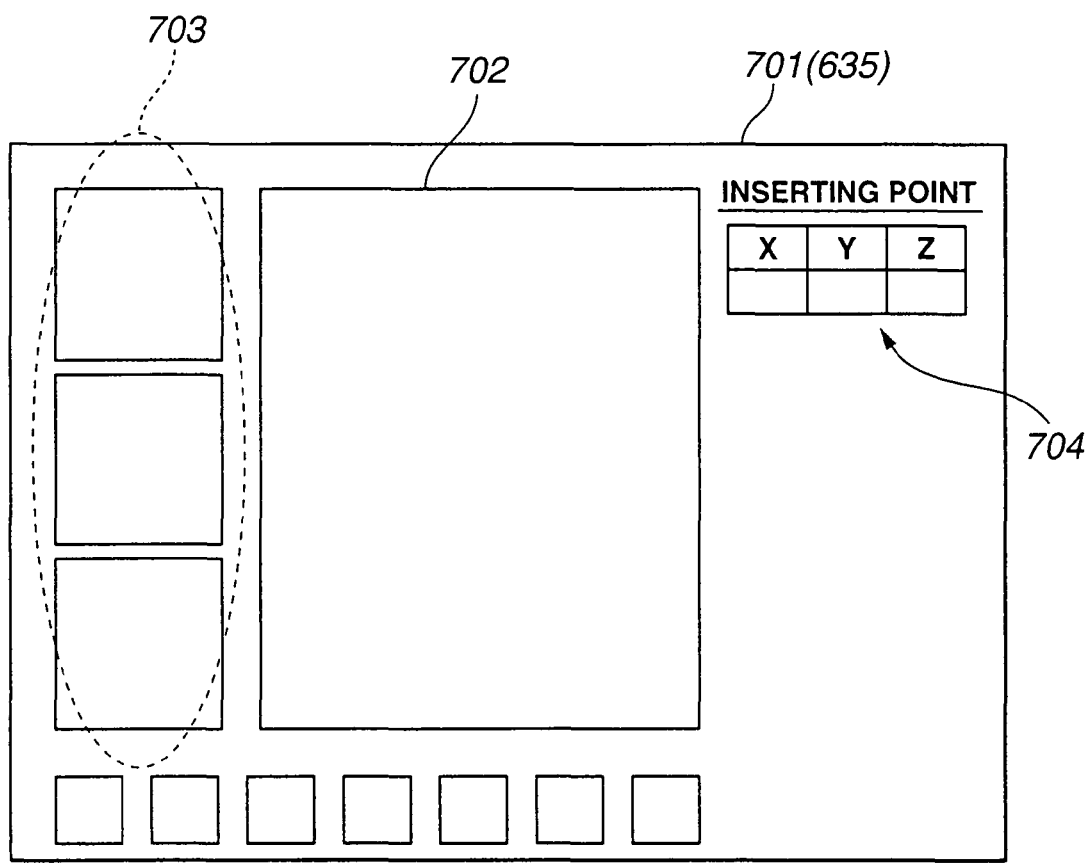
FIG. 46 is a diagram showing a VR display screen displaying a VR image constructed/created by processing in FIG. 39.
Figure 47:
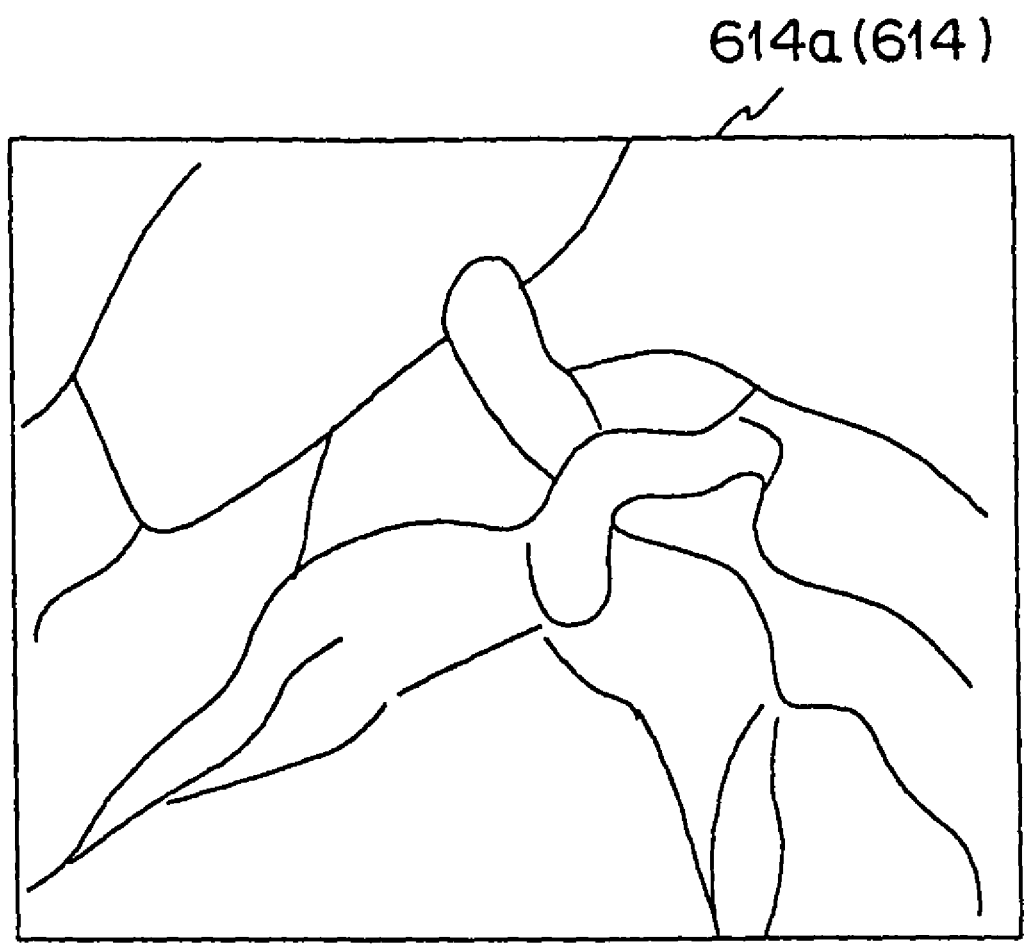
FIG. 47 is a diagram showing a first example of an endoscopic image displayed on an endoscopic image display monitor in FIG. 30.
Figure 48:
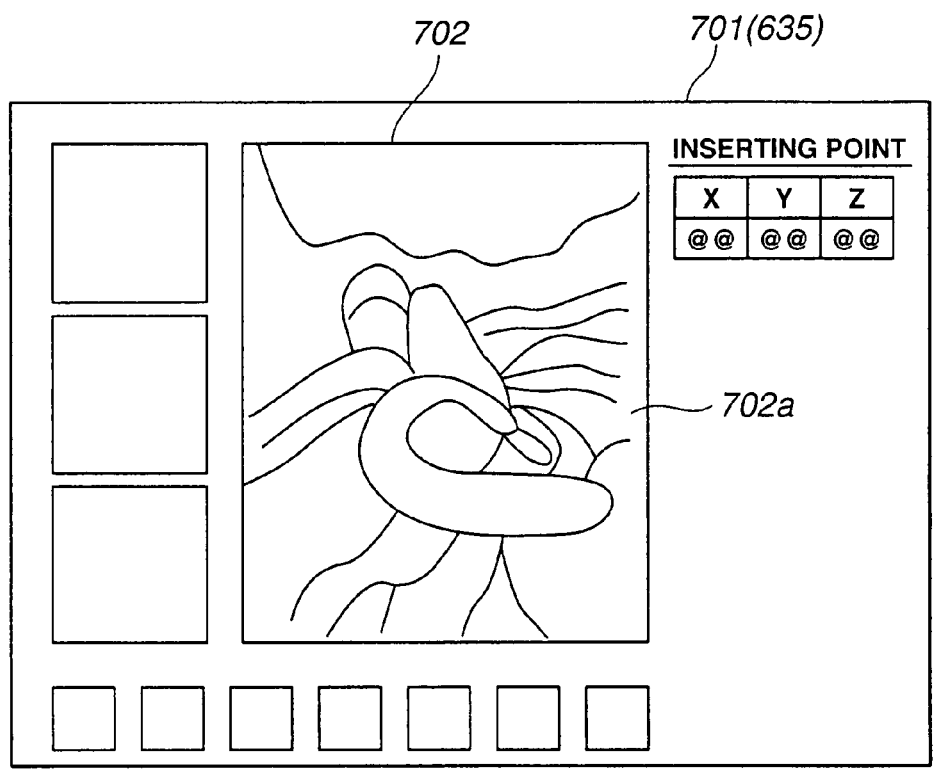
FIG. 48 is a diagram showing a VR display screen displayed in accordance with the endoscopic image in FIG. 47.
Figure 50:
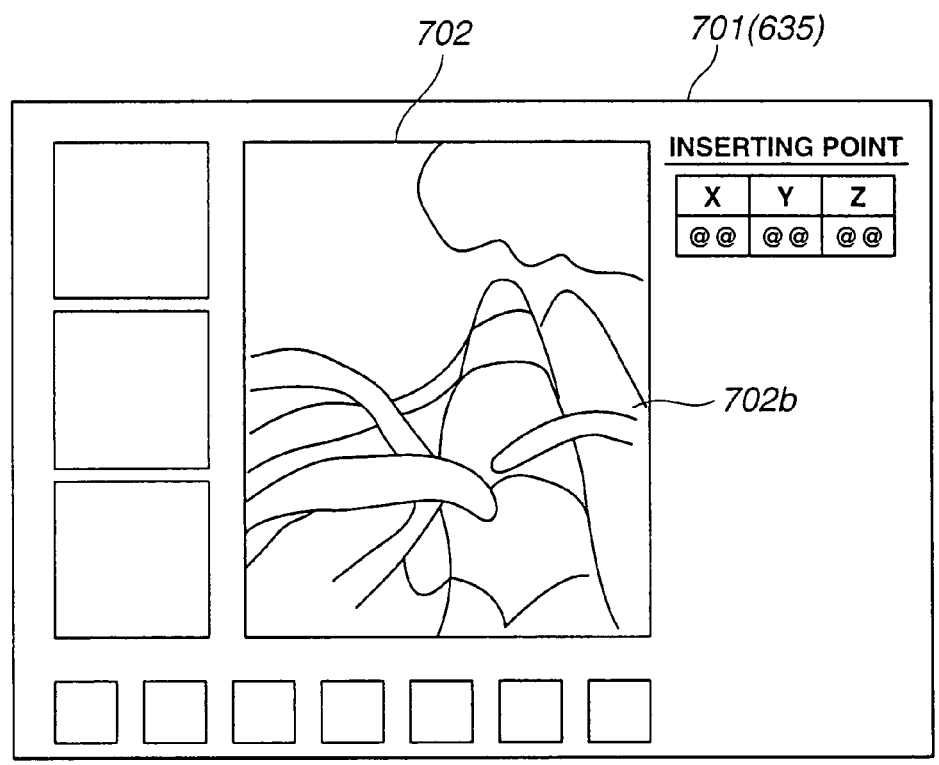
FIG. 50 is a diagram showing a VR display screen displayed in accordance with the endoscopic image in FIG. 49.
Figure 49:
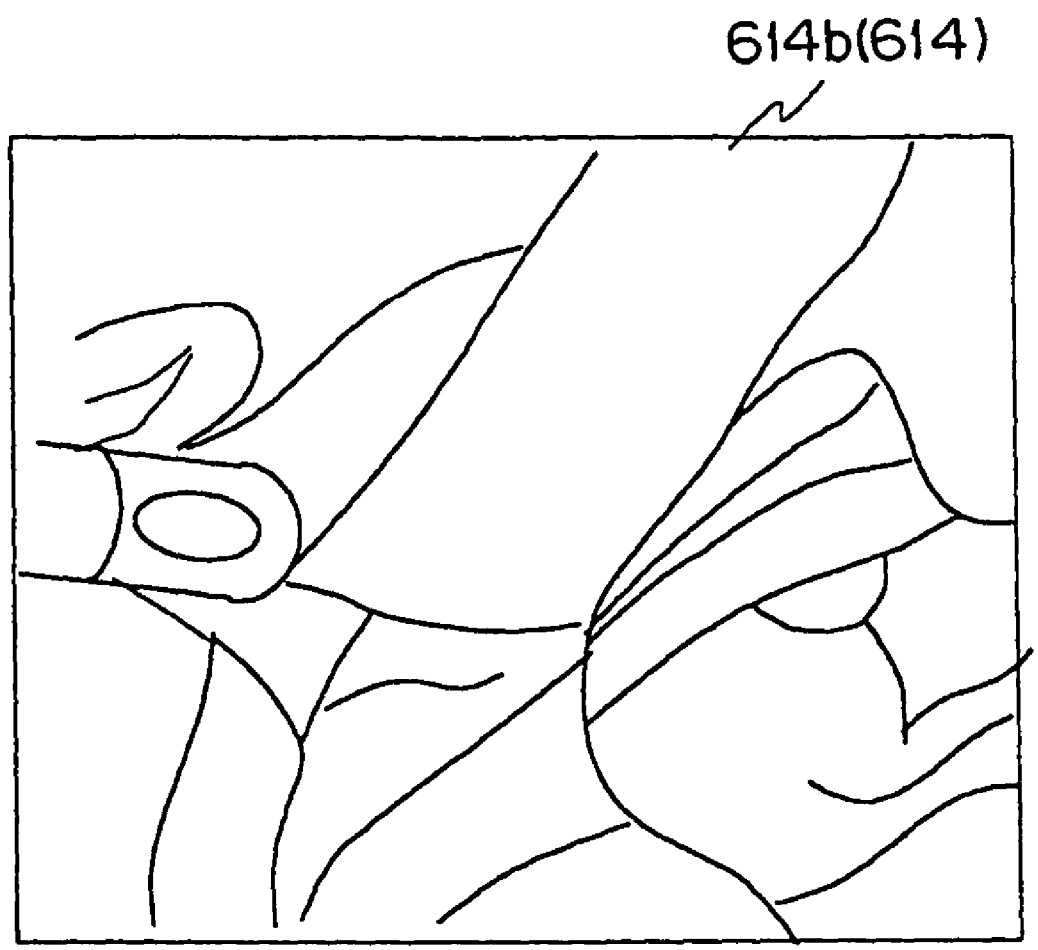
FIG. 49 is a diagram showing a second example of an endoscopic image displayed on the endoscopic image display monitor in FIG. 30.
Figure 51:
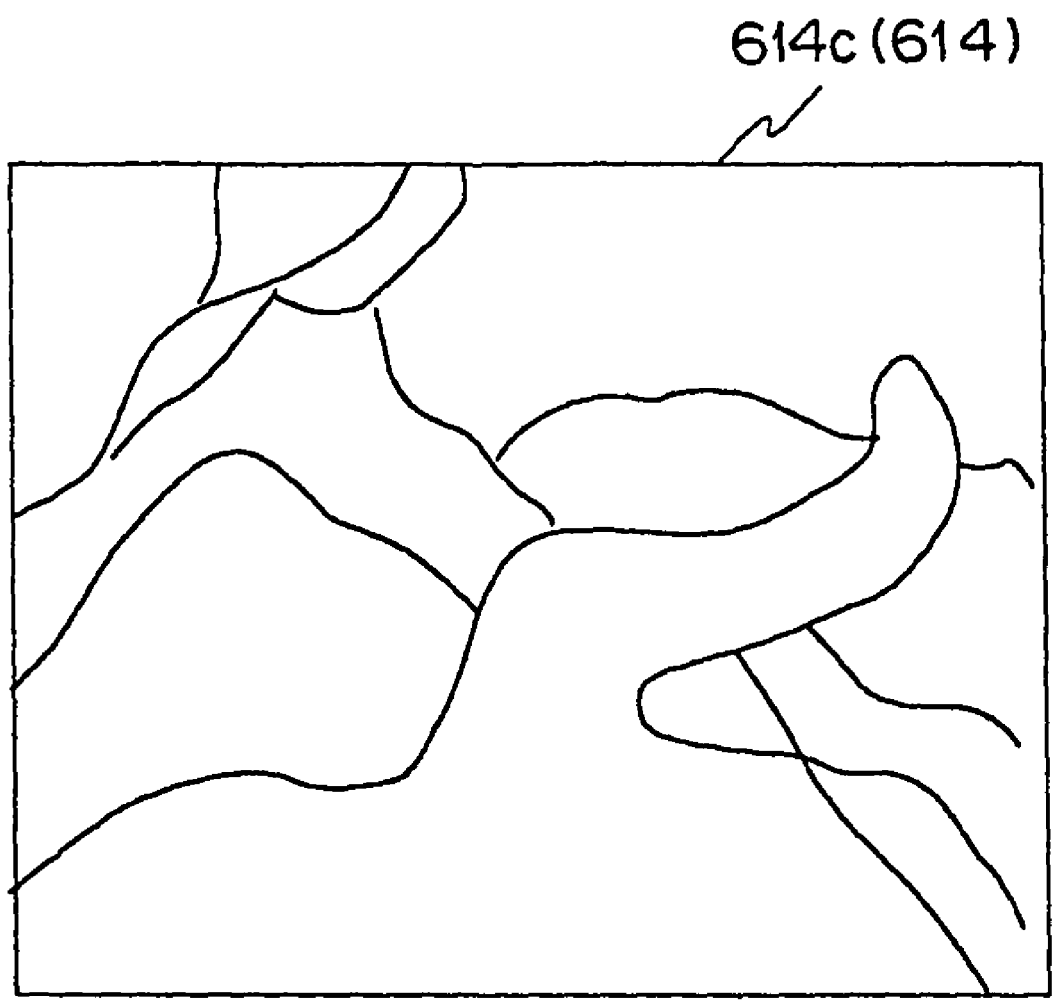
FIG. 51 is a diagram showing a third example of an endoscopic image displayed on the endoscopic image display monitor in FIG. 30.
Figure 52:
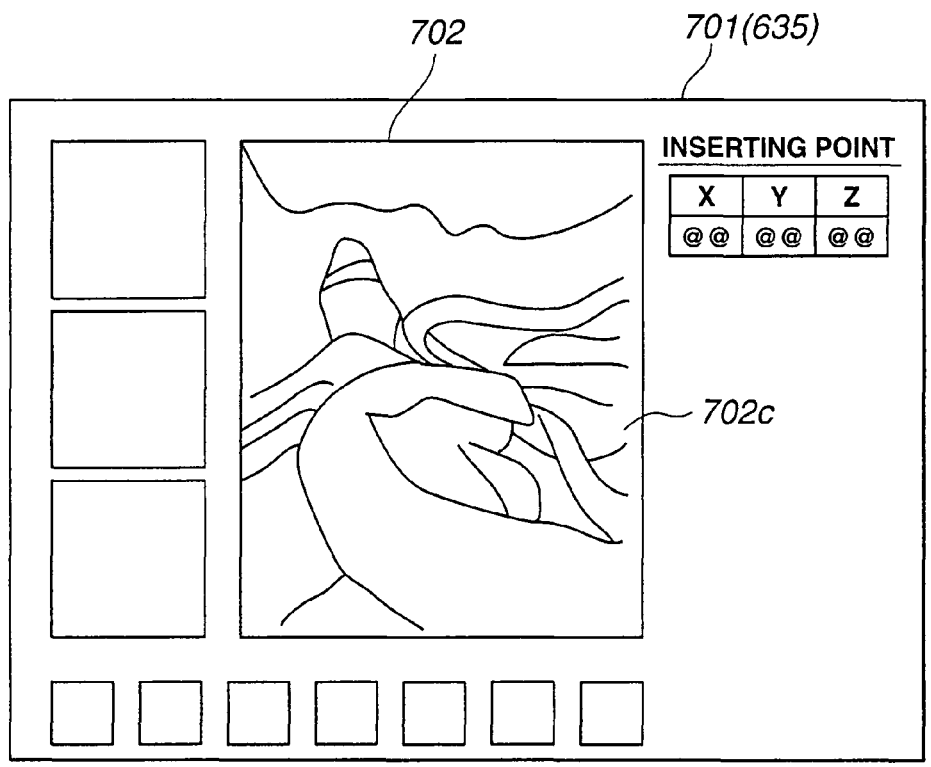
FIG. 52 is a diagram showing a VR display screen displayed in accordance with the endoscopic image in FIG. 51.
Figure 53:
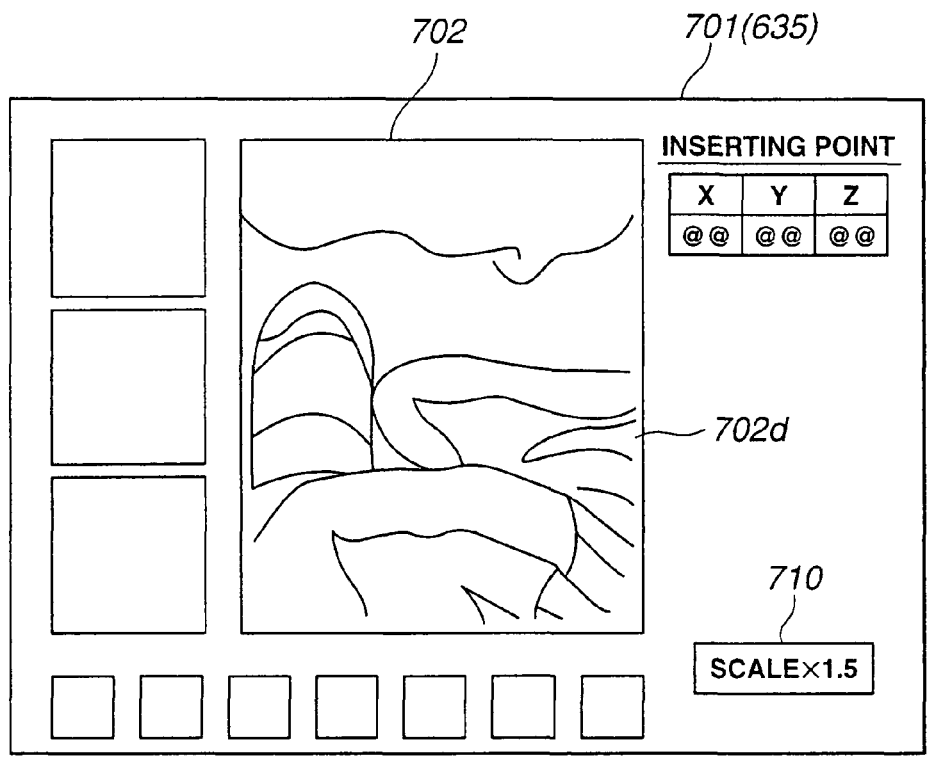
FIG. 53 is a diagram showing a VR display screen displaying a VR image having a different scale from that of the VR image in FIG. 52.

FIGS. 30 to 53 relate to the seventh embodiment of the invention. FIG. 30 is a configuration diagram showing a configuration of a surgery supporting apparatus. FIG. 31 is a diagram showing a state in which a rigid endoscope in FIG. 30 is being used. FIG. 32 is a diagram showing a construction of the rigid endoscope in FIG. 31. FIG. 33 is a diagram showing a construction of an essential part of a trocar in FIG. 31. FIG. 34 is a top view showing a top face of an XY-inserting point measuring apparatus in FIG. 30. FIG. 35 is a side view showing a side of the XY-inserting point measuring apparatus in FIG. 30. FIG. 36 is a back view showing a back face of the XY-inserting point measuring apparatus in FIG. 30. FIG. 37 is a diagram showing a construction of a Z-inserting point measuring apparatus in FIG. 30. FIG. 38 is a flowchart showing a processing flow of a surgery support apparatus in FIG. 30. FIG. 39 is a flowchart showing a flow of XY-inserting point measuring processing in FIG. 38. FIG. 40 is a first diagram illustrating the XY-inserting point measuring processing in FIG. 39. FIG. 41 is a second diagram illustrating the XY-inserting point measuring processing in FIG. 39. FIG. 42 is a third diagram illustrating the XY-inserting point measuring processing in FIG. 39. FIG. 43 is a flowchart showing a flow of Z-inserting point measuring processing in FIG. 38. FIG. 44 is a first diagram illustrating the Z-inserting point measuring processing in FIG. 43. FIG. 45 is a second diagram illustrating the Z-inserting point measuring processing in FIG. 43. FIG. 46 is a diagram showing a VR display screen displaying a VR image constructed/created by processing in FIG. 38. FIG. 47 is a diagram showing a first example of an endoscopic image displayed on an endoscopic image display monitor in FIG. 30. FIG. 48 is a diagram showing a VR display screen displayed in accordance with the endoscopic image in FIG. 47. FIG. 49 is a diagram showing a second example of an endoscopic image displayed on the endoscopic image display monitor in FIG. 30. FIG. 50 is a diagram showing a VR display screen displayed in accordance with the endoscopic image in FIG. 49. FIG. 51 is a diagram showing a third example of an endoscopic image displayed on the endoscopic image display monitor in FIG. 30. FIG. 52 is a diagram showing a VR display screen displayed in accordance with the endoscopic image in FIG. 51. FIG. 53 is a diagram showing a VR display screen displaying a VR image having a different scale from that of the VR image in FIG. 52.

As shown in FIG. 30, a surgery supporting apparatus 601 according to this embodiment has, in an operation room, a rigid endoscope 602, a VR image creating apparatus 603, a system controller 604, a CCU 605, a light source apparatus 606, a pneumoperitoneum apparatus 607, an electric knife 608, an ultrasonic treatment apparatus 609 and a VTR 610.

Image pickup signals picked up by an image pickup section 611 of the rigid endoscope 602 are transmitted to the CCU 605 and undergo image processing therein. Then, the result is output to the VTR 610 for recording images and the system controller 604.

The system controller 604 includes a communication I/F section 612, a memory 613, a display I/F section 615 and a CPU 616. The communication I/F section 612 exchanges setting information with the CCU 605, the light source apparatus 606, the pneumoperitoneum apparatus 607, an electric knife 608, an ultrasonic treatment apparatus 609, and the VTR 610. The memory 613 stores different kinds of programs. The display I/F section 615 causes an endoscopic image display monitor 614 to display image signals from the CCU 605. The CPU 616 controls these portions. A remote controller 617 is connected to the CPU 616 through the communication I/F section 612. Various kinds of data can be input through the remote controller 617.

The rigid endoscope 602 includes an amount-of-insertion detecting section 621, an inclination angle sensor 622, an XY-inserting point measuring apparatus 625 and a Z-point inserting point measuring apparatus 627. The amount-of-insertion detecting section 621 detects an inserting amount of the rigid endoscope 602. The inclination angle sensor 622 detects an inclination angle of insertion of the rigid endoscope 602. The XY-inserting point measuring apparatus 625 has an optical image sensor 623 and a switch 624. The optical image sensor 623 measures XY-coordinates of an inserting point of the rigid endoscope 602. The Z-point inserting point measuring apparatus 627 has an electromagnetic sensor 626 for measuring a Z-coordinate of an inserting point of the rigid endoscope 602.

Based on a CT image obtained by a CT apparatus (not shown) in advance, the VR image creating apparatus 603 creates a volume rendering image (VR image), which is a virtual image in real time and in a same direction of line of vision as that of an endoscopic image picked up by the rigid endoscope 602.

More specifically, the VR image creating apparatus 603 includes a CT image DB 631, a memory 632, a communication I/F section 633, a VR image constructing section 634, a display I/F section 636 and a CPU 637. The CT image DB 631 is a recording portion for storing a CT image database (DB) including multiple CT images. The memory 632 stores different kinds of programs. The communication I/F section 633 exchanges data with the communication I/F section 612 for the amount-of-insertion detecting section 621, the inclination angle sensor 622, the XY inserting point measuring apparatus 625, the Z-point inserting point measuring apparatus 627 and the system controller 604. The VR image constructing section 634 constructs a VR image based on different kinds of data obtained by the communication I/F section 633 and a CT image in the CT image DB 631. The display I/F section 636 causes the VR image display monitor 635 to display a VR image constructed by the VR image constructing section 634. The CPU 637 controls these portions. A keyboard 638 and a mouse 639 used for inputting various kinds of data are connected to the CPU 637.

As shown in FIG. 31, the rigid endoscope 602 is inserted into the body of a patient 640 along with a treating apparatus 643 such as an electric knife and an ultrasonic treating apparatus through the trocars 641 and 642.

As shown in FIG. 32, the rigid endoscope 602 includes an image pickup section 611 at the inserted proximal end and the inclination angle sensor 622 at a handle 645 on the inserted proximal end side. The inclination angle sensor 622 measures an insertion inclination angle of the rigid endoscope 602 by using a gyroscopic compass and outputs the result to the VR image creating apparatus 603.

As shown in FIG. 33, the amount-of-insertion detecting section 621 is provided on the proximal end side of the trocar 641 for guiding an insert portion 646 of the rigid endoscope 602 into the body of the patient 640. The amount-of-insertion detecting section 621 includes a roller 647 and a rotary encoder 648. The roller 647 is in contact with an outer surface of the insert portion 646 and rotates in accordance with the insertion of the insert portion 646. The rotary encoder 648 detects an amount of rotation of the roller 647 and outputs the amount of rotation to the VR image creating apparatus 603 as an amount of insertion of the insert portion 646.

As shown in FIGS. 34 to 36, the XY-inserting point measuring apparatus 625 has substantially the same construction as that of a publicly known optical mouse. The XY-inserting point measuring apparatus 625 has the switch 624 on the top face and a pointer 649 on the back face. The switch 624 is used for confirming an inserting point. The pointer 649 is used for printing a marker on the body surface of the patient 640 in connection with the optical image sensor 623 and the switch 624. The optical image sensor 623 detects a moved amount.

As shown in FIG. 37, the Z-point inserting point measuring apparatus 627 includes a fixing member 652, a trocar holding portion 653 and an measuring portion 654. The fixing member 652 supports and fixes a support rod 651 in perpendicular to an operation table 650 on which the patient 640 lies. The trocar holding portion 653 holds a trocar 641 extending from the support rod 651 at the right angle. The measuring portion 654 self-contains an electromagnetic induction sensor 626 which detects a moved amount in the axial direction (Z-direction) of the support rod 651 of the trocar holding portion 653 and outputs the result to the VR image creating apparatus 603.

Operations of this embodiment having the above-described construction will be described. As shown in FIG. 38, XY-inserting point measuring processing by the XY-inserting point measuring apparatus 625 is performed at a step S61. Details of the XY-inserting point measuring processing will be described later.

After an XY-inserting point is measured by the XY-inserting point measuring apparatus 625, the trocar 641 is placed at a position marked by a pointer 649 of the XY-inserting point measuring apparatus 625 and is inserted into the body of the patient 640 at a step S62. At a step S63, Z-point measuring processing is performed by the Z-inserting point measuring apparatus 27. Details of the Z-inserting point measuring processing will be described later.

In the processing at the steps S61 to S63, an inserting point of the rigid endoscope 602 is determined. The rigid endoscope 602 is inserted through the trocar 641. Then, at a step S64, an insertion inclination angle, that is, an attitude angle of the rigid endoscope 602 is measured by the inclination angle sensor 622. At a step S65, the direction of line of vision of an endoscopic image to be picked up by the rigid endoscope 602 is determined based on the insertion inclination angle at a step S65.

Once the insertion of the rigid endoscope 602 is started at a step S66, an amount of insertion of the rigid endoscope 602 is measured by the amount-of-insertion detecting section 621 at a step S67. At a step S68, a display scale of a VR image is determined based on the inserting amount (in accordance with the distance, that is, higher scale near an organ while lower scale away from the organ).

Once a direction of the line of vision and a display scale are determined, a VR image is created by the VR image constructing section 634 based on the direction of the line of vision and the display scale at a step S69. At a step S70, the VR image is displayed on the VR image display monitor 635 through the display I/F section 636, and the processing ends.

In the XY-inserting point measuring processing at the step S61, a starting point is set at "the navel" of the patient 640 at a step S71 as shown in FIG. 39. The XY-inserting point measuring apparatus 625 is placed on "the navel" as shown in FIG. 40. At a step S72, the switch 624 is pressed down. Thus, the origin (0,0) can be determined on the xy plane.

Next, at a step S73, the XY inserting point measuring apparatus 625 is moved to a position of the insertion of the trocar 641 as shown in FIG. 41. By pressing down the switch 624 at a step S74, a marker is stamped at the position as shown in FIG. 42 at a step S75. Thus, an inserting point (x0,y0) can be determined on the XY plane of the rigid endoscope 602.

In the Z-inserting point measuring processing at the step S63, after the trocar 641 held at the Z-point inserting point measuring apparatus 627 is placed and inserted at the inserting point (x0,y0), the position of the origin (x0,y0,0) in the z direction is detected, and measuring a Z-inserting point is started as shown in FIG. 44 upon starting the gas supply of the pneumoperitoneum apparatus 607 at step S81.

At a step S82, pressure of the abdominal cavity is set at a set pressure by the pneumoperitoneum apparatus 607. At a step S83, a moved amount ΔZ of the trocar 641 at the set pressure is measured by the Z-point inserting point measuring apparatus 627 as shown in FIG. 45. At a step S84, the moved amount ΔZ is an inserting point z0 in the Z direction of the rigid endoscope 602.

By performing the XY inserting point measuring processing and the Z-inserting point measuring processing, an inserting point (x0,y0,z0) of the rigid endoscope 602 is determined.

Next, a VR display screen to be displayed on the VR image display monitor 635 will be described. As shown in FIG. 46, a VR display screen 701 includes a VR image display area 702, a two-dimensional image display area 703 and an inserting point display field 704 and so on. The VR image display area 702 displays a VR image created by the VR image constructing section 634. The two-dimensional image display area 703 displays multiple two-dimensional CT images relating to a VR image. The inserting point display field 704 displays inserting point (x0,y0,z0) (=(@@,@@,@@)) of the rigid endoscope 602 determined by the XY-inserting point measuring processing and Z-inserting point measuring processing.

For example, when a live endoscopic image 614a as shown in FIG. 47 is displayed on the endoscopic image display monitor 614, a blood-vessel included virtual image 702a without an organ part, for example, as shown in FIG. 48 is displayed in the VR image display area 702 on the VR display screen 701. Here, the blood-vessel included virtual image 702a is in real time and has a same direction of line of vision and size (scale) as those of the live endoscopic image 614a.

When the rigid endoscope 2 is inclined from the state in FIG. 47 and the live endoscopic image 614b as shown in FIG. 49 is displayed on the endoscopic image display monitor 614, a blood-vessel included virtual image 702b without an organ part, for example, as shown in FIG. 50 is displayed in the VR image display area 702. Here, the blood-vessel included virtual image 702b is in real time and has a same direction of line of vision and size (scale) as those of the live endoscopic image 614b in accordance with (by tracking) the display.

When the live endoscopic image 614c as shown in FIG. 51 is displayed on the endoscopic image display monitor 614, a blood-vessel included virtual image 702c without an organ part, for example, as shown in FIG. 52 is displayed in the VR image display area 702 as described above. Here, the blood-vessel included virtual image 702c is in real time and has a same direction of line of vision and size (scale) as those of the live endoscopic image 614c. In this case, by manipulating the keyboard 638, for example, a blood vessel included virtual image 702d having a different scale as shown in FIG. 53 can be displayed in the VR image display area 702. The scale may be set arbitrarily. FIG. 53 shows a state magnified by 1.5 times, and the magnification scale is displayed in a scale display area 710.

In this way, according to this embodiment, an inserting point, insertion inclination angle, inserting amount of the rigid endoscope 602 are measured, and a real time VR image having a same direction of line of vision and size (scale) as those of a live endoscopic images is created and displayed based on the data of the inserting point, insertion inclination angle and inserting amount. Thus, information required for implementing a technique (such as blood-vessel included information) can be visually checked, and the technique can be supported safely and properly.

As described above, according to this embodiment, surgery can be advantageously supported by providing virtual images corresponding to live endoscopic images easily and in real time.

Eighth Embodiment

Figure 54:
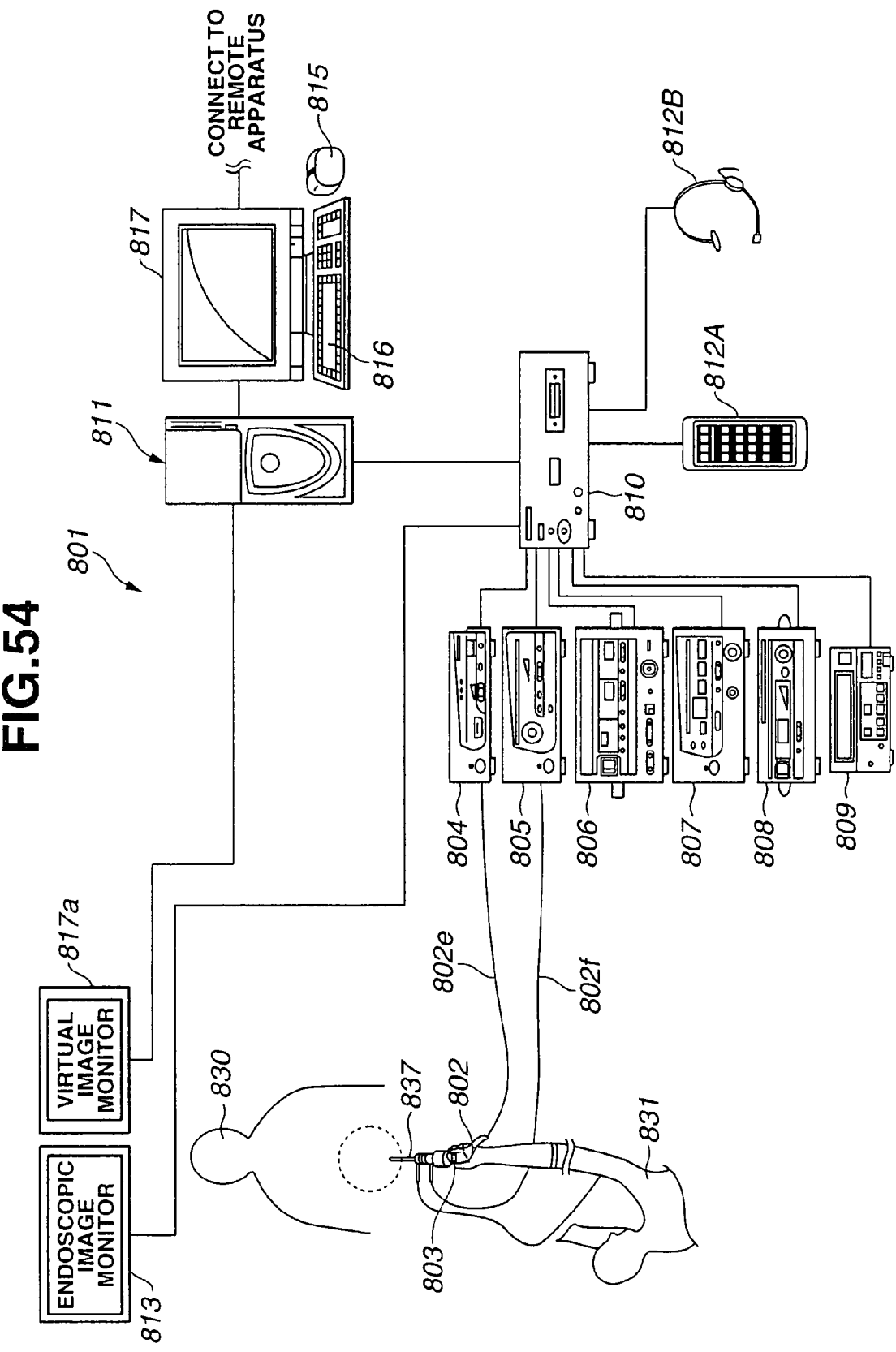
FIG. 54 is a construction diagram showing a construction of a technique support system according to an eighth embodiment of the invention.
Figure 55:
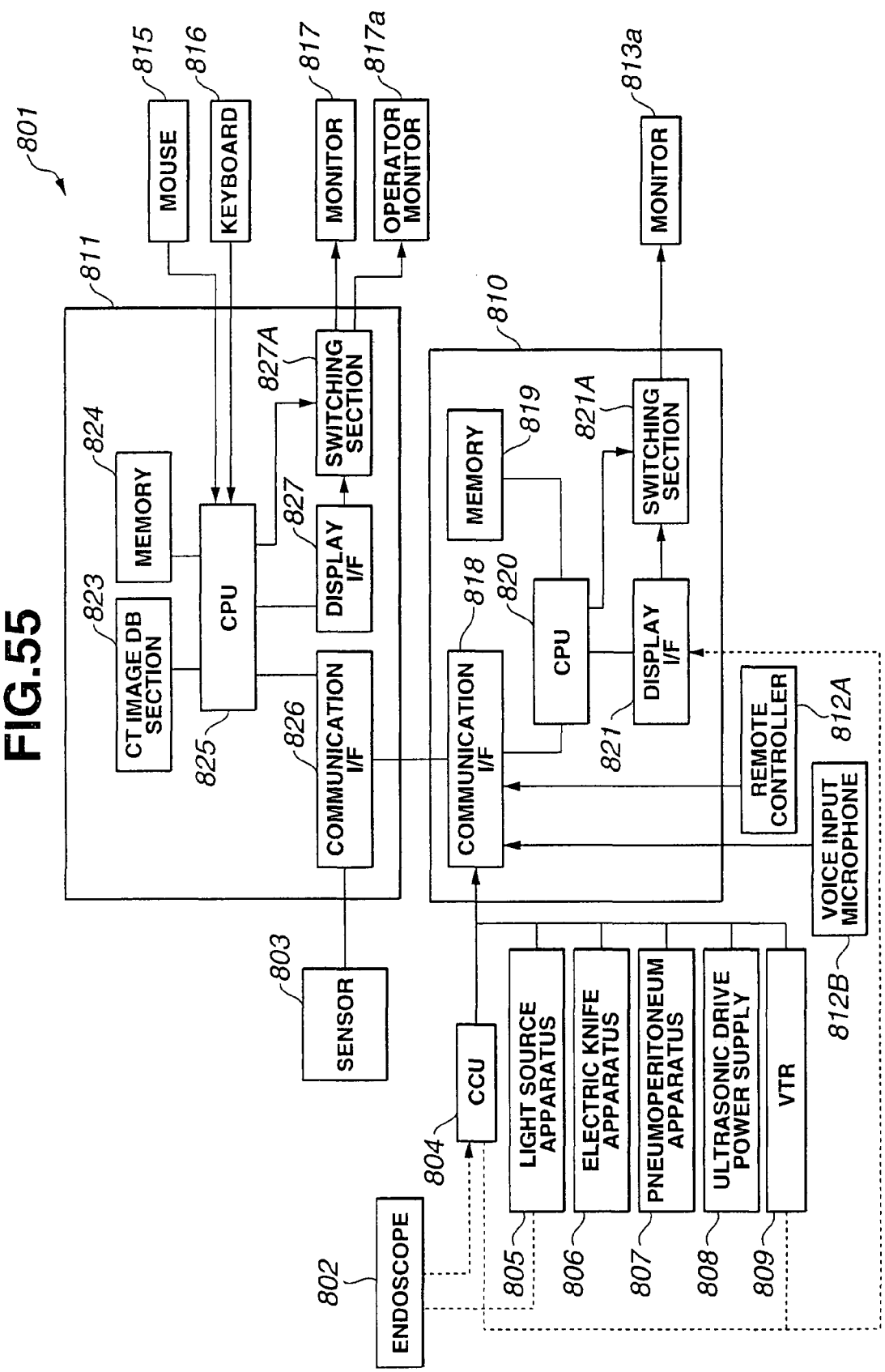
FIG. 55 is a block diagram showing an essential configuration of the technique support system in FIG. 54.
Figure 56:
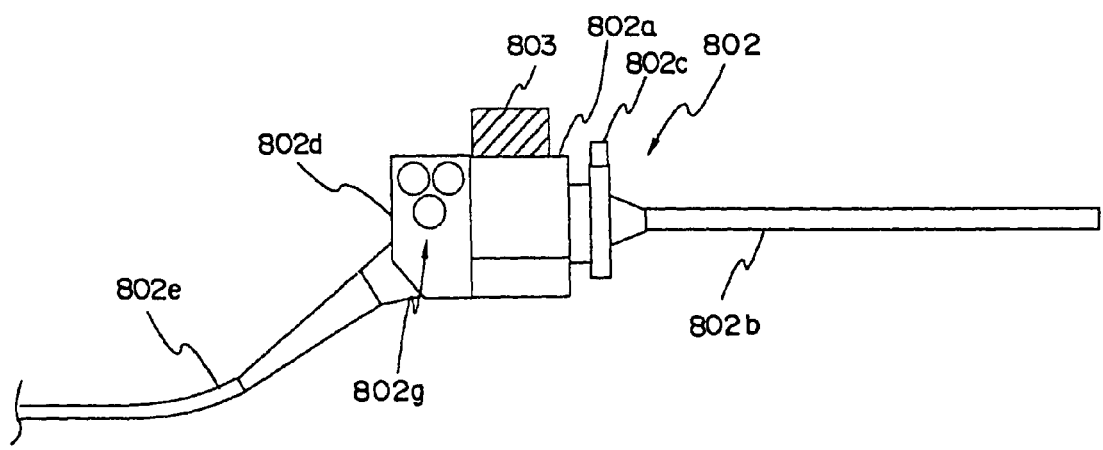
FIG. 56 is a diagram showing a construction of an endoscope in FIG. 54.
Figure 57:
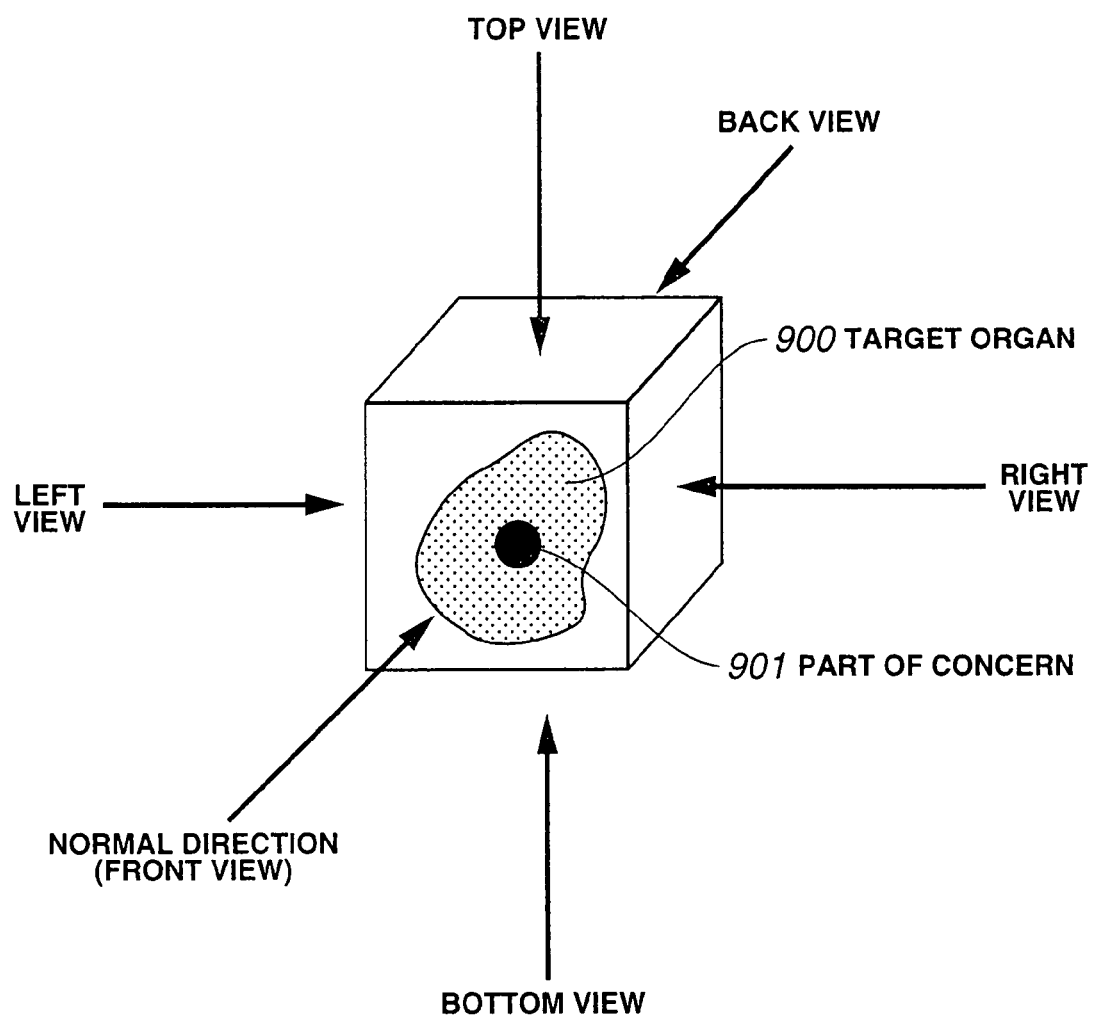
FIG. 57 is a diagram illustrating an operation of the technique support system in FIG. 54.
Figure 58:
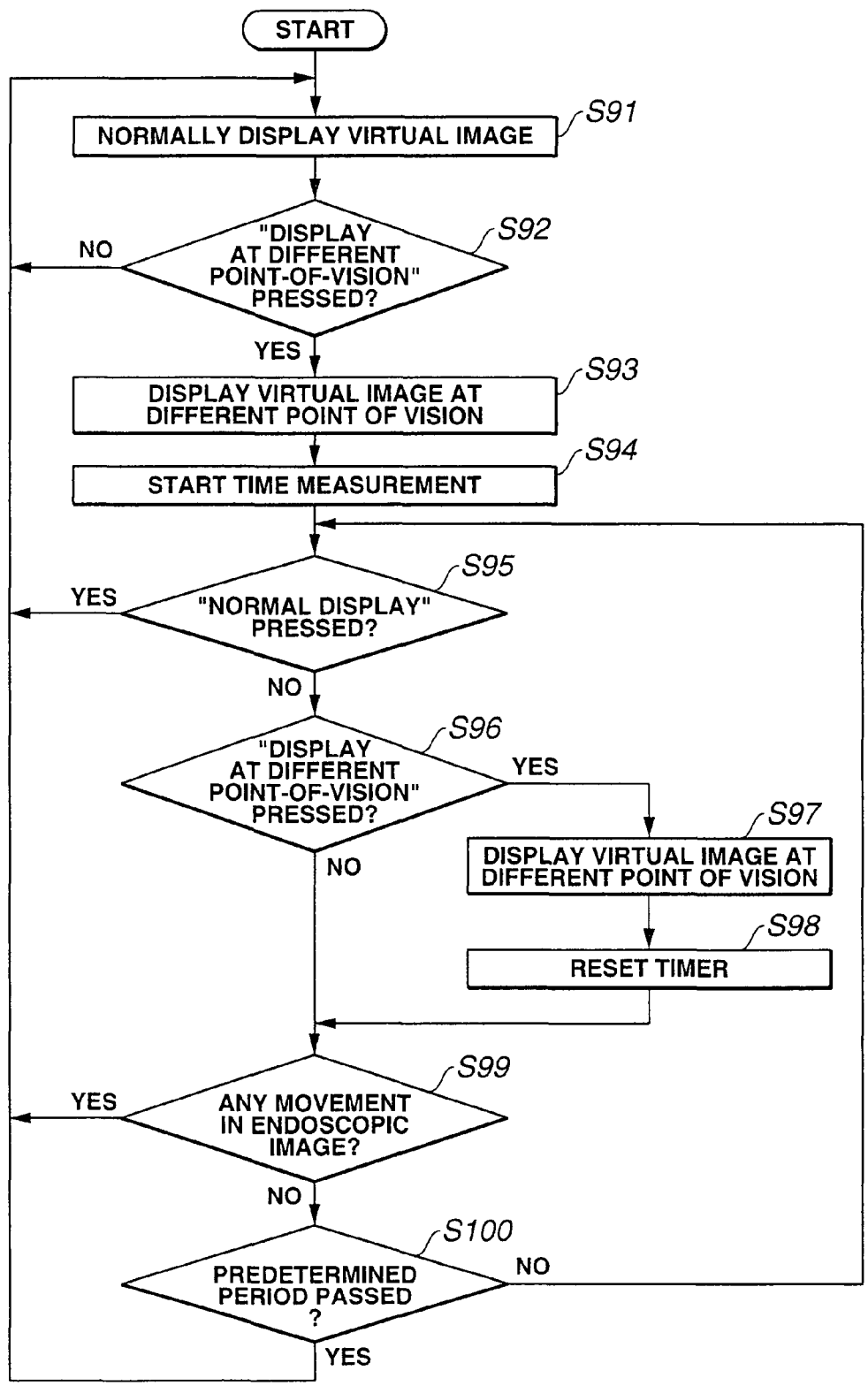
FIG. 58 is a flowchart showing a processing flow of the technique support system in FIG. 54.
Figure 59:
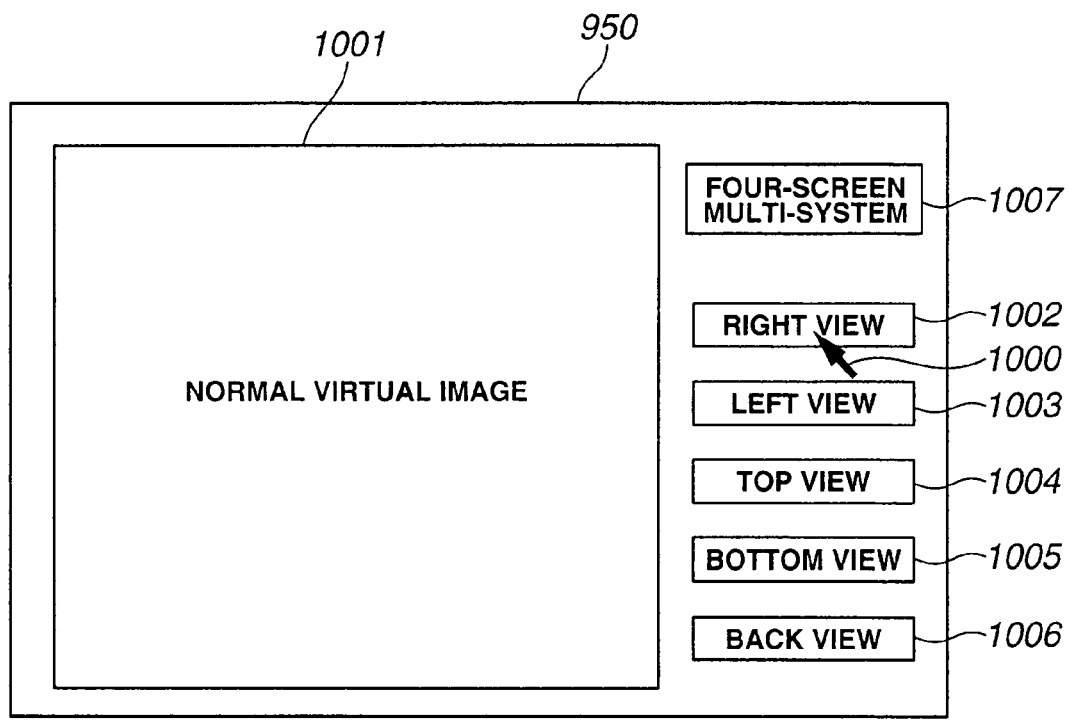
FIG. 59 is a first diagram showing a screen developed in the processing in FIG. 58.
Figure 60:
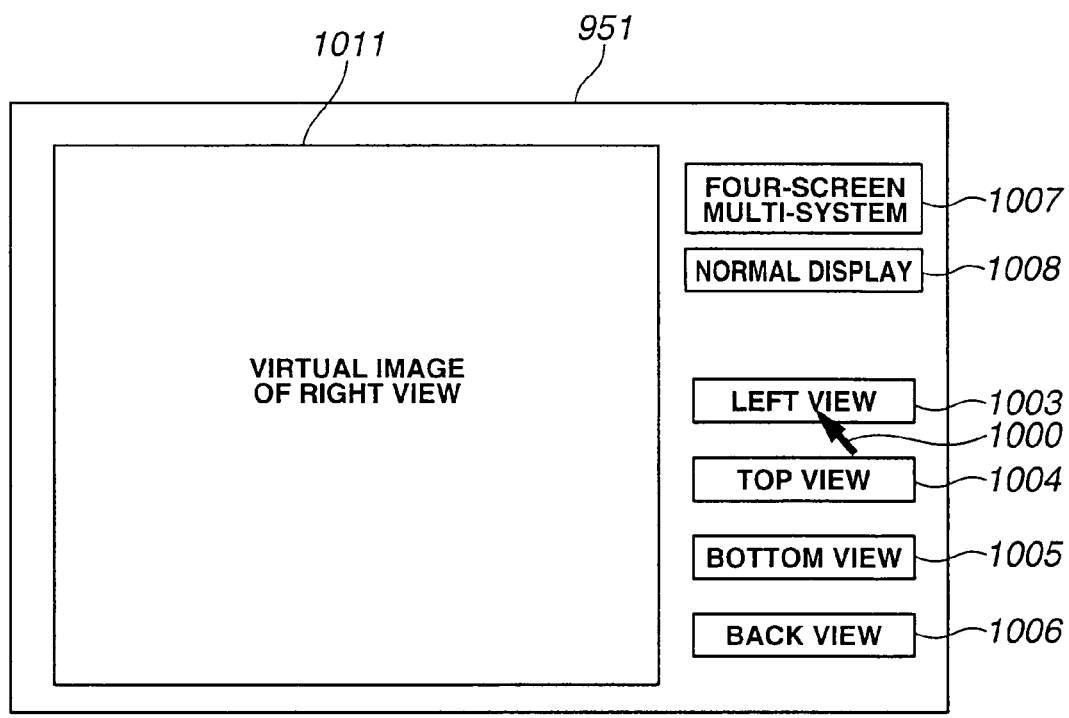
FIG. 60 is a second diagram showing a screen developed in the processing in FIG. 58.
Figure 61:
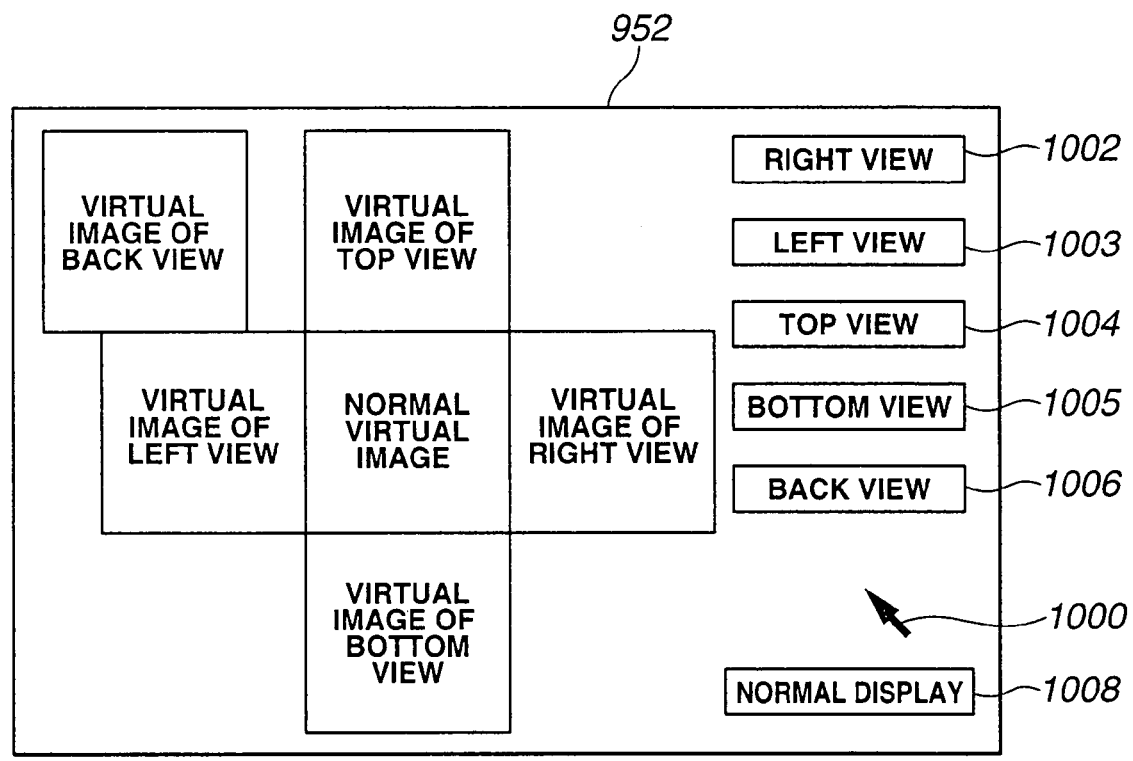
FIG. 61 is a third diagram showing a screen developed in the processing in FIG. 58.
Figure 62:
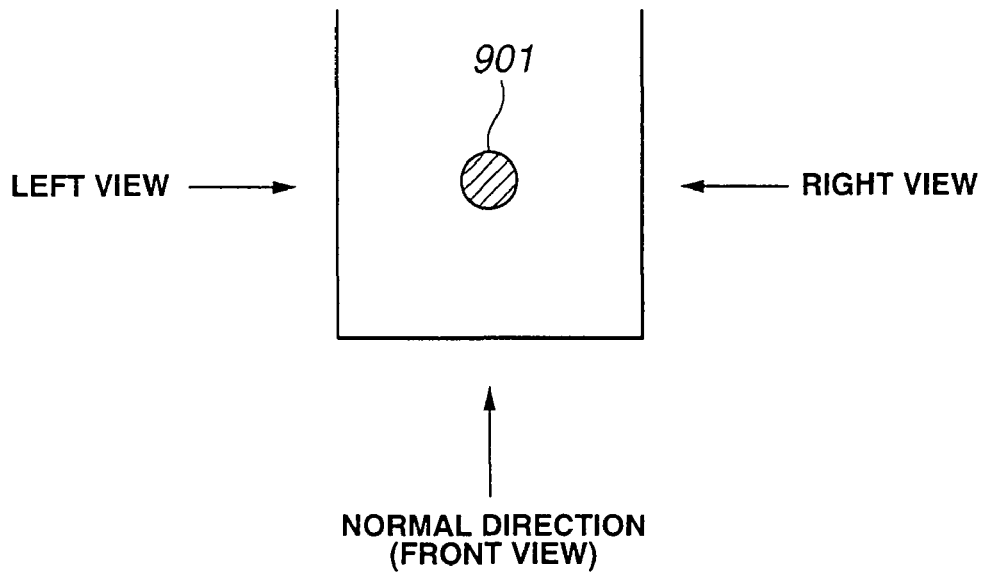
FIG. 62 is a first diagram illustrating a variation example of an operation of the technique support system in FIG. 54.
Figure 63:
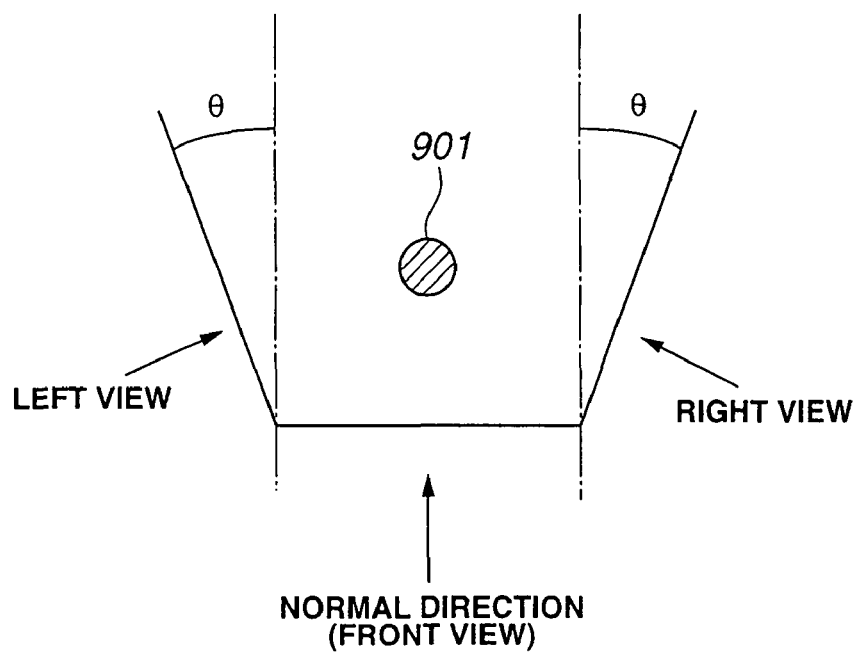
FIG. 63 is a second diagram illustrating a variation example of an operation of the technique support system in FIG. 54.
Figure 64:
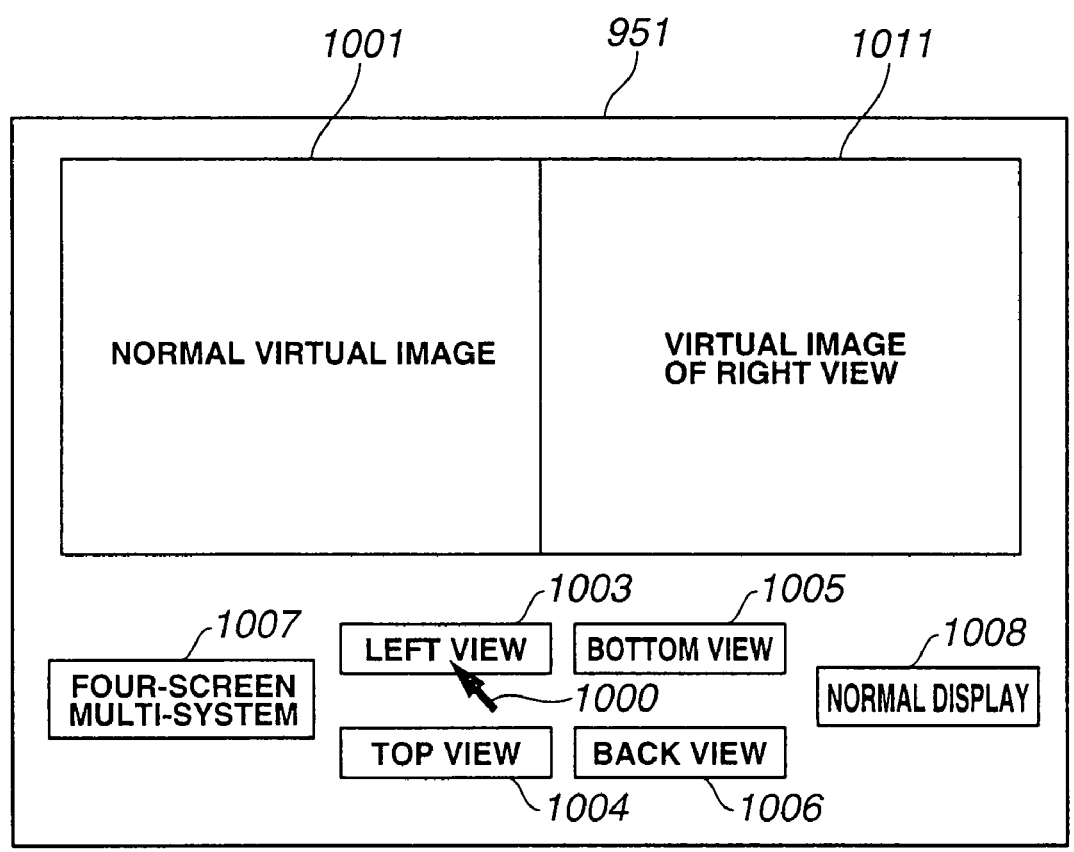
FIG. 64 is a diagram showing a first variation example of a screen developed in the processing in FIG. 58.
Figure 65:
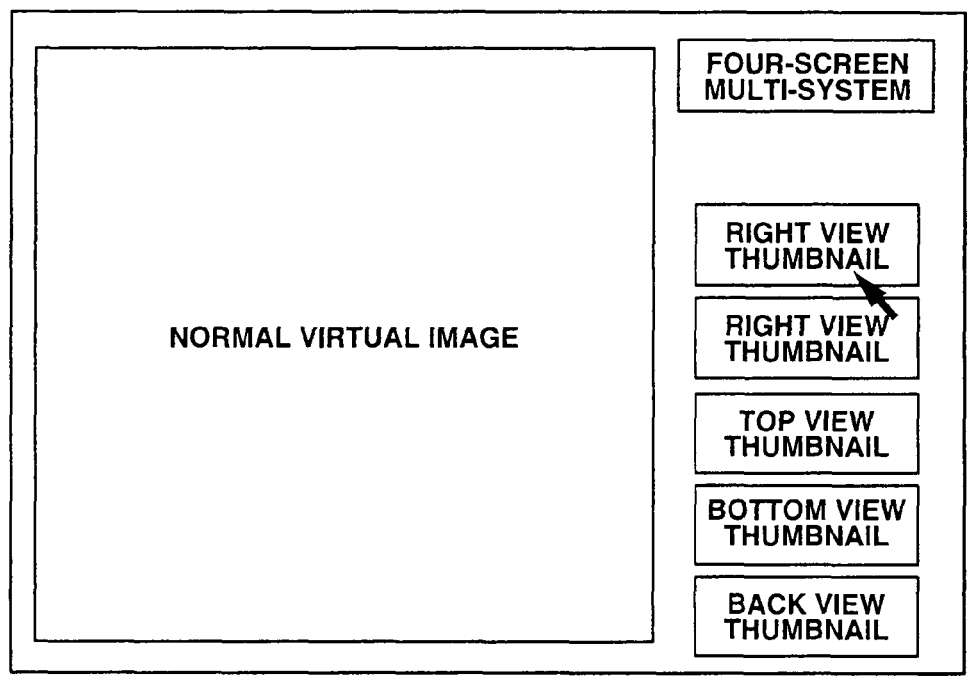
FIG. 65 is a first diagram showing a second variation example of a screen developed in the processing in FIG. 58.
Figure 66:
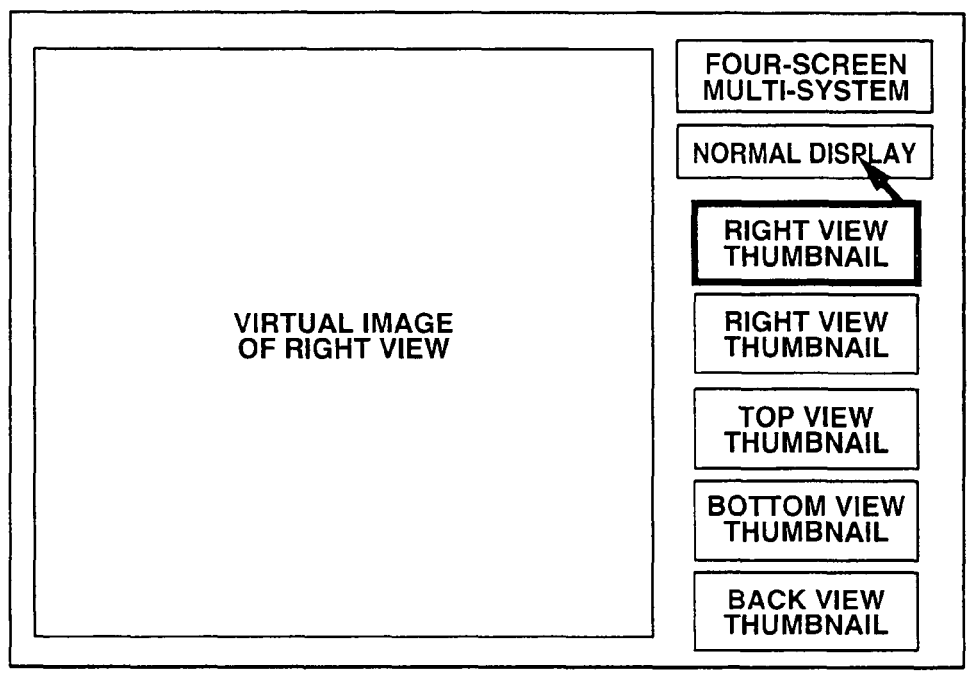
FIG. 66 is a second diagram showing a second variation example of a screen developed in the processing in FIG. 58.
Figure 67:
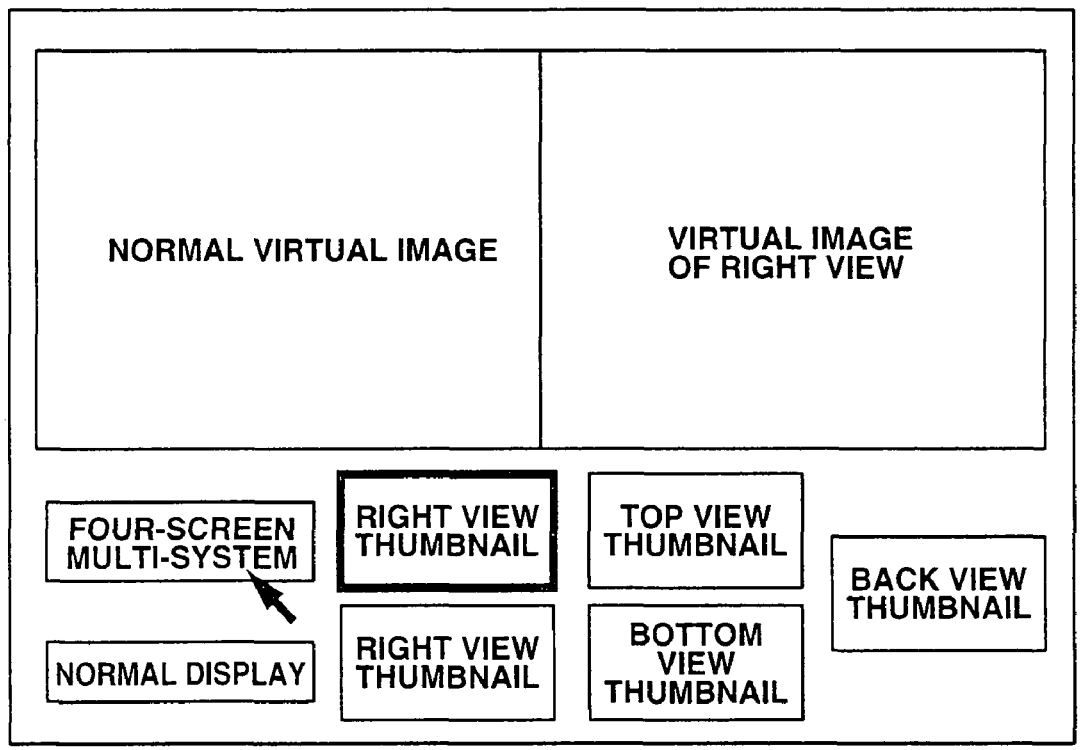
FIG. 67 is a third diagram showing the second variation example of a screen developed in the processing in FIG. 58.
Figure 68:
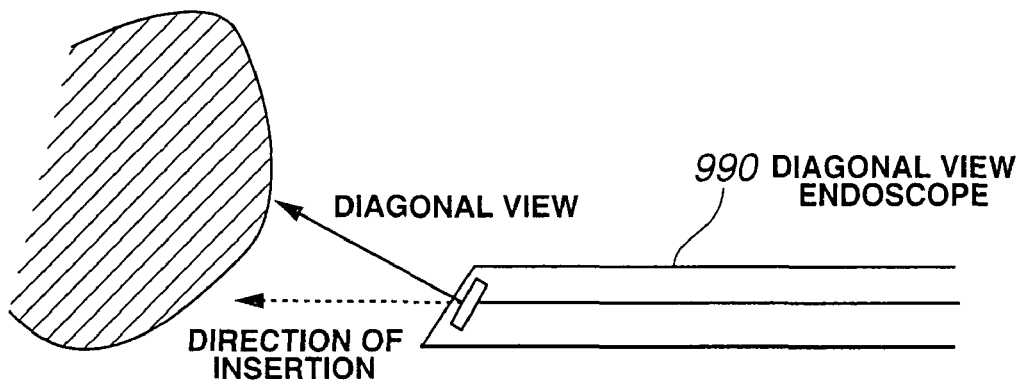
FIG. 68 is a diagram illustrating a side-view observation direction of a side-view endoscope in FIG. 54.
Figure 69:
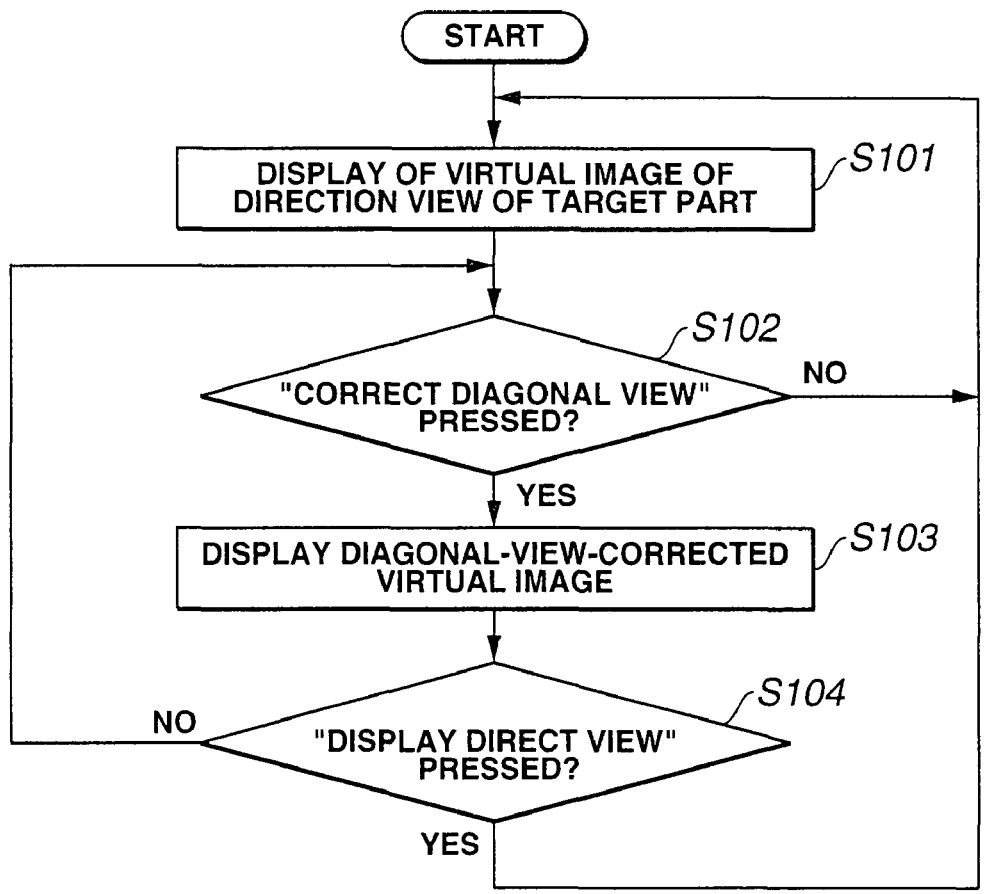
FIG. 69 is a flowchart showing processing for correcting a general virtual image, which is compliant with the side-view endoscope in FIG. 68.
Figure 70:
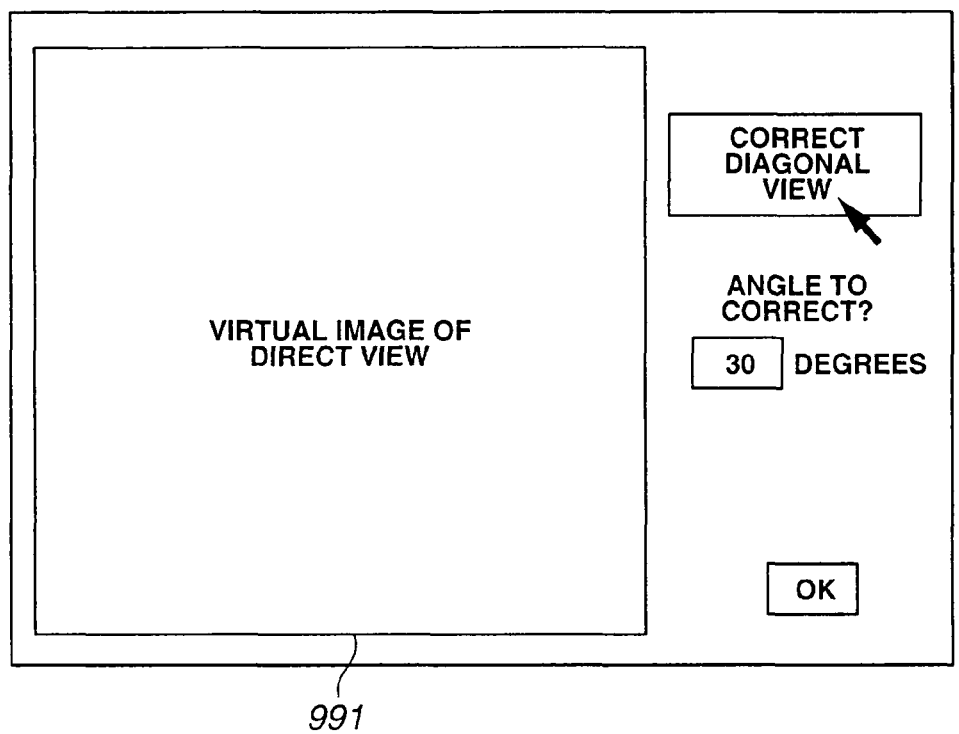
FIG. 70 is a first diagram showing a screen developed by the processing in FIG. 69.
Figure 71:
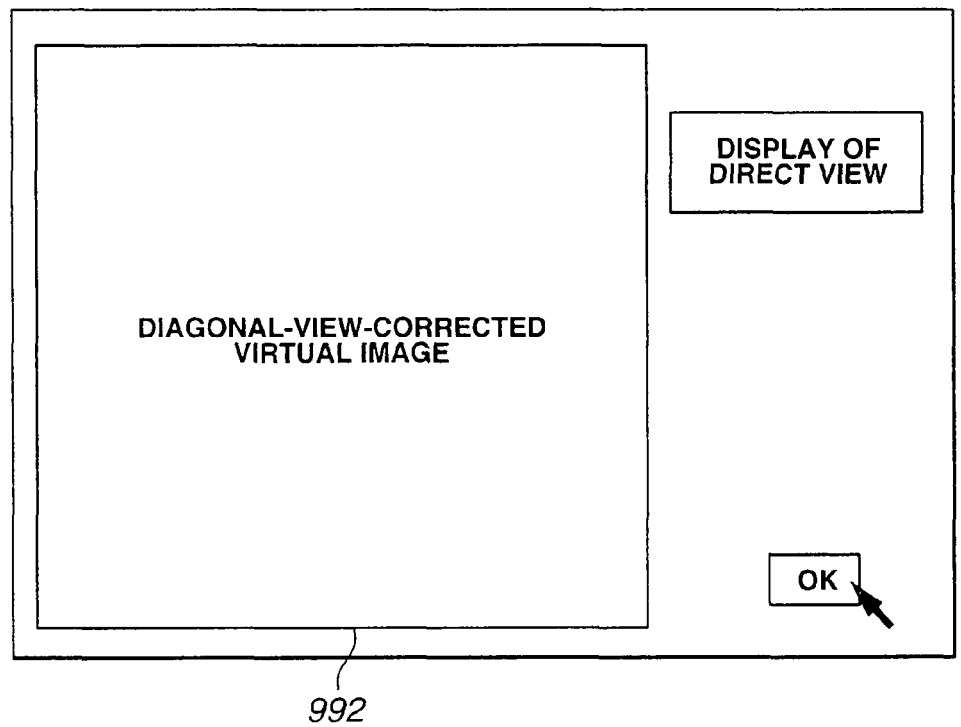
FIG. 71 is a second diagram showing a screen developed by the processing in FIG. 69.

FIGS. 54 to 71 relate to an eighth embodiment of the invention. FIG. 54 is a construction diagram showing a construction of a technique support system. FIG. 55 is a block diagram showing an essential configuration of the technique support system in FIG. 54. FIG. 56 is a diagram showing a construction of an endoscope in FIG. 54. FIG. 57 is a diagram illustrating an operation of the technique support system in FIG. 54. FIG. 58 is a flowchart showing a processing flow of the technique support system in FIG. 54. FIG. 59 is a first diagram showing a screen developed in the processing in FIG. 58. FIG. 60 is a second diagram showing a screen developed in the processing in FIG. 58. FIG. 61 is a third diagram showing a screen developed in the processing in FIG. 58. FIG. 62 is a first diagram illustrating a variation example of an operation of the technique support system in FIG. 54. FIG. 63 is a second diagram illustrating a variation example of an operation of the technique support system in FIG. 54. FIG. 64 is a diagram showing a first variation example of a screen developed in the processing in FIG. 58. FIG. 65 is a first diagram showing a second variation example of a screen developed in the processing in FIG. 58. FIG. 66 is a second diagram showing a second variation example of a screen developed in the processing in FIG. 58. FIG. 67 is a third diagram showing the second variation example of a screen developed in the processing in FIG. 58. FIG. 68 is a diagram illustrating a side-view observation direction of a side-view endoscope in FIG. 54. FIG. 69 is a flowchart showing processing for correcting a general virtual image, which is compliant with the side-view endoscope in FIG. 68. FIG. 70 is a first diagram showing a screen developed by the processing in FIG. 69. FIG. 71 is a second diagram showing a screen developed by the processing in FIG. 69.

As shown in FIG. 54, a technique support system 801 according to this embodiment is combined with an endoscope system. More specifically, the technique support system 801 has an endoscope 802 as observation means, which can observe the inside of a body cavity of a body to be examined, a CCU 804, a light source 805, an electric knife apparatus 806, a pneumoperitoneum apparatus 807, an ultrasonic drive power supply 808, a VTR 809, a system controller 810, a virtual image creating section 811, a remote controller 812A, a voice input microphone 812B, a mouse 815, a keyboard 816, a virtual image display monitor 817 and an endoscopic image monitor 813 and virtual image monitor 817a in an operation room.

As the endoscope 802 according to this embodiment, a laparoscope is used as shown in FIG. 56. The endoscope (laparoscope) 802 has an insert portion 802b to be inserted into an abdominal cavity of a body to be examined and a handle 802a disposed on the proximal end side of the insert portion 802b. An illumination optical system and an observation optical system are provided within the insert portion 802b. The illumination optical system and the observation optical system illuminate a part to be observed within an abdominal cavity of a body to be examined, and an observation image of the inside of the abdominal cavity of the body to be examined can be obtained.

A light guide connector 802c is provided at the handle 802a. One end of a light guide cable 802f (refer to FIG. 54) is connected to the light guide connector 802c having the other end connecting to the light source apparatus 805. Thus, illumination light from the light source apparatus 805 can be irradiated to a part to be observed through the illumination optical system within the insert portion 802b.

A camera head 802d having image pickup means such as a CCD is connected to an eyepiece (not shown) provided at the handle 802a. A remote switch 802g to be used for performing an operation such as zooming in/out of an observation image is provided in the camera head 802d. A camera cable 802e is extended from the proximal end side of the camera head 802d. A connection connector (not shown) for electrically connecting to the CCU 804 is provided at the other end of the camera cable 802e.

Referring back to FIG. 54, during surgery, the endoscope 802 is provided within a trocar 837 and is held at the abdominal part within the body of a patient by the trocar 837. By keeping this state, the insert portion of the endoscope 802 is inserted into the abdomen area, and the abdomen area is picked up by the image pickup section such as a CCD. Then, the picked-up image pickup signals are supplied to the CCU 804 through the camera head 802d.

The CCU 804 performs signal processing on the image pickup signals from the endoscope 802 and supplies image data (such as endoscopic live image data) based on the image pickup signals to the system controller 810 in an operation room. Under the control of the system controller 810, image data based on a still image or moving images of endoscopic live images is selectively output from the CCU 804 to the VTR 809. A detail construction of the system controller 810 will be described later.

Under the control of the system controller 810, the VTR 809 can record or play endoscopic live image data from the CCU 804. During the play, the played endoscopic live image data is output to the system controller 810.

The light source apparatus 805 is a light source apparatus for supplying illumination light to the endoscope 2 through a light guide.

The electric knife apparatus 806 is a surgical treatment apparatus for cutting an abnormal part within the abdomen area of a patient, for example, by using electric heat of an electric knife probe. The ultrasonic drive power supply 808 is a surgical treatment apparatus for cutting or coagulating the abnormal part by using an ultrasonic probe (not shown).

The pneumoperitoneum apparatus 807 has air supply and air-intake units, not shown. The pneumoperitoneum apparatus 807 supplies carbon dioxide to the abdomen area, for example, within the body of a patient through the trocar 837 connecting to the pneumoperitoneum apparatus 807.

The light source apparatus 805, the electric knife apparatus 806, the pneumoperitoneum apparatus 807 and the ultrasonic drive power supply 808 are electrically connected to the system controller 810 and are driven under the control of the system controller 810.

In addition to various kinds of equipment including the CCU 804, the VTR 809, the light source apparatus 805, the electric knife apparatus 806, the pneumoperitoneum apparatus 807 and the ultrasonic drive power supply 808, the system controller 810, the endoscopic image monitor 813, and a virtual image monitor 817a are placed within an operation room.

According to this embodiment, in order to perform treatment at a position as shown in FIG. 54 on the patient 830 by an operator 831 who picks up images of a body to be examined by inserting the insert portion into the abdominal part of the patient 830 through the trocar 837, the endoscopic image monitor 813 and the virtual image monitor 817a are placed at an easy-to-see position (in the direction of the field of vision) with respect to the position of the operator 831.

The system controller 810 controls different kinds of operations (such as display control and dimming control) of the entire endoscope system. As shown in FIG. 55, the system controller 810 has a communication interface (called communication I/F, hereinafter) 818, a memory 819, a CPU 820 as a control portion and a display interface (called display I/F, hereinafter) 821.

The communication I/F 818 is electrically connected to the CCU 804, the light source apparatus 805, the electric knife apparatus 806, the pneumoperitoneum apparatus 807, the ultrasonic drive power supply 808, the VTR 809 and the virtual image creating section 811, which will be described later. The exchange of drive control signal therefor and the exchange of endoscopic image data are controlled by the CPU 820. A remote controller 812A and voice input microphone 812B for an operator as remote operation means are electrically connected to the communication I/F 818. The communication I/F 818 captures operation instruction signals from the remote controller 812A and voice instruction signals from the voice input microphone 812B and supplies these signals to the CPU 820.

Though not shown, the remote controller 812A has a white balance button, a pneumoperitoneum button, a pressure button, a record button, a freeze button, a release button, a display button, an operation button for implementing two-dimensional display (2D display) for creating virtual images, an operation button for implementing three-dimensional display (3D display) for displaying virtual images, an inserting point button, a focus point button, buttons for instructing to change a display scale for 3D display (such as a zoom-in button and a zoom-out button), a display color button, a tracking button, an operation button for switching and/or determining setting input information for an operation setting mode determined by pressing one of buttons, a numeric keypad. The white balance button is used for display images displayed on an endoscopic image monitor 813 for endoscopic live images, the virtual image display monitor 817 or the virtual image monitor 817a. The pneumoperitoneum button is used for implementing the pneumoperitoneum apparatus 807. The pressure button is used for increasing or decreasing the pressure for implementing a pneumoperitoneum. The record button is used for recording endoscopic live images in the VTR 809. The freeze button and the release button are used for recording. The display button is used for displaying endoscopic live images or virtual images. The operation button for 2D display may includes an axial button, coronal button, and sagittal button in accordance with one of different kinds of 2D display mode. The inserting point button is used for indicating a direction of field of view of a virtual image displayed in a 3D display mode (and may be a button for displaying information on insertion to an abdomen area of the endoscope 802 such as numerical values in X-, Y- and Z-directions of the abdomen area to which the endoscope 802 is inserted). The focus button is a button for displaying a numerical value of the axial direction (angle) of the endoscope 802 inserted into the abdomen area). The display color button is used for change a display color. The tracking button is used for tracking. The numeric keypad is used for inputting numeric values and so on.

Thus, by using the remote controller 812A (or switch) including these buttons, an operator can operate to obtain desired information fast.

The memory 819 stores image data of endoscopic still images and data such as equipment setting information, for example. The data storing and reading are controlled by the CPU 820.

The display I/F 821 is electrically connected to the CCU 804, the VTR 809 and the endoscopic image monitor 813. The display I/F 821 exchanges endoscopic live image data from the CCU 4 or endoscopic image data having been played by the VTR 809 and outputs the received endoscopic live image data to the endoscopic image monitor 813. Thus, the endoscopic image monitor 813 displays endoscopic live images based on the supplied endoscopic live image data.

The endoscopic image monitor 813 can display not only endoscopic live images but also display setting information such as setting states and parameters of the apparatuses of the endoscope system under the display control of the CPU 820.

The CPU 820 controls different kinds of operations in the system controller 810, that is, performs control over exchanges of different kinds of signals by the communication I/F 818 and the display I/F 824, control over writing and/or reading of image data to/from the memory 819, control over display by the endoscopic image monitor 813, and control over different kinds of operations based on operation signals from the remote controller 812A (or switch).

On the other hand, the system controller 810 is electrically connected to the virtual image creating section 811.

As shown in FIG. 55, the virtual image creating section 811 has a CT image DB section 823, a memory 824, a CPU 825, a communication I/F 826, a display I/F 827 and switching section 827A.

The CT image DB section 823 includes a CT image data capturing portion (not shown) for capturing three-dimensional image data created by a publicly known CT apparatus, not shown, for imaging an X-ray tomographic image of a patient through a portable memory medium such as a magneto-optical (MO) disk and a digital versatile disk (DVD). Thus, the CT image DB section 823 can store the captured three-dimensional image data (CT image data). The reading and writing of the three-dimensional image data are controlled by the CPU 825.

The memory 824 stores the three-dimensional image data and data such as virtual image data created by the CPU 825 based on the three-dimensional image data. Thus, the storing and reading of these kinds of data are controlled by the CPU 825.

The communication I/F 826 is connected to the communication I/F 818 of the system controller 810 and exchanges control signals required for performing different kinds of operations in connection with the virtual image creating section 811 and the system controller 810. The communication I/F 826 is controlled by the CPU 825, and the control signals are captured into the CPU 825.

The display I/F 827 outputs virtual images created under the control of the CPU 825 to the virtual image monitors 817 and 817a through the switching section 827A. Thus, the virtual image monitors 817 and 817a display supplied virtual images. In this case, under the switching control of the CPU 825, the switching section 827A can switch the output of the virtual images and output the virtual images to the selected one of the virtual image monitors 817 and 817a. When switching the display of virtual images is not required, the switching section 827A is not required. A same virtual image may be displayed on both of the virtual image monitors 817 and 817a.

The mouse 815 and the keyboard 816 are electrically connected to the CPU 825. The mouse 815 and the keyboard 816 are operation means to be used for inputting and/or setting different kinds of setting information required for performing an operation for displaying virtual images by the virtual image display apparatus.

The CPU 825 performs different kinds of operations in the virtual image creating section 811, that is, performs control over exchanges different kinds of signals by the communication I/F 826 and the display I/F 827, control over writing and/or reading of image data to/from the memory 824, control over display by the monitors 817 and 817a, control over switching of the switching section 827A, and control over different kinds of operations based on operation signals from the mouse 815 and/or the keyboard 816.

According to this embodiment, the virtual image creating section 811 may be connected to a remotely provided virtual image creating section, for example, through communication means so as to be constructed as a remote surgery support system.

According to this embodiment, as shown in FIG. 56, the sensor 803 is provided at the handle 802a of the endoscope 802 in order to create and display virtual images based on a direction of field of vision of the endoscope 802. The sensor 803 accommodates a gyroscopic sensor, for example, and detects information such as an angle of insertion into the abdomen area of the endoscope 802. The detection information of the sensor 803 is supplied to the virtual image creating section 811 through the communication I/F 826 as shown in FIG. 55.

While the sensor 803 is electrically connected to the virtual image creating section 811 through a cable according to this embodiment, the sensor 803 may be connected to the virtual image creating section 811 in a wireless manner so as to implement data communication.

Next, operations of this embodiment having the above-described embodiment will be described. According to this embodiment, based on angle information of insertion of the endoscope 802 into the abdomen area by the sensor 803, the virtual image creating section 811 creates a virtual image in the normal direction (front) with respect to a part of concern (abnormal part 901 near a target organ 900 as shown in FIG. 57, which corresponds to the field of vision of the endoscope 802. At the same time, the virtual image creating section 811 creates multiple side virtual images viewed from the right, left, upper, lower and back of a cube with respect to the part of concern (abnormal part) 901 near the target organ 900. While the virtual image creating section 811 creates images of the right, left, upper, lower and back sides of the cube with respect to the part of concern abnormal part) 901 as planes having predetermined angles about an observation image plane in the direction of the field of vision of the endoscope 802, other planes of the sides in different directions may be adopted.

A virtual image at least in the normal direction (front plane) is created in real time in synchronization with live endoscopic images of the endoscope 802 based on detection information of the sensor 803.

According to this embodiment, multiple virtual images of the right, left, upper, lower back planes may be created in real time in synchronization with live endoscopic images like virtual images in the normal direction (front view). However, according to this embodiment, as described later, a side virtual images is created as a still image based on a frame image of the virtual image in the normal direction (front view) when an instruction for displaying the side virtual image is given.

Once a technique is started and an observation image of the inside of a body to be examined is picked up by the camera head 802d, an endoscopic image is displayed on the endoscopic image monitor 813.

Then, as shown in FIG. 58, the virtual image creating section 811 creates a virtual image in the normal direction (front view) based on angle information of insertion of the endoscope 802 into the abdomen area by the sensor 803 at a step S91. Then, a normal-direction virtual screen 950 is displayed on the virtual image monitor 817a as shown in FIG. 59.

The normal-direction virtual screen 950 in FIG. 59 includes command buttons 1002, 1003, 1004, 1005 and 1006 for instructing to display multiple side virtual images viewed from the right, left, upper, lower and back directions in addition to a normal-direction (front view) virtual image 1001, and a multi-command button 1007 for instructing to display the sides at the same time.

Then, at a step S92, one of the command buttons 1002, 1003, 1004, 1005 and 1006 and the multi-command button 1007 is selected by a pointer 1000 on the normal-direction virtual screen 950. Then, it is judged whether or not a display with another point of vision is implemented.

While the selection by the pointer 1000 is performed by using a pointing device or the like above, the operator may select by voice by using the voice input microphone 812B. For example, by producing a sound, "BACK", the back view may be selected by voice recognition.

When one of the command buttons 1002, 1003, 1004, 1005 and 1006 and the multi-command button 1007 is selected by the pointer 1000 on the normal-direction virtual screen 950, a virtual image from a point of vision corresponding to a command button selected at the step S93 is displayed on the virtual image monitor 817a.

For example, when the command button 1002 for displaying right-side display as shown in FIG. 59 is selected by the pointer 1000, a different point-of-vision virtual screen 951 having the right-side virtual image 1011 instead of the virtual image 1001 in the normal direction (front view) as shown in FIG. 60 is displayed on the virtual image monitor 817a.

The different point-of-vision virtual screen 951 in FIG. 60 includes the right-side virtual image 1011, the command buttons 1003, 1004, 1005 and 1006 for instructing to display multiple side virtual images of the left, upper, lower and back views, the multi-command button 1007 for instructing to display sides at the same time, and a normal display button 1008 for instructing to display a normal-direction (front view) virtual image 1001.

At a step S94, an internal timer within the CPU 825 of the virtual image creating section 811 is set, and measuring a time is started.

Subsequently, at a step S95, it is judged whether the normal display button 1008 is selected by the pointer 1000 on the different point-of-vision virtual screen 951. If the normal display button 1008 is selected, the processing returns to the step S91. If the normal display button 1008 is not selected, it is judged whether or not one of the command buttons 1003, 1004, 1005 and 1006 and the multi-command button 1007 is selected by the pointer 1000 on the different point-of-vision virtual screen 951 at a step S96.

If one of the command buttons 1003, 1004, 1005 and 1006 and the multi-command button 1007 is selected by the pointer 1000 on the different point-of-vision virtual screen 951, a virtual image at a point of vision in accordance with a command button selected is displayed on the virtual image monitor 817a at a step S97. At a step S98, the internal timer within the CPU 825 is reset, and a time measurement is restarted. Then, the processing goes to a step S99. If a command button is not selected, the processing goes from the step S96 to the step S99 directly.

At the step S99, the CPU 825 judges whether or not live endoscopic images of the endoscope 802 has a predetermined amount of movement based on a motion vector due to image processing by the CPU 820 of the system controller 810. If the live endoscopic images have a predetermined amount of movement or larger than the predetermined amount, the processing returns to the step S91. If the live endoscopic images does not have the predetermined amount of movement or larger than the predetermined amount, it is judged whether or not a predetermined amount of time has passed in the internal timer within the CPU 825 at a step S100. If the predetermined amount of time has passed, the processing returns to the step S91. If the predetermined amount of time has not passed, the processing returns to the step S95.

At the step S93 or step S97, if the multi-command button 1007 is selected by the pointer 1000, a multi-point-of-vision virtual screen 952 as shown in FIG. 61 is displayed on the virtual image monitor 817a. The multi-point-of-vision virtual screen 952 has images including the normal direction (front view) virtual image and multiple side virtual images of the right, left, upper, lower, back views with the normal direction (front view) virtual image as the center.

As described above, according to this embodiment, biological image information of different views of the surroundings of a part of concern (abnormal part) (such as image information having arteries and veins, which are hidden by organs and image information of the position of the part of concern) can be provided to an operator for a predetermined period of time during a technique. If live endoscopic images have a predetermined amount of movement or larger than the predetermined amount (change), the normal direction (front view) virtual image based on the angle information of insertion of the endoscope 2 to the abdomen area can be displayed again. Thus, various virtual images can be provided during the technique in real time.

According to this embodiment, while, as shown in FIG. 62, a side virtual image orthogonal to the normal-direction (front view) virtual image is created, the invention is not limited thereto. As shown in FIG. 63, a side virtual image of a side displaced by an offset angle θ from the plane orthogonal to the normal direction (front view) virtual image may be created. The plane of the side virtual image according to this embodiment is just an example, and the advantages of this embodiment can be obtained as far as the plane of the side virtual image is an arbitrary plane suitable for a technique.

While, according to this embodiment, an image to be displayed on the virtual image monitor 817a is one of the normal direction (front view) virtual image and the side virtual image, the invention is not limited thereto. For example, as shown in FIG. 64, a (right) side virtual image may be displayed next to the normal direction (front view) virtual image.

Instead of the command buttons, as shown in FIG. 65, thumbnail images of the side virtual images may be displayed. As shown in FIG. 66, by highlighting the frame of a thumbnail image of a selected side virtual image, the displayed side virtual image can be identified easily. Furthermore, a state of another side virtual image can be visually recognized through the thumbnail image display. Thus, the side virtual image can be provided more effectively. FIG. 67 shows a display example of a thumbnail image of a side virtual image, in which a (right) side virtual image is displayed next to the normal-direction (front view) virtual image.

By the way, according to this embodiment, the endoscope 802 is a straight vision endoscope rather than a diagonal vision endoscope. Thus, as shown in FIG. 68, since the direction of insertion of the diagonal vision endoscope 990 does not agree with the side vision direction, an image is obtained which has a different direction of the direction of the normal-direction (front view) only depending on the live endoscopic images for diagonal vision and the direction of insertion of the endoscope.

Accordingly, the CPU 825 of the virtual image creating section 811 corrects the normal-direction (front view) virtual image of the diagonal vision endoscope 990 and determines an observation direction as follows.

As shown in FIG. 69, at a step S101, a straight vision virtual image 991 in the direction of insertion of the diagonal vision endoscope 990 as shown in FIG. 70 is displayed on the virtual image monitor 817a. At a step S102, a correction angle corresponding to the diagonal vision angle of diagonal vision endoscope 990 on the virtual image 991 is input, and a diagonal vision correction button is selected. Thus, at a step S103, a diagonal vision corrected virtual image 992 as shown in FIG. 71 is displayed on the virtual image monitor 817a. When a straight-vision direction display button is selected at a step S104 while the diagonal vision corrected virtual image 992 is being displayed, the processing returns to the step S101. If the straight-vision direction display button is not selected, the processing returns to the step S102.

When the OK button is selected while the straight-vision virtual image 991 or the diagonal vision corrected virtual image 992 is being displayed, the straight-vision virtual image 991 or the diagonal vision corrected virtual image 992 is registered as a normal-direction (front view) virtual image.

Thus, normal direction (front view) virtual images compliant with the straight-vision type and the diagonal vision type can be obtained.

A normal-direction (front view) virtual image having a same direction as the direction of an observation image of a side-vision endoscope can be obtained from a side-vision endoscope as well as from a diagonal vision endoscope by performing a same angle correction (90 degree correction) as the angle correction for a diagonal vision endoscope.

As described above, according to this embodiment, a virtual image suitable for technique support can be advantageously provided during a technique in real time.

Ninth Embodiment

Figure 72:
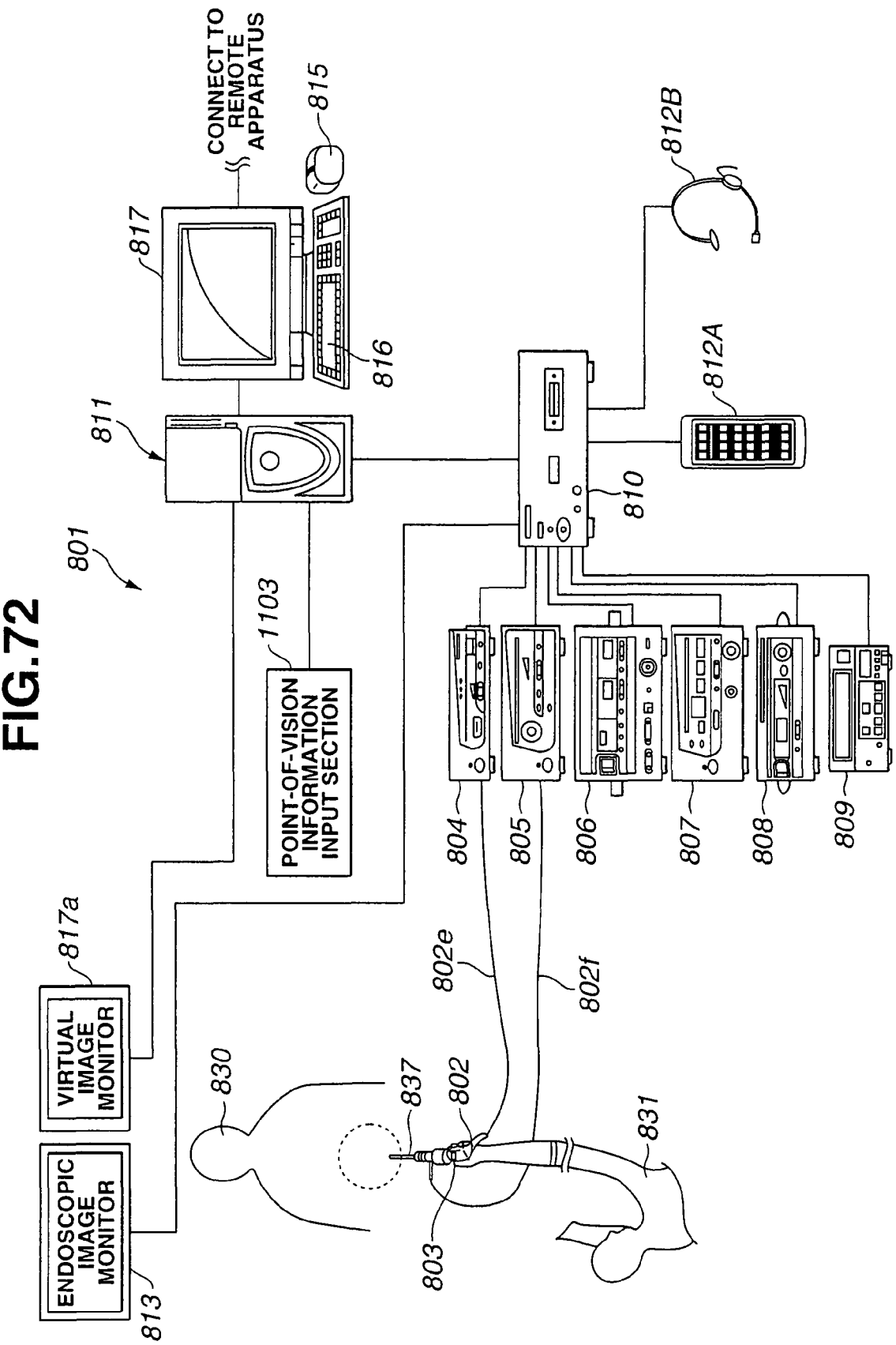
FIG. 72 is a construction diagram showing a construction of a technique support system according to a ninth embodiment of the invention.
Figure 73:
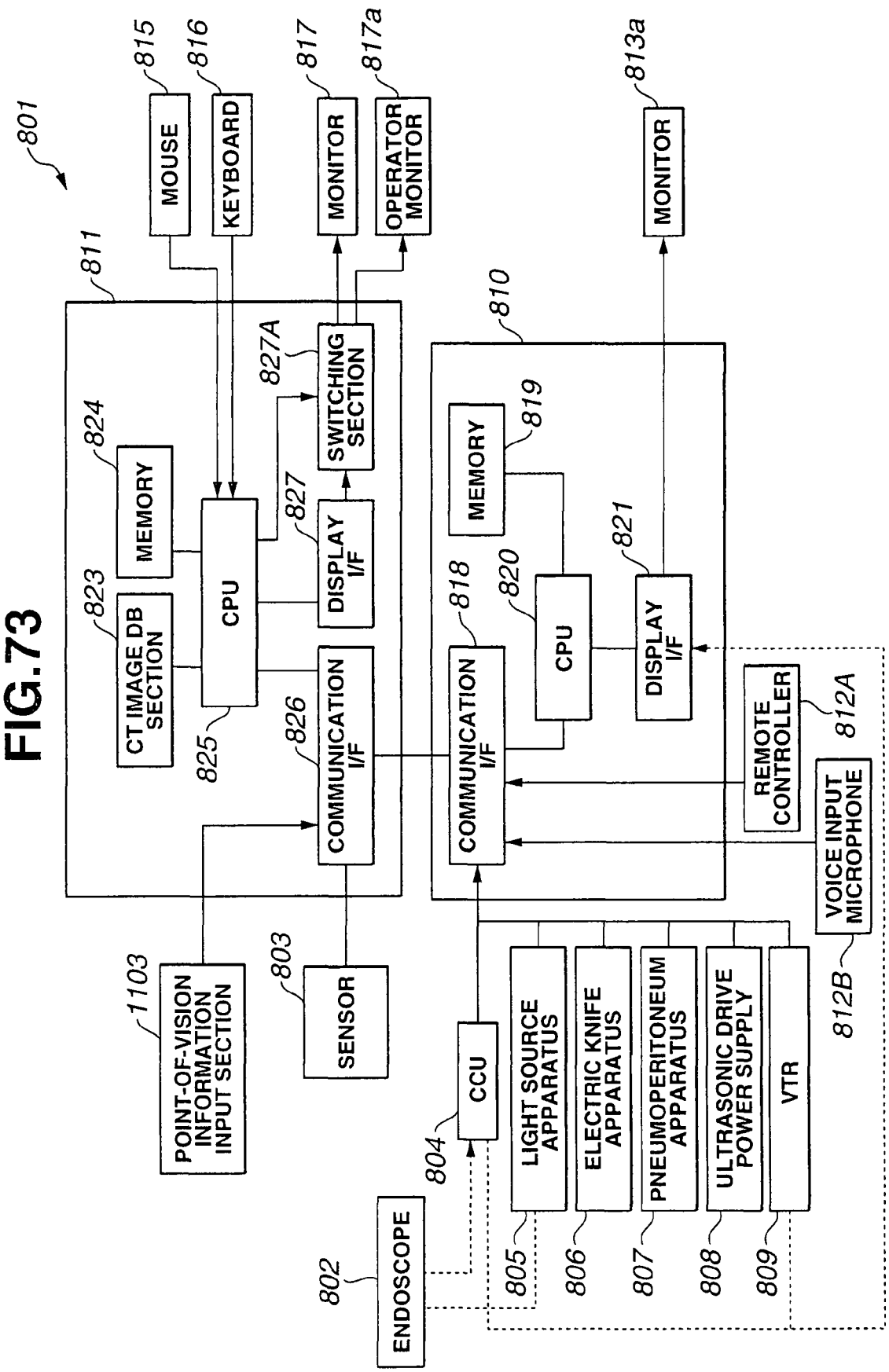
FIG. 73 is a block diagram showing an essential configuration of the technique support system in FIG. 72.
Figure 74:
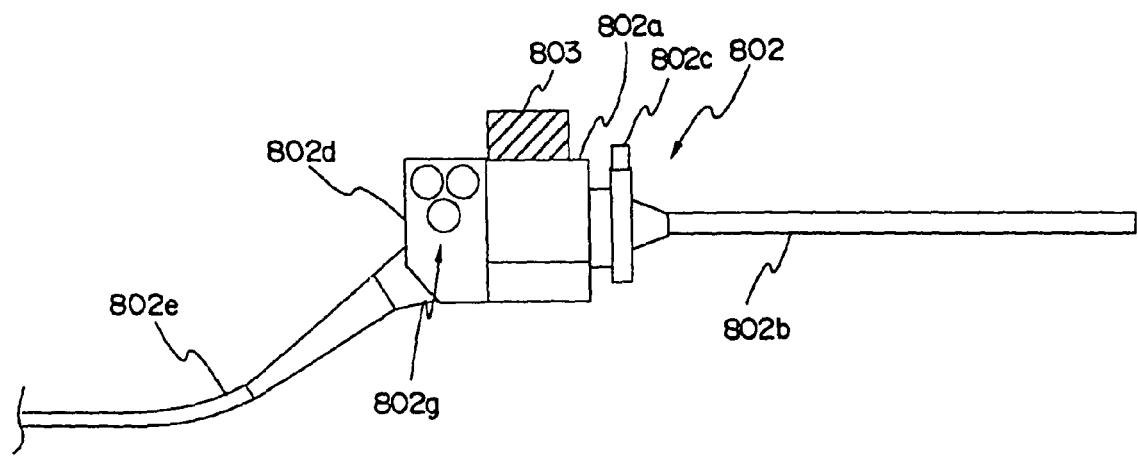
FIG. 74 is a diagram showing a construction of an endoscope in FIG. 72.
Figure 75:
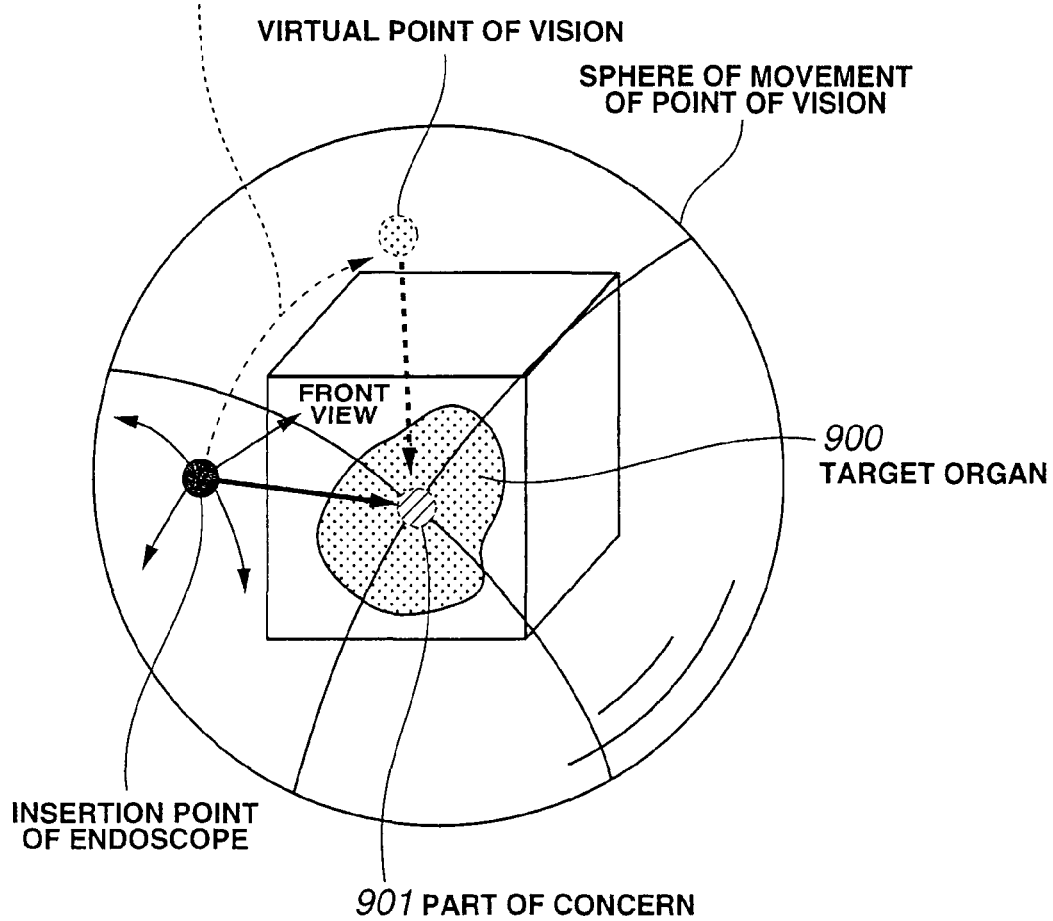
FIG. 75 is a diagram illustrating an operation of the technique support system in FIG. 72.
Figure 76:
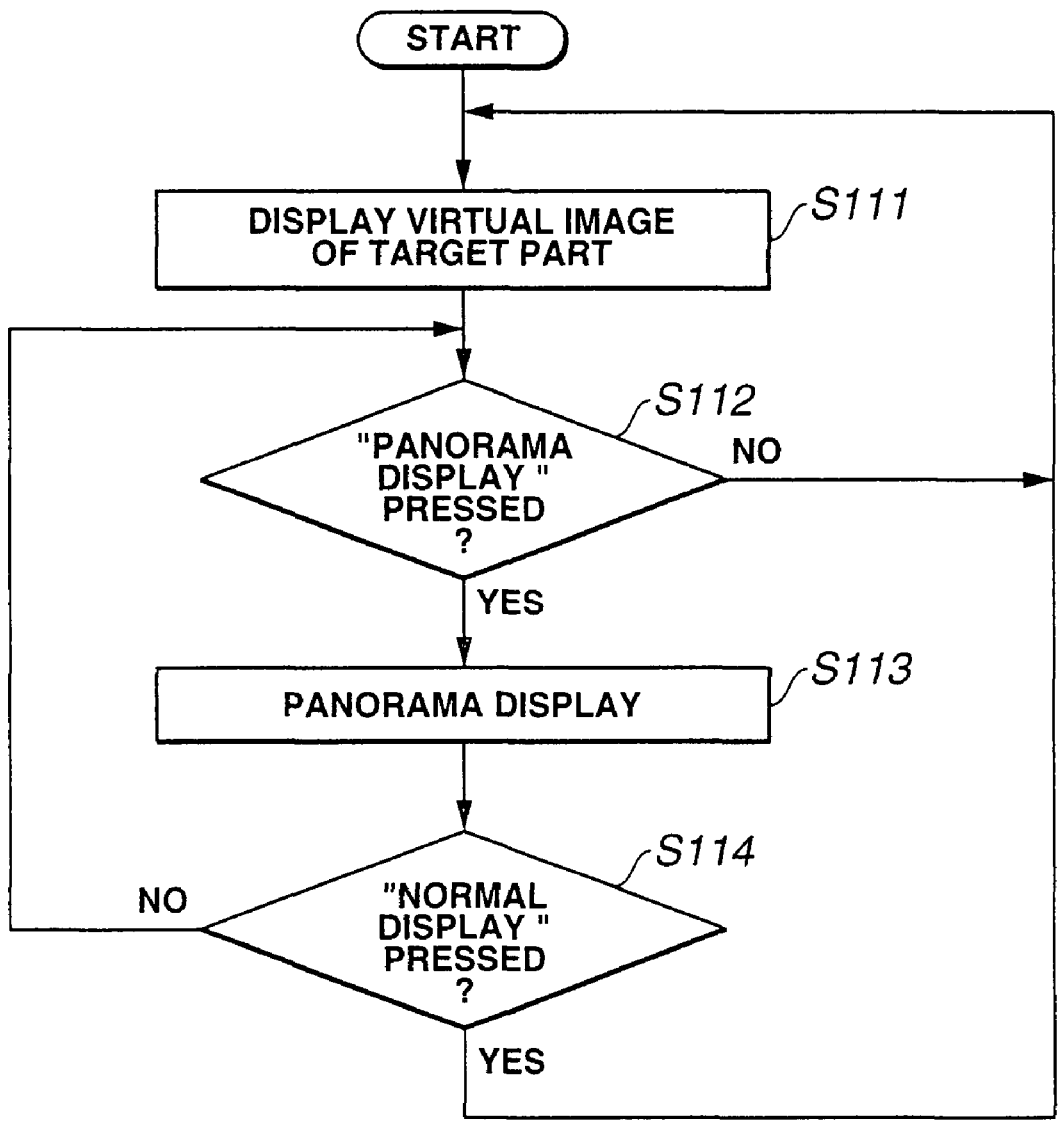
FIG. 76 is a flowchart showing a processing flow of the technique support system in FIG. 72.
Figure 77:
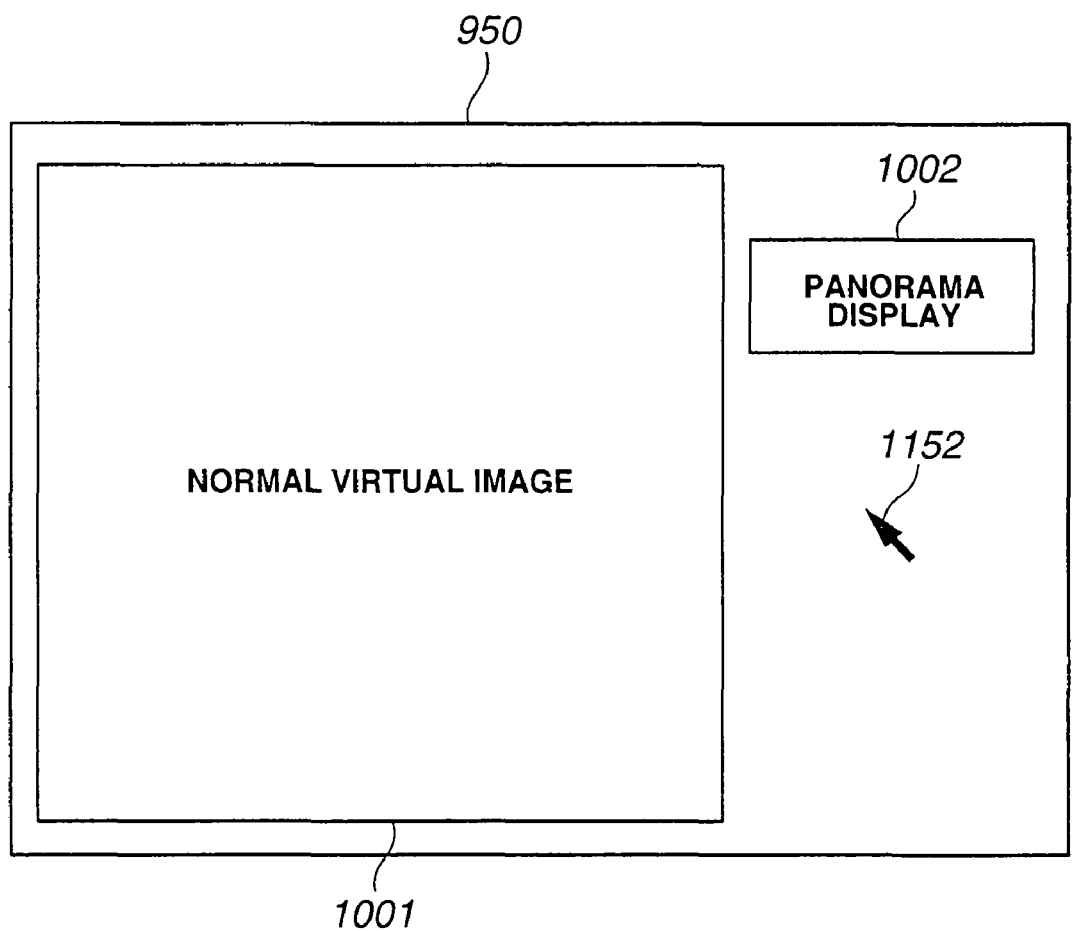
FIG. 77 is a first diagram showing a screen developed in the processing in FIG. 76.
Figure 78:
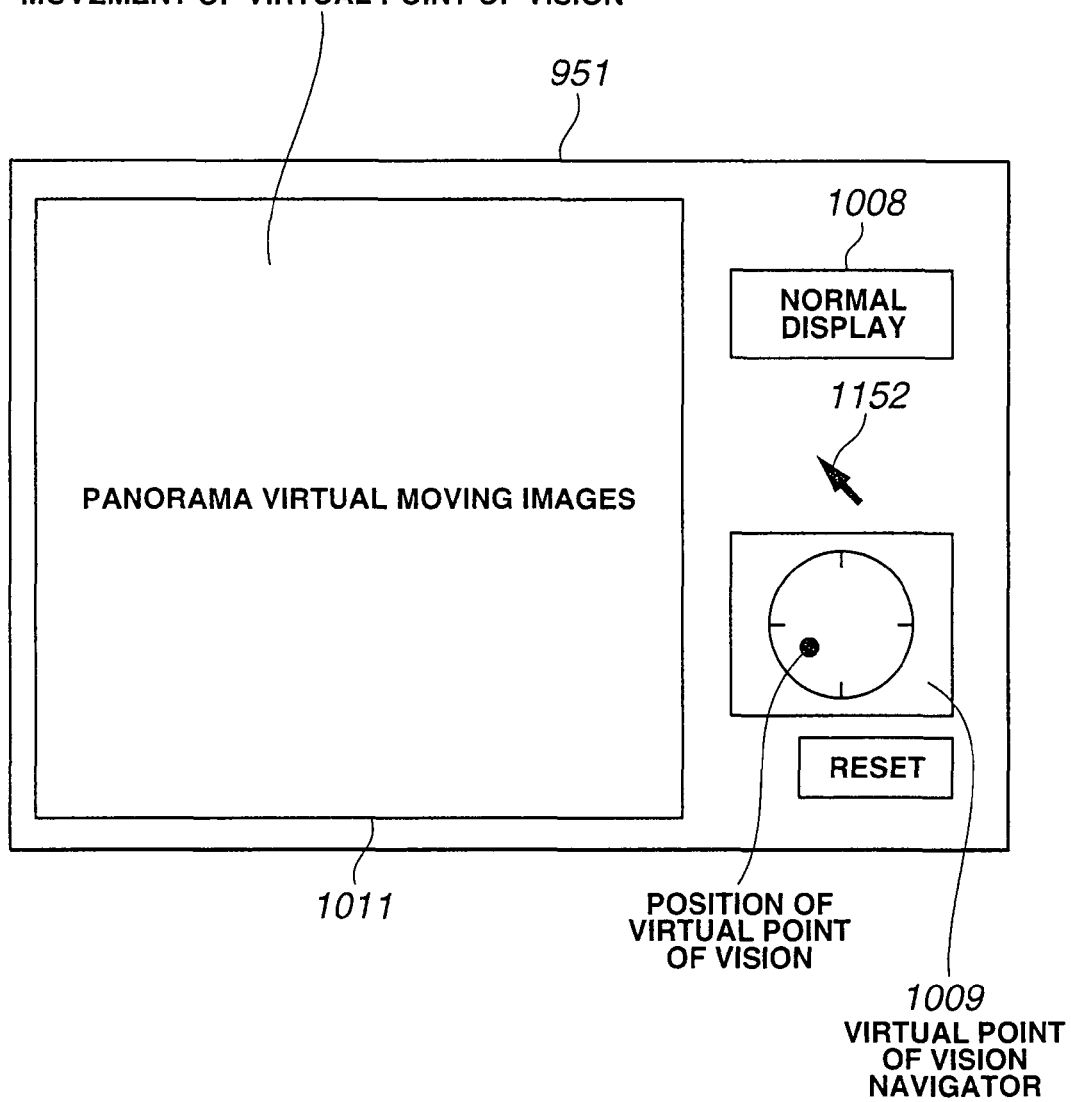
FIG. 78 is a second diagram showing a screen developed by the processing in FIG. 76.
Figure 79:
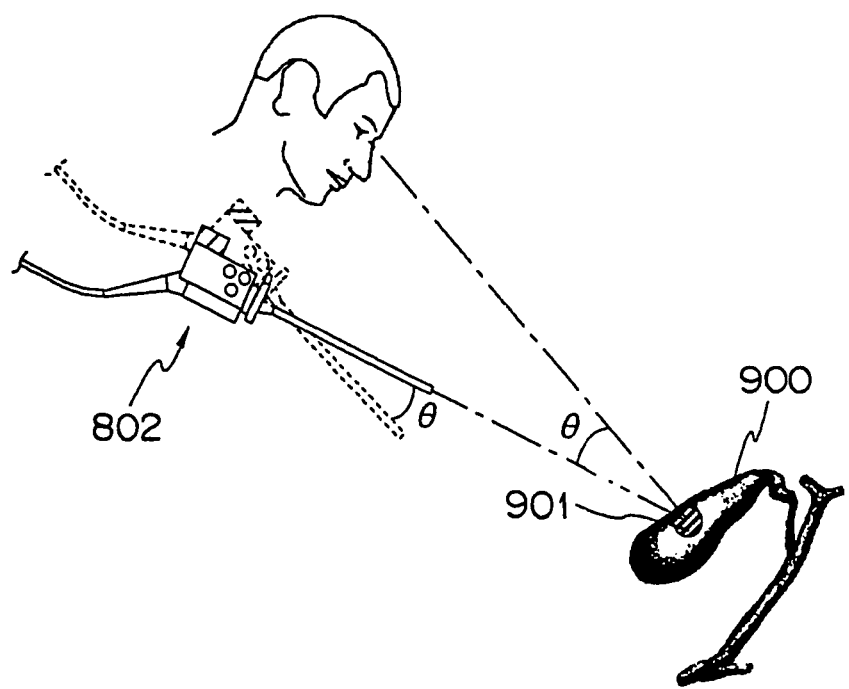
FIG. 79 is a first diagram illustrating an operation in which a point-of-vision information input portion in FIG. 72 is a sensor provided at a handle of the endoscope.
Figure 80:
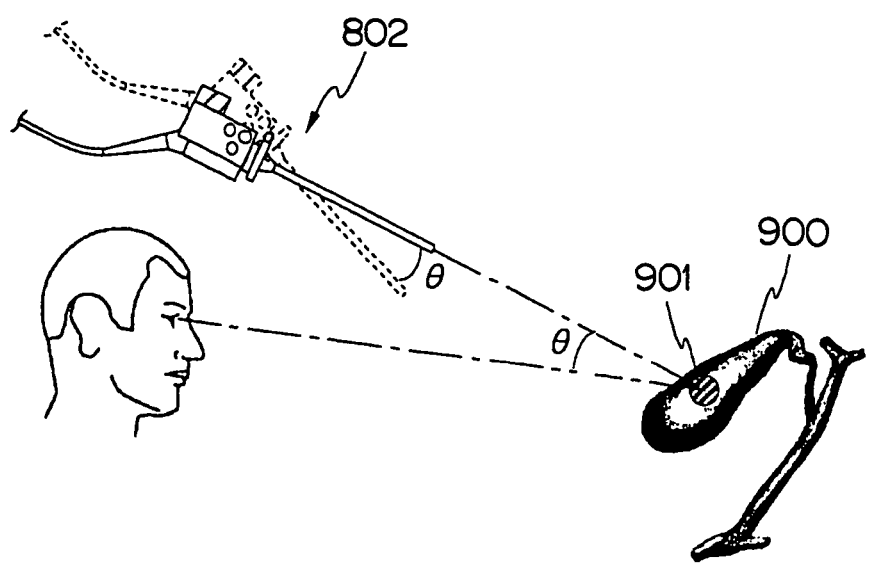
FIG. 80 is a second diagram illustrating an operation in which the point-of-vision information input portion in FIG. 72 is a sensor provided at the handle of the endoscope.
Figure 81:
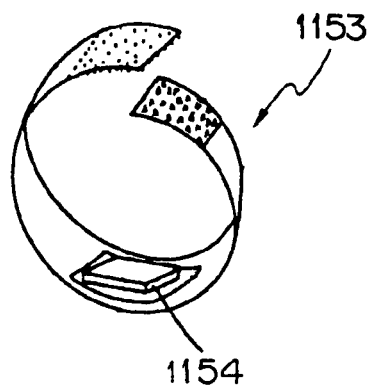
FIG. 81 is a diagram showing a head band having the point-of-view input portion in FIG. 72.
Figure 82:
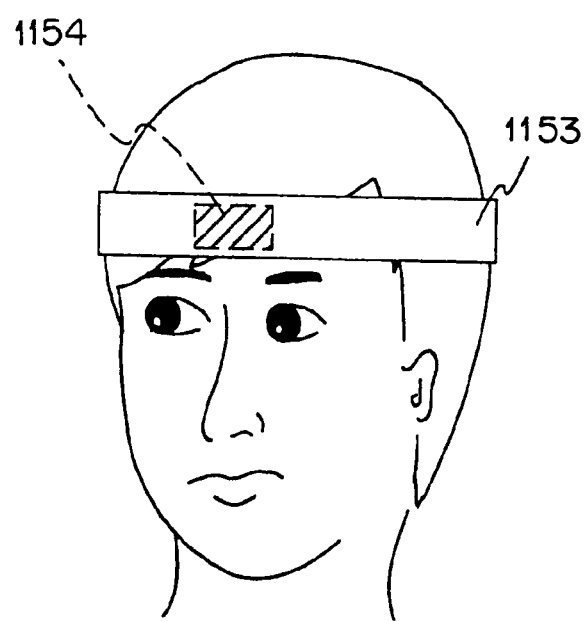

FIGS. 72 to 82 relate to a ninth embodiment. FIG. 72 is a construction diagram showing a construction of a technique support system. FIG. 73 is a block diagram showing an essential configuration of the technique support system in FIG. 72. FIG. 74 is a diagram showing a construction of an endoscope in FIG. 72. FIG. 75 is a diagram illustrating an operation of the technique support system in FIG. 72. FIG. 76 is a flowchart showing a processing flow of the technique support system in FIG. 72. FIG. 77 is a first diagram showing a screen developed by the processing in FIG. 76. FIG. 78 is a second diagram showing a screen developed by the processing in FIG. 76. FIG. 79 is a first diagram illustrating an operation in which a point-of-vision information input portion in FIG. 72 is a sensor provided at a handle of the endoscope. FIG. 80 is a second diagram illustrating an operation in which the point-of-vision information input portion in FIG. 72 is a sensor provided at the handle of the endoscope. FIG. 81 is a diagram showing a head band having the point-of-view input portion in FIG. 72. FIG. 82 is a diagram showing a state that the head band in FIG. 81 is worn.

In the following description of the ninth embodiment, the same reference numerals are given to the same components as those of the eighth embodiment, the descriptions of which will be omitted.

As shown in FIG. 72, a technique support system 801 according to this embodiment further includes a point-of-view information input portion 1103 having a joystick or the like. The point-of-vision information input portion 1103 is connected to a communication I/F 826 as shown in FIG. 73.

Next, operations of this embodiment having the above-described embodiment will be described. According to this embodiment, based on angle information of insertion of the endoscope 802 into the abdomen area by the sensor 803, the virtual image creating section 811 creates a virtual image in a direction with respect to a part of concern (abnormal part 901 near a target organ 900 as shown in FIG. 75, which corresponds to the field of vision of the endoscope 802. More specifically, as shown in FIG. 75, serial virtual images resulting from a process in which a position of the point of vision toward the part of concern 901 moves from a position of an inserting point of the endoscope to a virtual point of vision specified by a point-of-vision position changing portion such as a mouse, a joystick and a footswitch. As shown in FIG. 75, when a point of vision is moved arbitrarily on a sphere of the movement of the point of vision by the point-of-vision position changing portion, virtual images are created in series in accordance with the movement of the point of vision. In other words, serial virtual images are created based on an axial angle with respect to the part of concern, that is, an axial angle specifying a position of the point of vision or an axial angle or position of point of vision specified by a point-of-vision position specifying portion.

At least a virtual image is created in real time in synchronization with live endoscopic images of the endoscope 802 based on detection information of the sensor 803.

Once a technique is started and the inside of a body to be examined is imaged by the camera head 802, an endoscopic image is displayed on the endoscopic image monitor 813.

Then, as shown in FIG. 76, the virtual image creating section 811 creates a virtual image in the normal direction based on angle information of insertion of the endoscope 802 into the abdomen area by the sensor 803 at a step S111. Then, a normal-direction virtual screen 950 is displayed on the virtual image monitor 817a as shown in FIG. 77.

The normal-direction virtual screen 950 in FIG. 77 includes a panorama command button 1151 for instructing panorama display, which is a display of virtual images in accordance with the movement of the point of vision in addition to a normal-direction virtual image 1001.

Then, at a step S112, it is judged whether or not the panorama command button 1151 is selected by a pointer 1152 on the normal-direction virtual screen 950.

While the selection by the pointer 1152 is performed by using a pointing device above, the operator may select by voice by using the voice input microphone 812B, for example. (For example, by producing a sound, "BACK", the back view may be selected by voice recognition.)

When the panorama command button 1151 is selected by the pointer 1152 on the normal-direction virtual screen 950 in FIG. 77, the panorama virtual screen 961 having the panorama virtual image 1111 as shown in FIG. 78 is displayed on the virtual image monitor 817a at a step S113.

The panorama virtual screen 961 in FIG. 78 includes a normal display button 1008 and a virtual point-of-vision navigator 1009. The normal display button 1008 is used for instructing to display a normal-direction virtual image 1001. The virtual point-of-vision navigator 1009 indicates a relative position of a virtual point-of-vision with respect to the endoscope 802 of the panorama virtual image 1111.

At a step S114, it is judged whether or not the normal display button 1008 is selected.

Thus, according to this embodiment, a normal-direction virtual image and a panorama virtual image can be provided during surgery, and biological image information of different views of the surroundings of a part of concern (abnormal part) (such as image information having arteries and veins, which are hidden by organs and image information of the position of the part of concern) can be provided. Therefore, virtual images suitable for technique support can be provided during a technique in real time.

While the point-of-vision input portion 1103 is a joystick, the sensor 803 at the handle 802a of the endoscope 802 may be the point-of-vision information input portion 1103. When the sensor 803 is the point-of-vision information input portion 1103, a panorama virtual image for the point of vision moved by a predetermined angle θ resulting from the inclination of the endoscope 802 by the angle θ as shown in FIGS. 79 and 80. FIG. 79 shows an example that a panorama virtual image is moved in the opposite direction of that of the rotation angle of the endoscope 802 while FIG. 80 shows an example that a panorama virtual image is moved in the same direction as that of the rotation angle of the endoscope 802.

As shown in FIG. 81, a motion sensor 1154 as the point-of-vision information input portion 1103 is provided in a one-touch head band 1153, which can be sterilized. The head band 1153 may be attached to the head of an operator as shown in FIG. 82.

According to this embodiment, a virtual image suitable for technique support can be provided in real time during a technique.

Tenth Embodiment

Figure 83:
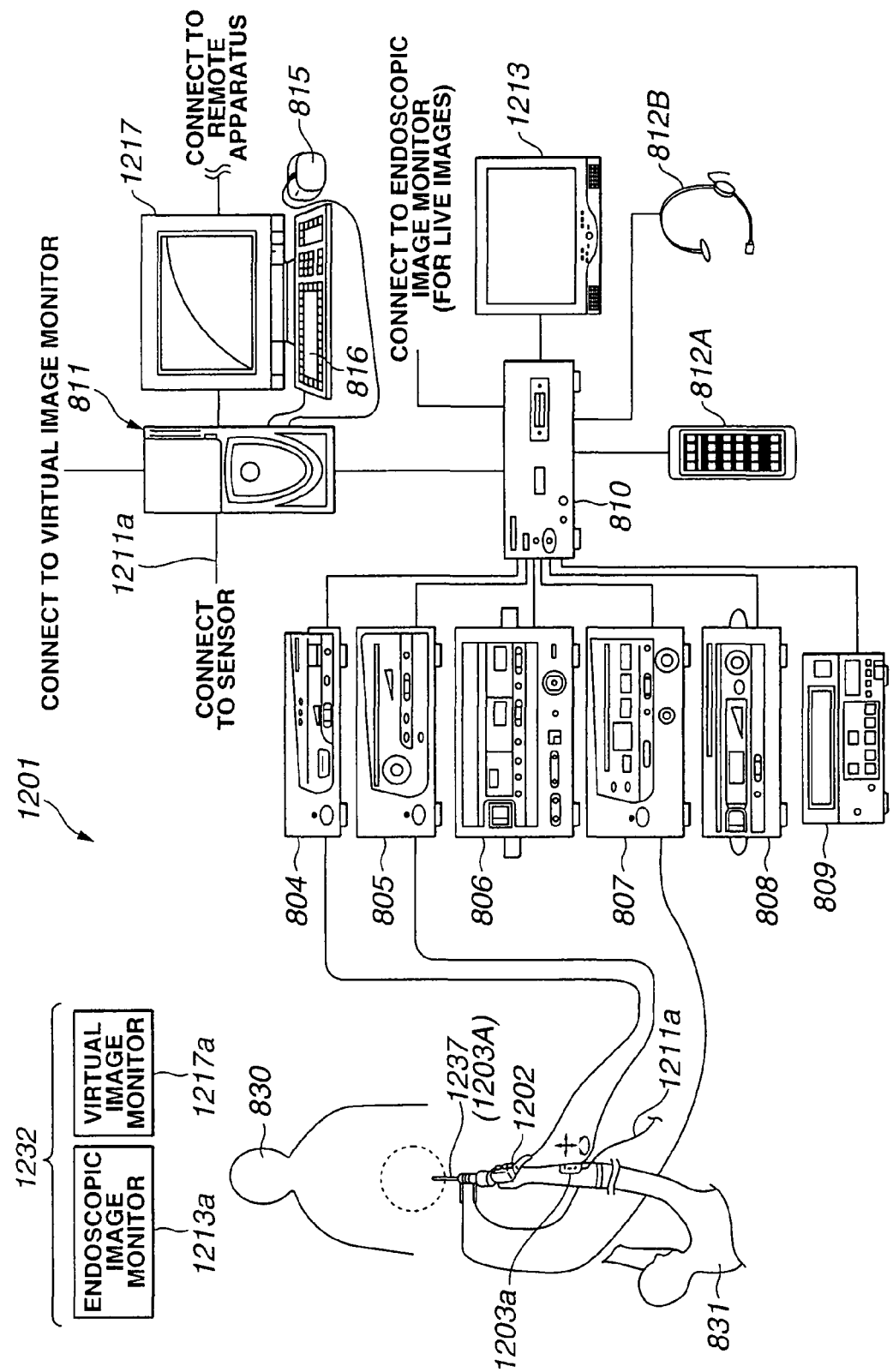
FIG. 83 is a schematic construction diagram showing a virtual image display apparatus according to a tenth embodiment of the invention and showing an entire construction of an endoscope system including the apparatus.
Figure 84:
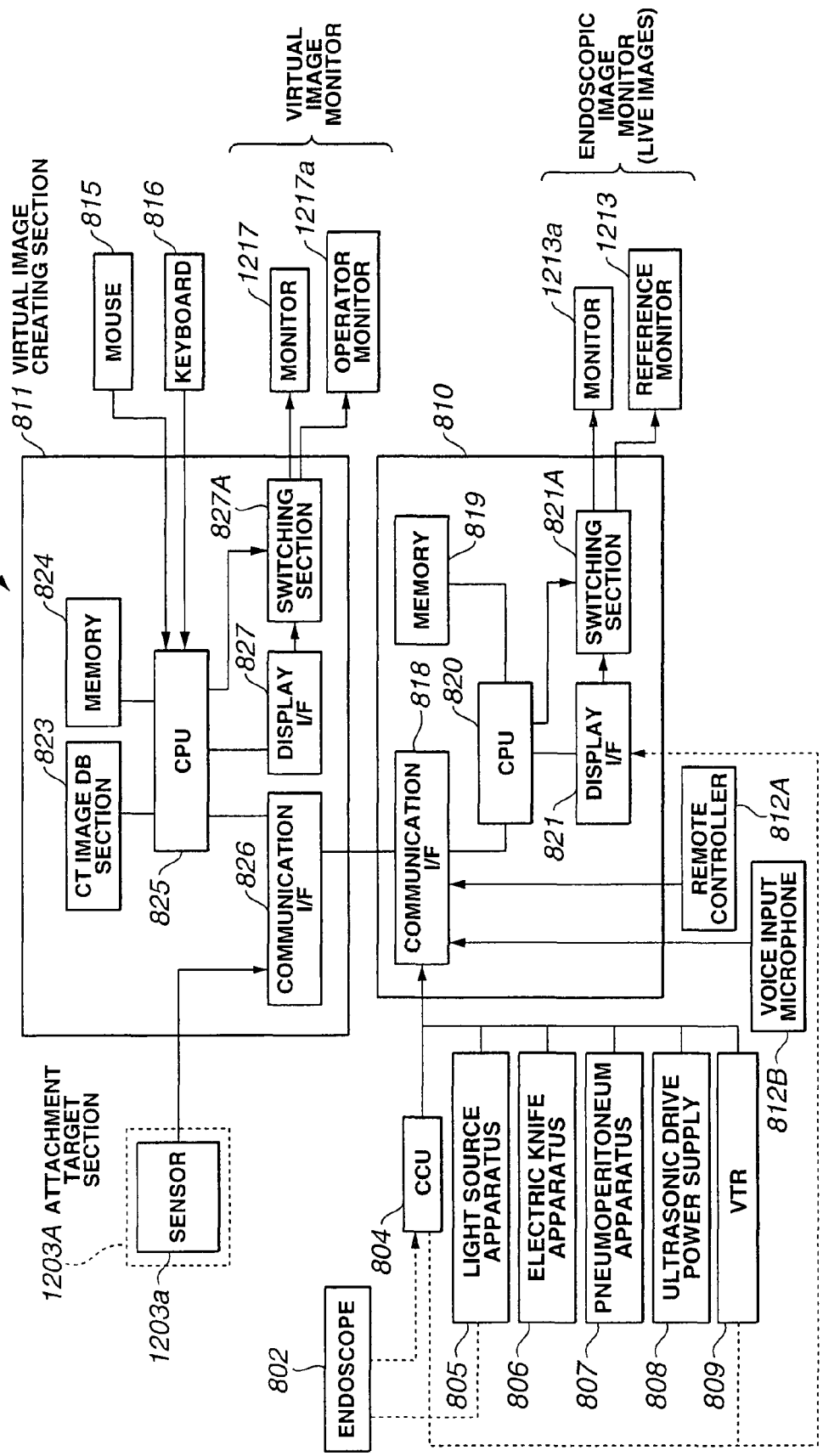
FIG. 84 is a block diagram showing an entire configuration of the endoscope system in FIG. 83.
Figure 85:
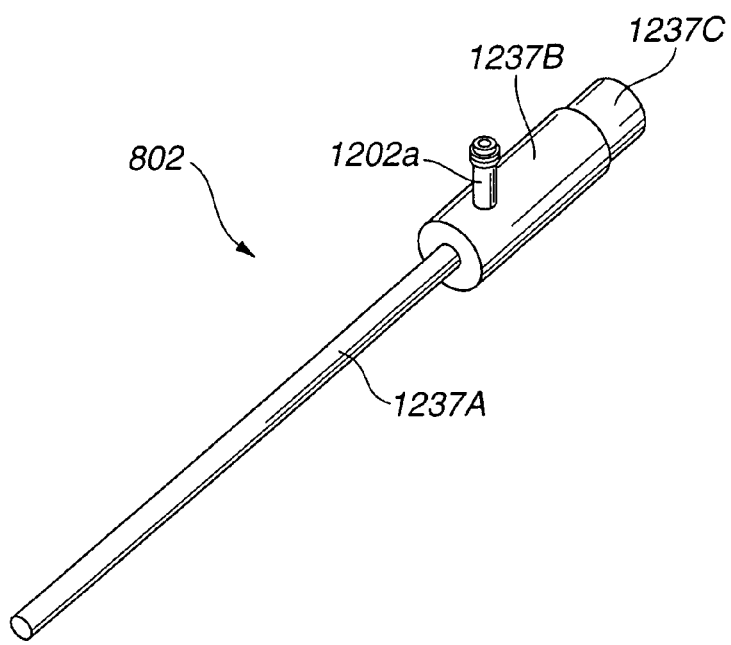
FIG. 85 is a perspective view showing an external construction of the endoscope in FIG. 83.
Figure 86:
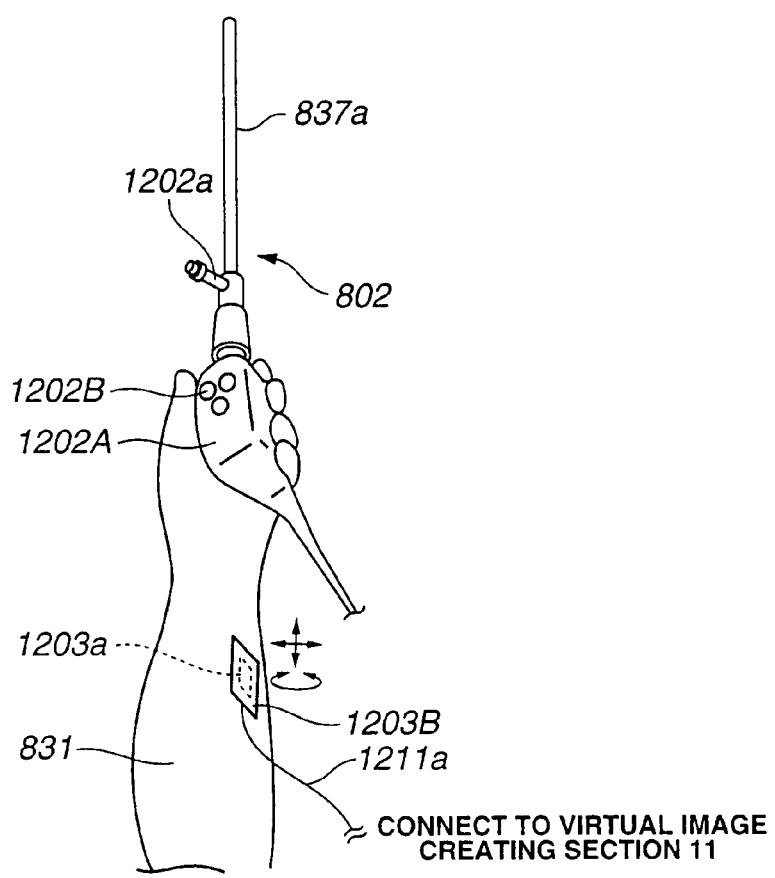
FIG. 86 is a perspective view showing a construction example in which the system is attached to the arm of an operator.
Figure 87:
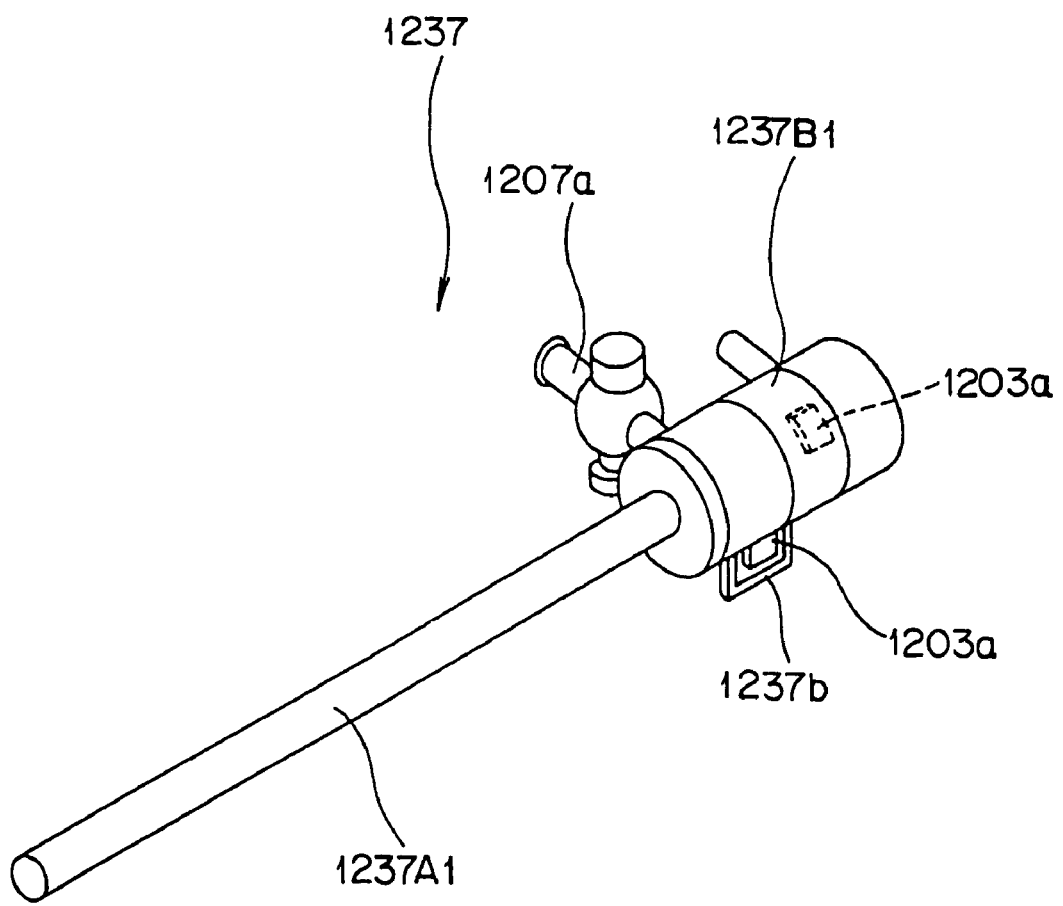
FIG. 87 is a perspective view showing an external construction of a trocar, which is an attachment target portion to which a sensor is attached.
Figure 88:
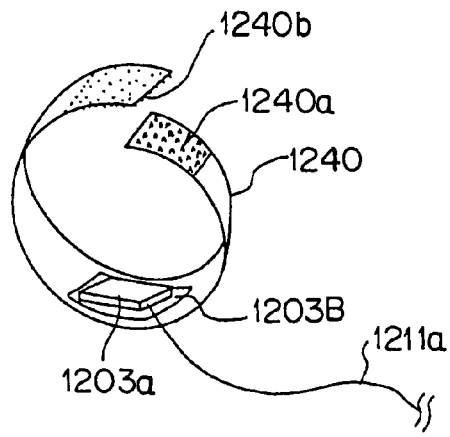
FIG. 88 is a construction perspective view showing a first variation example of the attachment target portion.
Figure 89:
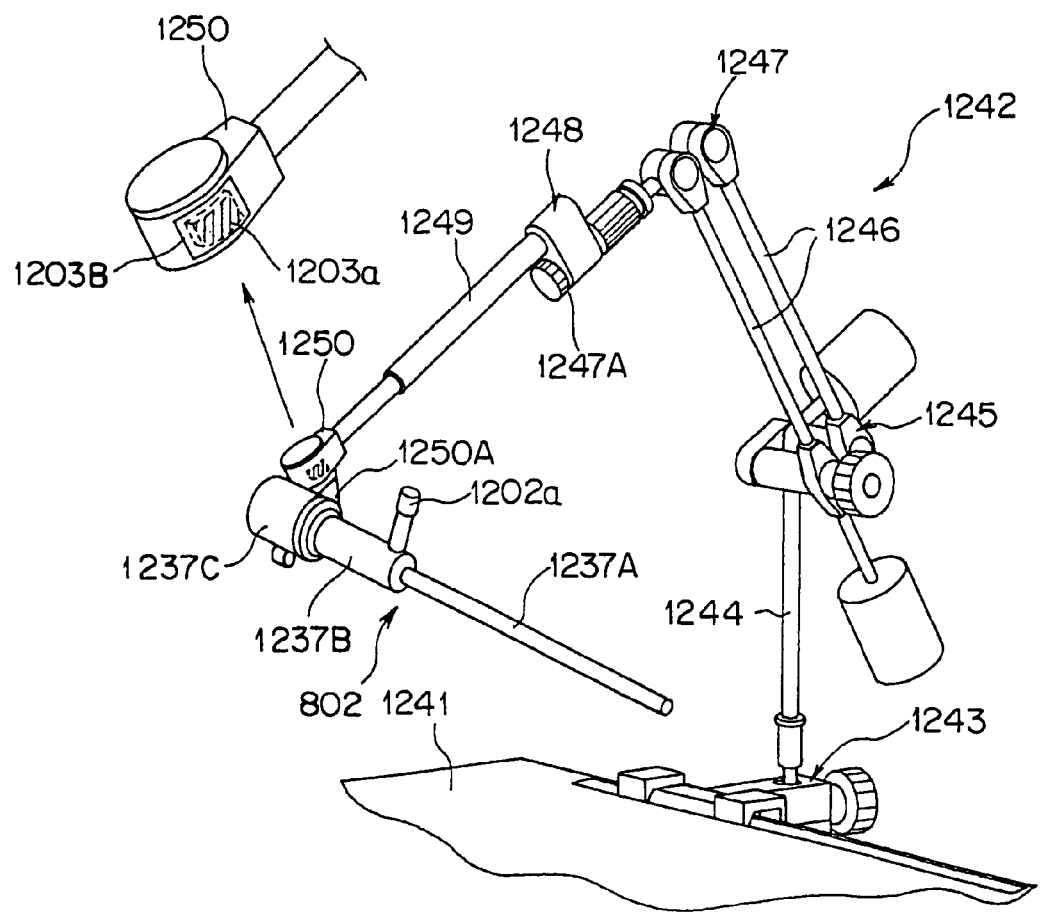
FIG. 89 is a construction perspective view showing a second variation example of the attaching target portion.
Figure 90:
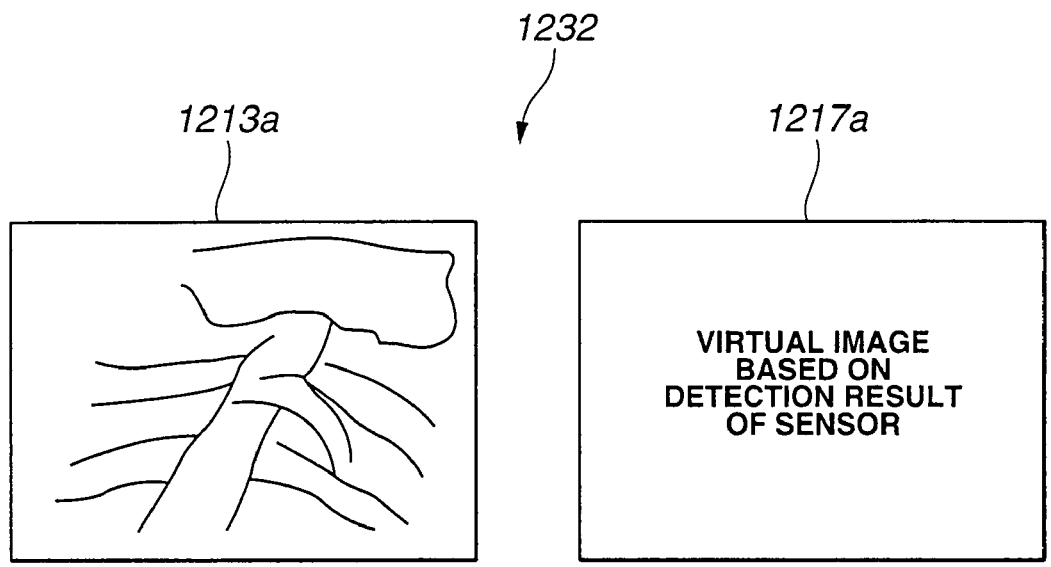
FIG. 90 is a diagram illustrating a display operation of this embodiment and showing a display example of an operator monitor shown in FIG. 83.
Figure 91:
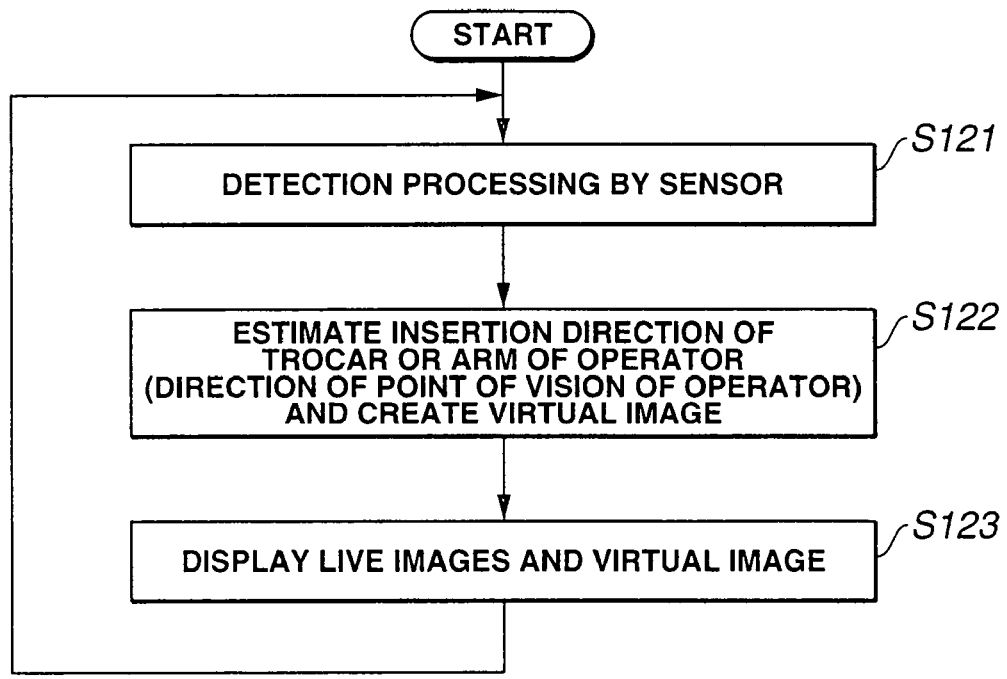
FIG. 91 is a flowchart illustrating a display operation of this embodiment and showing main control processing by a CPU of a virtual image creating section.

FIGS. 83 to 91 show a virtual image display apparatus according to a tenth embodiment of the invention. FIG. 83 is a schematic construction diagram showing an entire construction of an endoscope system including the virtual image display apparatus. FIG. 84 is a block diagram showing an entire configuration of the endoscope system in FIG. 83. FIG. 85 is a perspective view showing an external construction of the endoscope in FIG. 83. FIG. 86 is a perspective view showing a construction example in which the system is attached to the arm of an operator. FIG. 87 is a perspective view showing an external construction of a trocar, which is an attachment target portion to which a sensor is attached. FIG. 88 is a construction perspective view showing a first variation example of the attachment target portion. FIG. 89 is a construction perspective view showing a second variation example of the attachment target portion. FIGS. 90 and 91 are diagrams illustrating a display operation of this embodiment. FIG. 90 shows a display example of an operator monitor shown in FIG. 83. FIG. 91 is a flowchart illustrating main control processing by a CPU of a virtual image creating section.

The same reference numerals are given to the same components as those of the eighth embodiment, the descriptions of which will be omitted.

As shown in FIG. 83, a virtual image display apparatus 1201 according to this embodiment is combined with an endoscope system. More specifically, the virtual image display apparatus 1201 has an endoscope 802 as observation means, a sensor 1203a, an attachment target portion 1203A (such as a trocar 1237) for attaching the sensor 1203a to the endoscope 802, a camera control unit (CCU) 804, a light source 805, an electric knife apparatus 806, a pneumoperitoneum apparatus 807, an ultrasonic drive power supply 808, a VTR 809, a system controller 810, a virtual image creating section 811, a remote controller 812A, a voice input microphone 812B, a reference monitor 1213 for endoscopic live image display, a mouse 815, a keyboard 816, a virtual image display monitor 1217 and an operator monitor 1232 in an operation room.

As the endoscope 802, a laparoscope is used as shown in FIGS. 85 and 86. The laparoscope has an insert portion 1237A to be inserted into an abdominal cavity of a body to be examined, a handle 1237B disposed on the proximal end side of the insert portion 1237A, and an eye piece 1237C provided at the handle 1237B. An illumination optical system and an observation optical system are provided within the insert portion 1237A. The illumination optical system and the observation optical system illuminate a part to be observed within an abdominal cavity of a body to be examined, and an observation image of the inside of the abdominal cavity of the body to be examined can be obtained. A light guide connector 1202a is provided at the handle 1237B. A connector at one end of a light guide cable having the other end connecting to the light source apparatus is connected to the light guide connector 1202a. Thus, illumination light from the light source apparatus 805 can be irradiated to a part to be observed through the illumination optical system.

A camera head 1202A self-containing a CCD as shown in FIG. 86 is connected to the eyepiece 1237C. A remote switch 1202B to be used for performing an operation such as zooming in/out of an observation image is provided in the camera head 1202A. A camera cable is extended from the proximal end side of the camera head 1202A. A connection connector for electrically connecting to the CCU 804 is provided at the other end of the camera cable.

The endoscope (laparoscope) 802 is used within the trocar 1237 (refer to FIG. 87), which is an attachment target portion for attaching the sensor 1203a, which will be described later, during surgery.

As shown in FIG. 87, the trocar 1237 has an insert portion 1237A1 to be inserted into a body cavity of a body to be examined, a body 1237B1 on the proximal end side of the insert portion 1237A1 and an extension 1237b extending on the outer surface of the body 1237B1. The sensor 1203a is attached onto the extension 1237b. An air-supply connector 1207a is provided in the body 1237B1. A connector provided at one end of an air-supply tube having the other end connecting to the pneumoperitoneum apparatus 807 is connected to the air-supply connector 1207a. Thus, the inside of the abdominal cavity is inflated by air supply from the pneumoperitoneum apparatus 807 so that a spatial area can be established for a field of vision of and/or treatment by the endoscope 802.

The endoscope 802 is provided within the trocar 1237 having the above-described construction and is held at the abdominal part within the body of a patient by the trocar 1237. By keeping this state, the insert portion 1237A is inserted into the abdomen area. Observation images of the inside of the abdominal cavity having been obtained through the observation optical system are supplied to the CCU 804 through the camera head 1202A.

As shown in FIG. 84, the CCU 804 performs signal processing on the image pickup signals from the endoscope 802 and supplies image data (such as endoscopic live image data) based on the image pickup signals to the system controller 810 and the VTR 809 in an operation room. Under the control of the system controller 810, image data based on a still image or moving images of endoscopic live images is selectively output from the CCU 804. A detail construction of the system controller 810 will be described later.

As described above, the light source apparatus 805 is a light source apparatus for supplying illumination light to an illumination optical system provided in the endoscope 802 through a light guide within the light guide cable.

As described above, the electric knife apparatus 806 includes a surgical treatment apparatus for cutting an abnormal part within the abdomen area of a patient, for example, by using electric heat and a high-frequency output apparatus for outputting high frequency current to the treatment apparatus. The ultrasonic drive power supply 808 is a surgical treatment apparatus for cutting or coagulating the abnormal part by using an ultrasonic probe (not shown).

In addition to the above-described various kinds of equipment, the system controller 810 and an operator monitor 1232 are placed within an operation room.

According to this embodiment, in order to perform treatment at a position as shown in FIG. 83 by an operator 831 who images a body to be examined by inserting the insert portion into the abdominal part of the patient 830 through the trocar 1237, the operator monitor 1232 is placed at an easy-to-see position (in the direction of the field of vision) with respect to the position of the operator 831.

The operator monitor 1232 has an endoscopic image monitor 1213a and a virtual image monitor 1217a in parallel.

According to this embodiment, the sensor 1203a is provided on the arm of the operator 831 or the attachment target portion 1203A such as the trocar 1237 holding the endoscope 802 therethrough in order to create and display virtual images based on a direction of field of vision of the endoscope 802. The sensor 1203a is a sensor such as a gyroscopic sensor accommodated in a unit and detects information such as an angle of insertion of the attachment target portion 1203A such as the trocar 1237 into the abdomen area. The detection information of the sensor 1203a is supplied to the virtual image creating section 811, which will be described later, through a connection line 1211a. While the sensor 1203a is electrically connected to the virtual image creating section 811 through the connection line 1211a, the sensor 1203a may be connected to the virtual image creating section 811 in a wireless manner so as to implement data communication. A specific construction of the attachment target portion 1203A will be described later.

Though not shown, the remote controller 812A has a white balance button, a pneumoperitoneum button, a pressure button, a record button, a freeze button, a release button, a display button, an operation button for implementing two-dimensional display (2D display) for displaying volume rendering images, an operation button for implementing three-dimensional display (3D display) for displaying virtual images, an inserting point button, a focus point button, buttons for instructing to change a display scale for 3D display (such as a zoom-in button and a zoom-out button), a display color button, a tracking button, an operation button for switching and/or determining setting input information for an operation setting mode determined by pressing one of buttons, a numeric keypad. The white balance button is used for display images displayed on a reference monitor 1213 for endoscopic live images, the virtual image display monitor 1217 or the operator monitor 1232. The pneumoperitoneum button is used for implementing the pneumoperitoneum apparatus 807. The pressure button is used for increasing or decreasing the pressure for implementing a pneumoperitoneum. The record button is used for recording endoscopic live images in the VTR 809. The freeze button and the release button are used for recording. The display button is used for displaying endoscopic live images or virtual images. The operation button for 2D display may includes an axial button, coronal button, and sagittal button in accordance with one of different kinds of 2D display mode. The inserting point button is used for indicating a direction of field of view of a virtual image displayed in a 3D display mode (and may be a button for displaying information on insertion to the abdomen area of the endoscope 802 such as numerical values in X-, Y- and Z-directions of the abdomen area to which the endoscope 2 is inserted). The focus button is a button for displaying numerical values of the X-, Y- and Z- directions of a focused abdomen area. The display color button is used for changing a display color. The tracking button is used for tracking. The numeric keypad is used for inputting numeric values and so on.

According to this embodiment, a press-switch may be provided in a unit having the sensor 1203a. By pressing the switch, functions can be implemented by manipulating buttons on the remote controller 812A.

The display I/F 821 is electrically connected to the CCU 804, the VTR 809 and the reference monitor 1213. The display I/F 821 exchanges endoscopic live image data from the CCU 804 or endoscopic image data having been played by the VTR 809 and outputs the received endoscopic live image data to the reference monitor 1213 and the endoscopic image monitor 1213a, which will be described later, through a switching section 821A. Thus, the reference monitor 1213 and the endoscopic image monitor 1213a display endoscopic live images based on the supplied endoscopic live image data. In this case, the switching section 821A switches the output of endoscopic live image data under the switching control of the CPU 820 and outputs the endoscopic live image data to the reference monitor 1213 and/or the endoscopic image monitor 1213a.

The reference monitor 1213 and the endoscopic image monitor 1213a can not only display endoscopic live images but also display setting information such as setting states and parameters of the apparatuses of the endoscope system under the display control of the CPU 820.

The CPU 820 controls different kinds of operations in the system controller 810, that is, performs control over exchanges of different kinds of signals by the communication I/F 818 and the display I/F 821, control over writing and/or reading of image data to/from the memory 819, control over display by the reference monitor 13 and the endoscopic image monitor 1213a, and control over different kinds of operations based on operation signals from the remote controller 812A (or switch).

The communication I/F 826 is connected to the communication I/F 818 of the system controller 810 and the sensor 1203a provided in the attachment target portion 1203A. The communication I/F 826 exchanges control signals required for performing different kinds of operations in connection with the virtual image creating section 811 and the system controller 810 and receives detection signals from the sensor 1203a. The communication I/F 826 is controlled by the CPU 825, and the control signals are captured into the CPU 825.

The display I/F 827 outputs virtual images created under the control of the CPU 825 to the virtual image monitors 1217 and 1217a through the switching section 827A. Thus, the virtual image monitors 1217 and 1217a display supplied virtual images. In this case, under the switching control of the CPU 825, the switching section 827A can switch the output of the virtual images and output the virtual images to the selected one of the virtual image monitors 1217 and 1217a. When switching the display of virtual images is not required, the switching section 827A is not required. A same virtual image may be displayed on both of the virtual image monitors 1217 and 1217a.

The CPU 825 includes image processing means, not shown, for creating a virtual image based on a detection result from the sensor 1203a that the operator 831 has by using three-dimensional image data (CT image data) read from the CT image DB section 823. The CPU 825 performs display control for causing one of the monitors 1217 and 1217a, which is switched and specified by the switching section 827A, to display a virtual image created by using the image processing means in accordance with a detection result, that is, a virtual image corresponding to an endoscopic real image.

Next, a method of attaching a sensor by using the attachment target portion 1203A will be described with reference to FIG. 87.

According to this embodiment, as shown in FIG. 87, the sensor 1203a is provided at the trocar 1237 as the attachment target portion 1203A used by the operator 831.

As described above, the trocar 1237 has the extension 1237b extended on the outer surface of the body 1237B1, and the sensor 1203a is attached onto the extension 1237b. The sensor 1203a may be attached on the outer surface of the body 1237B1 as indicated by the shown dotted line. Alternatively, an extension, not shown, removably fitting with the outer surface of the body 1237B1 may be provided, and the sensor 1203a may be attached to the extension.

Therefore, by attaching the sensor 1203a to the trocar 1237 in this way, the direction of the insertion of the endoscope 2 within the trocar 1237 substantially agrees with the direction of the insertion of the trocar 1237. Therefore, information such as an angle of the insertion of the endoscope 802 can be detected by the sensor 1203a.

According to this embodiment, the attachment target portion 1203A may be the arm of the operator 831 as shown in FIGS. 83 and 86 instead of the trocar 1237, and the sensor 1203a may be attached to the arm. In this case, the sensor 1203a is accommodated within a sterilized tape member 1203B having a bag form and is stuck to the arm of the operator 831. Therefore, also in this case, the direction of the arm of the operator 831 is similar to a scope direction (inserting direction) of the endoscope 802 within the trocar 1237 and can be matched as described above. Therefore, information such as an insertion angle of the endoscope 802 can be detected by the sensor 1203a.

According to this embodiment and a first variation example in FIG. 88, a one-touch arm band 1240, which can be sterilized, may be provided as the attachment target portion 1203A, and the sensor 1203a accommodated in the tape member 1203B may be attached to an internal surface of the arm band 1240. When the arm band 1240 itself is sterilized and has a bag form, the sensor 1203a may be accommodated in the bag-form arm band 1240 and be fixed tightly instead of accommodating in the tape member 1203B.

In the first variation example, removable Velcro convex 1240a and concave 1240b are provided on the both sides of the arm band 1240. Therefore, the sensor 1203a can be attached thereto by the operator 831 more easily.

According to this embodiment and a second variation example in FIG. 89, as the attachment target portion 1203A, a movable scope holder 1242 may be used which holds the endoscope (laparoscope) 802 on the operation table 1241.

For example, as shown in FIG. 89, the scope holder 1242 has a fixing portion 1243, a support portion 1244, a first connecting portion 1245, a second connecting portion 1247, a slide portion 1248, a second arm portion 1249 and a third connecting portion 1250. The fixing portion 1243 fixes the scope holder 1242 to the operation table 1241. The support portion 1244 is fixed to the fixing portion 1243. The first connecting portion 1245 vertically movably support a first arm portion 1246 at the support portion 1244. The second connecting portion 1247 is provided on the opposite side of the first connecting portion 1245, and a slide support portion 1247A is rotatably connected to the second connecting portion 1247. The slide portion 1248 can slide on the slide support portion 1247A. The second arm portion 1249 is strechably provided in the slide portion 1248. The third connecting portion 1250 is provided on the opposite side of the slide portion 1248 and holds the endoscope 802. The third connecting portion 1250 has a holding portion 1250A for holding and fixing a handle 1237B of the endoscope 802 (more specifically, a part around the border of the insert portion 1237A and the handle 1237B of the endoscope 802). The endoscope 802 is rotatably held by the holding portion 1250A.

With the scope holder 1242 according to the second variation example, the sensor 1203a accommodated in the tape member 1203B is attached onto, for example, the side of the third connecting portion 1250. Thus, like the configuration example of the trocar 1237 shown in FIG. 87, the insertion direction of the endoscope 802 held by the holder 1250A can substantially agree with the direction of the movement of the third connecting portion. Therefore, information such as an insertion angle of the endoscope 802 can be detected by the sensor 1203a.

While, according to this embodiment, the sensor 1203a is attached to the trocar 1237, the arm of the operator 831 or the third connecting portion 1250 of the scope holder 1242, the invention is not limited thereto. For example, the sensor 1203a may be attached to a cap, a slipper or the like of the operator 831.

Next, an example of control over a virtual image display apparatus according to this embodiment will be described with reference to FIGS. 90 and 91.

Here, surgery on a body to be examined within the abdomen area of a patient is performed by using an endoscope system of the virtual image display apparatus 1201 shown in FIG. 83. In this case, when the endoscope system is powered on and when the CPU 825 of the virtual image creating section 811 receives an instruction for virtual image display from an operator through the mouse 815 or the keyboard 816, the CPU 825 starts a virtual image display program recorded in a recording portion, not shown. Thus, the CPU 825 causes the monitor 1217 to display a screen required for displaying a virtual image.

Then, the operator inputs information on the position within the abdomen area of the patient, for example, to which the endoscope 802 is inserted (that is, numeric value in the X, Y, and Z directions of the abdomen area (inserting point)) by using the mouse 815 or the keyboard 816 with reference to the screen displayed on the monitor 1217. Then, similarly, the operator inputs, that is, specifies a numeric value in the axial direction of the endoscope 802, which is being inserted into the abdomen area (that is, a focus point).

The image processing means (not shown) creates a virtual image corresponding to an inserting point and a focus point of the endoscope 802 based on input information. The CPU 825 displays data of the created virtual image on the virtual image monitor 1217 and the virtual image monitor 1217a of the operator monitor 1232.

Here, endoscopic live images are displayed on the endoscopic image monitor 1213a within the operator monitor 1232 for an operator performing surgery under the display control of the CPU 820 of the system controller 810. The operator 831 performs surgery with reference to the display. In this case, the endoscope 802 is used with the sensor 1203a set in the trocar 1237 as shown in FIG. 87.

While surgery is being performed, the CPU 825 of the virtual image creating section 811 activates a detection program shown in FIG. 91 according to this embodiment. The detection program detects an insertion direction of the trocar 1237 or the arm of the operator 831 (or direction of point of vision of the operator when the sensor 1203a is attached to the cap or slipper of the operator 831) by using the sensor 1203a and displays a virtual image based on the detection result.

For example, it is assumed that, during surgery, the operator 831 inclines the insert portion of the endoscope 802 with respect to the abdomen area. In this case, when endoscopic live images in accordance with the inclination of the endoscope 802 is displayed on the reference monitor 1213 and the endoscopic image monitor 1213a (refer to FIG. 90), the inclination of the endoscope 802 is always detected by the sensor 1203a under the control of the CPU 825 according to this embodiment (step S121). Based on the detection result, an insertion direction of the trocar or the arm of the operator or a direction of point of vision of the operator is estimated, and a virtual image is created by the image processing means within the CPU 825 (step S122). The created image is displayed on the monitor 1217 and the virtual image monitor 1217*a* (refer to FIG. 90) of the operator monitor 1232 (step S123).

Thus, since a virtual image corresponding to an endoscopic live image upon inclination of the insert portion of the endoscope 802 can be displayed on the virtual image monitor 1217*a*, biological image information (virtual image) of a body to be examined within an observed area of an endoscopic observation image can be obtained under endoscopic observation.

Thus, according to this embodiment, only by attaching the sensor 1203*a* to the trocar 1237 or the arm of the operator 831, a virtual image corresponding to an insertion angle of the endoscope 802 can be displayed automatically along with endoscopic live images. Therefore, an operator can securely obtain biological image information (virtual image) of a body to be examined within an observed area of an endoscopic observation image while performing surgery, and the surgery can be performed smoothly. As a result, an easy-to-use virtual display apparatus having a simple construction can be obtained at low costs.

Since, according to this embodiment, the sensor 1203*a* is provided on the trocar 1237 holding the endoscope 802 or the arm of the operator 831, the weight of the operation portion of the endoscope 802 can be reduced. Therefore, the operability of the endoscope 802 can be improved.

Furthermore, according to this embodiment, when the sensor 1203*a* is attached to a cap, a slipper or the like of the operator 831 and when the operator 831 moves his/her head or leg toward the direction he/she needs to see, the orientation (the direction of point of vision) of the operator can be detected by the sensor 1203*a*. Thus, a virtual image in accordance with the orientation (direction of point of vision) of the operator can be displayed under the control of the CPU 825. In other words, the operator 831 can display a virtual image in the direction that the operator 831 needs to see only by moving his/her body toward the direction that he/she needs to see. Thus, the operator 831 can easily identify a three-dimensional, positional relationship of blood vessels and the like behind an observed part displayed in an endoscopic image and can securely perform a treatment.

According to this embodiment, the sensor 1203*a* is provided only at the trocar 1237 holding the endoscope 802. However, when surgery is performed by an operator operating the endoscope 802, an operator performing forceps treatment by using treating devices and an assistant operator, the sensors 1203*a* may be provided at the trocars 1237 holding the treating devices in addition to the trocar 1237 holding the endoscope 802. Furthermore, operator monitors may be provided for the operators, and a virtual image based on a detection result of the sensors 1203*a* may be displayed.

According to this embodiment, the endoscope 802 may be an endoscope having a bending portion of which insert portion has the distal end that is freely bendable. In this case, when a function for detecting a bending angle of the bending portion is provided to the sensor 1203*a*, a virtual image in accordance with a bending angle of the bending portion can be displayed. When a magnetic sensor is provided in unit accommodating the sensor 1203*a* and when means for irradiating magnetism is provided to the magnetic sensor, an amount of insertion of the endoscope 802 can be detected by performing computation processing by the CPU 825. In other words, a virtual image based on an amount of insertion of the endoscope 802 can be displayed. In this case, an amount of insertion of the endoscope 802 may be detected by using a rotary encoder instead of a magnetic sensor.

With a virtual image display apparatus having a simple construction according to this embodiment, biological image information of a body to be examined within an observed area of an endoscopic observation image can be securely obtained at low costs under endoscopic observation, which is an advantage.

Since, with a virtual image display apparatus having a simple construction according to this embodiment, biological image information of a body to be examined within an observed area of an endoscopic observation image can be obtained at low costs under endoscopic observation, the virtual image display apparatus is especially effective for performing surgery for a case requiring further biological image information of a body to be examined, which cannot be obtained from endoscopic observation images.

Eleventh Embodiment

Figure 92:
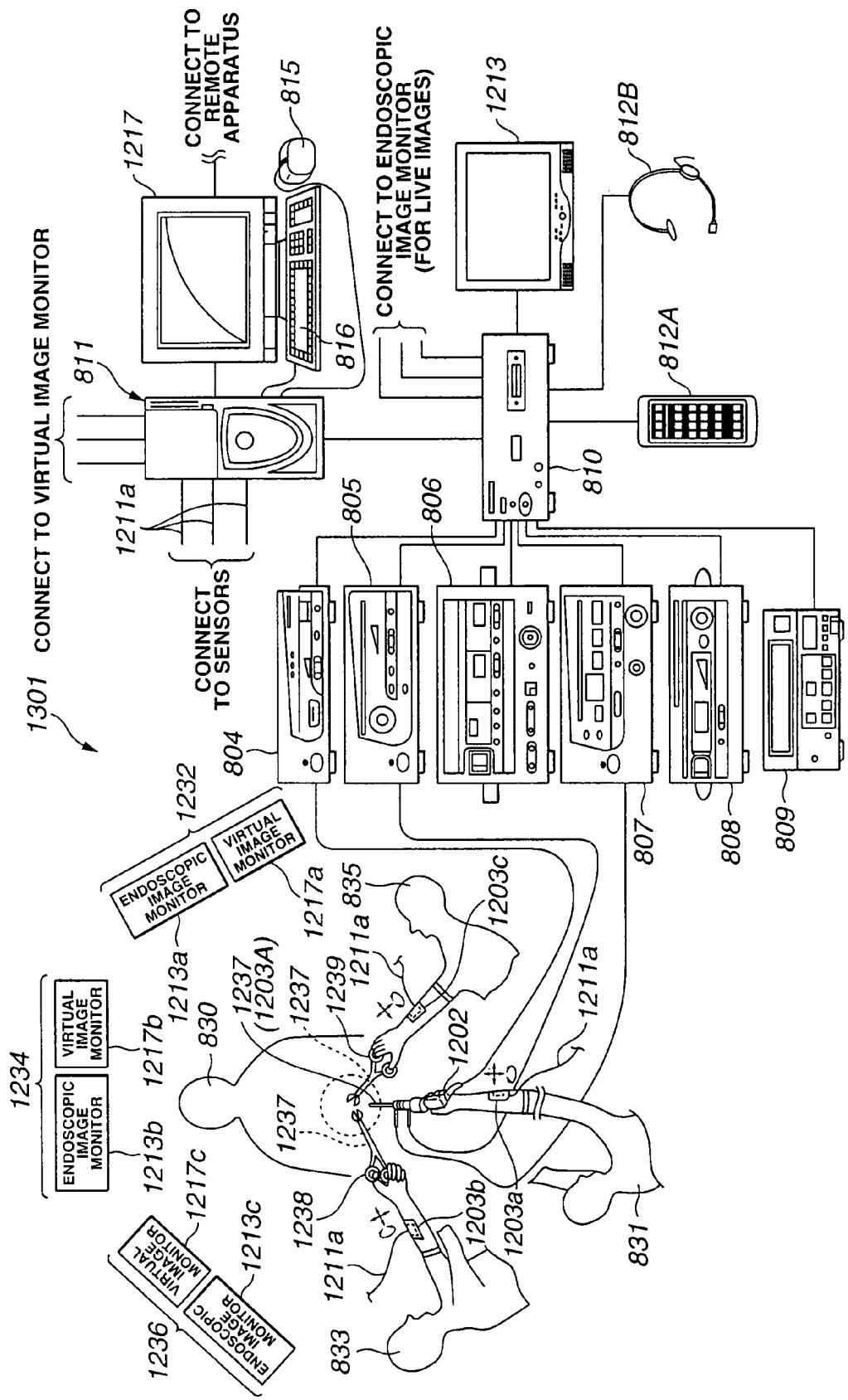
FIG. 92 is a schematic construction diagram showing a virtual image display apparatus according to an eleventh embodiment of the invention and showing an entire construction of an endoscope system including the apparatus.
Figure 93:
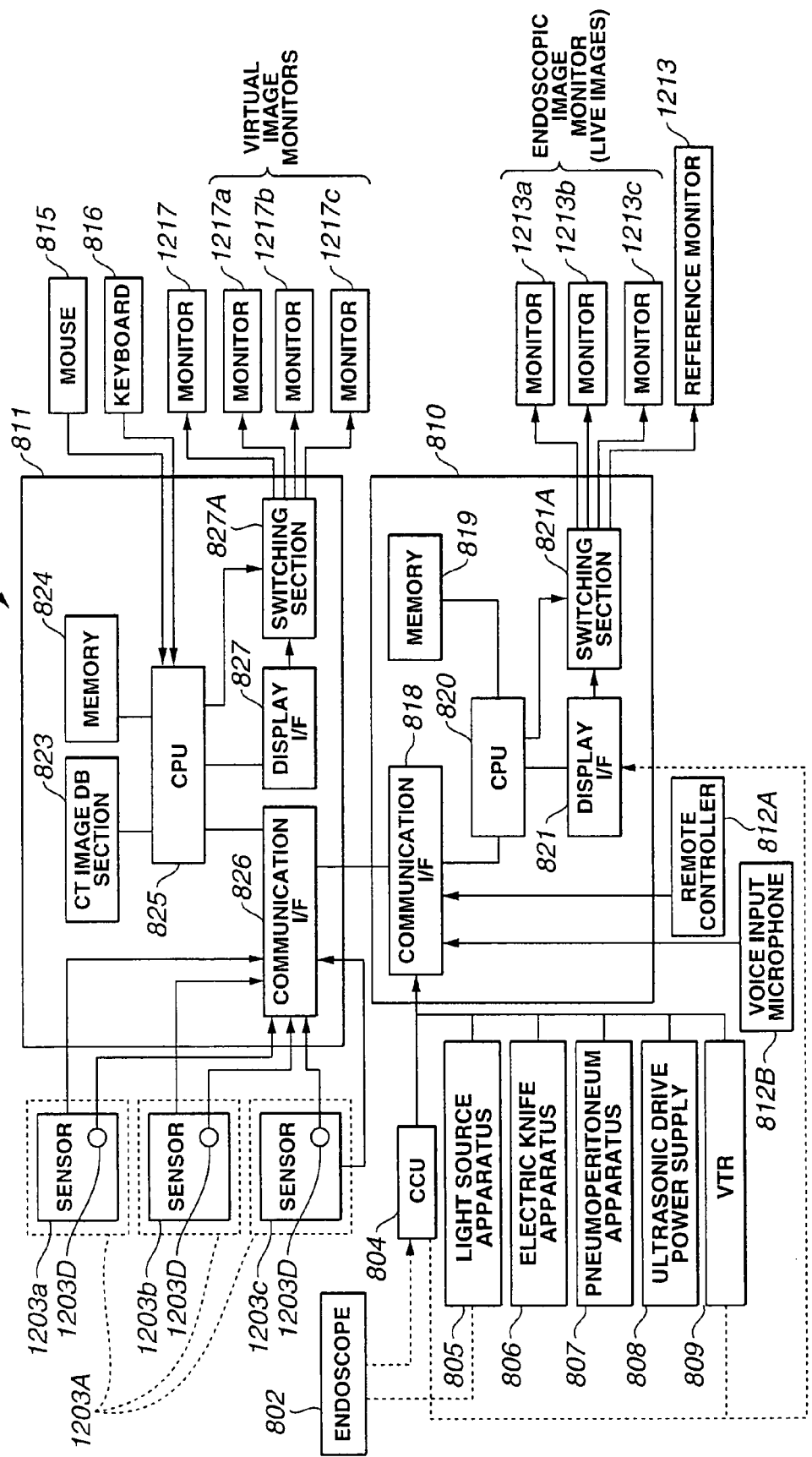
FIG. 93 is a block diagram showing an entire configuration of the endoscope system in FIG. 92.
Figure 94:
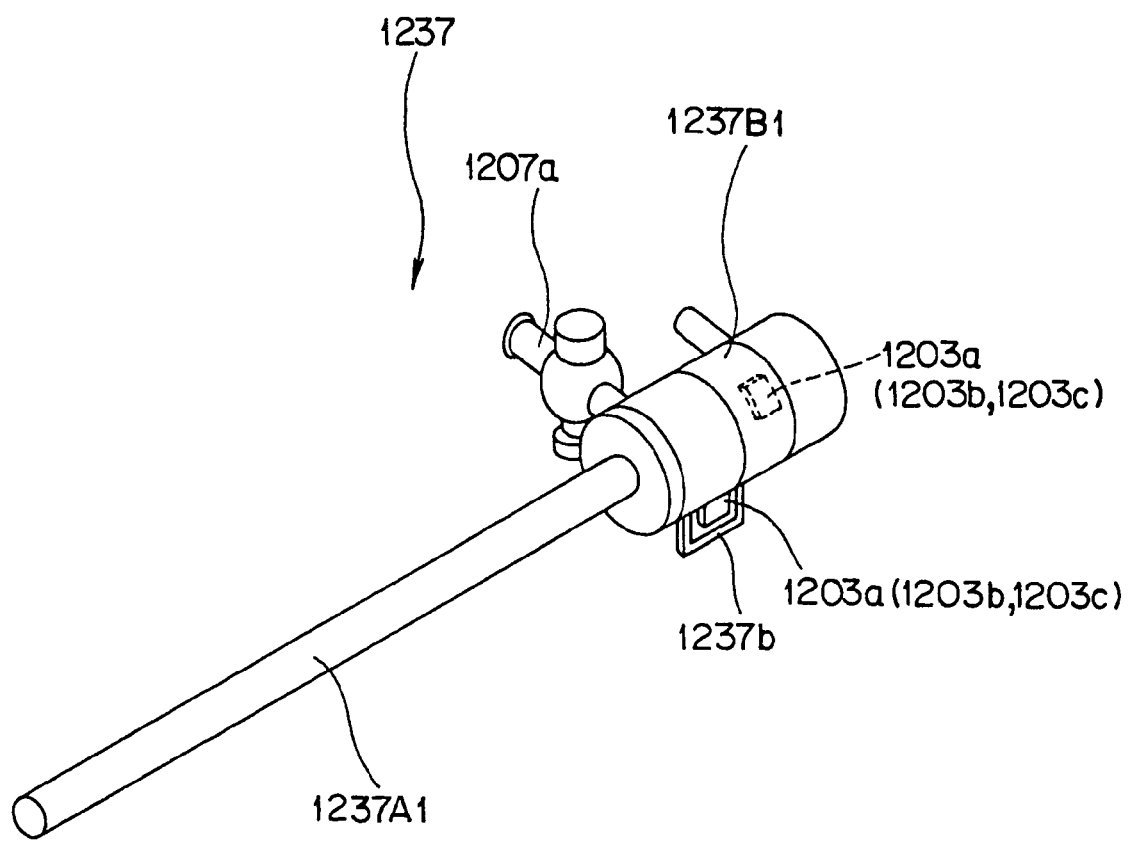
FIG. 94 is a perspective view showing an external construction of a trocar, which is an attachment target portion to which a sensor is attached.
Figure 95:
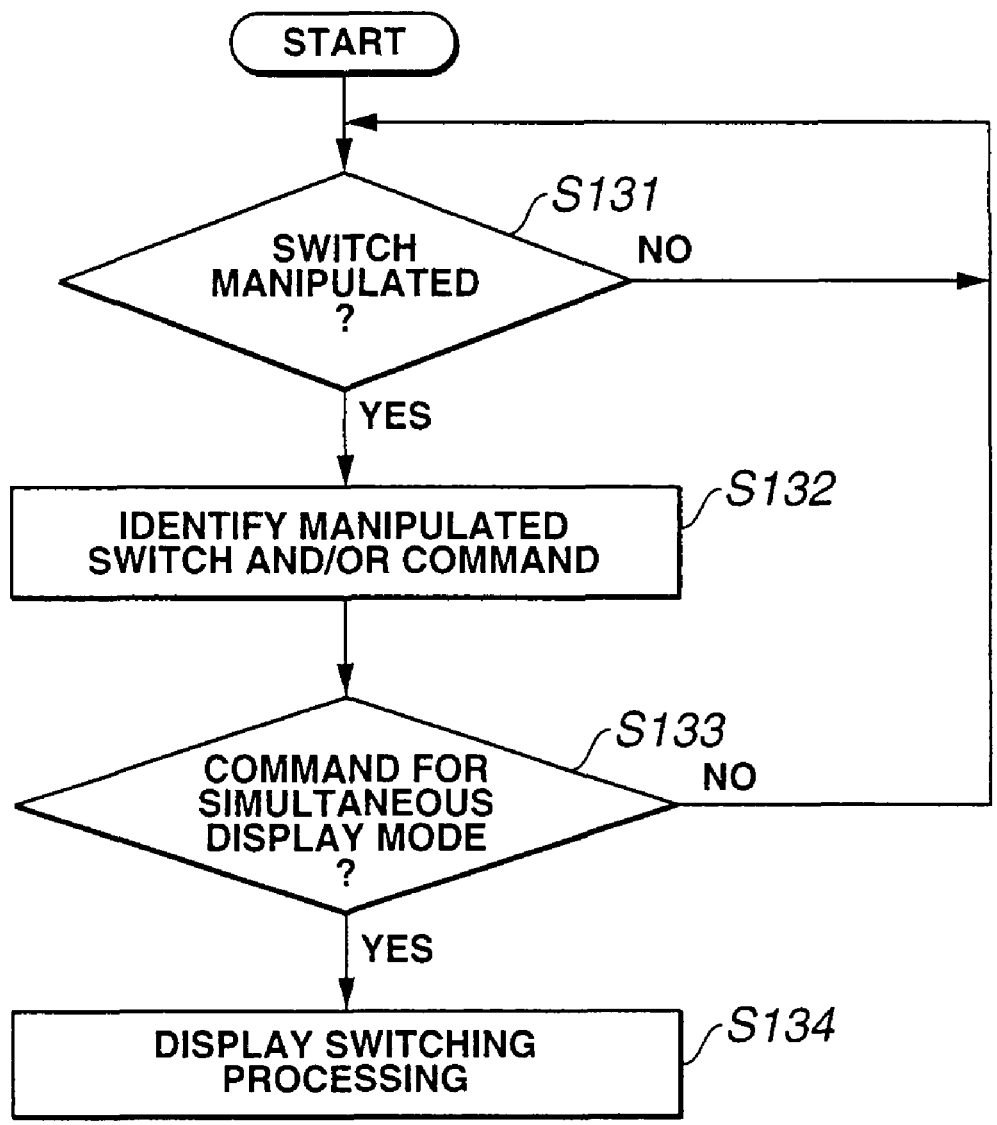
FIG. 95 is a flowchart illustrating a display operation of the eleventh embodiment and showing main control processing by a CPU of a virtual image creating section.
Figure 96:
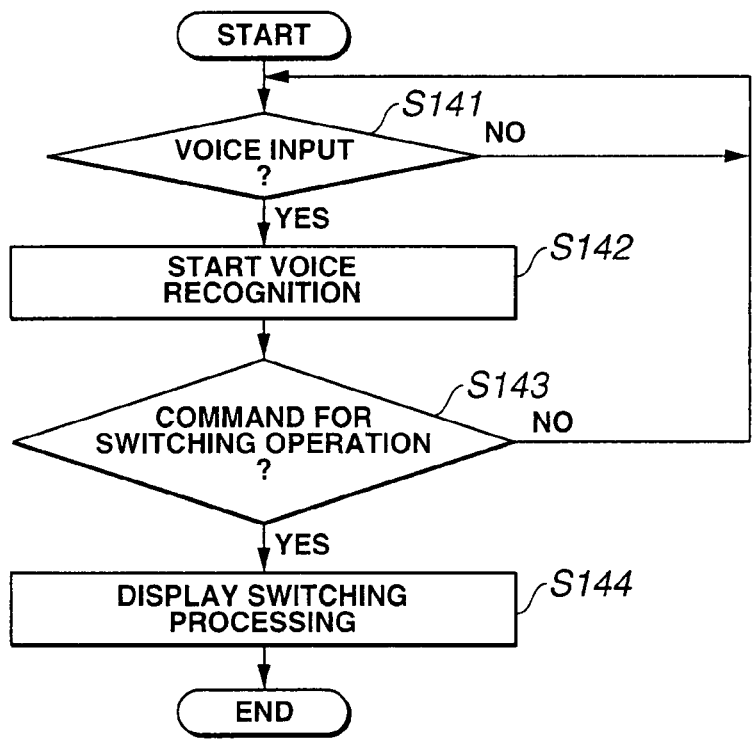
FIG. 96 is a flowchart illustrating a display operation of the eleventh embodiment and showing voice control processing by the CPU.

FIGS. 92 to 96 show a virtual image display apparatus according to an eleventh embodiment of the invention. FIG. 92 is a schematic construction diagram showing an entire construction of an endoscope system including the virtual image display apparatus. FIG. 93 is a block diagram showing an entire configuration of the endoscope system in FIG. 92. FIG. 94 is a perspective view showing an external construction of a trocar, which is an attachment target portion to which a sensor is attached. FIGS. 95 and 96 illustrate display operations of the virtual image display apparatus according to this embodiment. FIG. 95 is a flowchart showing main control processing by a CPU of a virtual image creating section. FIG. 96 is a flowchart showing voice control processing by the CPU.

The same reference numerals are given to the same components as those of the eighth and tenth embodiment, the descriptions of which will be omitted.

As shown in FIG. 92, a virtual image display apparatus 1301 according to this embodiment is combined with an endoscope system. More specifically, the virtual image display apparatus 1301 has an endoscope 802 as observation means, at least two of first and second treating devices 1238 and 1239 for treating a body to be examined, an attachment target portion 1203A (such as a trocar 1237) for attaching sensors 1203*a* to 1203*c* to the endoscope 802 and the first and second treating devices 1238 and 1239, a camera control unit (CCU) 804, a light source apparatus 805, an electric knife apparatus 806, a pneumoperitoneum apparatus 807, an ultrasonic drive power supply 808, a VTR 809, a system controller 810, a virtual image creating section 811, a remote controller 812A, a voice input microphone 812B, a reference monitor 1213 for endoscopic live image display, a mouse 815, a keyboard 816, a virtual image display monitor 1217 and three of first to third operator monitors 1232, 1234, 1236 in an operation room.

In addition to these devices and apparatus, the system controller 810 and the first to third operator monitors 1232, 1234 and 1236 are disposed in an operation room.

As shown in FIG. 92, surgery under endoscopic observation may be performed by three people including an operator operating the endoscope 802, an operator performing a forceps treatment and an assistant operator. The virtual image display apparatus 1301 according to this embodiment is compliant with surgery by three operators.

For example, an operator performing a forceps treatment on a body to be examined of the patient 830 by using the first treating device 1238 such as forceps is called first operator 833. An operator operating the endoscope 802 is called second operator 831. An assistant operator assisting the first operator by using the second treating device 1239 is called third operator 835. When the first to third operators 833, 831 and 835 perform a treatment at a position as shown in FIG. 92, for example, the first to third operator monitors 1232, 1234 and 1236 are disposed at easy-to-see positions (direction of field of vision) corresponding to positions of the first to third operators 833, 831 and 835.

The first operator monitor 1232 has an endoscopic image monitor 1213a and a virtual image monitor 1217a in parallel and is disposed at a position, which can be seen easily by the first operator 833. The second operator monitor 1234 has an endoscopic image monitor 1213b and a virtual image monitor 1217b in parallel and is disposed at a position, which can be seen easily by the second operator 831. The third operator monitor 1236 has an endoscopic image monitor 1213c and a virtual image monitor 1217c in parallel and is disposed at a position, which can be seen easily by the third operator 835.

According to this embodiment, the sensors 1203a to 1203c are attached on the arms of the first to third operators 833, 831 and 835 or the attachment target portion 1203A such as the trocars 1237 holding the endoscope 802 and the first and second treating devices 1238 and 1239 therethrough in order to create and display virtual images based on a direction of directions of insertion of the endoscope 802 and the first and second treating devices 1238 and 1239.

The sensors 1203a to 1203c are sensors such as gyroscopic sensors accommodated in units and detect information such as an angle of insertion of the attachment target portion 1203A such as the trocar 1237 into the abdomen area. The detection information of the sensors 1203a to 1203c is supplied to the virtual image creating section 811, which will be described later, through a connection line 1211a. While the sensors 1203a to 1203c are electrically connected to the virtual image creating section 811 through the connection line 1211a, the sensors 1203a to 1203c may be connected to the virtual image creating section 811 in a wireless manner so as to implement data communication.

A press-button switch 1203D to be used by an operator for, for example, implementing, changing or switching a display mode of virtual images is provided in each of the sensors 1203a to 1203c (refer to FIG. 93). A specific construction of the attachment target portion 1203A will be described later.

Though not shown, the remote controller 812A has a white balance button, a pneumoperitoneum button, a pressure button, a record button, a freeze button, a release button, a display button, an operation button for implementing two-dimensional display (2D display) for displaying volume rendering images, an operation button for implementing three-dimensional display (3D display) for displaying virtual images, an inserting point button, a focus point button, buttons for instructing to change a display scale for 3D display (such as a zoom-in button and a zoom-out button), a display color button, a tracking button, an operation button for switching and/or determining setting input information for an operation setting mode determined by pressing one of the buttons, a numeric keypad. The white balance button is used for display images displayed on a reference monitor 1213 for endoscopic live images, the virtual image display monitor 1217 or the operator monitors 1232, 1234 and 1236. The pneumoperitoneum button is used for implementing the pneumoperitoneum apparatus 807. The pressure button is used for increasing or decreasing the pressure for implementing a pneumoperitoneum. The record button is used for recording endoscopic live images in the VTR 809. The freeze button and the release button are used for recording. The display button is used for displaying endoscopic live images or virtual images. The operation button for 2D display may includes an axial button, coronal button, and sagittal button in accordance with one of different kinds of 2D display mode. The inserting point button is used for indicating a direction of field of view of a virtual image displayed in a 3D display mode (and may be a button for displaying information on insertion to the abdomen area of the endoscope 802 such as numerical values in X-, Y- and Z-directions of the abdomen area to which the endoscope 2 is inserted). The focus button is a button for displaying numerical values of the X-, Y- and Z-directions of a focused abdomen area. The display color button is used for changing a display color. The tracking button is used for tracking. The numeric keypad is used for inputting numeric values and so on. By pressing the switch 1203D provided to each of the sensors 1203a to 1203b (refer to FIG. 93), functions can be implemented by manipulating buttons on the remote controller 812A.

By using the remote controller 12A or the switch 1203D including these buttons, an operator can operate to obtain desired information promptly.

The display I/F 821 is electrically connected to the CCU 804, the VTR 809 and the reference monitor 1213. The display I/F 821 exchanges endoscopic live image data from the CCU 804 or endoscopic image data having been played by the VTR 809 and outputs the received endoscopic live image data to the reference monitor 1213 and the endoscopic image monitors 1213a to 1213c, which will be described later, through the switching section 821A. Thus, the reference monitor 1213 and the endoscopic image monitors 1213a to 1213c display endoscopic live images based on the supplied endoscopic live image data. In this case, under the switching control of the CPU 820, the switching section 821A can switch the output of the endoscopic live image data and output the endoscopic live image data to the selected one of the reference monitor 1213 and endoscopic image monitors 1213a to 1213c.

The reference monitor 1213 and the endoscopic image monitors 1213a to 1213c can not only display endoscopic live images but also display setting information such as setting states and parameters of the apparatuses of the endoscope system under the display control of the CPU 820.

The CPU 820 controls different kinds of operations in the system controller 810, that is, performs control over exchanges of different kinds of signals by the communication I/F 818 and the display I/F 821, control over writing and/or reading of image data to/from the memory 819, control over display by the reference monitor 1213 and the endoscopic image monitors 1213a to 1213c, and control over different kinds of operations based on operation signals from the remote controller 812A or the switch 1203D.

The communication I/F 826 is connected to the communication I/F 818 of the system controller 810, the sensors 1203a to 1203c provided in the attachment target portions 3A for the first to third operators 833, 831 and 835 and the switch 1203D. The communication I/F 826 exchanges control signals required for performing different kinds of operations in connection with the virtual image creating section 811 and the system controller 810, receives detection signals from the sensors 1203a to 1203c and receives an operation signal from the switch 1203D. The communication I/F 826 is controlled by the CPU 825, and the control signals are captured into the CPU 825.

The display I/F 827 outputs virtual images created under the control of the CPU 825 to the virtual image monitors 1217 and 1217a to 1217c through the switching section 827A. Thus, the virtual image monitors 1217 and 1217a to 1217c display supplied virtual images. In this case, under the switching control of the CPU 825, the switching section 827A can switch the output of the virtual images and output the virtual images to the selected one of the virtual image monitors 1217 and 1217a to 1217c.

The CPU 825 controls different kinds of operations in the virtual image creating section 811, that is, performs control over exchanges of different kinds of signals by the communication I/F 826 and the display I/F 827, control over writing and/or reading of image data to/from the memory 824, control over display by the monitors 1217 and 1217a to 1217c, control over switching of the switching section 827A and control over different kinds of operations based on operation signals from the mouse 815 and/or the keyboard 816.

The CPU 825 includes image processing means, not shown, for creating a virtual image based on a detection result from the sensors 1203a to 1203c that the first to third operators 833, 831 and 835 have by using three-dimensional image data (CT image data) read from the CT image DB section 823. The CPU 825 performs display control for causing one of the monitors 1217 and 1217a to 1217c, which is switched and specified by the switching section 827A, to display a virtual image created by using the image processing means in accordance with a detection result, that is, a virtual image corresponding to an endoscopic real image.

Also according to this embodiment, the virtual image creating section 811 may be connected to a remotely provided virtual image creating section, for example, through communication means so as to be constructed as a remote surgery support system.

Next, a method of attaching a sensor by using the attachment target portion 1203A will be described with reference to FIG. 94.

According to this embodiment, as shown in FIG. 94, the sensors 1203a to 1203c are provided in the trocars 1237, which are the attachment target portion 1203A used by the respective first to third operators 833, 831 and 835. The trocar 1237 can be attached by holing the endoscope 2 and the first and second treating devices 1238 and 1239 therethrough used by the first and second operators 833 and 835.

The trocar 1237 has the extension 1237b extended on the outer surface of the body 1237B1, and the sensor 1203a (1203b and 1203c) having the switch 1203D is attached onto the extension 1237b. The sensor 1203a (1203b and 1203c) may be attached on the outer surface of the body 1237B1 as indicated by the shown dotted line. Alternatively, an extension, not shown, removably fitting with the outer surface of the body 1237B1 may be provided, and the sensor 1203a (1203b, 1203c) may be attached to the extension.

Therefore, by attaching the sensor 1203a (1203b, 1203c) to the trocar 1237 in this way, the direction of the insertion of the endoscope 802 and/or the first and second treating devices 1238 and 1239 within the trocar 1237 substantially agrees with the direction of the insertion of the trocar 1237. Therefore, information such as an angle of the insertion of the endoscope 802 and the first and second treating devices 1238 and 1239 can be detected by the sensor 1203a to 1203c.

According to this embodiment, the attachment target portion 1203A may be the arms of the first to third operators 833, 831 and 835 as shown in FIGS. 92 and 86 instead of the trocar 1237, and the sensors 1203a to 1203c may be attached to the arms. In this case, each of the sensors 1203a to 1203c is accommodated within a sterilized tape member 1203B having a bag form and is stuck to the arm of each of the first to third operators 833, 831 and 835. Therefore, also in this case, the direction of the arm of each of the first to third operators 833, 831 and 835 is similar to a scope direction of the endoscope 802 within the trocar 1237 or a direction of insertion of one of the first and second treating devices 1238 and 1239 and can be matched as described above. Therefore, information such as an insertion angle of the endoscope 802 and the first and second treating devices 1238 and 1239 can be detected by the sensors 1203a to 1203c.

Also in this embodiment, like the tenth embodiment, the attachment target portion 1203A may be the place in the variation example in FIG. 88 or the variation example in FIG. 89.

By the way, by manipulating the switch 1203D (or the remote controller 812A) provided in the sensors 1203a (1203b, 1203c) in the virtual image display apparatus according to this embodiment, a display mode for virtual images can be selected, implemented or switched.

For example, one of the first to third operators 833, 831 and 835 can select and implement a display mode for virtual display image by properly pressing the switch 1203D (refer to FIG. 93).

Next, a control example of the virtual image display apparatus according to this embodiment to be implemented by a switching operation will be described with reference to FIG. 95.

First of all, a basic operation of the virtual image display apparatus according to this embodiment will be described.

Here, an operator on a body to be examined within the abdomen area of a patient is performed by using an endoscope system of the virtual image display apparatus 1301 shown in FIG. 92. In this case, when the endoscope system is powered on and when the CPU 825 of the virtual image creating section 811 receives an instruction for virtual image display from an operator through the mouse 815 or the keyboard 816, the CPU 825 starts a virtual image display program recorded in a recording portion, not shown. Thus, the CPU 825 causes the monitor 1217 to display a screen required for displaying a virtual image.

Then, the operator inputs information on the position within the abdomen area of the patient, for example, to which the endoscope 802 is inserted (that is, numeric value in the X, Y, and Z directions of the abdomen area (inserting point)) by using the mouse 815 or the keyboard 816 with reference to the screen displayed on the monitor 1217. Then, similarly, the operator inputs a numeric value in the axial direction of the endoscope 802, which is being inserted into the abdomen area (that is, focus point). Also for the first and second treating devices 1238 and 1239, respective required information are input with reference to screens, not shown.

The image processing means (not shown) creates virtual images corresponding to an inserting point and focus point of the endoscope 802 and inserting points and focus points of the first and second treating devices 1238 and 1239 based on input information. The CPU 825 displays data of the created virtual images on the virtual image monitor 1217 and the first to third operator monitors 1232, 1234 and 1236. In this case, virtual images corresponding to the endoscope 802 are mainly displayed on the virtual image monitor 1217. In addition, virtual images corresponding to the first and second treating devices 1238 and 1239 may be selected and be displayed.

Here, endoscopic live images are displayed on the endoscopic image monitors 1213a to 1213c within the first to third operator monitors 1232, 1234 and 1236 for the first to third operators performing surgery under the display control of the CPU 820 of the system controller 810. The first to third operators 833, 831 and 835 perform surgery with reference to the display. In this case, the endoscope 802 and the first and second treating devices 1238 and 1239 are used with the sensors 1203a to 1203c set in the trocars 1237 as shown in FIG. 94. The sensors 1203a to 1203c may be attached onto the arms of the respective operators through the tape portions 1203B instead of the trocars 1237.

While surgery is being performed, the CPU 825 of the virtual image creating section 811 according to this embodiment creates a virtual image in accordance with endoscopic live images and based on a detection result from the sensor 1203a of the endoscope 802 by means of the image processing means within the CPU 825. Then, the CPU 825 causes the virtual image monitors 1217b of the monitor 1217 and the second operator monitor 1234 to display the created image. At the same time, the CPU 825 creates virtual images by means of the image processing means within the CPU 825 based on detection result from the sensors 1203b and 1203c of the first and second treating devices 1238 and 1239 and causes the virtual image monitors 1217a and 1217c of the first and third operator monitors 1232 and 1236 to display the created images.

For example, it is assumed that, during surgery, the second operator 831 inclines the insert portion of the endoscope 802 with respect to the abdomen area. In this case, when endoscopic live images in accordance with the inclination of the endoscope 802 is displayed on the reference monitor 1213 and the endoscopic image monitors 1213a to 1213c, the inclination of the endoscope 802 is always detected by the sensor 1203a according to this embodiment. The CPU 825 creates a virtual image based on the detection result by means of the image processing means within the CPU 825. The CPU 825 causes the monitor 1217 and the virtual image monitor 1217b of the second operator monitor 1234 to display the created image. Similarly, for the first and second treating devices 1238 and 1239, the CPU 825 creates virtual images based on detection results from the sensors 1203b and 1203c by means of the image processing means within the CPU 825. The CPU 825 causes the virtual image monitors 1217a and 1217c of the first and third operator monitors 1232 and 1236 to display the created images.

Thus, since virtual images corresponding to endoscopic live images upon inclination of the insert portion of the endoscope 802 and/or the first and second treating devices 1238 and 1239 can be displayed on the virtual image monitors 1217a to 1217b, the first to third operators 833, 831 and 835 can obtain biological image information of a body to be examined within an observed area of an endoscopic observation image under endoscopic observation.

In the control example according to this embodiment, the CPU 825 activates a detection program shown in FIG. 95 during display of virtual images. In response to a change instruction request of a display mode from an operator through the switch 1203D during surgery, the detection program detects the operation signal and displays a virtual image based on the detection result.

The CPU 825 always detects the presence of a switch manipulation on the switch 1203D in judgment processing at a step S131. In this case, if it is judged that a switch manipulation has been performed on the switch 1203D, the CPU 825 identifies the switch 1203D pressed in the processing at a subsequent step S132 (that is, the switch 1203D pressed by one of the first to third operators 833, 831 and 835) and the type of the operation instruction (command), and the processing goes to judgment processing at a step S133. On the other hand, if it is judged that no switch operation has been performed, the CPU 825 continuously performs judgment processing until a switch manipulation is performed on the switch 1203D.

Then, the CPU 825 judges whether or not the type of the operation instruction (command) by the switch 1203D, which is recognized in the judgment processing at the step S133, is for the simultaneous display mode. If not, the processing returns to the step S131. If for the simultaneous display mode, the processing goes to a step S134.

Then, in the processing at the step S134, the CPU 825 performs display switching processing based on the type of the operation instruction (command) at the step S132. In other words, since the type of the operation instruction (command) by the switch 1203D is a command for the simultaneous display mode, the CPU 825 controls, in the processing at the step S134, the switching section 827A shown in FIG. 93 such that a virtual image corresponding to the treating device of one of the first to third operators 833, 831 and 835 having pressed the switch 1203D can be output and displayed on the virtual image monitors 1217a to 1217c of the first to third operator monitors 1232, 1234 and 1236. Thus, the virtual image corresponding to the treating device (such as one treating device of the endoscope 802 and the first and second treating devices 1238 and 1239) of the operator having pressed the switch 1203D can be simultaneously displayed on the virtual image monitors 1217a to 1217c disposed in the directions of the fields of vision of the operators.

The virtual image display apparatus 1301 according to this embodiment can select and execute a virtual display mode not only through the switch 1203D but also by voice of an operator. The control example by voice input will be described with reference to FIG. 96. The voice input microphone 812B shown in FIGS. 92 and 93 are used by all of the first to third operators 833, 831 and 835.

The CPU 825 activates the detection program shown in FIG. 96 during display of virtual images based on detection results from the sensors 1203a to 1203c of the endoscope 802 and the first and second treating devices 1238 and 1239. In response to a change instruction request of a display mode from an operator through the voice input microphone 812B during surgery, the detection program detects the type of the voice instruction and displays a virtual image based on the detection result.

The CPU 825 exchanges signals with the communication I/F 818 of the system controller 810 and always detects the presence of a voice input through the voice input microphone 812B in judgment processing at a step S141. In this case, if it is judged that a voice input instruction through the voice input microphone 812B has been performed, the CPU 825 identifies the voice input microphone 812B input in the processing at a subsequent step S142 (that is, the voice input microphone 812B of one of the first to third operators 833, 831 and 835) and the type of the voice instruction (command), and the processing goes to judgment processing at a step S143. On the other hand, if it is judged that no voice input instruction has been performed, the CPU 825 continuously performs judgment processing until a voice input instruction is performed through the voice input microphone 812B.

Then, the CPU 825 judges whether or not the type of the voice instruction (command) through the voice input microphone 812B, which is recognized in the judgment processing at the step S143, is a switching operation command. If not, the processing returns to the step S141. If the command is for a switching operation, the processing goes to a step S144.

Then, since the type of voice instruction (command) through the voice input microphone 812B is a command for a switching operation, the CPU 825 controls to perform virtual image display based on the type of the voice instruction. For example, the CPU 825 controls the switching section 827A shown in FIG. 93 such that a virtual image corresponding to the treating device of one of the first to third operators 833, 831 and 835 having given the voice instruction through the voice input microphone 812B can be output and displayed on the virtual image monitors 1217*a* to 1217*c* of the first to third operator monitors 1232, 1234 ad 1236. Thus, the virtual image corresponding to the treating device (such as one treating device of the endoscope 802 and the first and second treating devices 1238 and 1239) of the operator who inputs the voice instruction by using the voice input microphone 812B can be simultaneously displayed on the virtual image monitors 1217*a* to 1217*c* disposed in the directions of the fields of vision of the operators.

Therefore, according to this embodiment, only by performing a switching operation through the switch 1203D or inputting a voice instruction through the voice input microphone 812B, a virtual image corresponding to the treating device (such as one treating device of the endoscope 802 and the first and second treating devices 1238 and 1239) of the operator having pressed the switch 1203D or input the voice instruction can be simultaneously displayed on the virtual image monitors 1217*a* to 1217*c* disposed in the directions of the fields of vision of the operators. Therefore, an operator can securely obtain biological image information (virtual image) of a body to be examined within an observed area of an endoscopic observation image while performing surgery, and the surgery can be performed smoothly. As a result, an easy-to-use virtual display apparatus having a simple construction can be obtained at low costs.

Since, according to this embodiment, the sensors 1203*a* are provided on the trocars 1237 holding the endoscope 802 and the first and second treating devices 1238 and 1239 or the arms of the first to third operators, the weight of the endoscope 802 and first and second treating devices 1238 and 1239 can be reduced. Therefore, the operability of these apparatuses can be improved.

Twelfth Embodiment

Figure 97:
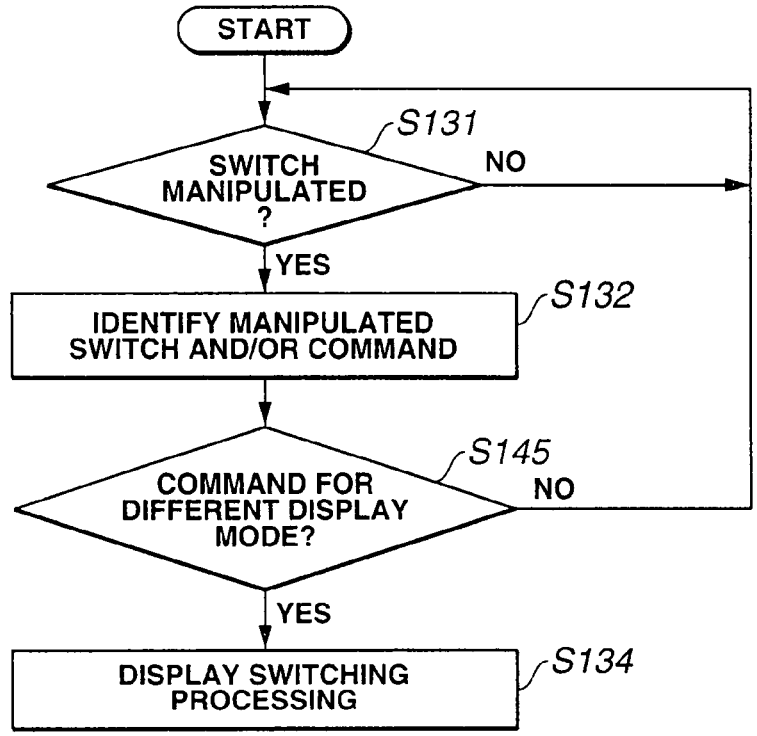
FIG. 97 relates to a virtual image display apparatus of a twelfth embodiment and is a flowchart showing main control processing by a CPU of a virtual image creating section.

FIG. 97 relates to a virtual image display apparatus of a twelfth embodiment and is a flowchart showing control processing by a CPU of a virtual image creating section. In FIG. 97, the same reference numerals are given to the same steps S as those of the processing shown in FIG. 95 of the eleventh embodiment.

The virtual image display apparatus according to this embodiment is substantially the same as the virtual image display apparatus according to the eleventh embodiment, but virtual display control processing by the CPU 825 is different.

A control example by the virtual image display apparatus according to this embodiment will be described with reference to FIG. 97.

Like the eleventh embodiment, the CPU 825 activates a processing routine shown in FIG. 97 during display of virtual images based on detection results from the sensors 1203*a* to 1203*c* of the endoscope 802 and the first and second treating devices 1238 and 1239 and always detects the presence of a switch manipulation on the switch 1203D in judgment processing at a step S131. In this case, if it is judged that a switch manipulation has been performed on the switch 1203D, the CPU 825 identifies the switch 1203 pressed in the processing at a subsequent step S132 (that is, the switch 1203D pressed by one of the first to third operators 833, 831 and 835) and the type of the operation instruction (command), and the processing goes to judgment processing at a step S145. On the other hand, if it is judged that no switch operation has been performed, the CPU 825 continuously performs judgment processing until a switch manipulation is performed on the switch 1203D.

Then, the CPU 825 judges whether or not the type of the operation instruction (command) by the switch 1203D, which is recognized in the judgment processing at the step S145, is for a different display mode. If not, the processing returns to the step S131. If for a different display mode, the processing goes to a step S134.

Then, in the processing at the step S134, the CPU 825 performs display switching processing based on the type of the operation instruction (command) at the step S132. In other words, since the type of the operation instruction (command) by the switch 1203D is a command for a different display mode, the CPU 825 controls, in the processing at the step S134, the switching section 827A shown in FIG. 93 such that virtual images corresponding to the treating devices used by the first to third operators 833, 831 and 835 can be output and displayed on the virtual image monitors 1217*a* to 1217*c* of the first to third operator monitors 1232, 1234 and 1236 irrespective of one of the first to third operators 833, 831 and 835 having pressed the switch 1203D. Thus, the virtual images corresponding to the operators' treating devices (such as the endoscope 802 and the first and second treating devices 1238 and 1239) in accordance with the directions of the fields of vision of the operators can be displayed on the virtual image monitors 1217*a* to 1217*c* disposed in the directions of the fields of vision of the operators.

Also according to this embodiment, virtual display control may be performed by using the voice input microphone 812B like the eleventh embodiment.

Therefore, according to this embodiment, only by performing a switching operation through the switch 1203D or inputting a voice instruction through the voice input microphone 812B, virtual images corresponding to treating devices (such as the endoscope 802 and the first and second treating devices 1238 and 1239) of the operator can be separately displayed on the virtual image monitors 1217*a* to 1217*c* disposed in the directions of the fields of vision of the operators. Therefore, surgery can be performed smoothly. The other advantages are the same as those of the eleventh embodiment.

In the eleventh and twelfth embodiments according to the invention, the endoscope 802 may be an endoscope having a bending portion, the distal end of the insert portion of which is freely bendable. In this case, when a function for detecting a bending angle of the bending portion is provided to the sensor 1203*a*, a virtual image in accordance with a bending angle of the bending portion can be displayed. When a magnetic sensor is provided in a unit accommodating the sensor 1203*a* and when means for irradiating magnetism is provided to the magnetic sensor, an amount of insertion of the endoscope 802 can be detected by performing computation processing by the CPU 825. In other words, virtual images based on amounts of insertion of the endoscope 802 and first and second treating devices 1238 and 1239 can be displayed. In this case, amounts of insertion of the endoscope 802 and first and second treating devices 1238 and 1239 may be detected by using a rotary encoder instead of a magnetic sensor.

With a virtual image display apparatus having a simple construction according to this embodiment, biological image information of a body to be examined within an observed area of an endoscopic observation image can be obtained at low costs under endoscopic observation and be securely provided to multiple operators during surgery as required, which is an advantage.

Since, with a virtual image display apparatus having a simple construction according to this embodiment, biological image information of a body to be examined within an observed area of an endoscopic observation image can be obtained at low costs under endoscopic observation and be securely provided to multiple operators during surgery as required, the virtual image display apparatus is especially effective for performing surgery by an operator operating an endoscope and an operator and assistant performing a forceps treatment by using the first and second treating devices.

Thirteenth Embodiment

Figure 98:
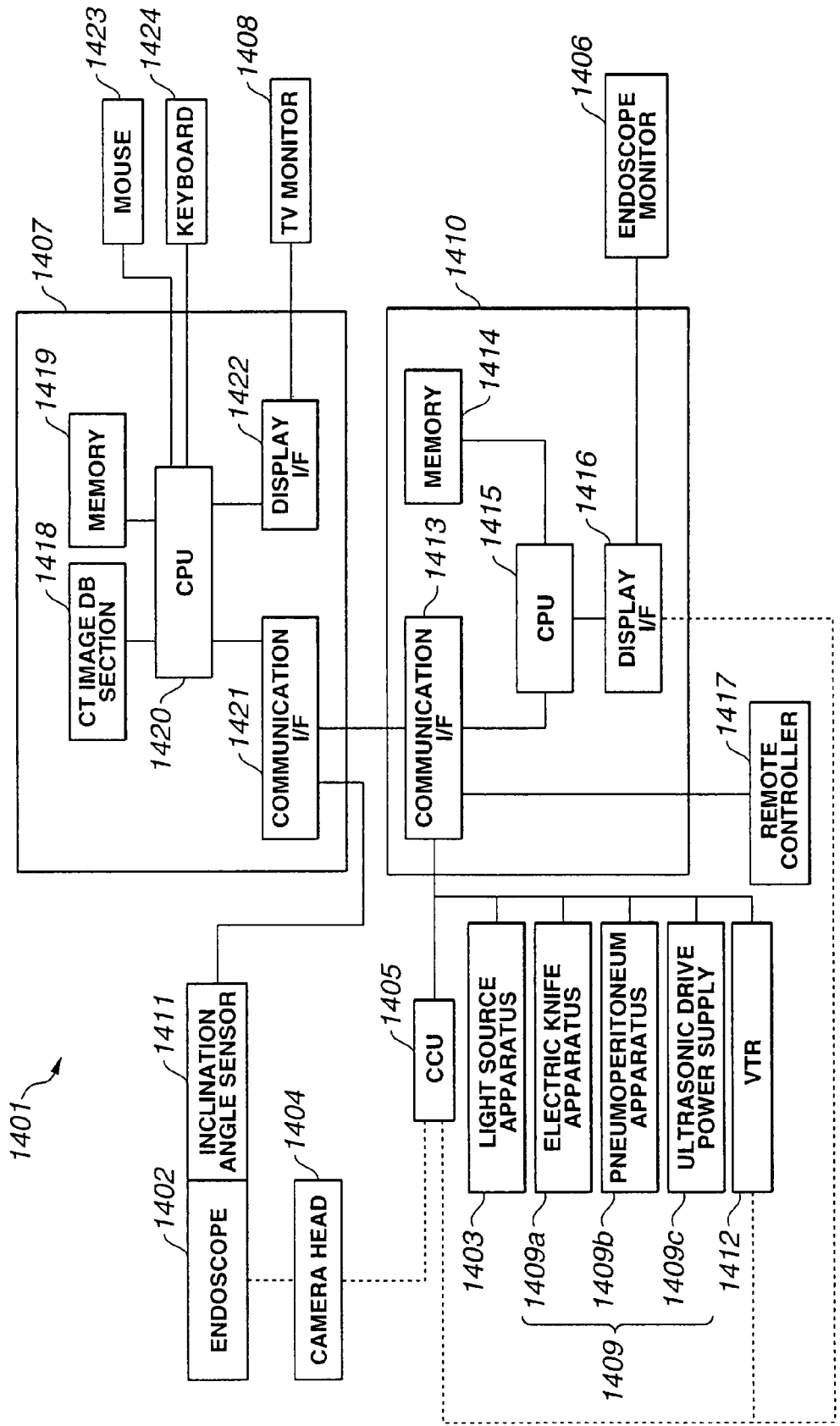
FIG. 98 is an entire configuration diagram showing an object observation system according to a thirteenth embodiment.
Figure 99:
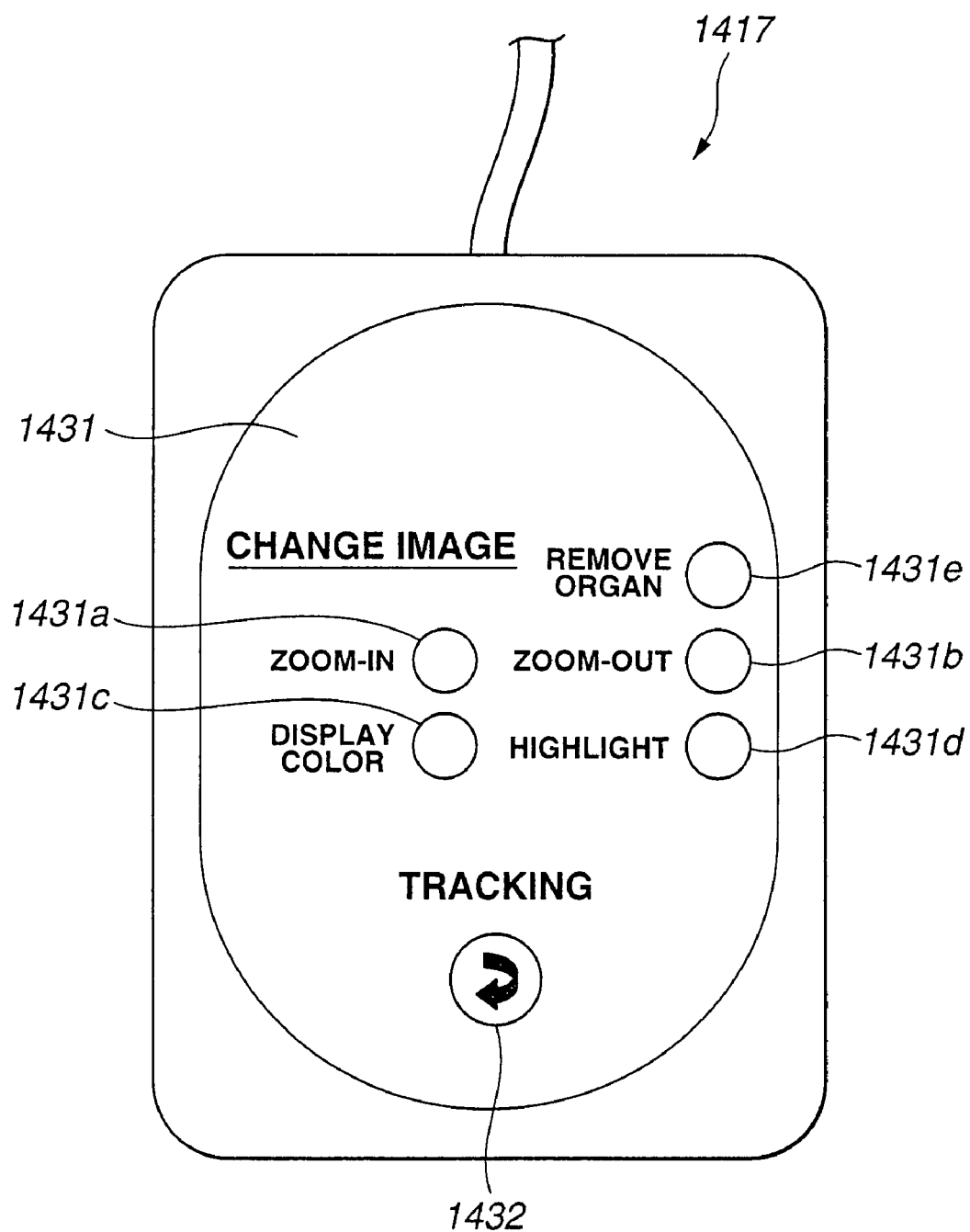
FIG. 99 is a construction diagram showing a construction of a remote controller for an operator in FIG. 98.
Figure 100:
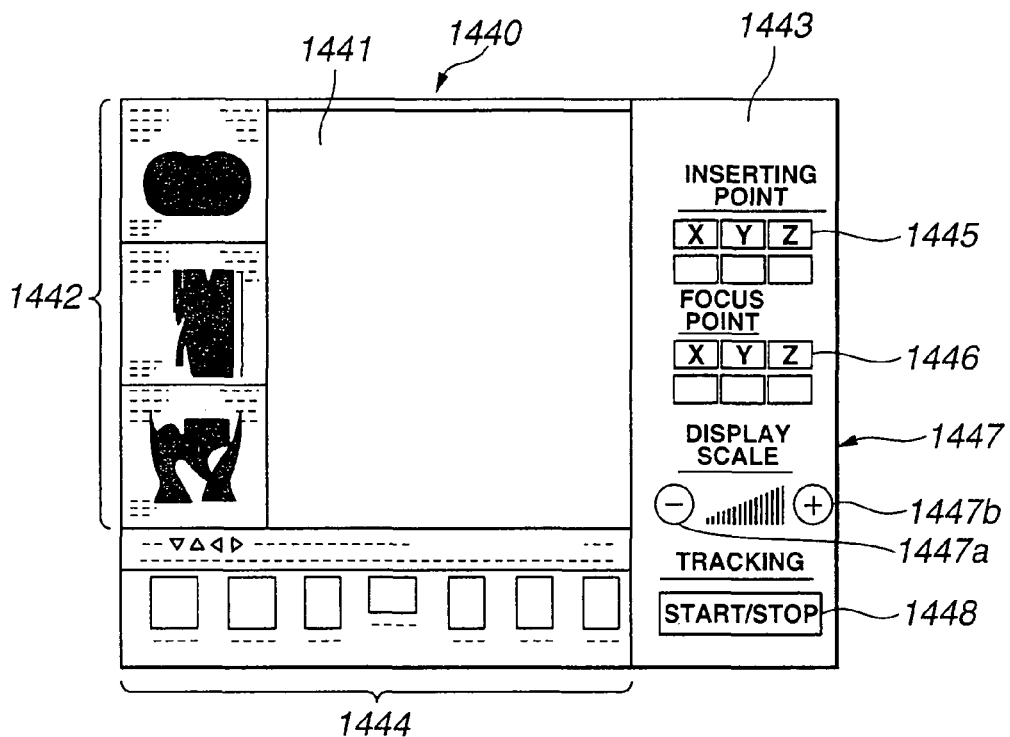
FIG. 100 is a screen display example of a virtual image display screen displayed on a VR monitor in FIG. 98.
Figure 101:
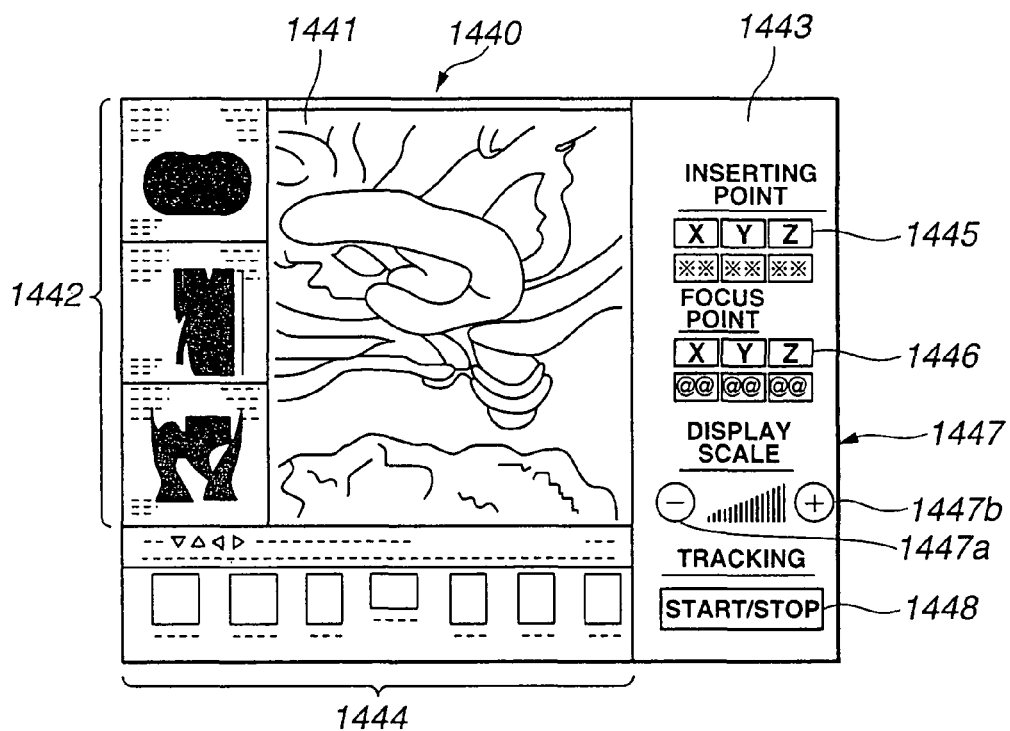
FIG. 101 is a screen display example on which a virtual image is displayed in a virtual image display area in FIG. 100.
Figure 102:
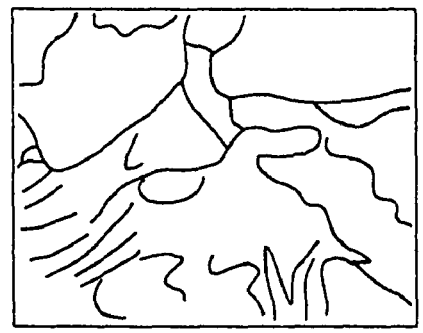
FIG. 102 is an example of an endoscopic live image displayed on an endoscope monitor in FIG. 98.
Figure 103:
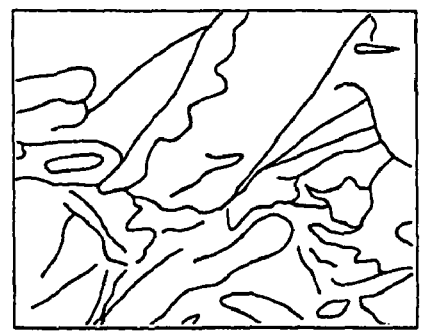
FIG. 103 is an example of an endoscopic live image displayed on the endoscope monitor when the endoscope is moved.
Figure 104:
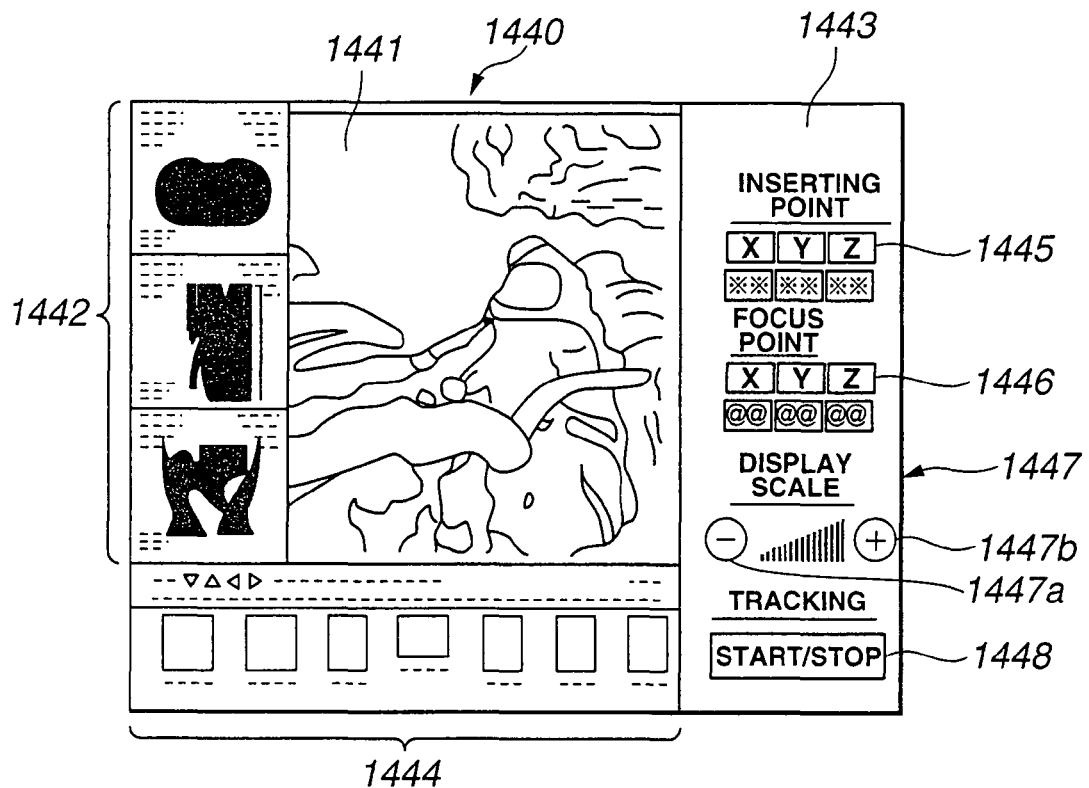
FIG. 104 is a screen display example in which a virtual image agreeing with the endoscopic live image in FIG. 103 is displayed on the virtual image display area.
Figure 106:
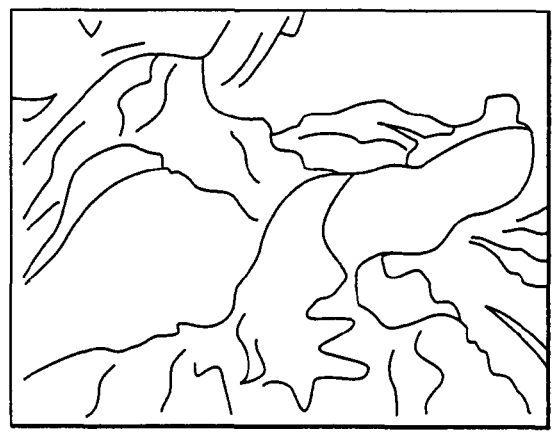
FIG. 106 is an example of an endoscopic live image for illustrating an operation of the thirteenth embodiment.
Figure 105:
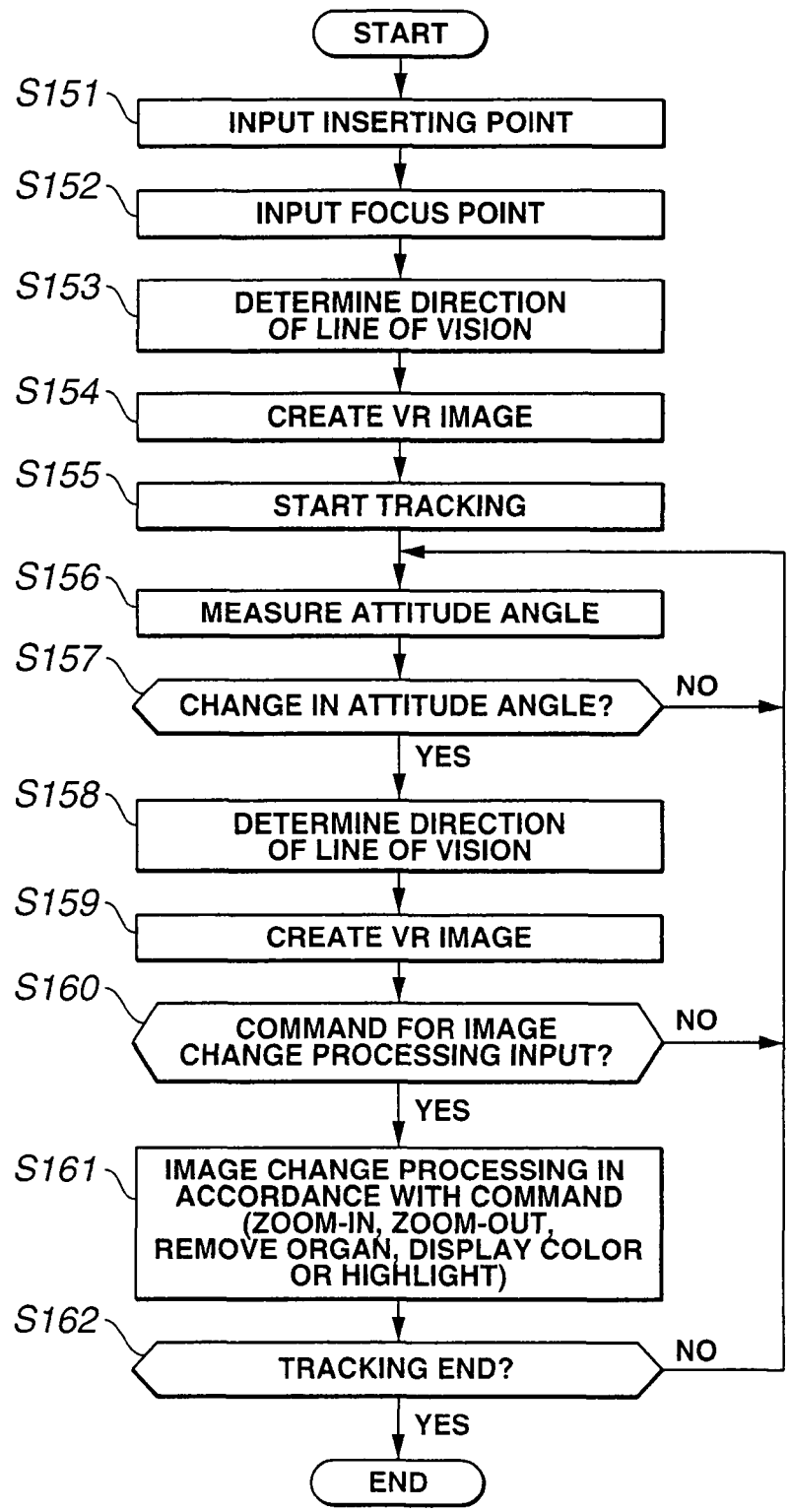
FIG. 105 is a flowchart showing a processing operation, which is a feature of the thirteenth embodiment.
Figure 107:
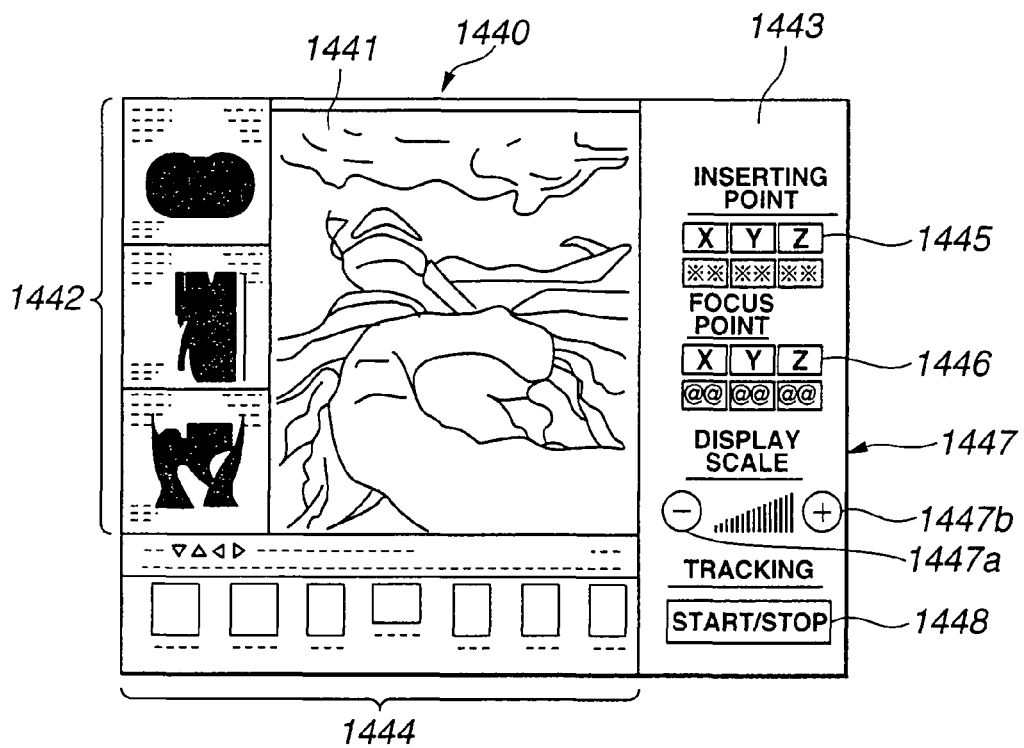
FIG. 107 is a first screen display example of a virtual image display screen for illustrating the operation of the thirteenth embodiment.
Figure 108:
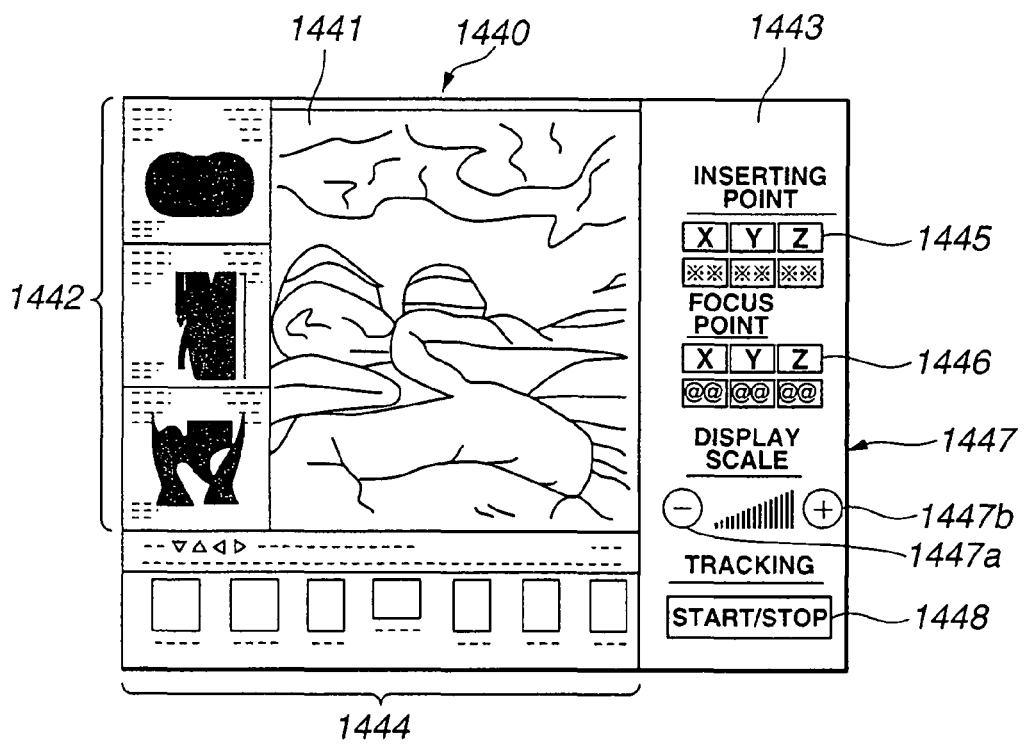
FIG. 108 is a screen display example of a virtual image display screen on which a virtual image in FIG. 107 is enlarged.
Figure 109:
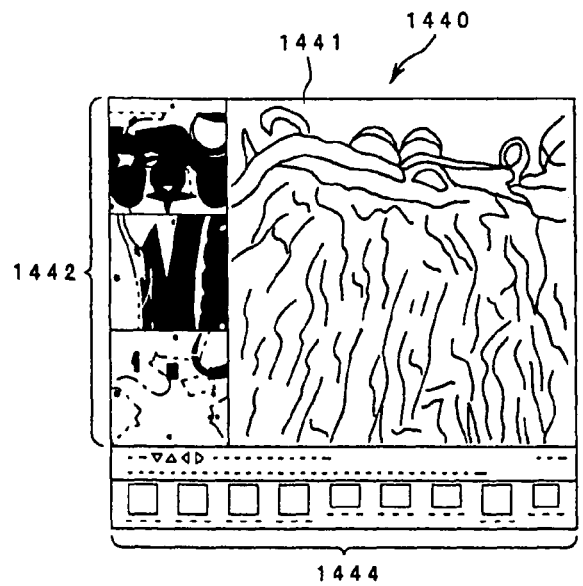
FIG. 109 is a second screen display example of a virtual image display screen for illustrating an operation of the thirteen embodiment.
Figure 110:
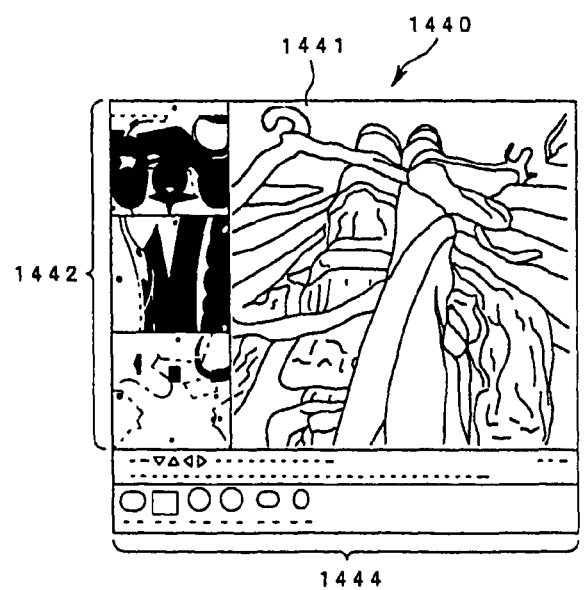
FIG. 110 is a screen display example of a virtual image display screen when organ removal processing is performed on the virtual image in FIG. 108.
Figure 111:
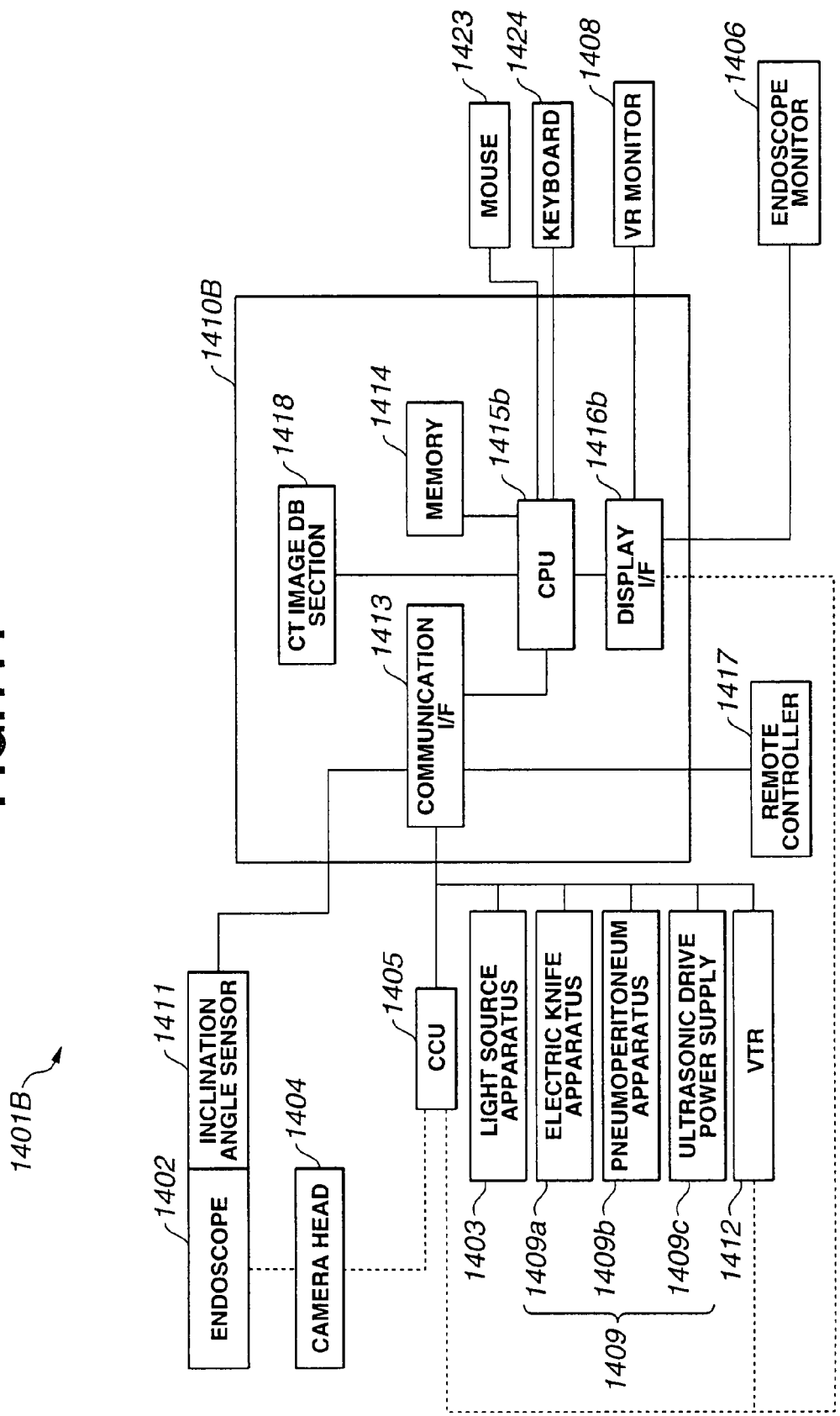
FIG. 111 is an entire configuration diagram of an object observation system showing a variation example of the thirteenth embodiment.

FIGS. 98 to 111 relate to a thirteenth embodiment of the invention. FIG. 98 is an entire configuration diagram showing an object observation system according to a thirteenth embodiment. FIG. 99 is a construction diagram showing a construction of a remote controller for an operator in FIG. 98. FIG. 100 is a screen display example of a virtual image display screen displayed on a VR monitor in FIG. 98. FIG. 101 is a screen display example on which a virtual image is displayed in a virtual image display area in FIG. 100. FIG. 102 is an example of an endoscopic live image displayed on an endoscope monitor in FIG. 98. FIG. 103 is an example of an endoscopic live image displayed on the endoscope monitor when the endoscope is moved. FIG. 104 is a screen display example in which a virtual image agreeing with the endoscopic live image in FIG. 103 is displayed on the virtual image display area. FIG. 105 is a flowchart showing a processing operation, which is a feature of the thirteenth embodiment. FIG. 106 is an example of an endoscopic live image for illustrating an operation of this embodiment. FIG. 107 is a first screen display example of a virtual image display screen for illustrating the operation of this embodiment. FIG. 108 is a screen display example of a virtual image display screen on which a virtual image in FIG. 107 is enlarged. FIG. 109 is a second screen display example of a virtual image display screen for illustrating an operation of this embodiment. FIG. 110 is a screen display example of a virtual image display screen when organ removal processing is performed on the virtual image in FIG. 108. FIG. 111 is an entire configuration diagram of an object observation system showing a variation example of the thirteenth embodiment.

According to this embodiment, the invention is applied to a surgical system for an endoscopic surgery.

As shown in FIG. 98, an object observation system 1401 according to the thirteenth embodiment includes an endoscope 1402, a light source apparatus 1403, a camera head 1404, a camera control unit (CCU) 1405, an endoscope monitor 1406, a virtual image creating section 1407, a volume rendering (VR, hereinafter) monitor 1408, multiple medical equipment 1409 and a system controller 1410. The endoscope 1402 is observation means which can observe a body to be examined. The light source apparatus 1403 supplies illumination light to the endoscope 1402. The camera head 1404 is removably attached to the endoscope 1402 and self-contains an image pickup apparatus for picking up a body to be examined image obtained by the endoscope 1402. The CCU 1405 performs signal processing on the image pickup apparatus of the camera head 1404. The endoscope monitor 1406 displays endoscopic optical image resulting from signal processing by the CCU 1405 as endoscopic live images. The virtual image creating section 1407 performs image processing on pre-stored virtual image data and creates a volume rendering image (simply called virtual image, hereinafter). The VR monitor 1408 displays a virtual image resulting from image processing by the virtual image creating section 1407 as a reference image. The multiple medical equipment 1409 performs a treatment on an affected part of a patient, which is a body to be examined. The system controller 1410 centrally controls the light source apparatus 1403, the CCU 1405, the virtual image creating section 1407 and the medical equipment 1409.

Though not shown, the endoscope 1402 has a long and narrow insert portion and an eyepiece connected to the proximal end of the insert portion. The endoscope 1402 holds a light guide (not shown) therethrough for transmitting illumination light. The light guide transmits illumination light from the light source apparatus 1403. The illumination light having been transmitted from the light guide illuminates a body to be examined such as an affected part from an illumination optical system (not shown) disposed at the distal end of the insert portion.

The endoscope 1402 captures a body to be examined image from an objective optical system (not shown) adjacent to the illumination optical system. The captured subject image is transmitted to the eyepiece by an image transmitting optical system (not shown) such as a relay lens and an image guide and is enlarged from an eyepiece optical system (not shown) in the eyepiece so that the body to be examined image can be observed as an endoscopic optical image.

According to this embodiment, the endoscope 1402 includes an inclination angle sensor 1411 for detecting an inclination angle of the insert portion. Inclination angle data detected by the inclination angle sensor 1411 is supplied to the virtual image creating section 1407. By starting tracking, which will be described later, the virtual image creating section 1407 performs image processing on virtual image data based on inclination angle data detected by the inclination angle sensor 1411 such that the result can agree with endoscopic live images.

The camera head 1404 removably attached to the endoscope eyepiece can capture an endoscopic optical image transmitted from the eyepiece optical system of the endoscope eyepiece. The camera head 1404 optoelectronically converts the endoscopic optical image captured from the endoscope 1402 to image pickup signals by means of an image pickup apparatus (not shown) such as a CCD and outputs the image pickup signals to the CCU 1405.

The CCU 1405 performs signal processing on image pickup signals from the camera head 1404 and generates standard video signals thereby. Then, the CCU 1405 outputs the standard video signals to the endoscope monitor 1406 through the system controller 1410. The endoscope monitor 1406 displays an endoscopic optical image on the display screen as an endoscopic live image.

While the object observation system 1401 according to this embodiment has an optical endoscope which can observe, through the eyepiece, a body to be examined image captured from the distal end of the insert portion and transmitted by image transmitting means to the eyepiece and a camera head, which is mounted at the eyepiece of the optical endoscope, for picking up an endoscopic optical image from the eyepiece, the invention is not limited thereto. The object observation system 1401 may include an electronic endoscope self-containing, at the distal end of the insert portion, an image pickup apparatus for picking up a body to be examined image. In this case, the electronic endoscope may have a scaling function by which an objective optical system can be moved in the optical axis direction.

The CCU 1405 supplies generated video signals to the VTR 1412. The VTR 1412 is connected to the system controller 1410 and records and stores a desired endoscopic optical image in response to an operation instruction from an operator.

The medical equipment 1409 includes a pneumoperitoneum apparatus 1409*a*, an electric knife apparatus 1409*b*, and an ultrasonic surgical apparatus 1409*c*. The pneumoperitoneum apparatus 1409*a* supplies gas such as carbon dioxide into the abdomen area of a patient through a pneumoperitoneum tube (not shown) in order to establish a field of vision within the abdomen area. The electric knife apparatus 1409b performs coagulation/resection treatments on an affected part by supplying high frequency power to an electric knife (not shown). The ultrasonic surgical apparatus 1409c performs coagulation/resection treatments on an affected part by supplying electric energy to an ultrasonic treating device (not shown) and using ultrasonic vibration generated by the ultrasonic treating device.

These medical equipment 1409 are connected to the system controller 1410.

The system controller 1410 centrally controls different kinds of operations of the entire system. The system controller 1410 has a communication interface (called communication I/F, hereinafter) 1413, a memory 1414, a CPU (central processing unit) 1415 as a control portion and a display interface (called display I/F, hereinafter) 1416.

The communication I/F 1413 communicates with the light source apparatus 1403, the CCU 1405, the virtual image creating section 1407 and the medical equipment 1409. The exchange of control signals and the exchange of image data are controlled by the CPU 1415. A remote controller 1417 as virtual image change instruction means is connected to the communication I/F 1413. The remote controller 1417 is used by an operator to instruct to perform image processing on a virtual image displayed on the VR monitor 1408 as described later. A detail construction of the remote controller 1417 will be described later.

The memory 1414 stores image data of endoscopic still images and data such as equipment setting information, for example. The data storing and reading are controlled by the CPU 1415.

The display I/F 1416 outputs video signals from the CCU 1405 or the VTR 1412 to the endoscope monitor 1406. Thus, an endoscopic live image can be displayed on a display screen of the endoscope monitor 1406.

The CPU 1415 controls different kinds of operations in the system controller 1410, that is, performs control over exchanges of different kinds of signals by the communication I/F 1413 and the display I/F 1416, control over writing and/or reading of image data to/from the memory 1414, control over display by the endoscope monitor 1406, and control over different kinds of operations based on operation instruction signals from the remote controller 1417.

The system controller 1410 controls the medical equipment 1409 under the control of the CPU 1415. The system controller 1410 outputs video signals from the CCU 1405 to the endoscope monitor 1406. Thus, endoscopic live images can be displayed on a display screen of the endoscope monitor 1406.

In the system controller 1410, the CPU 1415 controls the virtual image creating section 1407 based on an operation instruction signal from the remote controller 1417.

The virtual image creating section 1407 has a CT image DB section 1418, a memory 1419, a CPU 1420, a communication I/F 1421 and a display I/F 1422.

The CT image DB section 1418 includes a CT image data capturing portion (not shown) for capturing virtual image data created by a publicly known CT apparatus, not shown, for imaging an X-ray tomographic image of a body to be examined through a portable memory medium such as a magneto-optical (MO) disk and a digital versatile disk (DVD). Thus, the CT image DB section 1418 can store the captured virtual image data. That is, the CT image DB section 1418 includes virtual image data storing means. The reading and writing of the virtual image data from/to the CT image DB section 1418 are controlled by the CPU 1420.

The memory 1419 stores the virtual image data from a portable recording medium and data such as virtual image data image-processed by the CPU 1420. Thus, the storing and reading data are controlled by the CPU 1420.

The communication I/F 1421 is connected to the communication I/F 1413 of the system controller 1410 and the inclination angle sensor 1411. The communication I/F 1421 exchanges control signals required for performing different kinds of operations in connection with the virtual image creating section 1407 and the system controller 1410. The communication I/F 1421 is controlled by the CPU 1420, and the received signals are captured into the CPU 1420.

The display I/F 1422 sends virtual image data created under the control of the CPU 1420 to the VR monitor 1408. Thus, a virtual image is displayed on the VR monitor 1408 connecting to the display I/F 1422.

The mouse 1423 and the keyboard 1424 are connected to the CPU 1420. The mouse 1423 and the keyboard 1424 are operation means to be used for inputting and/or setting different kinds of setting information. As described later, the mouse 1423 and the keyboard 1424 may be used as observation information input means to input inserting point information and focus point information of the endoscope 1402 with respect to a body to be examined.

The CPU 1420 performs different kinds of operations in the virtual image creating section 1407, that is, performs control over exchanges different kinds of signals by the communication I/F 1421 and the display I/F 1422, control over writing and/or reading of image data to/from the memory 1419, control over display by the VR monitor 1408, and control over different kinds of operations based on operation signals from the mouse 1423 and/or the keyboard 1424.

The CPU 1420 performs display control such that image processing can be performed on virtual image data read from the CT image DB section 1418 based on inclination angle data from the inclination angle sensor 1411 and the virtual image can be displayed on the VR monitor 1408.

The CPU 1420 further performs virtual image change processing for changing a virtual image based on an operation instruction from the remote controller 1417 for a virtual image displayed on the VR monitor 1408 under the control of the CPU 1415 of the system controller 1410. In other words, the CPU 1415 of the system controller 1410 and the CPU 1420 of the virtual image creating section 1407 are included in virtual image processing means.

The remote controller 1417 includes, as shown in FIG. 99, an image change operation portion 1431 for performing different kinds of image change processing and a tracking button 1432 for implementing tracking, for example.

The image change operation portion 1431 includes, as image change commands, a zoom-out button 1431a, a zoom-in button 1431b, a display color button 1431c, a highlight button 1431d and a remove organ button 1431e. The zoom-out button 1431a is used for decreasing a display scale. The zoom-in button 1431b is used for increasing a display scale. The display color button 1431c is used for changing a display color of a predetermined area. The highlight button 1431d is used for highlighting a predetermined area by increasing or decreasing the intensity. The remove organ button 1431e is used for removing an organ so as to view a predetermined area easily.

By using the remote controller 1417 having these image change commands (buttons 1431a to 1431e), an operator can perform operations for obtaining a desired virtual image.

Next, a display example, which is a feature of the object observation system 1401, will be described with reference to FIGS. 100 to 104.

In response to an operation instruction through a manipulation on the remote controller 1417 by an operator, the CPU 1415 of the system controller 1410 controls the CPU 1420 of the virtual image creating portion 1407 to display a virtual image display screen 1440 shown in FIG. 100, for example, on the display screen of the VR monitor 1408.

The virtual image display screen 1440 includes a virtual image display area 1441, a 2D image display area 1442, an operation setting area 1443 and a selected display area 1444. The virtual image display area 1441 is the center of the screen and displays a virtual image. The 2D image display area 1442 is a part close to the left end of the screen and displays multiple 2D images. The operation setting area 1443 is a part close to the right end of the screen and is used for manipulating and/or setting the virtual image display area 1441. The selected display area 1444 is disposed in a part close to the lowest end of the screen and is used for implementing 3D display of one of the other multiple reference images (thumbnail images).

The operation setting area 1443 includes an inserting point input area 1445, and a focus-point input area 1446. The inserting point input area 1445 is used for inputting values (called inserting point) in the X, Y and Z directions of the abdomen area into which the endoscope 1402 is inserted. The focus-point input area 1446 is used for inputting values (in angle, called focus point) in the X, Y and Z directions of the axial direction of the endoscope 1402 where the endoscope 1402 is inserted into the abdomen area.

In accordance with inputs to these inserting point input area 1445 and focus point input area 1446, the CPU 1420 of the virtual image creating section 1407 determines a direction of line of vision of a virtual image in order to implement virtual image display.

The operation setting area 1443 includes a zoom-in/zoom out operation area 1447 and a tracking start/stop button 1448. The zoom-in/zoom out area 1447 includes a zoom-in switch 1447*a* and zoom-out switch 1447*b* for increasing and decreasing a display scale. The tracking start/stop button 1448 is used for starting/stopping tracking.

In order to activate the object observation system 1401, the virtual image display screen 1440 shown in FIG. 100 is displayed on the VR monitor 1408 first of all. Then, information (inserting point) indicating into which point of the abdomen area of a patient the endoscope 1402 is to be inserted is input to the inserting point input area 1445 by using the mouse 1423 or the keyboard 1424. After that, the focus-point input area 1446 is selected, and a value (focus point) in the axial direction of the endoscope 1402 is required to input in a similar way the focus point input area 1446 where the endoscope 1402 is inserted into the abdomen area.

In other words, the CPU 1420 of the virtual image creating section 1407 determines a direction of line of vision based on positional information (inserting point and focus point) of the endoscope 1402, performs image processing on virtual image data and displays the virtual image on the virtual display area 1441.

Thus, as shown in FIG. 101, a display screen displaying a virtual image in response to an input of positional information (inserting point and focus point) of a predetermined endoscope is obtained on the virtual image display area 1441. Here, an endoscopic live image is displayed on the endoscope monitor 1406 as shown in FIG. 102.

Upon starting tracking, endoscopic live images are displayed on the endoscope monitor 1406 in response to movement of the endoscope as shown in FIG. 103, for example. Thus, based on inclination angle data detected by the inclination angle sensor 1411, the CPU 1420 of the virtual image creating section performs image processing on virtual image data in accordance with the endoscopic live images and display the virtual image on the virtual image display area 1441 as shown in FIG. 104.

According to this embodiment, based on an operation instruction by an operator during surgery through the remote controller 1417, image change processing can be implemented such as zooming-in, zooming-out and organ removal.

A processing operation, which is a feature of this embodiment, will be described in detail with reference to FIGS. 106 to 109 based on a flowchart shown in FIG. 105.

Here, surgery is performed on a body to be examined within the abdomen area of a patient by using the object observation system 1401 shown in FIG. 98. In this case, when the object observation system 1401 has power applied thereto, a program based on a control method for the object observation system of the invention, which is stored in the CPU 1415 of the system controller 1410, is started first of all. Thus, the CPU 1415 of the system controller 1410 controls the CPU 1420 of the virtual image creating section 1407. As described above, the virtual image display screen 1440 shown in FIG. 100 is displayed on the VR monitor 1408.

Then, by using the mouse 1423 or the keyboard 1424 and with reference to a virtual image displayed on the virtual image display area 1441 of the VR monitor 1408, a nurse or an operator inputs, in the inserting point input area 1445, information (inserting point) regarding which position in the abdomen area of a patient the endoscope 1402 is inserted into (step S151). Then, the nurse or operator selects the focus-point input area 1446 and inputs an axial value (focus point) of the endoscope 1402 thereto where the endoscope 1402 is inserted to the abdomen area similarly in the focus-point input area 1446 (step S152). Thus, the direction of the line of vision is determined (step S153). The steps S151 and S152 are included in an observation information input process.

Hence, the virtual image data in accordance with the inserting point and focus point of the endoscope 1402 undergoes image processing by the CPU 1420 of the virtual image creating section 1407. Then, the result is displayed in the virtual image display area 1441 of the virtual image display screen 1440 as shown in FIG. 101, for example.

Then, the operator inserts the endoscope 1402 into the abdomen area of the patient. In a body to be examined image obtaining process, the object observation system 1401 causes the endoscopic live images obtained by the endoscope 1402 to be displayed on the display screen of the endoscope monitor 1406 under the display control of the CPU 1415 of the system controller 1410 as shown in FIG. 102, for example.

The operator performs surgery with reference to the endoscopic live images and sometimes with reference to the virtual image display screen 1440.

Then, the operator starts tracking by pressing the tracking button 1432 of the remote controller 1417 (step S155).

Thus, the CPU 1420 of the virtual image creating section 1407 measures an attitude angle (step S156) by always detecting an inclination of the endoscope 1402 by using the inclination angle sensor 1411 and determines whether the attitude angle is changed or not (step S157).

Here, during surgery, an operator moves the endoscope 1402. Then, endoscopic live images in accordance with the inclinations of the endoscope 1402 are displayed as shown in FIG. 102, for example, on the endoscope monitor 1406.

On the other hand, when the CPU 1420 of the virtual image creating section 1407 determines the attitude angle has been changed here, the CPU 1420 determines a direction of a line of vision (focus point) of the endoscope 1402 based on the detected inclination angle data (step S157). Then, the CPU

1420 of the virtual image creating section 1407 performs image processing on the virtual image data such that the virtual images can agree with the endoscopic live images, creates virtual images (step S159) and causes the VR monitor 1408 (in the virtual image display area 1441 of the virtual display screen 1440) to display the virtual images. In other words, the step S159 is a virtual image processing process.

Here, when the endoscope is an electronic endoscope having a scaling function, the display scale of virtual images may be changed such that the virtual images can agree with the endoscopic live images, which are scaled in accordance with a scaling operation of the electronic endoscope, in the virtual image processing process.

Thus, the virtual images, as shown in FIG. 103, corresponding to the endoscopic live images in accordance with different states of the position, direction, display scale and so on of the endoscope can be displayed on the virtual display screen 1440 of the VR monitor 1408. The operator can obtain more detail image information fast and securely thereby.

Based on an operation instruction signal by the operator through the remote controller 1417, the CPU 1415 of the system controller 1410 detects whether an image change command is input or not (step S160). If so, the CPU 1415 controls the CPU 1420 of the virtual image creating section 1407 to perform image change processing in accordance with the command (step S161). In other words, the step S161 is included in a virtual image change process.

Here, for example, as shown in FIG. 106, an endoscopic live image is displayed on the display screen of the endoscope monitor 1406, and the virtual display screen 1440 is displayed on the display screen of the VR monitor 1408 as shown in FIG. 107.

In this case, the operator manipulates the zoom-in button 1431b of the remote controller 1417 in order to increase the display scale of the virtual image displayed on the virtual image display area 1441. Thus, the CPU 1420 of the virtual image creating section 1407 performs zoom-in processing on the virtual image currently displayed on the virtual image display area 1441 in accordance with the manipulation on the zoom-in button 1431b of the remote controller 1417 and causes the virtual image to be displayed on the virtual image display area 1441 as shown in FIG. 108.

When the virtual display screen 1440 is displayed as shown in FIG. 109, the operator may manipulate the remove organ button 1431e of the remote controller 1417 in order to check how the blood vessels lie by getting the organ out of the virtual image.

Thus, the CPU 1420 of the virtual image creating section 1407 performs organ removal processing on the virtual image currently displayed on the virtual image display area 1441 in accordance with the manipulation on the organ remove button 1431e of the remote controller 1417 and causes the virtual image to be displayed on the virtual image display area 1441 as shown in FIG. 110.

The virtual display screen 1440 shown in FIGS. 109 and 110 has the virtual image display area 1441 extended to the right end without the operation setting area 1443.

According to this embodiment, a virtual image can be changed by zooming-in, zooming-out, removing organs and/or the like based on an operation instruction through the remote controller 1417 by an operator during surgery.

Subsequently, the processing from the step S156 is repeated until the tracking is terminated (step S162) in response to the manipulation on the tracking button 1432 again by the operator.

Therefore, the operator can obtain required information fast and securely by performing simple manipulations while he/she is performing surgery.

As a result, according to this embodiment, an easy-to-use object observation system can be obtained which can display a virtual image intended by an operator as a reference image. Thus, the security of an operation can be improved, which can largely contribute to the reduction of an operation time.

The object observation system may have a construction as shown in FIG. 111. FIG. 111 is an entire configuration diagram of an object observation system according to a variation example of the thirteenth embodiment.

The object observation system 1401B has a system controller 1410B integrated to the virtual image creating section 1407 as shown in FIG. 111.

The system controller 1410B includes a CT image DB section 1418b, a communication I/F 1413b, a memory 1414b, a CPU 1415b and a display I/F 1416b. The CT image DB section 1418b performs the same operations as those of the CT image DB section 1418 of the virtual image creating section 1407. The communication I/F 1413b is connected to the light source apparatus 1403, the CCU 1405, the medical equipment 1409, the VTR 1412, the inclination angle sensor 1411 and the remote controller 1417 and also functions as the communication I/F 1421 of the virtual image creating section 1407. The memory 1414b also functions as the memory 1419 of the virtual image creating section 1407. The CPU 1415b is connected to the mouse 1423, the keyboard 1424 and the remote controller 1417 and also functions as the CPU 1420 of the virtual image creating section 1407. The display I/F 1416b is connected to the endoscope monitor 1406 and the VR monitor 1408 and also functions as the display I/F 1422 of the virtual image creating section 1407.

Since the object observation system 1401B has substantially the same construction and operations as those of the thirteenth embodiment except that the system controller 1410B also functions as the virtual image creating section 1407, the description thereof will be omitted herein.

Thus, since the object observation system 1401B can obtain substantially the same advantages as those of the thirteenth embodiment, and since the system controller 1410B can also function as the virtual image creating section 1407, the object observation system 1401B can be reduced in size as a whole and can be constructed at low costs.

Fourteenth Embodiment

Figure 112:
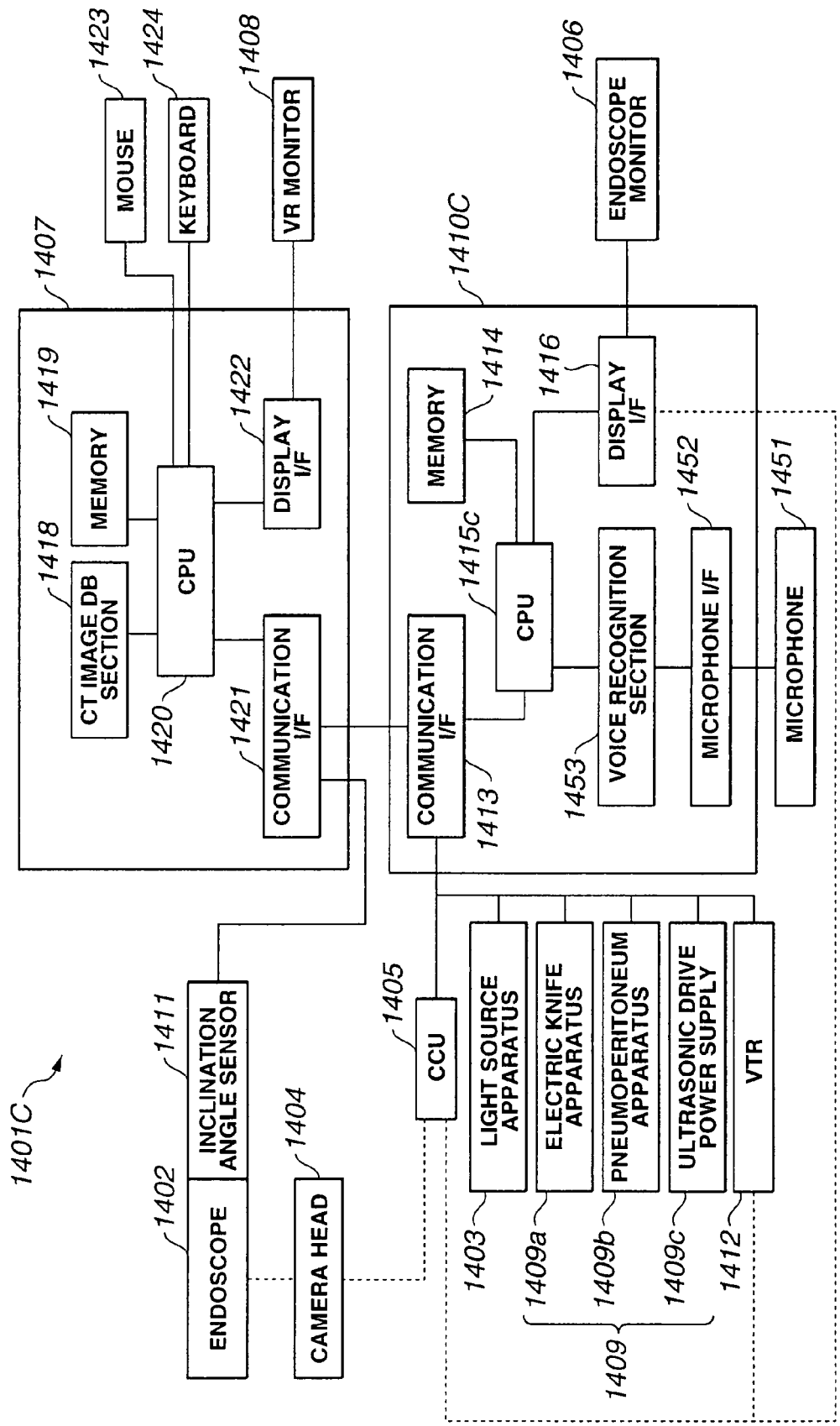
FIG. 112 is an entire configuration diagram showing an object observation system according to a fourteenth embodiment.
Figure 113:
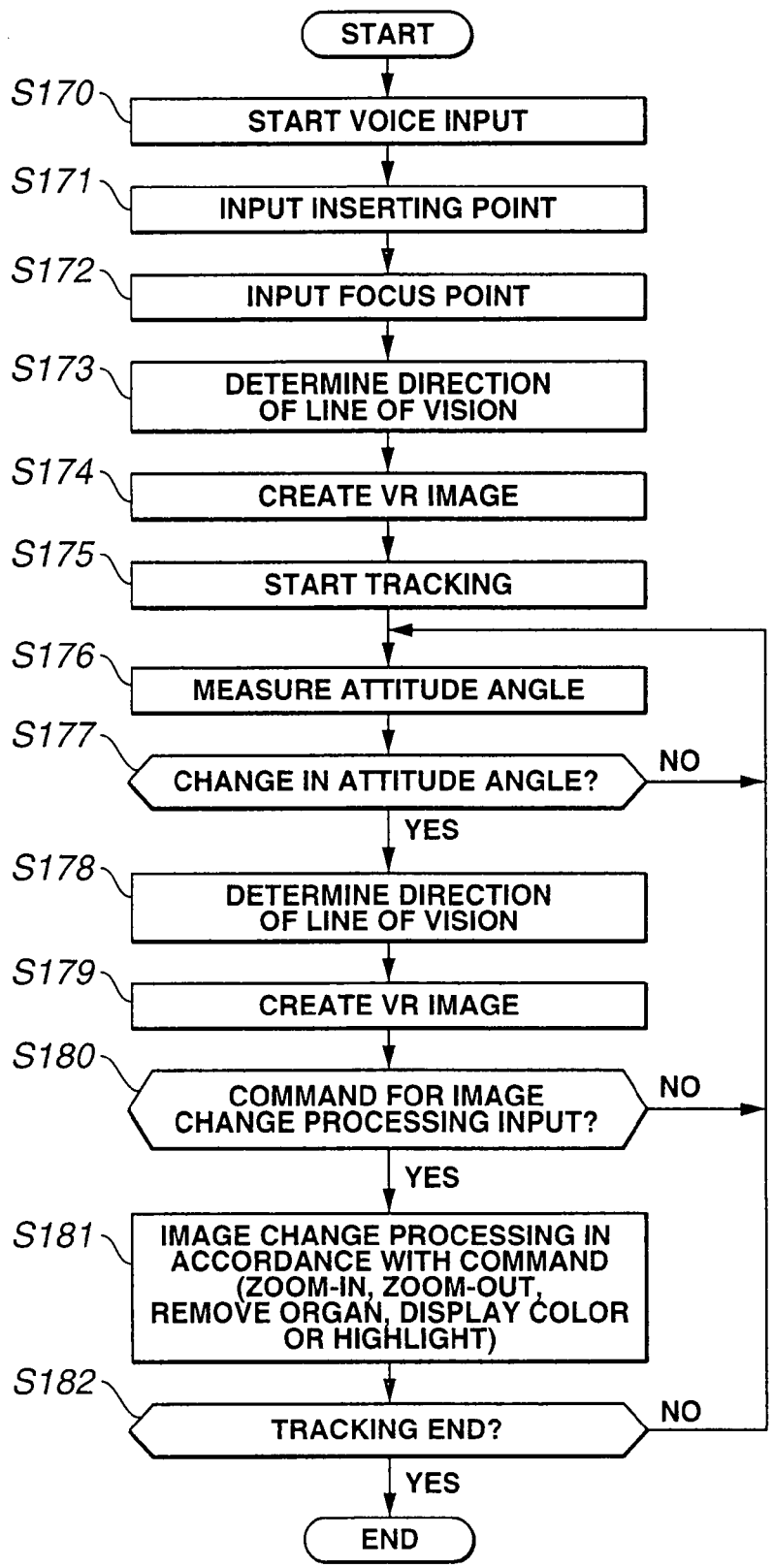
FIG. 113 is a flowchart showing processing operation, which is a feature of the fourteenth embodiment.

FIGS. 112 and 113 relate to a fourteenth embodiment of the invention. FIG. 112 is an entire configuration diagram showing an object observation system according to the fourteenth embodiment. FIG. 113 is a flowchart showing processing operation, which is a feature of the fourteenth embodiment.

While the thirteenth embodiment has the remote controller 1417 to be manipulated and used to instruct by an operator as virtual image change instructing means, the fourteenth embodiment has a microphone to be manipulated and used to instruct by an operator as the virtual image change instructing means. Since the other components are the same as those of the thirteenth embodiment, the description thereof will be omitted. The same reference numerals are given to the same components in the description.

In other words, as shown in FIG. 112, an object observation system 1401C according to the fourteenth embodiment includes a system controller 1410C connecting to the microphone 1451 for capturing voice of an operator. As described later, the microphone 1451 can be used for inputting inserting point information and focus-point information of the endoscope 1402 with respect to a body to be examined as observation information input means.

The microphone 1451 is, for example, mounted on the head set, not shown, to be attached to the head of an operator and is removably connected to the system controller 1410C. The microphone 1451 may be a pin microphone, which can be attached to an operator.

The system controller 1410C has a microphone I/F 1452 connecting to the microphone 1451 and a voice recognizing portion 1453 for signal-converting voice signals received by the microphone I/F 1452, recognizing the voice command and outputting a command signal in accordance with the recognized voice command to the CPU 1415c.

The rest of the construction is substantially the same as that of the thirteenth embodiment, and the description thereof will be omitted herein.

Then, in the object observation system 1401C, the CPU 1415c of the system controller 1410C controls the entire system under the voice control of an operator through the microphone 1451.

In the same manner as that of the thirteenth embodiment, the object observation system 1401C can perform image processing and display processing on virtual image data and image change processing on virtual images such as zoom-in, zoom-out and organ removal in response to inputs of an inserting point and a focus point under the voice control of an operator during surgery through the microphone 1451.

A processing operation, which is a feature of the fourteenth embodiment, is shown in FIG. 113.

In the flowchart shown in FIG. 113, the object observation system 1401C is powered on in order to perform surgery on a body to be examined within the abdomen area of a patient so that voice input to the system controller 1410C through the microphone 1451 can be performed, which is the start of a voice input (step S170). Then, the operator himself/herself inputs an inserting point and a focus point by voice (steps S171 and S172), which is an observation information input process.

Like the thirteenth embodiment, inputting an inserting point and a focus point (steps S171 and S172) may be performed by a nurse or an operator by using the mouse 1423 or the keyboard 1424.

The subsequent operations (steps S173 to S182) are the same as those according to the thirteenth embodiment except that other commands are voice-input by an operator himself/ herself.

As a result, in addition to the same advantages as those of the thirteenth embodiment, the object observation system 1401C according to the fourteenth embodiment can be easily controlled by voice without the inconvenience of remote control manipulations and can have good operability and a simple construction at low costs.

Fifteenth Embodiment

Figure 114:
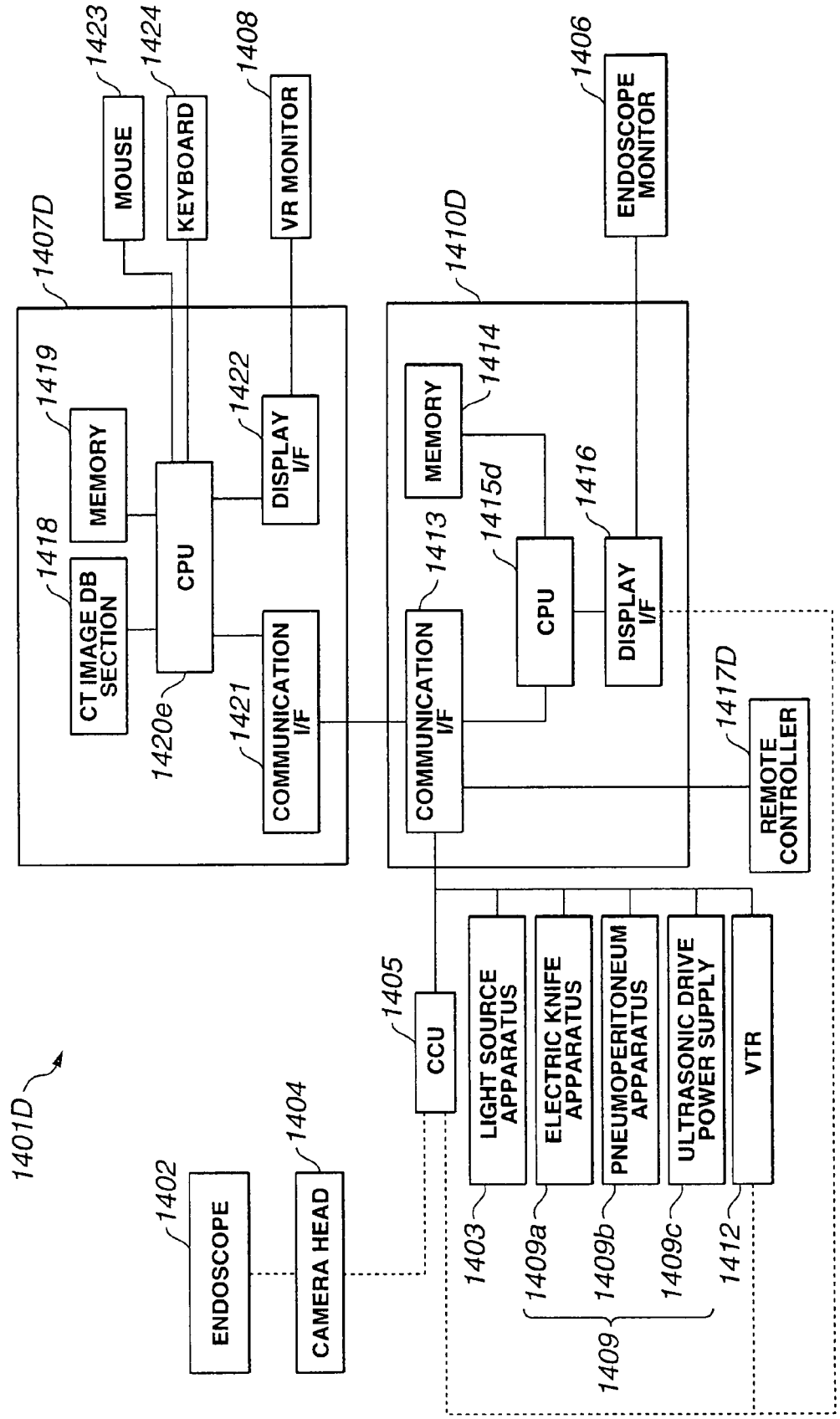
FIG. 114 is an entire configuration diagram showing an object observation system of a fifteenth embodiment.
Figure 115:
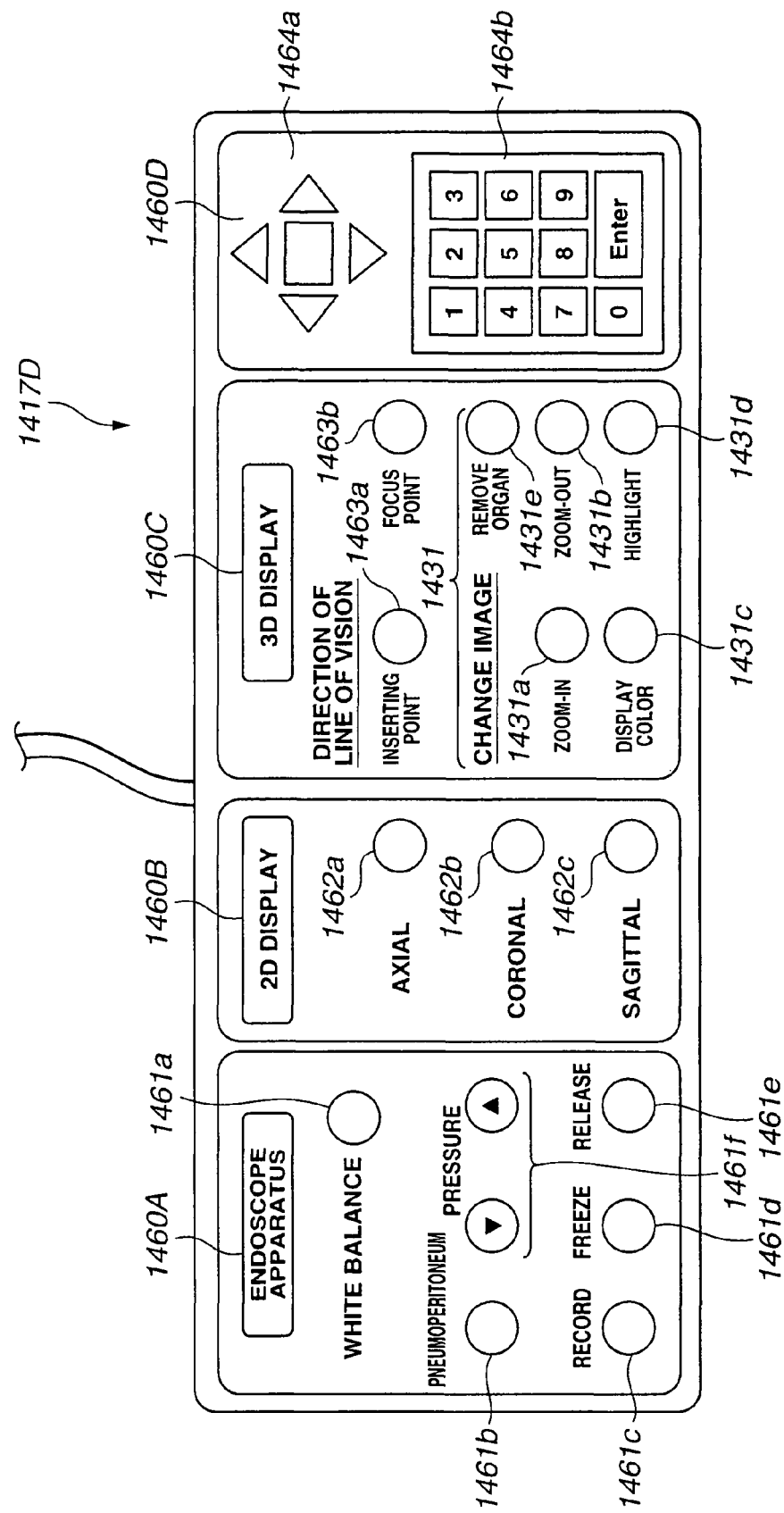
FIG. 115 is a construction diagram showing a construction of an operator's remote controller in FIG. 114.
Figure 116:
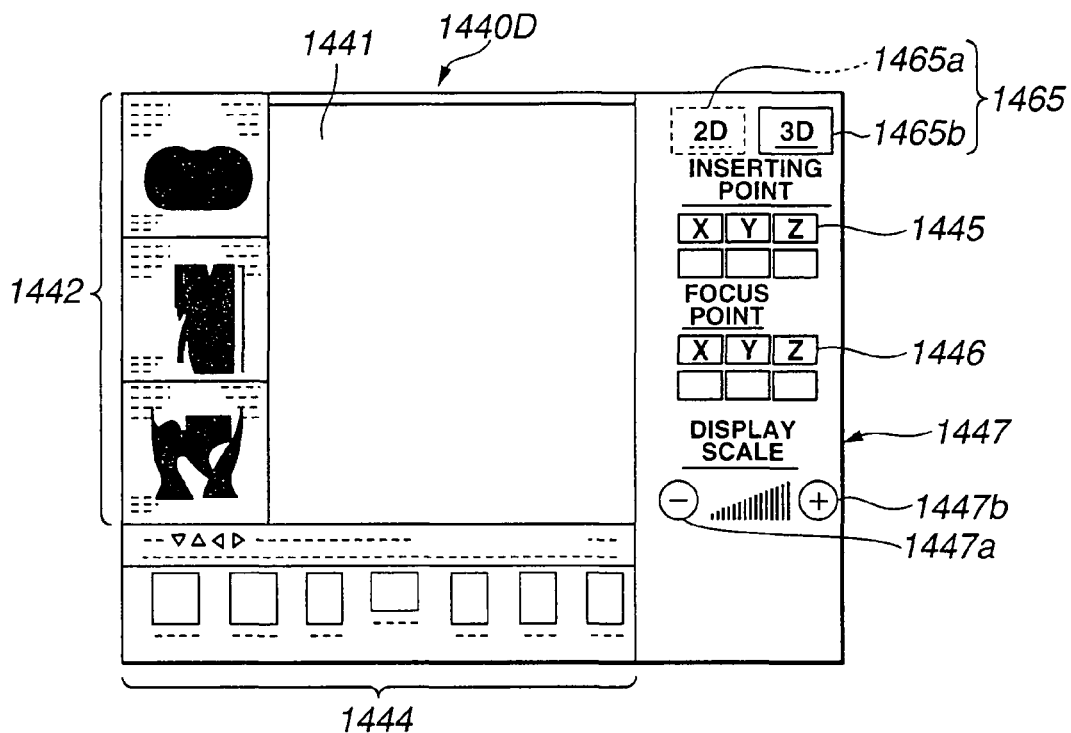
FIG. 116 is a screen display example of a virtual image display screen in a three-dimensional display form, which is displayed on a VR monitor in FIG. 114.
Figure 117:
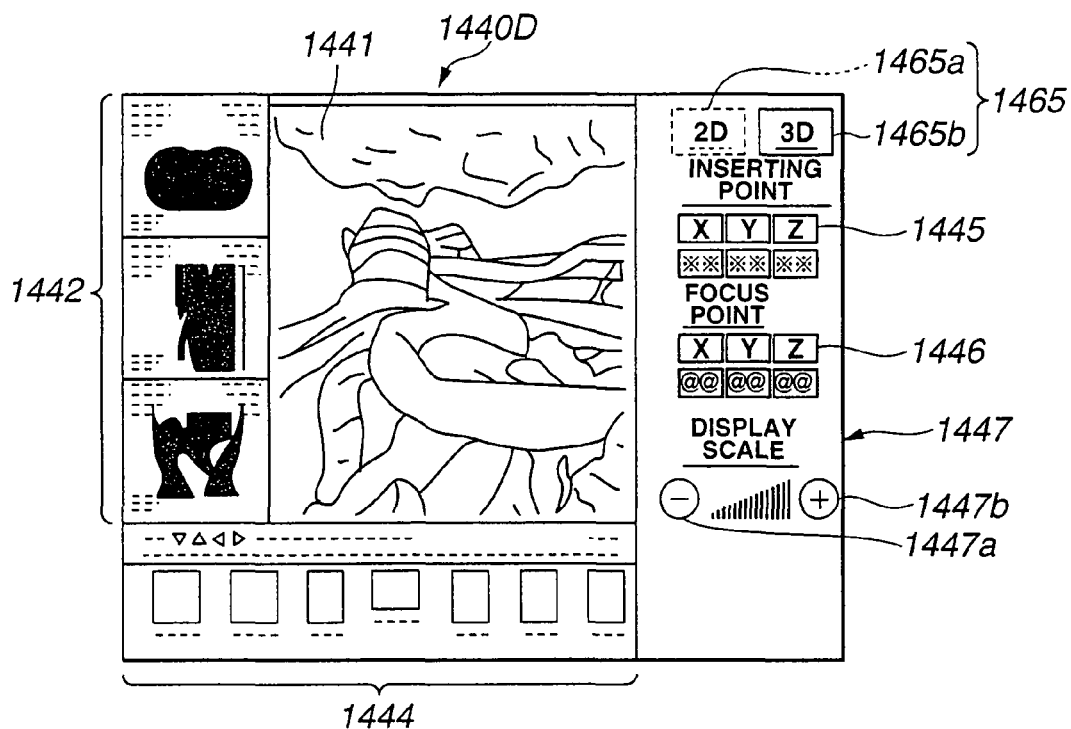
FIG. 117 is a screen display example on which a virtual image is displayed in a virtual image display area in FIG. 116.
Figure 118:
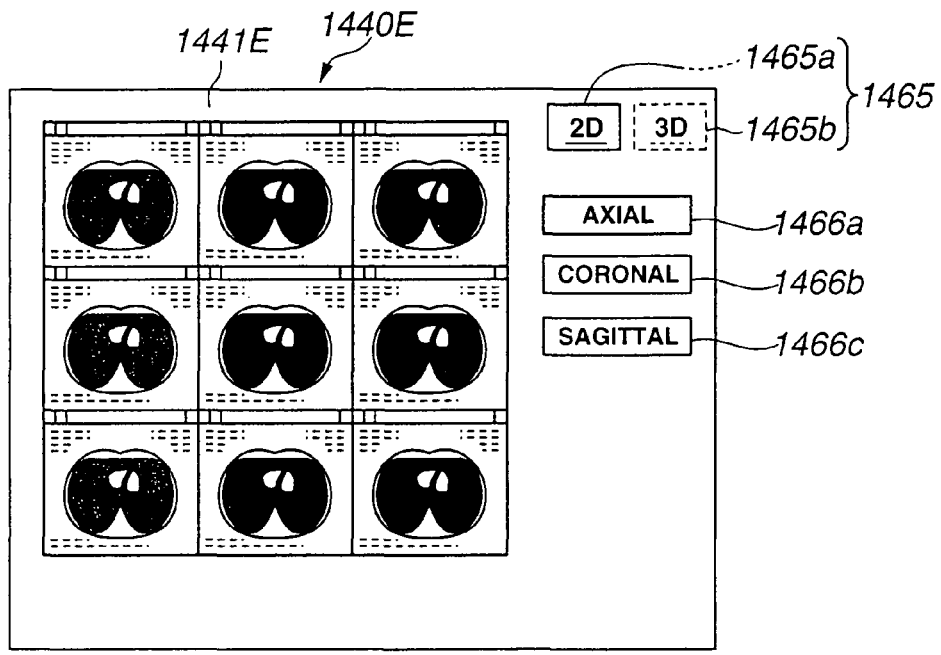
FIG. 118 is a screen display example of a virtual image display screen in a two-dimensional display form, which is displayed on the VR monitor in FIG. 114.
Figure 119:
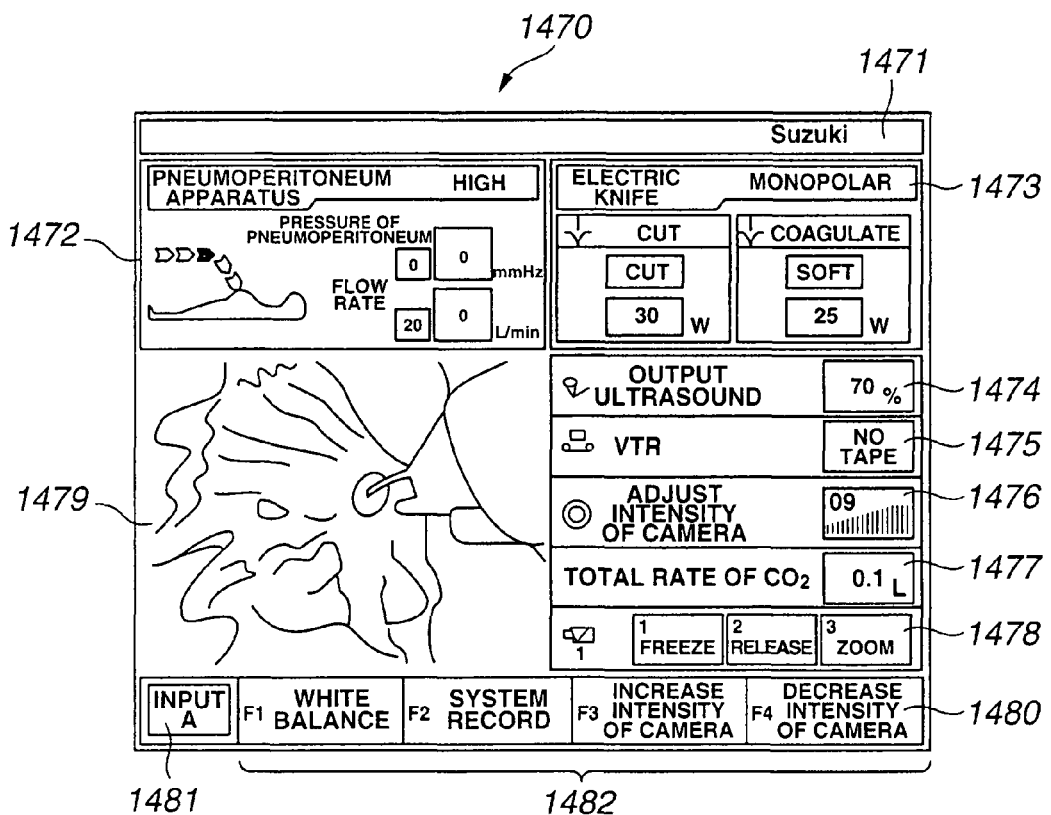
FIG. 119 is a screen display example of an equipment setting information screen displayed on the VR monitor in FIG. 114.
Figure 120:
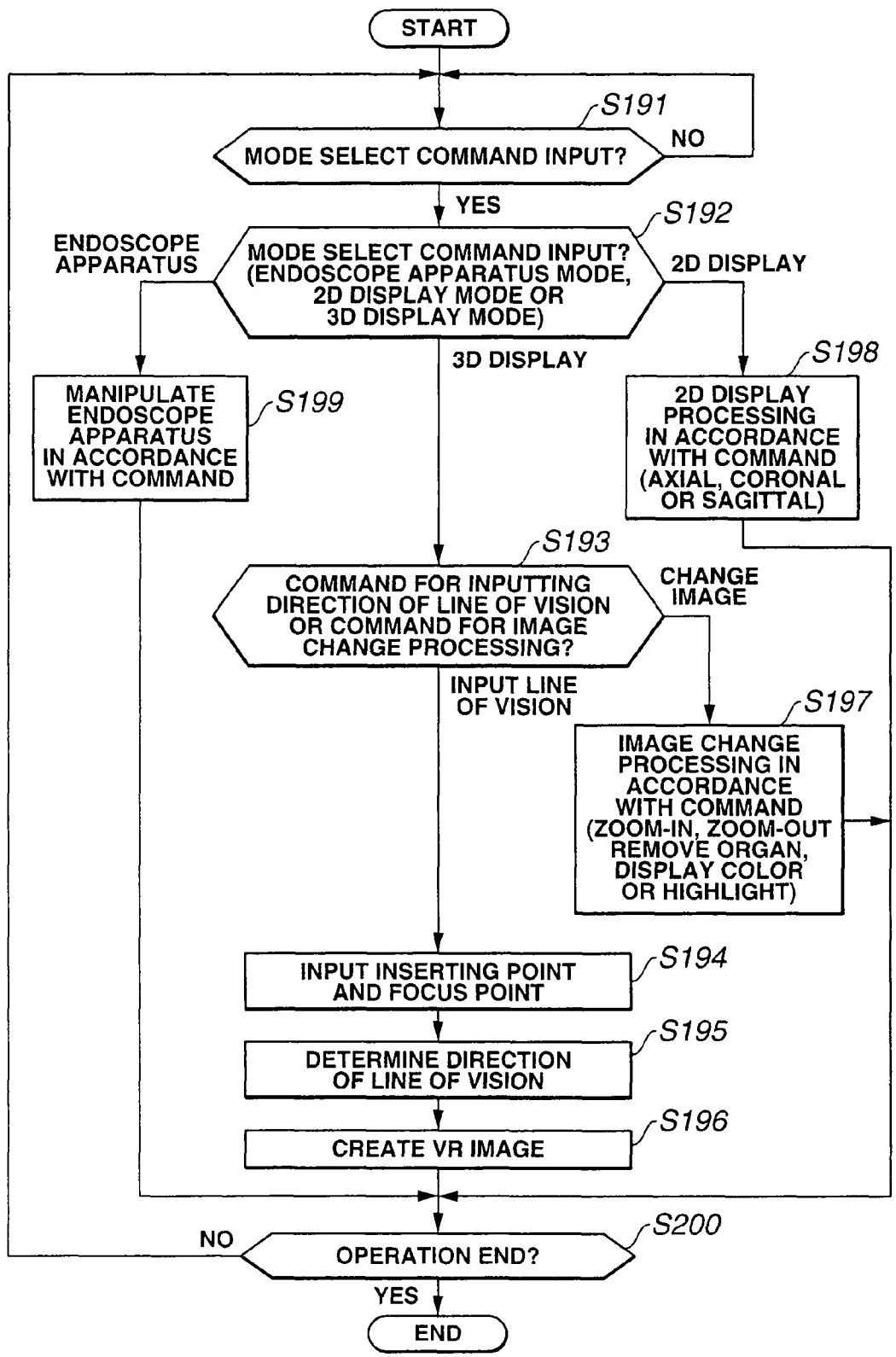
Figure 121:
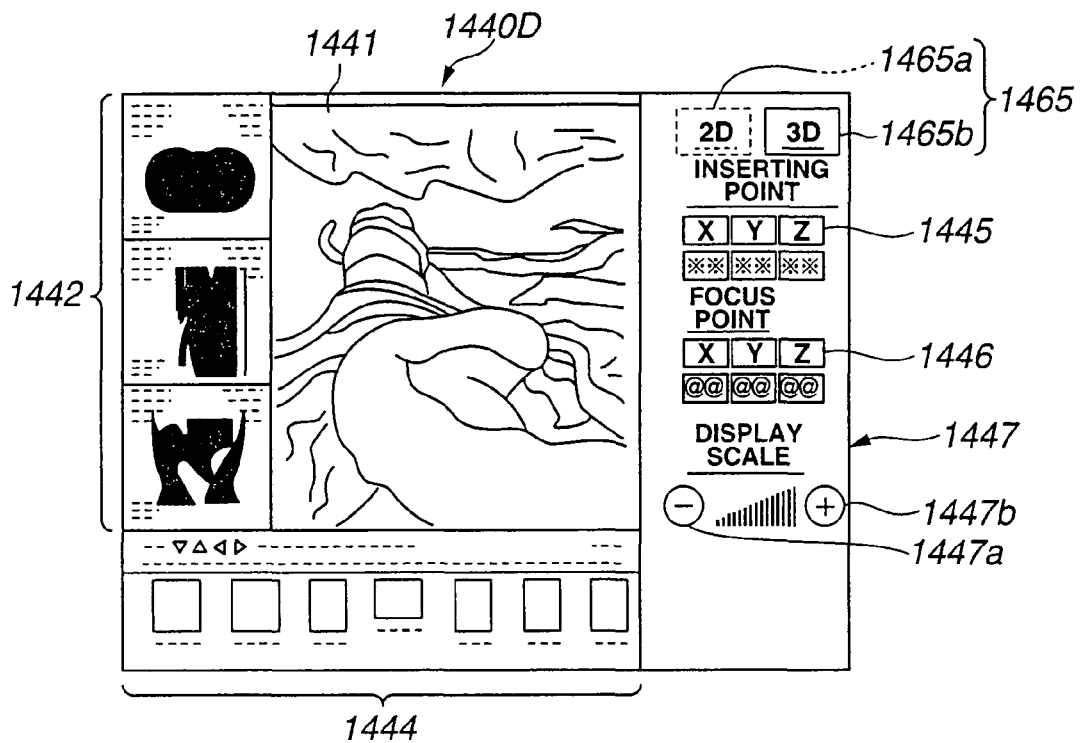
Figure 122:
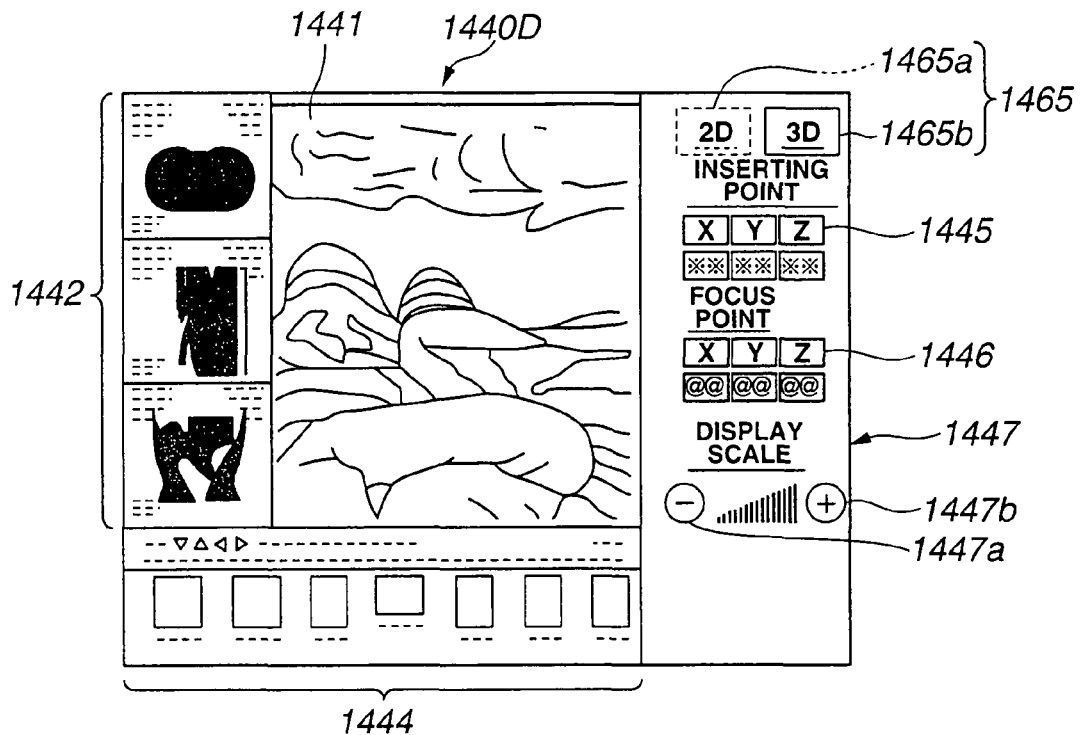

FIGS. 114 to 122 relate to a fifteenth embodiment of the invention. FIG. 114 is an entire configuration diagram showing an object observation system of the fifteenth embodiment. FIG. 115 is a construction diagram showing a construction of an operator's remote controller in FIG. 114. FIG. 116 is a screen display example of a virtual image display screen in a three-dimensional display form, which is displayed on a VR monitor in FIG. 114. FIG. 117 is a screen display example on which a virtual image is displayed in a virtual image display area in FIG. 116. FIG. 118 is a screen display example of a virtual image display screen in a two-dimensional display form, which is displayed on the VR monitor in FIG. 114. FIG. 119 is a screen display example of an equipment setting information screen displayed on the VR monitor in FIG. 114. FIG. 120 is a flowchart showing a processing operation, which is a feature of the fifteenth embodiment. FIG. 121 is a screen display example of a virtual image display screen for illustrating an operation of this embodiment. FIG. 122 is a screen display example of a virtual image display screen on which the virtual image in FIG. 121 is enlarged.

According to the thirteenth and fourteenth embodiments, a virtual image corresponding to an endoscopic live image can be displayed based on inclination angle data detected by an inclination angle sensor by tracking during surgery with the inclination angle sensor 1411 in the endoscope 1402. On the other hand, according to the fifteenth embodiment, an operator can freely input an inserting point and a focus point without tracking by using a remote controller for inputting an inserting point and a focus point as observation information input means. The rest of the construction is the same as that of the thirteenth embodiment, and the same reference numerals are given to the same components for description.

In other words, as shown in FIG. 114, an object observation system 1401D according to the fifteenth third embodiment has an operator's remote controller 1417D, a virtual image creating section 1407D and a system controller 1410D. The operator's remote controller 1417D can be used for inputting an inserting point and a focus point as observation information input means. The virtual image creating section 1407D creates a virtual image by performing image processing on virtual image data based on inserting point data and focus-point data input through the remote controller 1417D. The system controller 1410D controls the virtual image creating section 1407D.

The system controller 1410D has a CPU 1415d for controlling a CPU 1420d of the virtual image creating section 1407D based on an operation instruction through the remote controller 1417D on a virtual image displayed on the VR monitor 1408.

The CPU 1420d of the virtual image creating section 1407D creates a virtual image by performing image processing on virtual image data based on inserting point data and focus-point data input through the remote controller 1417D.

As shown in FIG. 115, for example, the remote controller 1417D includes an endoscope equipment operation portion 1460A, a 2D display operation portion 1460B, a 3D display operation portion 1460C and a setting operation portion 1460D. The endoscope equipment operation portion 1460A checks and sets an operation of an endoscope equipment. The 2D display operation portion 1460B is used for implementing two-dimensional display (2D display) of a virtual image on a display screen of the VR monitor 1408. The 3D display operation portion 1460C is used for implementing three-dimensional display (3D display) of a virtual image.

The endoscope equipment operation portion 1460A includes a white balance button 1461a, a pneumoperitoneum button 1461b, a pressure button 1461f, a record button 1461c, a freeze button 1461d and a release button 1461e. The white balance button 1461a can be used for a display image displayed on the endoscope monitor 1406. The pneumoperitoneum button 1461b can be used for executing a pneumoperitoneum apparatus 1409a. A pressure button 1461f can be used for increasing and decreasing pressure for establishing a pneumoperitoneum. The record button 1461c can be used for recording endoscopic live images in the VTR 1412. The freeze button 1461d and the release button 1461e can be used when recording is implemented.

The 2D display operation portion 1460B includes an axial button 1462a, coronal button 1462b and sagittal button 1462c, which are compliant with different kinds of 2D display modes.

The axial button 1462a can be used for display an axial plane having upper (head) and lower (foot) divisions of a body. The coronal button 1462b can be used for displaying a coronal plane having front (front) and rear (back) divisions of a body with respect to the major axis. The sagittal button 1462c can be used for displaying a sagittal plane having left and right divisions of a body.

The 3D display operation portion 1460C includes an inserting point button 1463a, a focus button 1463b and an image change operation portion 1431. The inserting point button 1463a can be used for inputting an inserting point as a direction of a line of vision. The focus button 1463b can be used for inputting a focus point. The image change operation portion 1431 is the same as the one according to the thirteenth embodiment.

The 3D display operation portion 1460C includes the same image change operation portion 1431 as the image change operation portion 1431 of the remote controller 1417 according to the thirteenth embodiment.

The setting operation portion 1460D includes an operation button 1464a and a numeric keypad 1464b. The operation button 1464a and the numeric keypad 1464b can be used for switching and/or determining setting input information and for inputting numeric values and so on, respectively, for an operation setting mode determined by the endoscope apparatus operation portion 1460A, the 2D display operation portion 1460B and the 3D display operation portion 1460C.

An operator can use the remote controller 1417D including these operation portions 1460A to 1460D to obtain desired information fast.

With the object observation system 1401D according to this embodiment, the virtual image display screen 1440D is displayed on the display screen of the VR monitor 1408 as shown in FIG. 116, for example.

The virtual image display screen 1440D has the same construction as that of the virtual image display screen 1440 according to the thirteenth embodiment except that a switched display portion 1465 on the upper part close to the right end of the screen. The switched display portion 1465 has a 2D mode display portion 1465a for indicating 2D display of virtual images and a 3D mode display portion 1465b for indicating 3D display of virtual images.

A direction of a line of vision of virtual images is determined in accordance with an inserting point and focus point input by an operator by manipulating (the numeric keypad 1464b of) the remote controller 1417D when the virtual image display screen 1440D shown in FIG. 116 is displayed on the display screen of the VR monitor 1408. Thus, virtual images are displayed in 3D display form on the virtual image display area 1441 as shown in FIG. 117.

On the other hand, in order to check a state of a body to be examined on a 2D display, the virtual image display screen 1440D shown in FIG. 117 can be switched to the virtual image display screen 1440E in 2D display as shown in FIG. 118 in response to a manipulation on (the operation button 1464a of) the remote controller 1417D by an operator. As a result the virtual image display screen 1440E in 2D display form can be displayed on the display screen of the VR monitor 1408.

As shown in FIG. 118, the virtual image display screen 1440E includes a 2D image display area 1441E on the center of the screen and an operation setting area 1443E on the right end of the screen. The 2D image display area 1441E displays a virtual image two-dimensionally. The operation setting area 1443E can be used for manipulating and/or setting the 2D image display area 1441E.

The operation setting area 1443E includes a switched display portion 1465, which is the same as that of the virtual image display screen 1440D, on the upper part. The lower part of the switched display portion 1465 includes an axial display switch 1466a, coronal display switch 1466b and sagittal display switch 1466c, which are compliant with the 2D display modes.

On the virtual image display screen 1440E, one of the display switches (that is, the axial display switch 1466a, coronal display switch 1466b and sagittal display switch 1466c) in the operation setting area 1443E can be selected in accordance with a manipulation on a respective 2D display mode button (of the axial button 1462a, the coronal button 1462b and the sagittal button 1462c) of the remote controller 1417D by an operator. Thus, a virtual image in a selected 2D display mode is displayed two-dimensionally on the 2D image display area 1441E.

On the other hand, in order to check an operation and settings of the endoscope apparatus, the virtual image display screen 1440D shown in FIG. 117 can be switched to the equipment setting information screen 1470 as shown in FIG. 119, which is displayed on the display screen of the VR monitor 1408, in response to a manipulation on (the operation button 1464a of) the remote controller 1417D by an operator.

As shown in FIG. 119, the equipment setting information screen 1470 includes, for example, a patient's name display portion 1471 on the upper part of the screen, a pneumoperitoneum display portion 1472, electric knife display portion 1473, ultrasonic treatment display portion 1474, VTR display portion 1475, camera intensity adjusting portion 1476, $CO_2$ capacity display portion 1477, CCU operation display potion 1478 and live image display portion 1479 under the patient's name display portion 1471 and a setting input display portion 1480 on the lowest part of the screen. The patient's name display portion 1471 shows a patient's name. The pneumoperitoneum display portion 1472 shows information such as an operation state, a pneumoperitoneum pressure and a temperature of the pneumoperitoneum apparatus 1409a. The electric knife display portion 1473 shows a setting and operation state of the electric knife apparatus 1409b. The ultrasonic processing display portion 1474 shows an ultrasonic output state by the ultrasonic treatment apparatus 1409c. The VTR display portion 1475 shows a remaining amount of a tape in the VTR 1412. The camera intensity adjusting portion 1476 shows an intensity adjustment (iris) state of the camera head 1404. The $CO_2$ capacity display portion 1477 shows a total output capacity (the integral of the capacity) of $CO_2$ into a body cavity. The CCU operation display portion 1478 shows an operation state (freeze, release or zoom) of the CCU 1405. The live image display portion 1479 displays endoscopic live images. The setting input display portion 1480 can be used for inputting settings of each equipment.

The setting input display portion 1480 includes an input switch 1481 and a function key portion 1482. The input switch 1481 is used for inputting different settings. Different setting modes are registered with the function key portion 1482 in advance.

The function key portion 1482 includes Functions F1 to F4. A white balance switch for implementing white balance is registered with Function F1. A system record switch for implementing system recording is registered with Function F2. A camera intensity-up switch for increasing the camera intensity is registered with Function F3. A camera intensity-down switch for decreasing the camera intensity is registered with Function F4.

In the equipment setting information screen 1470, an operator can manipulate the endoscope apparatus operation portion 1460A of the remote controller 1417D, select one of different equipment settings to be displayed, input a numeric value as required so that the equipment setting information can be changed and/or set.

In the object observation system 1401D, the CPU 1415d of the system controller 1410D controls the entire system according to an operation instruction signal from an operator through the remote controller 1417D.

Processing operations, which are features of the fifteenth embodiment, are shown in the flowchart in FIG. 120.

Here, surgery is performed on a body to be examined within the abdomen area of a patient by using the object observation system 1401D shown in FIG. 114. In this case, when the object observation system 1401D has power applied thereto, a nurse or an operator starts a program based on a control method for the object observation system of the invention, which is stored in the CPU 1420d, by using the mouse 1423 or the keyboard 1424 first of all.

Then an operator inserts the endoscope 1402 into the abdomen area of the patient. The object observation system 1401D causes an endoscopic live image obtained by the endoscope 1402 to be displayed on the display screen of the endoscope monitor 1406 under the display control of the CPU 1415d of the system controller 1410D as a body to be examined image obtaining operation.

Then, the operator manipulates the setting operation portion 1460D of the remote controller 1417D, selects and inputs the 2D display mode or 3D display mode of the endoscope apparatus operation mode or virtual image display mode as a mode select command and performs manipulations with the selected display mode.

The CPU 1415d of the system controller 1410D judges the presence of the input of a mode selection command based on an operation instruction on (the setting operation portion 1460D of) the remote controller 1417D by an operator (step S191) and, if yes, judges whether the mode selection command is a 2D display mode or 3D display mode of the endoscope equipment operation mode or the virtual image display mode (step S192). Based on the judgement result, the CPU 1415d switches to the display mode.

Here, if the 3D display mode of the virtual image display mode is selected and input, the CPU 1415d of the system controller 1410D identifies the input of the selection of the 3D display mode of the virtual image display mode and switches to and displays the virtual image display screen 1440D in the 3D display form as shown in FIG. 116 on the VR monitor 1408.

Then, on the virtual image display screen 1440D in the 3D display form, an operator needs to input an inserting point and a focus point by manipulating the remote controller 1417D.

First of all, the operator selects and inputs the direction-of-line-of-vision input command by manipulating the operation button 1464a of the remote controller 1417D and inputs numeric values for an inserting point and focus point by manipulating the numeric keypad 1464b.

Thus, the CPU 1415d of the system controller 1410D recognizes the input of the selection of the direction-of-line-of-vision input command (step S193), inputs an inserting point and a focus point based on the numeric values input from the numeric keypad 1464b (step S194), and determines the direction of the line of vision (step S195). In other words, the step S194 is an observation information input process.

Then, the CPU 1415d of the system controller 1410D controls the CPU 1420d of the virtual image creating section 1407D to perform image processing on virtual image data in accordance with the determined direction of the line of vision and to display the virtual image in the virtual image display area 1441 as shown in FIG. 117 (step S196). In other words, the step S196 is a virtual image processing process.

After that, the operator needs to perform image change processing on the virtual image displayed in the virtual image display area 1441.

Here, for example, the virtual display screen 1440D is displayed on the display screen of the VR monitor 1408 as shown in FIG. 121. Then, in order to increase the display scale of the virtual image, the operator manipulates the zoom-in button 1431b of the remote controller 1417D as an image processing change command.

Thus, the CPU 1415d of the system controller 1410D recognizes the selection of the image processing change (step S193) and controls the CPU 1420d of the virtual image creating section 1407D to zoom-in the virtual image currently displayed in the virtual image display area 1441 in response to the manipulation on the zoom-in button 1431b of the remote controller 1417D as the image change processing (step S197) corresponding to the input command and to display the virtual image in the virtual image display area 1441 as shown in FIG. 122. In other words, the step S197 is a virtual image change process.

On the other hand, in order to check the state of the body to be examined in 2D display mode, the operator selects and inputs the 2D display mode by manipulating the operation button 1464a of the remote controller 1417D.

Thus, the CPU 1415d of the system controller 1410D recognizes the input of the selection of the 2D display mode (step S193), switches to and displays the virtual image display screen 1440E in the 2D display mode shown in FIG. 118 on the display screen of the VR monitor 1408.

Then, with reference to the virtual image display screen 1440E, the operator manipulates the operation buttons of the 2D display operation portion 1460B of the remote controller 1417D.

Thus, the CPU 1415d of the system controller 1410D controls the CPU 1420d of the virtual image creating section 1407D to display the virtual image in the 2D display mode corresponding to the input command (step S198).

On the other hand, in order to check and set an operation of the endoscope apparatus during surgery, the operator manipulates the operation button 1464a of the remote controller 1417D and selects and inputs the endoscope operation mode.

Thus, the CPU 1415d of the system controller 1410D recognizes the input of the selection of the endoscope apparatus operation mode (step S193) and switches to and displays the equipment setting information screen 1470 shown in FIG. 199 on the display screen of the VR monitor 1408.

Then, the operator changes and/or sets equipment setting information by manipulating buttons for the endoscope apparatus 1460A on the remote controller 1417D with reference to the equipment setting information screen 1470.

Thus, the CPU 1415d of the system controller 1410D operates the endoscope apparatus in accordance with the input command (step S199).

After that, the processes from the step S191 are repeated to the end of the operation (step S200).

The commands may be input by a nurse or an operator by using the mouse 1423 or the keyboard 1424.

As a result, with the object observation system 1401D according to the fifteenth embodiment having the remote controller 1417D allowing the input of an inserting point and a focus point, an operator can freely input an inserting point and a focus point and view a virtual image of a desired area in addition to the same advantages as those of the thirteenth embodiment, which can advantageously improve the operability.

Furthermore, with the object observation system 1401D according to the fifteenth embodiment, an operator can freely check and set an operation of the endoscope apparatus by using the remote controller 1417D, which can advantageously further improve the operability.

Sixteenth Embodiment

FIGS. 123 and 124 relate to a sixteenth embodiment of the invention. FIG. 123 is an entire configuration diagram showing an object observation system according to the sixteenth embodiment. FIG. 124 is a flowchart showing a processing operation, which is a feature of the sixteenth embodiment.

While the remote controller 1417D to be manipulated by an operator is provided as virtual image change instructing means according to the fifteenth embodiment, a microphone to be used by an operator for instructing a manipulation is provided as virtual image change instructing means according to the sixteenth embodiment. Since the other components are the same as those of the fifteenth embodiment, the description thereof will be omitted. The same reference numerals are given to the same components for description.

In other words, an object observation system 1401E according to the sixteenth embodiment includes a system controller 1410E to which the microphone 1451E is connected as shown in FIG. 123.

For example, the microphone 1451E is attached to a head set (not shown) to be attached to the head of an operator and is removably connected to the system controller 1410E. The microphone 1451E may be a pin microphone, which can be attached to an operator.

The system controller 1410E has a microphone I/F 1452e connecting to the microphone 1451E and a voice recognizing portion 1453e for signal-converting voice signals received by the microphone I/F 1452e, recognizing the voice command and outputting a command signal in accordance with the recognized voice command to the CPU 1415e.

The rest of the construction is substantially the same as that of the fifteenth embodiment, and the description thereof will be omitted herein.

Then, in the object observation system 1401E, the CPU 1415e of the system controller 1410E controls the entire system under the voice control of an operator through the microphone 1451E.

In the same manner as that of the fifteenth embodiment, the object observation system 1401E can be operated in a display mode selected between the 2D display mode and the 3D display mode of one of the endoscope apparatus mode and the virtual image display mode under the voice control of an operator during surgery through the microphone 1451E.

A processing operation, which is a feature of the sixteenth embodiment, is shown in FIG. 124.

In the flowchart shown in FIG. 124, the object observation system 1401E is powered on in order to perform surgery on a body to be examined within the abdomen area of a patient so that voice input to the system controller 1410E through the microphone 1451E can be performed, which is the start of a voice input (step S300). Then, the operator himself/herself inputs each command by voice.

The subsequent operations (steps S191 to S200) are the same as those according to the fifteenth embodiment except that other commands are voice-input by an operator himself/herself.

Like the fifteenth embodiment, inputting each command may be performed by a nurse or an operator by using the mouse 1423 or the keyboard 1424.

As a result, in addition to the same advantages as those of the fifteenth embodiment, the object observation system 1401E according to the sixteenth embodiment can be easily controlled by voice without the inconvenience of remote control manipulations and can have good operability and a simple construction at low costs.

As described above, according to this embodiment, an easy-to-use object observation system and method of controlling an object observation system can be obtained which can display a virtual image intended by an operator as a reference image.

The invention is not limited to the first to sixteenth embodiments, and various changes and modifications of the invention can be made without departing from the spirit and scope of the invention.

What is claimed is:

1. A virtual image display system, comprising:
   an endoscope having a rigid insert portion, which is capable of being inserted into a cavity of a body to be examined and capable of being can be used for observing an image of the body to be examined;
   at least one treating device which is capable of being inserted into the cavity of the body to be examined from a position different from a position at which the endoscope is inserted into the cavity of the body to be examined for performing a treatment on the body to be examined;
   a first detecting portion for detecting information indicating an observation direction of the insert portion of the endoscope;
   a second detecting portion for detecting information indicating a treatment direction of the treating device;
   a three-dimensional virtual image data storing portion for storing three-dimensional image data relating to the body to be examined, which is prepared in advance;
   a virtual image data processing portion for creating data of an endoscope correspondent virtual image in the observation direction of the insert portion of the endoscope by processing the three-dimensional virtual image data based on information indicating the observation direction of the insert portion of the endoscope detected by the first detecting portion, and for creating data of a treating-device correspondent virtual image in the treatment direction of the treating device by processing the three-dimensional virtual image data based on the information indicating the treatment direction of the treating device detected by the second detecting portion;
   an endoscope-operator dedicated monitor provided with a first endoscopic observation image display device capable of displaying an endoscopic observation image as a live image, and a first virtual image display device capable of displaying the endoscope correspondent virtual image or the treating-device correspondent virtual image, the first endoscopic observation image display device and the first virtual image display device being disposed in a parallel;
   at least one treating-device-operator dedicated monitor which is a monitor disposed to have a display direction different from a display direction of the endoscope-operator dedicated monitor and provided with a second endoscope observation image display device which is different from the first endoscopic observation image display device and capable of displaying the endoscopic observation image as a live image, and a second virtual image display device capable of displaying the endoscope correspondent virtual image or the treating-device correspondent virtual image, the second endoscopic observation image display device and the second virtual image display device being disposed in a parallel; and switch sections provided to be respectively corresponding to the first detecting portion and the second detecting portion, for instructing change of a display mode of the first virtual image display device and/or a display mode of the second virtual image display device, wherein when change of the display mode is not instructed by one of the switch sections provided respectively corresponding to the first detecting portion and the second detecting portion, the endoscope correspondent virtual image is displayed in the first virtual image display device and the treating-device correspondent virtual image corresponding to a predetermined treating device is displayed on the second virtual image display device, and when change of the display mode to a simultaneous display mode is instructed by one of the switch sections provided respectively corresponding to the first detecting portion and the second detecting portion, the endoscope correspondent virtual image or the treating-device correspondent virtual image which corresponds to the switch portion by which the change of the display mode is instructed is displayed on both of the first virtual image display device and the second virtual image display device.

2. A virtual image display system according to claim 1, wherein change of the display mode to a different display mode is instructed by one of the switch sections provided respectively corresponding to the first detecting portion and the second detecting portion, the endoscope correspondent virtual image is displayed in the first virtual image display device and the treating-device correspondent virtual image corresponding to the predetermined treating device is displayed on the second virtual image display device.

3. A virtual image display system according to claim 1, wherein the endoscope and the treating device are inserted into the cavity of the body to be examined through trocars attached to places of the body to be examined, and the first detecting portion is disposed at a trocar for inserting the endoscope and the second detecting portion is disposed at a trocar for inserting the treating device.

4. A virtual image display system according to claim 1, wherein the switch portions are respectively disposed at the first detecting portion and the second detecting portion.

5. A virtual image display method for an object observation system including an endoscope having a rigid insert portion, which is capable of being inserted into a body to be examined and capable of being used for observing an image of the body to be examined, and at least one treating device which is capable of being inserted into the body to be examined at a position different from a position where the insert portion is inserted into the cavity of body to be examined for performing a treatment on the body to be examined, the method comprising:

providing a first detection portion for detecting information indicating an observation direction of the insert portion of the endoscope;

providing a second detection portion for of detecting information indicating a treatment direction of the treating device;

storing three-dimensional virtual image data relating to the body to be examined, which is prepared in advance;

creating data of an endoscope correspondent virtual image in the observation direction of the insert portion of the endoscope by processing the three-dimensional virtual image data based on the information indicating the observation direction of the insert portion of the endoscope detected by the first detecting portion, and creating data of a treating-device correspondent virtual image in the treatment direction of the treating device processing the three-dimensional virtual image data based on the information indicating the treatment direction of the treating device detected by the second detecting portion;

providing an endoscope-operator dedicated monitor provided with a first endoscope observation image display device capable of displaying an endoscopic observation image as a live image, and a first virtual image display device capable of displaying the endoscope correspondent virtual image or the treating-device correspondent virtual image, the first endoscope observation image display device and the first virtual image display device being disposed in parallel;

providing at least one treating-device-operator dedicated monitor which is a monitor disposed to have a display direction different from a display direction of the endoscope-operator dedicated monitor and provided with a second endoscope observation image display device which is different from the first endoscopic observation image display device and capable of displaying the endoscopic observation image as a live image, and a second virtual image display device capable of displaying the endoscope correspondent virtual image or the treating-device correspondent virtual image, the second endoscopic observation image display device and the second virtual image display device being disposed in a parallel;

instructing change of a display mode of the first virtual image display device and/or a display mode of the second virtual image display device by the switch sections provided respectively corresponding to the first detecting portion and the second detecting portion; and when change of the display mode is not instructed by one of the switch sections provided respectively corresponding to the first detecting portion and the second detecting portion, displaying the endoscope correspondent virtual image in the first virtual image display device and the treating-device correspondent virtual image corresponding to a predetermined treating device is displayed on the second virtual image display device, and when change of the display mode to a simultaneous display mode is instructed by one of the switch sections provided respectively corresponding to the first detecting portion and the second detecting portion, displaying the endoscope correspondent virtual image or the treating-device correspondent virtual image which corresponds to the switch portion by which the change of the display mode is instructed on both of the first virtual image display device and the second virtual image display device.

6. A virtual image display system according to claim 5, wherein change of the display mode to a different display mode is instructed by one of the switch sections provided respectively corresponding to the first detecting portion and the second detecting portion, the endoscope correspondent virtual image is displayed in the first virtual image display device and the treating-device correspondent virtual image corresponding to the predetermined treating device is displayed on the second virtual image display device.

7. A virtual image display system according to claim 5, wherein the endoscope and the treating device are inserted into the cavity of the body to be examined through trocars attached to places of the body to be examined, and the first detecting portion is disposed at a trocar for inserting the endoscope and the second detecting portion is disposed at a trocar for inserting the treating device.

8. A virtual image display system according to claim 5, wherein the switch portions are respectively disposed at the first detecting portion and the second detecting portion.

* * * * *

UNITED STATES PATENT AND TRADEMARK OFFICE
CERTIFICATE OF CORRECTION

PATENT NO. : 7,951,070 B2
APPLICATION NO. : 11/716308
DATED : May 31, 2011
INVENTOR(S) : Takashi Ozaki et al.

Page 1 of 1

It is certified that error appears in the above-identified patent and that said Letters Patent is hereby corrected as shown below:

Column 68, line 27 (claim 1, line 4), should read: examined and capable of being used for observ Signed and Sealed this
Eleventh Day of October, 2011

David J. Kappos
*Director of the United States Patent and Trademark Office*